US008076316B2

(12) United States Patent
Frincke

(10) Patent No.: US 8,076,316 B2
(45) Date of Patent: *Dec. 13, 2011

(54) STEROID COMPOUNDS AND FORMULATIONS

(75) Inventor: James M. Frincke, San Diego, CA (US)

(73) Assignee: Harbor BioSciences, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/957,661

(22) Filed: Dec. 1, 2010

(65) Prior Publication Data
US 2011/0098260 A1 Apr. 28, 2011

Related U.S. Application Data

(63) Continuation of application No. 11/835,397, filed on Aug. 7, 2007, now Pat. No. 7,863,261, which is a continuation of application No. 09/675,323, filed on Sep. 28, 2000, now abandoned.

(60) Provisional application No. 60/166,116, filed on Nov. 16, 1999.

(51) Int. Cl.
A61K 31/56 (2006.01)
C07J 1/00 (2006.01)

(52) U.S. Cl. .............................. 514/170; 514/178

(58) Field of Classification Search .................. 552/502
See application file for complete search history.

(56) References Cited

U.S. PATENT DOCUMENTS

| 2,243,887 A | 6/1941 | Serini et al. |
| 2,267,257 A | 12/1941 | Ruzicka |
| 2,308,833 A | 1/1943 | Ruzicka et al. |
| 2,830,063 A | 4/1958 | Clinton et al. |
| 3,029,263 A | 4/1962 | Campbell et al. |
| 3,128,292 A | 4/1964 | Counsell |
| 3,176,030 A | 3/1965 | Huffmann et al. |
| 3,200,113 A | 8/1965 | Christiansen et al. |
| 3,734,935 A | 5/1973 | Husbands et al. |
| 3,944,576 A | 3/1976 | Van den Broek |
| 4,898,694 A | 2/1990 | Schwartz et al. |
| 5,028,631 A | 7/1991 | Schwartz et al. |
| 5,075,464 A | 12/1991 | Blohm et al. |
| 5,206,008 A | 4/1993 | Loria |
| 5,292,730 A | 3/1994 | Lardy |
| 5,296,481 A | 3/1994 | Partridge et al. |
| 5,372,996 A | 12/1994 | Labrie |
| 5,387,583 A | 2/1995 | Loria |
| 5,424,463 A | 6/1995 | Lardy et al. |
| 5,461,042 A | 10/1995 | Loria |
| 5,506,223 A | 4/1996 | Lardy et al. |
| 5,593,981 A | 1/1997 | Labrie |
| 5,686,438 A | 11/1997 | Daynes et al. |
| 5,723,455 A | 3/1998 | Tanabe et al. |
| 5,763,433 A | 6/1998 | Morfin |
| 5,824,668 A | 10/1998 | Rubinfeld et al. |
| 5,859,000 A | 1/1999 | Dowell et al. |
| 5,912,240 A | 6/1999 | Loria |
| 5,922,701 A | 7/1999 | Araneo |
| 5,925,630 A | 7/1999 | Upasani et al. |
| 5,939,545 A | 8/1999 | Upasani et al. |
| 6,110,906 A | 8/2000 | Labrie et al. |
| 6,436,435 B1 | 8/2002 | Rubinfeld et al. |
| 6,573,289 B1 | 6/2003 | Tasaka et al. |
| 6,667,299 B1 | 12/2003 | Ahlem et al. |
| 6,767,903 B1 | 7/2004 | Cleve et al. |
| 7,462,610 B2 | 12/2008 | Lardy et al. |
| 7,482,334 B2 | 1/2009 | Frincke et al. |
| 7,524,835 B2 | 4/2009 | Frincke |
| 7,550,450 B2 | 6/2009 | Lardy et al. |
| 7,691,835 B2 | 4/2010 | Frincke |
| 7,696,189 B1 | 4/2010 | Frincke |
| 7,842,680 B2 | 11/2010 | Lardy et al. |
| 7,863,261 B2 | 1/2011 | Frincke |
| 2003/0060425 A1 | 3/2003 | Ahlem et al. |
| 2004/0043973 A1 | 3/2004 | Ahlem et al. |
| 2006/0079492 A1 | 4/2006 | Ahlem et al. |
| 2006/0088473 A1 | 4/2006 | Dowding et al. |
| 2007/0014719 A1 | 1/2007 | Reading et al. |
| 2007/0077201 A1 | 4/2007 | Reading et al. |
| 2007/0129282 A1 | 6/2007 | Ahlem et al. |
| 2008/0153792 A1 | 6/2008 | Frincke et al. |

FOREIGN PATENT DOCUMENTS

| EP | 0 363 128 | 4/1990 |
| WO | WO 91/00732 | 1/1991 |
| WO | WO 95/07926 | 3/1995 |
| WO | WO 95/10527 | 4/1995 |
| WO | WO 97/37662 | 10/1997 |
| WO | WO 99/63973 | 12/1999 |
| WO | WO 00/32201 | 6/2000 |
| WO | WO 00/56757 | 9/2000 |

OTHER PUBLICATIONS

U.S. Appl. No. 60/124,087, filed Nov. 3, 1999, Prendergast et al.
U.S. Appl. No. 60/126,056, filed Mar. 23, 1999, Ahlem et al.
Ben-David et al., Anti-hypocholterolemic effects of dihydroepiandersterone in rats *Proc. Soc. Exp. Biol. Med.*, 125:1136-40 1967.
Campbell, et al., 6-methyl steroids in the androstane series. *J. Amer. Chem. Soc.* 80:4717-4721 1958.
Campbell, et al., The synthesis of some 7α- and 7β-methyl steroid hormones, *J. Amer. Chem. Soc.*, 81:4069-4074 1959.
Chambaz, et al., Urinary steroids in neonates: Characterization of four androstenetetrols by gas chromatography and mass spectrometry. *Proceedings of Acad. Sc. Paris, Series D*, 268: 2817-2820 1969.
Chang, et al., Suppression of Δ5-Androstenediol-induced androgen receptor transactivation by selective steroids in human prostate cancer cells, *Proc. Natl. Acad. Sci. USA*. 96(20):11173-11177 1999.
Clinton, et al., Esters of 17α-Ethinylandrostane-3β,17β-diol and 17α-ethinylandrost-5-ene-3β,17β-diol, *J. Org. Chem.* 22:473-475 1957.
Ferrari, et al., Inhibition of β-hydroxysteroid dehydrogenase 1. Structural characteristics of some steroidal inhibitors, *Biochem. Biophys. Acta* 77:349-356 1963.
Gatto, et al., Dehydroepiandrosterone inhibits the growth of DMBA-induced rat mammary carcinoma via the androgen receptor *Oncol. Rep.* 5(1):241-3 1998.

(Continued)

Primary Examiner — Elli Peselev
(74) Attorney, Agent, or Firm — Darryl D. Muenchau

(57) ABSTRACT

The invention provides methods to treating conditions such as prostate cancer, or for ameliorating one or more symptoms associated with prostate cancer, or for agents that modulate the biological activity of the androgen receptor. The invention also provides methods and compositions suitable for therapeutic applications.

7 Claims, 6 Drawing Sheets

OTHER PUBLICATIONS

Gaunt, et al., Antagonists to cortisone: an ACTH-like action of steroids, *Endocrinol.* 52:407-423 1953.

Hackenberg et al., Estrogen and androgen receptor mediated stimulation and inhibition of proliferation by androst-5-ene-3β,17β-diol in human mammary cancer cells, *J. Steroid Biochem. Mol. Biol.*, 46(5):597-603 1993.

Henderson, Dehydroepiandrosterone and 16α-bromo-epiandrosterone: Inhibitors of Epstein-Barr virus-induced transformation of human lymphocytes, *Carcinogenesis*, 2(7):683-686 1981.

Lardy, et al., Ergosteroids. II: Biologically active metabolites and synthetic derivatives of dehydroepiandrosterone, *Steroids* 63:158-165 1998.

Marwah, et al., C19-Steroids as androgen receptor modulators: Design, discovery, and structure-activity relationship of new steroidal androgen receptor antagonists, *Bioorg. Med. Chem.*, 14:5933-5947 2006.

Miyamoto, et al., $\Delta^5$-androstenediol is a natural hormone with androgenic activity in human prostate cancer cells, *Proc. Natl. Acad. Sci. U.S.A.* 95(19):11083-11088 1998.

Miyamoto, et al.,3β-Acetoxyandrost-1,5-diene-17-ethylene ketal functions as a potent antiandrogen with marginal agonist activity, *Proc. Natl. Acad. Sci. USA*, 100:4440-4444 2003.

Moore, et al. Concentration of dihydrotestosterone and 3α-androstanediol in naturally occurring and androgen-induced prostatic hyperplasia in the dog, *J. Clin. Invest.* 64:1003-1010 1979.

Morfin, et al, Pregnenolone and dehydroepiandersterone as precursors of native 7-hydroxylated metabolites which increases the immune response in mice, *J. Steroid Biochem. Mol. Biol.* 50:91-100 1994.

Penning, et al., Human 3α-hydroxysteroid dehydrogenase isoforms (AKR1C1-AKR1C4) of the aldo-keto reductase superfamily: functional plasticity and tissue distribution reveals roles in the inactivation and formation of male and female sex hormones, *Biochem J.* 351:67-77 2000.

Segaloff, et al., Hormonal therapy in cancer of the breast IV. Effect of androstenediol on clinical course and hormonal excretion, *Cancer* 5(6):1179-1181 1952.

Segaloff, et al., Hormonal therapy in cancer of the breast. V. The effect of methyltestosterone on clinical course and hormonal excretion *Cancer*, 5(2):271-274 1952.

Segaloff, et al., Testosterone and miscellaneous steroids in the treatment of advanced mammary cancer, *Cancer*, 10(4):808-812 1957.

Shackleton, et al., Metabolism of fetal and neonatal adrenal steroids, *J. Steroid. Biochem.* 11:523-529 1979.

US 8,076,316 B2

STEROID COMPOUNDS AND FORMULATIONS

CROSS-REFERENCE TO RELATED APPLICATIONS

This application is a continuation of U.S. application Ser. No. 11/835,397, filed Aug. 7, 2007, now U.S. Pat. No. 7,863, 261, which is a continuation application of abandoned U.S. application Ser. No. 09/675,323, filed Sep. 28, 2000, which claims priority from abandoned U.S. provisional application Ser. No. 60/166,116, filed Nov. 16, 1999, all of which are incorporated herein by reference.

BACKGROUND OF THE INVENTION

The invention provides methods and compositions comprising steroids or analogs, such as analogs of androst-5-ene-3β,17β-diol ("AED") or 1,3,5(10)-estratriene-17α-ethynyl-3β,17β-diol ("EED") for use as agents to modulate the biological activity of the androgen receptor ("AR") or to treat androgen responsive or related conditions such as prostate cancer and benign prostatic hypertrophy ("BPH").

Prostate cancer represents the most commonly diagnosed non-cutaneous malignancy in aging males and is the second leading cause of cancer-related death in North American men. Androgen ablation has been the cornerstone of treatment for advanced forms of this disease, typically by a combination of surgical or medical antiandrogen therapy. Antiandrogens that are commonly used include hydroxyflutamide (HF), cyproterone acetate and bicalutamide (casodex). Androgen ablation treatments are used to reduce the level of endogenous androgens. However, most androgen-dependent prostate cancer cases appear to progress to androgen-independent malignancies. Limiting the availability of androgens to regional or metastatic prostate cancers usually induces remission, but after some time the cancer often becomes refractory to androgen ablation treatments. It has been suggested that genetic changes of the AR gene may contribute to a short response to anti-androgen therapy. However, the mechanisms responsible for conversion of prostate cancer cells to an androgen independent condition are not fully characterized.

BPH is a disease that affects approximately 60% of males older than about 60 years of age. An elevated accumulation of male hormones such as dihydrotestosterone ("DHT") in prostate tissue may contribute to prostate enlargement. The accumulation of DHT appears to result from elevated intracellular DHT receptor levels. The increase is associated with an elevation of estrogen levels relative to androgen levels, which decrease with age. The urological symptoms consist in an elevated frequency of miction due to elevated residual urine. This is typically accompanied by a weak flow of urine, a time-delayed start of miction, and repeated infections of the bladder and kidneys. BPH treatment includes surgery to remove the obstruction, but this is not always effective or has unwanted side-effects, e.g., incontinence or decreased libido. Other treatments such as androgen ablation by bilateral orchiectomy or androgen ablation chemotherapy are too invasive or have unwanted side-effects. Less invasive methods exist, e.g. balloon dilatation. treatment with hyperthermia or microwaves, but they can have limited efficacy.

Chemotherapy for conditions such as prostate cancer and BPH, or their symptoms, include administering androgen synthesis inhibitors such as 5α reductase inhibitors to inhibit production of sex hormones such as testosterone or dihydrotestosterone, or administering Naftopidil for dysuria. Treatment with 5α reductase inhibitors has been combined with other treatments such as anti-estrogens, aromatase (estrogen synthetase) inhibitors, inhibitors of 17β-hydroxysteroid dehydrogenase or lutenizing hormone releasing hormone agonists or antagonists. Other proposed treatments include administering aromatase inhibitors such as 4-hydroxyandrostene-3,17-dione. Chemotherapy typically has drawbacks. It can have unwanted side effects, particularly in older patients or it can become ineffective over time. Various treatments and their limitations have been described, see, e.g., U.S. Pat. Nos. 4,059,630, 4,310,523, 4,659,695, 4,970,204, 5,137,882, 5,372,996, 5,494,914, 5,561,124, 5,593,981, 5,994,334, 5,994,335, 5,998,377, 6,015,806, 6,093,722, 6,110,906 and European publication EP 0 401 653.

Biological properties of AED and related steroid compounds have been disclosed, see, e.g., U.S. Pat. No. 2,833, 793, 2,911,418, 3,148,198, 3,471,480, 3,710,795, 3,711,606 3,976,691, 4,268,441, 4,427,649, 4,542,129, 4,666,898, 4,898,694, 4,956,355, 4,978,532, 5,001,119, 5,043,165, 5,077,284, 5,028,631, 5,110,810, 5,157,031, 5,162,198, 5,175,154, 5,206,008, 5,277,907, 5,292,730, 5,296,481, 5,372,996, 5,387,583, 5,407,684, 5,424,463, 5,461,042, 5,478,566, 5,506,223, 5,518,725, 5,527,788, 5,527,789, 5,532,230, 5,559,107, 5,562,910, 5,583,126, 5,585,371, 5,587,369, 5,591,736, 5,593,981, 5,610,150, 5,635,496, 5,641,766, 5,641,768, 5,656,621, 5,660,835, 5,677,366, 5,686,438, 5,696,106, 5,700,793, 5,707,983, 5,709,878, 5,710,143, 5,714,481, 5,728,688, 5,736,537, 5,744,462, 5,753,237, 5,756,482, 5,776,921, 5,776,923, 5,780,460, 5,795,880, 5,798,347, 5,798,348, 5,804,576, 5,807,848, 5,807,849, 5,811,418, 5,824,313, 5,824,668, 5,824,671, 5,827,841, 5,837,269, 5,837,700, 5,843,932, 5,846,963, 5,856,340, 5,859,000, 5,869,090, 5,863,910, 5,872,114, 5,872,147 and 5,910,407; German patent numbers 2035738 and 2705917; PCT publication numbers WO 95/21617, WO 97/48367, WO 98/05338, WO 98/50040, WO 98/50041, WO 98/58650; European publication number 0020029.

The androgen receptor and co-activators such as $ARA_{70}$, $ARA_{24}$, $ARA_{54}$, $ARA_{55}$ and Rb, and methods to use them have been described, e.g., U.S. Pat. Nos. 5,789,170, 5,614, 620; International publication number WO 00/04152.

The invention methods and compositions accomplish one or more of several objects. Invention objects include providing methods and compositions to inhibit proliferation of prostate cancer cells a subject. Other objects are to provide methods to make and use compositions and formulations comprising EED analogs or other compounds disclosed herein. Additional objects will be apparent from the disclosure.

SUMMARY OF THE INVENTION

Figure 1:
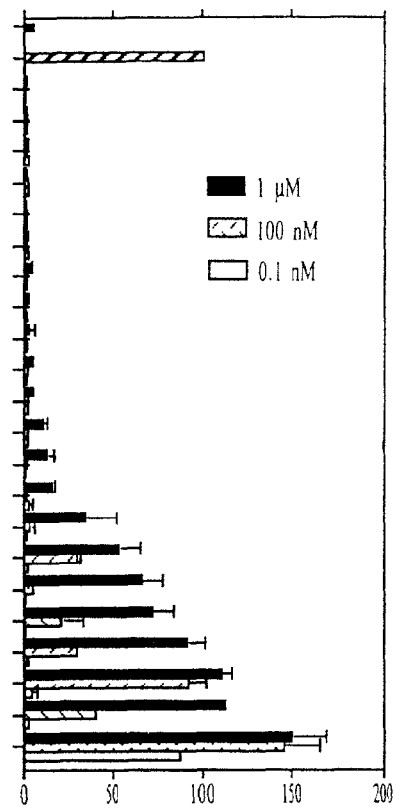
FIG. 1 shows effects of tested compounds on the transcriptional activity of the androgen receptor.

The invention methods and compositions accomplish one or more of several objects. Invention objects include providing methods and compositions to inhibit proliferation of prostate cancer cells a subject. Other objects are to provide methods to make and use compositions and formulations comprising EED analogs or other compounds disclosed herein. Additional objects will be apparent from the disclosure. In accordance with the objects, the invention provides a method to treat or prevent an androgen responsive disease such as prostate cancer, benign prostatic hyperplasia or breast cancer in a subject, or to ameliorate one or more symptoms thereof, comprising administering to a subject, or delivering to the subject's tissues, an effective amount of a compound of formula 1 or 2

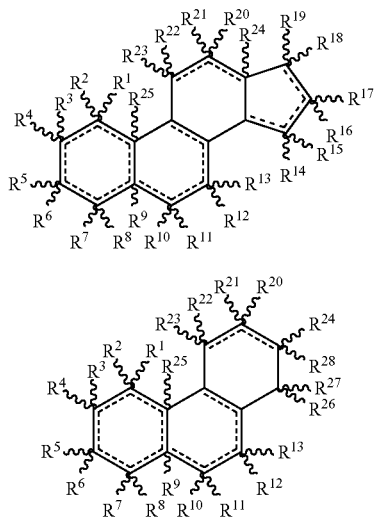

wherein, $R^1$-$R^{28}$ independently are —H, —$OR^{PR}$, —$SR^{PR}$, —$N(R^{PR})_2$, —O—Si—$(R^A)_3$, —CN, —$NO_2$, —$OSO_3H$, —$OPO_3H$, an ester, a phosphoester, a phosphonoester, a sulfite ester, a sulfate ester, an amide, an amino acid, a peptide, an ether, a thioether, an acyl group, a carbonate, a carbamate, a slufonamide, a halogen, an optionally substituted alkyl group, an optionally substituted alkenyl group, an optionally substituted alkynyl group, an optionally substituted aryl moiety, an optionally substituted heterocycle, an optionally substituted heteroaryl moiety, an optionally substituted monosaccharide, an optionally substituted oligosaccharide, a nucleoside, a nucleotide, an oligonucleotide, a polymer, or, when two of $R^1$-$R^{28}$ are linked to the same carbon atom (e.g., $R^5$ and $R^6$ or $R^{12}$ and $R^{13}$), they independently comprise a double bond, such as =O, =S, =$CH_2$ or =N—OH, at one or more ring carbons, and provided that when one or more of the rings comprises a double bond, one of the variable groups that is bonded to the double bonded ring carbon is absent; each $R^A$ independently is $C_{1-8}$ alkyl; each $R^{PR}$ independently is —H or a protecting group; and the dotted lines are optional double bonds, provided that 2, 3, 4 or more of $R^1$-$R^{28}$ are not hydrogen, and provided that compound is not 17α-ethynyl-17β-hydroxy-4-estrene-3-one, 17α-ethynyl-17β-hydroxy-5(10)-estrene-3-one, 1, 3, 5(10)-estratriene-17α-ethynyl-3β,17β-diol, 17α-ethynyl-androst-5-ene-3β,17β-diol, 17α-ethynyl-17β-hydroxy-4-androsten-3-one, 3β,17β-dihydroxy-androst-5-en-16-one, 3β,17β-dihydroxy-androst-4-en, 3β,-methylcarbonate-androst-5-en-7α,17β-dione, 3β,17β-dihydroxy-androst-5-en-11-one, 3β,17β-diacetoxy-androst-5-ene-7α,17β-diol, 3β,17β-diacetoxy-androst-5-ene-7-one, 3β-methoxy-androst-5-ene-7α, 17β-diol, 17β-methoxy-androst-3,5-diene-7-one, 17β-hydroxy-androst-3,5-diene-7-one, 5α-androstane-3α,17β-diol or an ester, ether or salt of any of these compounds.

Other objects will become apparent on reading the disclosure.

DETAILED DESCRIPTION OF THE INVENTION

As used herein and unless otherwise stated or implied by context, the following terms have the meanings defined here.

A "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, felines, e.g., domestic cat, dogs, e.g., domestic dog, wolf, birds, e.g., chicken, turkey, emu, ostrich, and fish, e.g., trout, catfish and salmon. Subject includes any subset of the foregoing, e.g., all of the above, but excluding one or more groups or species such as humans, primates or rodents.

Expressions that refer to "a formula 1 compound", "a compound of formula 1", "a formula 2 compound" or the like means compounds, compositions or formulations where one or more than one formula 1 (or formula 2) compound is present, typically 1, 2, 3 or 4, usually 1.

A "mimetic of a formula 1 or 2 compound" or a "mimetic of EED" means any compound, steroid or non-steroid (e.g., a compound disclosed in one or more of the references cited herein), that qualitatively or quantitatively induces the same or similar biological responses to a any significant degree that one or more formula 1 compounds or EED induces. Biological responses include modulation of AR-mediated transcription or inhibition of replication of cells, e.g., prostate cancer cells. In general, a mimetic of a formula 1 or 2 compound, e.g. EED, will induce at least about 35%, preferably at least about 50%, of the biological response that the formula 1 or 2 compound induces as optionally compared to suitably controlled and untreated reference cells, cell populations (in vitro or in vivo) or subjects. Typically the biological response will be defined by measuring one, two, three or more parameters, e.g., modulation of the synthesis of one or more gene products or modulation of cell replication.

"Alkyl" as used here means linked normal, secondary, tertiary or cyclic carbon atoms, i.e., linear, branched or cyclic. The number of carbon atoms in an alkyl group or moiety is 1 to about 20, unless otherwise specified, e.g., $C_{1-8}$ alkyl means an alkyl moiety containing 1, 2, 3, 4, 5, 6, 7 or 8 carbon atoms. Examples include methyl, ethyl, 1-propyl (n-propyl), 2-propyl (i-propyl, —$CH(CH_3)_2$), 1-butyl (n-butyl), 2-methyl-1-propyl (i-butyl, —$CH_2CH(CH_3)_2$), 2-butyl (s-butyl, —CH($CH_3$)$CH_2CH_3$), 2-methyl-2-propyl (t-butyl, —$C(CH_3)_3$), 1-pentyl (n-pentyl), 2-pentyl (—$CH(CH_3)CH_2CH_2CH_3$), 3-pentyl (—$CH(CH_2CH_3)_2$), 2-methyl-2-butyl (—$C(CH_3)_2$ $CH_2CH_3$), β-methyl-2-butyl (—$CH(CH_3)CH(CH_3)_2$), β-methyl-1-butyl (—$CH_2CH_2CH(CH_3)_2$), 2-methyl-1-butyl (—$CH_2CH(CH_3)CH_2CH_3$), 1-hexyl, 2-hexyl (—$CH(CH_3)$ $CH_2CH_2CH_2CH_3$), 3-hexyl (—$CH(CH_2CH_3)$ ($CH_2CH_2CH_3$)), 2-methyl-2-pentyl (—$C(CH_3)_2$ $CH_2CH_2CH_3$), β-methyl-2-pentyl (—$CH(CH_3)CH(CH_3)$ $CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), cyclopropyl, cyclobutyl, cyclopentyl and cyclohexyl.

"Alkenyl" means linked normal, secondary, tertiary or cyclic carbon atoms where one or more double bonds (e.g., —CH=CH—) are present, typically 1, 2 or 3, usually 1 or 2. The number of carbon atoms in an alkenyl group or moiety is 2 to about 20, unless otherwise specified, e.g., $C_{2-8}$ alkenyl means an alkenyl moiety containing 2, 3, 4, 5, 6, 7 or 8 carbon atoms.

"Alkynyl" means linked normal, secondary, tertiary or cyclic carbon atoms where one or more triple bonds (—C≡C—) are present, typically 1, 2 or 3, usually 1. The number of carbon atoms in an alkynyl group or moiety is 2 to about 20, unless otherwise specified, e.g., $C_{2-8}$ alkynyl means an alkynyl moiety containing 2, 3, 4, 5, 6, 7 or 8 carbon atoms.

"Aryl" means phenyl or naphthyl.

"Aryl-alkyl", aryl-alkenyl" and aryl-alkynyl" respectively mean an aryl moiety bonded to an alkyl, alkenyl or alkynyl group, wherein aryl, alkyl, alkenyl and alkynyl have the meanings defined above. Exemplary aryl-alkyl moieties have the structure aryl-$C_{1-20}$ alkyl- or aryl-$C_{2-20}$ alkenyl-, e.g., aryl-$CH_2$—, phenyl-$CH_2$—, phenyl-$CH_2$—CH=CH—$CH_2$—. Typically the alkyl groups will comprise 1-8 carbon atoms that are linear or branched and typical alkenyl and alkynyl groups will comprise 1-8 carbon atoms that are linear or branched.

"Substituted alkyl", "substituted alkenyl", "substituted alkynyl" "substituted aryl-alkyl", "substituted aryl-alkenyl" and "substituted aryl-alkynyl" mean an alkyl, alkenyl, alkynyl, aryl-alkyl, aryl-alkenyl or aryl-alkynyl group respectively, that comprises 1, 2, 3 or more independently selected substituents bonded to a carbon atom or 1, 2, 3 or more independently selected substituents that replace or interrupt any carbon atom chain or ring. Substituents include ethers (—O—), ketones (—C(O)—), —$OR^{PR}$(including —OH), —C(O)$OR^{PR}$(including —C(O)OH), —C(O)O—, —C(S)$OR^{PR}$, —C(S)O—, —OC(O)—, —C(O)H, —$OCH_2$—, —$OCH_2CH_2$—, —$OCH_2O$—, —$OCH_2CH_2O$—, —$NR^{PR}$—, —$N(R^{PR})_2$, —$NHR^{PR}$, —NHC(O)—, —$CH_2$—$NR^{PR}$—, —$CH_2$—$NHR^{PR}$, —$CH_2$—NHC(O)—, —C(O)NH—, —C(O)$NHR^{PR}$, —OC(O)$NR^{PR}$—, —OC(O)$NHR^{PR}$, —$NR^{PR}$C(O)$NR^{PR}$—, —$NR^{PR}$C(O)$NHR^{PR}$, —$NR^{PR}$$CH_2$—, —$NR^{PR}$$CH_2CH_2$—, —S—, —$SR^{PR}$, —S(O)—, —S(O)(O)—, —S(O)$OR^{PR}$, —S(O)H, —CN, —$NO_2$, —O—$CH_2$—O—C(O)—$OR^{PR}$ (including —O—$CH_2$—O—C(O)—OH), —O—$CH_2$—O—C(O)—$SR^{PR}$ (including —O—$CH_2$—O—C(O)—SH), —O—$CH_2$—C(O)—$NHR^{PR}$ (including —O—$CH_2$—C(O)—$NH_2$), —O—$CH_2$—C(O)—$R^{PR}$ (including —O—$CH_2$—C(O)—OH), —O—$CH_2$—C(O)—$SR^{PR}$ (including —O—$CH_2$—C(O)—SH), —O—$CH_2$—$OR^{PR}$ (including —O—$CH_2$—OH), —O—$CH_2$—$CH_2$—$OR^{PR}$ (including —O—$CH_2$—$CH_2$—OH), —O—$CH_2$—$CH_2$—O—$CH_2$—$CH_2$—$OR^{PR}$ (including —O—$CH_2$—$CH_2$—$OCH_2$—$CH_2$—OH), halogen, and combinations of these moieties where $R^{PR}$ independently is hydrogen, a protecting group or both $R^{PR}$ together are a protecting group. In some embodiments, alkenyl, alkynyl, aryl-alkenyl and aryl-alkynyl groups comprise one, two, three or more substituents, and such substituents are optionally bonded to a carbon atom that is one or more methylene moiety removed from the double bond, i.e., the substituent is separated at least by 1, 2, 3 or more —$CH_2$— moieties from a double bond.

Heterocycle. "Heterocycle" or "heterocyclic" includes by way of example and not limitation these heterocycles described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* 1960, 82:5566.

Examples of heterocycles include by way of example and not limitation pyridyl, thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H, 6H-1,5,2-dithiazinyl, thienyl, thianthrenyl, pyranyl, isobenzofuranyl, chromenyl, xanthenyl, phenoxathiinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Typically, nitrogen bonded heterocycles include 1-aziridyl, 1-azetedyl, 1-pyrrolyl, 1-imidazolyl, 1-pyrazolyl, and 1-piperidinyl.

"Heteroaryl" or "heteroaromatic" means an aromatic ring or two or more fused rings that contain one or more aromatic rings where the ring or fused rings comprise 1, 2, 3 or more heteroatoms, usually oxygen (—O—), nitrogen (—$NR^{PR}$—) or sulfur (—S—) where $R^{PR}$ is —H, a protecting group, optionally substituted $C_{1-8}$ alkyl, optionally substituted $C_{2-8}$ alkenyl or optionally substituted $C_{2-8}$ alkynyl, usually —H. Examples are as described for heterocycle and heteroaryl or heteroaromatic groups comprise a subset of heterocycles.

"Alcohol" as used herein means an alcohol that comprises a $C_{1-20}$ alkyl moiety substituted at one, two or more hydrogen atoms with one, two or more hydroxyl groups. Alcohols include ethanol, n-propanol, i-propanol, n-butanol, i-butanol, s-butanol, t-butanol, n-pentanol, i-pentanol, n-hexanol, cyclohexanol, n-heptanol, n-octanol, n-nonanol, n-decanol, ethylene glycol and glycerol. The carbon atoms in alcohols can be straight, branched or cyclic. Alcohol includes any subset of the foregoing, e.g., $C_{1-6}$ alcohols (alcohols having 1, 2, 3, 4, 5 or 6 carbon atoms).

"Halogen" means fluorine, chlorine, bromine or iodine.

"Protecting group" or "$R^{PR}$" means a moiety that prevents the atom to which it is linked from participating in unwanted reactions, or it limits such reactions. For example, for —$OR^{PR}$, $R^{PR}$ may be hydrogen or a protecting group for the oxygen atom found in a hydroxyl. For —C(O)—$OR^{PR}$, $R^{PR}$ may be hydrogen or a carboxyl protecting group, for —$SR^{PR}$, $R^{PR}$ may be hydrogen or a protecting group for sulfur in thiols for instance, and for —$NHR^{PR}$ or —$N(R^{PR})_2$—, $R^{PR}$ may be hydrogen or a nitrogen atom protecting group for primary or secondary amines. One or more hydroxyl, thiol, amine or other reactive groups may be found in formula 1 or formula 2 compounds. These groups may require protection against reactions taking place elsewhere in the molecule. The protecting groups for oxygen, sulfur or nitrogen atoms, or for reactive groups containing heteroatoms, are used, for example, to prevent unwanted reactions with electrophilic compounds, such as acylating used, e.g., in steroid chemistry.

"Protecting groups" as used herein comprise noncyclic or cyclic protecting groups, which have been extensively described, e.g., "Protective Groups in Organic Chemistry", Theodora W. Greene (John Wiley & Sons, Inc., New York, 1991, ISBN 0-471-62301-6) (hereafter "Greene") and will not be detailed here. The corresponding cleavage reactions have also been described, e.g., Greene. In the context of the present invention, these protecting groups are groups that can be removed from the molecule of the invention without irreversibly changing the covalent bond structure or oxidation/reduction state of the remainder of the molecule. For example, when —$R^{PR}$ is a removable protecting group that is bonded to a —O— or —NH— group, it is removed to form —OH or —$NH_2$, respectively, without affecting other covalent bonds in the molecule. In some embodiments, the protecting group will not be removable without affecting other covalent bonds in the molecule. More than one protecting group can be removed at a time, or they can be removed sequentially. The formula 1 or 2 compounds may contain one or more than one protecting group, which may be the same or different.

Removable protecting groups are usually removed by known procedures, although it will be understood that the protected intermediates fall within the scope of this invention. The removal of the protecting group may require several steps or removal may be straight-forward, depending upon the economics and nature of the conversions involved. In general, one will use a protecting group with exocyclic amines or with carboxyl groups during synthesis of a formula 1 or 2 compound. For most therapeutic applications protected groups will be deprotected, unless the protecting group is one that can be removed under physiological conditions. Protecting groups commonly are employed to protect against covalent modification of a sensitive group in reactions such as alkylation or acylation. Ordinarily, protecting groups are removed by, e.g. hydrolysis, elimination or aminolysis. Thus, simple functional considerations will suffice to guide the selection of a reversible or an irreversible protecting group at a given locus on the invention compounds. Suitable protecting groups and criteria for their selection are described in T. W. Greene and P. G. M. Wuts, Eds. "Protective Groups in Organic Synthesis" 2nd edition, Wiley Press, at pps. 10-142, 143-174, 175-223, 224-276, 277-308, 309-405 and 406-454.

Determination of whether a group is a protecting group is made in the conventional manner, e.g., as illustrated by Kocienski, Philip J.; *"Protecting Groups"* (Georg Thieme Verlag Stuttgart, New York, 1994) (hereafter "Kocienski"), Section 1.1, page 2, and Greene Chapter 1, pages 1-9. In particular, a group is a protecting group if when, based on mole ratio, 90% of that protecting group has been removed by a deprotection reaction, no more than 50%, preferably no more than 25%, more preferably no more than 10%, of the deprotected product molecules have undergone changes to their covalent bond structure or oxidation/reduction state other than those occasioned by the removal of the protecting group. When multiple protecting groups of the same type are present in the molecule, the mole ratios are determined when all of the groups of that type are removed. When multiple protecting groups of different types are present in the molecule, each type of protecting group is treated (and the mole ratios are determined) independently or together with others depending on whether the deprotection reaction conditions pertinent to one type are also pertinent to the other types present. In one embodiment of the invention, a group is a protecting group if when, based on mole ratio determined by conventional techniques, 90% of that protecting group has been removed by a conventional deprotection reaction, no more than 50%, preferably 25%, more preferably 10%, of the deprotected product molecules of the invention have undergone irreversible changes to their covalent bond structure or oxidation/reduction state other than those occasioned by the removal of the protecting group. Irreversible changes require chemical reactions (beyond those resulting from aqueous hydrolysis, acid/base neutralization or conventional separation, isolation or purification) to restore the covalent bond structure or oxidation/reduction state of the deprotected molecule of the invention.

"Ester" means a moiety that comprises a —C(O)—O— structure. Typically, esters as used here, comprise an organic moiety containing about 1-50 carbon atoms, usually about 2-18 carbon atoms, and 0 to about 10 independently selected heteroatoms (e.g., O, S, N, P, Si, F, Cl, Br, I), usually about 1-6 heteroatoms, linked to a formula 1 or formula 2 steroid nucleus at 1, 2, 3, 4 or more of $R^1$-$R^{28}$ through the —C(O)—O— structure, e.g., organic moiety-C(O)—O-steroid or organic moiety-O—C(O)-steroid. When more than one ester is present, e.g., 2, 3 or 4 esters, each ester moiety is independently selected. The organic moiety usually comprises one or more of any of the organic groups described above, e.g., $C_{1-20}$ alkyl moieties, $C_{2-20}$ alkenyl moieties, $C_{2-20}$ alkynyl moieties, aryl moieties, $C_{2-9}$ heterocycles, an ester moiety or substituted derivatives of any of these. Typical substitutions for these organic groups include 1, 2, 3, 4 or more, usually 1 or 2 independently selected, —O—, —S—, —$NR^{PR}$—, —C(O)—, —$N(R^{PR})_2$, —C(O)$OR^{PR}$, —OC(O)$R^{PR}$, —$OR^{PR}$, —$SR^{PR}$, —$NO_2$, =O, =S, —CN, —NHC(O)—, —C(O)NH—, —OC(O)—, —C(O)O—, —O-A8, —S-A8, —C(O)-A8, —OC(O)-A8, —C(O)O-A8, =N—, —N=, —$OPO_3(R^{PR})_2$, —$OSO_3H_2$ or halogen moieties or atoms, where $R^{PR}$ independently is —H, a protecting group or both $R^{PR}$ together are a protecting group and A8 is $C_{1-8}$ alkyl, $C_{1-8}$ alkenyl, $C_{1-8}$ alkynyl, $C_{1-6}$ alkyl-$C_{2-9}$ aryl (e.g., benzyl), aryl (e.g. phenyl) or $C_{0-6}$ alkyl-$C_{1-7}$ heterocycle. Substitutions are independently chosen. The organic moieties exclude obviously unstable moieties, e.g., —O—O—, except where such unstable moieties are transient species that one can use to make a compound with sufficient chemical stability for the one or more of the uses described herein. The substitutions listed above are typically substituents that one can use to replace a one or more carbon atoms, e.g., —O— or —C(O)—, or one or more hydrogen atom, e.g., halogen, —$NH_2$ or —OH. In some embodiments, the ester is unsubstituted, i.e., H—C(O)—O-steroid.

"Thioester" means a moiety that comprises a —C(S)—O— structure. Typically, thioesters as used here comprise a hydrogen atom or an organic moiety containing about 1-50 carbon atoms and 0 to about 10 independently selected heteroatoms (e.g., O, S, N, P, Si) linked to a formula 1 or 2 steroid nucleus at 1, 2, 3, 4 or more of $R^1$-$R^{28}$ through the —C(S)—O— structure, e.g., organic moiety-C(S)—O-steroid or organic moiety-O—C(S)-steroid. The organic moiety is as described above for esters. In some embodiments, the thioester is unsubstituted, i.e., H—C(S)—O-steroid.

"Phosphoester" or "phosphate ester" means a moiety that comprises a —O—P($OR^{PR}$)(O)—O— structure where $R^{PR}$ is hydrogen (—H), a protecting group or an organic moiety as described for esters. Typically, phosphoesters as used here comprise a hydrogen atom, a protecting group or an organic moiety containing about 1-50 carbon atoms and 0 to about 10 independently selected heteroatoms (e.g., O, S, N, P, Si) linked to a formula 1 or 2 steroid nucleus at 1, 2, 3, 4 or more of $R^1$-$R^{28}$ through the —O—P($OR^{PR}$)(O)—O— structure, i.e., organic moiety-O—P($OR^{PR}$)(O)—O-steroid. The organic moiety is as described above for esters. In some embodiments, the phosphate ester is unsubstituted, e.g., HO—P($OR^{PR}$)(O)—O-steroid.

"Phosphonoester" means a moiety that comprises 1, 2, 3, 4 or more, typically only 1, —P($OR^{PR}$)(O)—O— structure where $R^{PR}$ is —H, a protecting group or an organic moiety as described for esters. Typically, phosphonoesters as used here comprise a hydrogen atom, a protecting group or an organic moiety containing about 1-50 carbon atoms and 0 to about 10 independently selected heteroatoms (e.g., O, S, N, P, Si) linked to a formula 1 or 2 steroid nucleus at 1, 2, 3, 4 or more of $R^1$-$R_{28}$ through the —P($OR^{PR}$)(O)—O— structure, i.e., organic moiety-P($OR^{PR}$)(O)—O-steroid or steroid-P($OR^{PR}$)(O)—O-organic moiety. The organic moiety is as described above for esters. In some embodiments, the phosphonoester is unsubstituted, e.g., H—P($OR^{PR}$)(O)—O-steroid.

"Sulfate ester" means a moiety that comprises 1, 2, 3, 4 or more —O—S(O)(O)—O— structure, usually 1. Typically, sulfate esters as used here comprise a hydrogen atom, a protecting group or an organic moiety containing about 1-50 carbon atoms and 0 to about 10 independently selected heteroatoms (e.g., O, S, N, P, Si) linked to a formula 1 or 2 steroid nucleus at 1, 2, 3, 4 or more of $R^1$-$R^{28}$ through the —O—S(O)(O)—O— structure, e.g., organic moiety-O—S(O)(O)—O-steroid. The organic moiety is as described above for esters. In some embodiments, the sulfate ester is unsubstituted, i.e., HO—S(O)(O)—O-steroid.

"Sulfite ester" means a moiety that comprises 1, 2, 3, 4 or more —O—S(O)—O-structures, usually 1. Typically, sulfite esters as used here comprise an organic moiety containing about 1-50 carbon atoms and 0 to about 10 independently selected heteroatoms (e.g., O, S, N, P, Si) linked to a formula 1 or 2 steroid nucleus at 1, 2, 3, 4 or more of $R^1$-$R^{28}$ through the —O—S(O)—O— structure, e.g., organic moiety-O—S(O)—O-steroid. The organic moiety is as described above for esters. In some embodiments, the sulfite ester is unsubstituted, i.e., HO—S(O)—O-steroid.

"Sulfonamide" means a moiety that comprises 1, 2, 3, 4 or more —S(O)(O)—N($R^A$)($R^B$) or —S(O)(O)—N($R^A$)— structures, usually 1, where $R^A$ and $R^B$ independently are —H, a protecting group, an organic moiety (as described for esters), or both $R^A$ and $R^B$ together comprise a protecting group. Typically, sulfonamides as used here comprise an organic moiety containing about 1-50 carbon atoms and 0 to about 10 independently selected heteroatoms (e.g., O, S, N, P, Si) linked to a formula 1 or 2 steroid nucleus at 1, 2, 3, 4 or more of $R^1$-$R^{28}$ through the —O—S(O)—O— structure, e.g., organic moiety-S(O)(O)—NH-steroid or N($R^A$)($R^B$)—S(O)(O)-steroid. The organic moieties are as described above for esters, e.g., moieties that comprise 1 to about 22 carbon atoms and up to about 10 independently selected heteroatoms. In some embodiments, the sulfonamide is unsubstituted, e.g., $H_2N$—S(O)(O)-steroid.

"Amide" means an organic moiety as described for ester that comprises 1, 2, 3, 4 or more —C(O)$NR^{PR}$— moieties, usually 1 or 2, where $R^{PR}$ is —H or a protecting group, $R^{PR}$ is usually H. In some embodiments, the —C(O)$NR^{PR}$— group is linked to the steroid nucleus at 1, 2, 3, 4 or more of $R^1$-$R^{28}$ through the —$NR^{PR}$— moiety, e.g., organic moiety-C(O)—$NR^{PR}$-steroid or steroid-C(O)—$NR^{PR}$-organic moiety. The organic moiety is as described above for esters. In some embodiments, the amide is unsubstituted, i.e., $H_2N$—C(O)-steroid or HC(O)—NH-steroid.

"Ether" means an organic moiety as described for ester that comprises 1, 2, 3, 4 or more —O— moieties, usually 1 or 2. In some embodiments, the —O— group is linked to the steroid nucleus at 1, 2, 3, 4 or more of $R^1$-$R^{28}$ through the —O— moiety, e.g., organic moiety-O-steroid. The organic moiety is as described above for esters.

"Thioether" means an organic moiety as described for ester that comprises 1, 2, 3, 4 or more —S— moieties, usually 1 or 2. In some embodiments, the —S— group is linked to the steroid nucleus at 1, 2, 3, 4 or more of $R^1$-$R^{28}$ through the —S— moiety, e.g., organic moiety-S-steroid. The organic moiety is as described above for ester.

"Acyl group" means an organic moiety as described for ester that comprises 1, 2, 3, 4 or more —C(O)— groups. In some embodiments, the —C(O)— group is linked to the steroid nucleus at 1, 2, 3, 4 or more of $R^1$-$R^{28}$, e.g., organic moiety-C(O)-steroid. The organic moiety is as described above for esters. An unsubstituted acyl group comprises a HC(O)— moiety, e.g., linked to the steroid nucleus.

"Carbonate" means an organic moiety as described for ester that comprises 1, 2, 3, 4 or more —O—C(O)—O— structures. Typically, carbonate groups as used here comprise an organic moiety containing about 1-50 carbon atoms and 0 to about 10 independently selected heteroatoms (e.g., O, S, N, P, Si) linked to a formula 1 or formula 2 steroid nucleus at 1, 2, 3, 4 or more of $R^1$-$R^{28}$ through the —O—C(O)—O-structure, e.g., organic moiety-O—C(O)—O-steroid. The organic moiety is as described above for esters. An unsubstituted carbonate group comprises a HO—C(O)—O-moiety, e.g., linked to the steroid nucleus.

"Carbamate" means an organic moiety as described for ester that comprises 1, 2, 3, 4 or more —O—C(O)$NR^{PR}$— structures where $R^{PR}$ is —H, a protecting group or an organic moiety as described for ester. Typically, carbamate groups as used here comprise an organic moiety containing about 1-50 carbon atoms and 0 to about 10 independently selected heteroatoms (e.g., O, S, N, P, Si) linked to a formula 1 or formula 2 steroid nucleus at one or more of $R^1$-$R^{28}$ through the —O—C(O)—$NR^{PR}$-structure, e.g., organic moiety-O—C(O)—$NR^{PR}$-steroid or steroid-O—C(O)—$NR^{PR}$-organic moiety. The organic moiety is as described above for esters. An unsubstituted carbamate group comprises a HO—C(O)—NH— or $H_2N$—C(O)—O— moiety, e.g., linked to the steroid nucleus.

As used herein, "monosaccharide" means a polyhydroxy aldehyde or ketone having the empirical formula $(CH_2O)_n$ where n is 3, 4, 5, 6 or 7. Monosaccharide includes open chain and closed chain forms, but will usually be closed chain forms. Monosaccharide includes hexofuranose and pentofuranose sugars such as 2'-deoxyribose, ribose, arabinose, xylose, their 2'-deoxy and 3'-deoxy derivatives and their 2',3'- dideoxy derivatives. Monosaccharide also includes the 2',3' dideoxydidehydro derivative of ribose. Monosaccharides include the D-, L- and DL-isomers of glucose, fructose, mannose, idose, galactose, allose, gulose, altrose, talose, fucose, erythrose, threose, lyxose, erythrulose, ribulose, xylulose, ribose, arabinose, xylose, psicose, sorbose, tagatose, glyceraldehyde, dihydroxyacetone and their monodeoxy derivatives such as rhamnose. Monosaccharides are optionally protected or partially protected. The formula 1 and formula 2 compounds may comprise 1, 2, 3 or more independently selected monosaccharides at one or more of $R^1$-$R^{28}$.

Disaccharide and oligosaccharide mean a moiety that comprises respectively two or more linked monosaccharides. Substituted disaccharide or substituted oligosaccharide means a moiety that comprises two or more linked monosaccharides, at least one of which is a substituted monosaccharide. The formula 1 and formula 2 compounds may comprise 1, 2, 3 or more independently selected disaccharides or oligosaccharides at one or more of $R^1$-$R^{28}$.

Optionally substituted alkyl group, optionally substituted alkenyl group, optionally substituted alkynyl group, optionally substituted aryl moiety and optionally substituted heterocycle mean substitutions of $C_{1-20}$ alkyl moieties, $C_{2-20}$ alkenyl moieties, $O_{2-20}$ alkynyl moieties, aryl moieties, $C_{2-9}$ heterocycles or substituted derivatives of any of these. Typical substitutions for these organic groups include 1, 2, 3, 4 or more, usually 1 or 2 independently chosen, —O—, —S—, —$NR^{PR}$—, —C(O)—, —N($R^{PR}$)$_2$, —C(O)O$R^{PR}$, —OC(O)$R^{PR}$, —O$R^{PR}$ (including —OH), —S$R^{PR}$ (including —SH), —NO$_2$, —CN, —NHC(O)—, —C(O)NH—, —OC(O)—, —C(O)O—, —O-A8, —S-A8, —C(O)-A8, —OC(O)-A8, —C(O)O-A8, =N—, —N=, —OPO$_2$$R^{PR}$, —OSO$_3$H or halogen moieties or atoms, where $R^{PR}$ independently is —H, a protecting group or both $R^{PR}$ together are a protecting group and A8 is $C_{1-8}$ alkyl, $C_{1-8}$ alkenyl, $C_{1-8}$ alkynyl, $C_{1-4}$ alkyl-aryl (e.g., benzyl), aryl (e.g. phenyl) or $C_{1-4}$ alkyl-$C_{1-5}$ heterocycle. Substitutions are independently chosen. The organic moieties as described here, and for other any other moieties described herein, exclude obviously unstable moieties, e.g., —O—O—, except where such unstable moieties are transient species that one can use, for example, to make a compound with sufficient chemical stability for the one or more of the uses described herein.

Optionally substituted "monosaccharide" comprise any $C_3$-$C_7$ sugar, in the D-, L- or DL-configurations, e.g., erythrose, glycerol, ribose, deoxyribose, arabinose, glucose, mannose, galactose, fucose, mannose, glucosamine, N-acetylneuraminic acid, N-acetylglucosamine, N-acetylgalactosamine or glucuronic acid, that is optionally substituted at one or more hydroxyl groups. Suitable substitutions include hydrogen, protected hydroxyl, carboxyl, azido, cyano, acetyl, —O—$C_{1-6}$ alkyl, —S—$C_{1-6}$ alkyl, —O—$C_{2-6}$ alkenyl, —S—$C_{2-6}$ alkenyl, optionally protected amine, optionally protected carboxyl, halogen, thiol, protected thiol or substituents as described for substituted alkyl groups. The linkage between the monosaccharide the steroid is α or β.

Optionally substituted "oligosaccharide" comprises two, three, four or more of any C3-C7 sugars that are covalently linked to each other. The linked sugars may have D-, L- or DL-configurations. Suitable sugars and substitutions are as described for monosaccharides. The linkage between the oligosaccharide and the steroid is α or β, as are the linkages between the monosaccharides that comprise the oligosaccharide.

Nucleoside includes 3TC, AZT, D4T, ddI, ddC, G, A, U, C, T, dG, dA, dT and dC.

Polymer includes biocompatible organic polymers, e.g., PEGs and polyhydroxyalkyl polymers. PEG means an ethylene glycol polymer that contains about 20 to about 2000000 linked monomers, typically about 50-1000 linked monomers, usually about 100-300. Polyethylene glycols include PEGs containing various numbers of linked monomers, e.g., PEG 20, PEG 30, PEG 40, PEG 60, PEG 80, PEG 100, PEG 115, PEG 200, PEG 300, PEG 400, PEG 500, PEG 600, PEG 1000, PEG 1500, PEG 2000, PEG 3350, PEG 4000, PEG 4600, PEG 5000, PEG 6000, PEG 8000, PEG 11000, PEG 12000, PEG 2,000,000 and any mixtures thereof.

Amino acid. "Amino acid" means an amino acid moiety that comprises any naturally-occurring or synthetic amino acid residue, i.e., any moiety comprising at least one carboxyl and at least one amino residue directly linked by one, two three or more carbon atoms, typically one (α) carbon atom. The nature and identity of the intervening structure located between the carboxyl and amino groups can have a variety of structures including those described herein. Typically, amino acids linked to the steroid through the amine group have sufficient conformation and length to be capable of autocatalytic hydrolysis of the amino acid-steroid bond and release of the steroid. This can occur when the free carboxyl is generated in vivo by deesterification, deamidation or peptidolytic cleavage of the precursor containing a linkage between the amino acid's amine group and the steroid. Hydrolysis of the bond between an amino acid's carboxyl or amino group and the steroid can also occur by chemical or enzymatic activity, e.g., esterase cleavage or non-enzymatic hydrolysis.

In general, the amino acids corresponding to the residues employed in the invention compounds are naturally occurring and have no significant pharmacological activity per se. However, optimal pharmacokinetic activity, (substantially complete hydrolysis upon hydrolysis of the distal amide or ester bond) may be achieved by using non-naturally occurring amino acid residues. The intervening structure may be as simple as methylene when the amino acid residue is glycyl, or substituted methylene for other a amino acids. The structure ordinarily contains up to about 5 carbon or heteroatoms in the direct linkage between the amino acid's carboxyl carbon and the amine nitrogen. Thus, amino acids can comprise intervening ethylene, propylene, butylene, or pentylene groups or their substituted analogs, such as for example, oxyesters or ethers in which oxygen replaces carbon and, as appropriate, hydrogen. An example of such an intervening structure would be —CH—O—C($R^{22}$)($R^{23}$)—, where $R^{22}$ and $R^{23}$ are independently selected hydrogen or organic moieties as described above for esters. In some embodiments one of $R^{22}$ and $R^{23}$ is hydrogen and the other is a $C_{2-20}$ organic moiety. Typically the organic moieties contain about 1-20 carbon atoms and 0, 1, 2, 3, 4 or 5 independently selected heteroatoms, which are typically selected from oxygen, nitrogen, sulfur and phosphorus. In general, fewer intervening atoms are used when more rapid hydrolysis is desired, although larger structures are suitable if, e.g., they possess sufficient flexibility or have conformations to allow positioning of the carboxyl group in proximity to the amino acid-steroid bond.

Ordinarily, $R^{22}$ is —H, methyl or hydroxymethyl, usually —H, and $R^{23}$ is a side chain or group of a naturally occurring amino acid. Amino acid side chains include analogs where the side chain is a $C_{1-15}$ homolog of the corresponding natural compound, e.g., methylene, ethylene, propylene, butylene or a substituted derivative thereof, e.g., an alkyl, ether or alkoxy (e.g., methoxy, ethoxy, propoxy) substituted derivative. In general, for carboxyl-containing side chains, if the C atom of the side chain carboxyl is linked by 5 or less atoms to the N then the carboxyl optionally will be blocked, e.g. by esterification or amidation wherein the ester or amide bonds are hydrolyzable in vivo. $R^{22}$ also is taken together with $R^{30}$ to form a proline residue ($-CH_2-)_3$. Thus, $R^{23}$ is generally a side group such as —H, —CH$_3$, —CH(CH$_3$)$_2$, —CH$_2$—CH(CH$_3$)$_2$, —CHCH$_3$—CH$_2$—CH$_3$, —CH$_2$—C$_6$H$_5$, —CH$_2$CH$_2$—S—CH$_3$, —CH$_2$OH, —CH(OH)—CH$_3$, —CH$_2$—SH, —CH$_2$—C$_6$H$_4$OH, —CH$_2$—CO—NH$_2$, —CH$_2$—CH$_2$—CO—NH$_2$, —CH$_2$—COOH, —CH$_2$—CH$_2$—COOH, —(CH$_2$)$_4$—NH$_2$ and —(CH$_2$)$_3$—NH—C(NH$_2$)—NH$_2$. $R^{23}$ also includes 1-guanidinoprop-3-yl, benzyl, 4-hydroxybenzyl, imidazol-4-yl, indol-3-yl, methoxyphenyl and ethoxyphenyl. The optimal $R^{30}$ group is readily selected using routine assays.

In general, the amino acid residue has the structure shown in the formulas below. Ordinarily, n is 1 or 2, $R^{22}$ is —H and $R^{23}$ is a moiety containing one or more of the following groups: amino, carboxyl, amide, carboxyl ester, hydroxyl, $C_6$-$C_7$ aryl, ether (—O—), thioether (—S—), n-, s- or t-alkyl ($C_1$-$C_6$), guanidinyl, imidazolyl, indolyl, sulfhydryl, sulfoxide, and phosphoryl. The $R^{22}$ and $R^{23}$ substituents can have a wide variety of structures including those disclosed herein, e.g., esters, ethers or carbonates.

When the amino acid residues contain one or more chiral centers, any of the D, L, meso, threo or erythro (as appropriate) racemates or mixtures thereof, fall within the scope of this invention. In general, if it is desired to rely on non-enzymatic means of hydrolysis, D isomers should be used. On the other hand, L isomers may be more versatile since they can be susceptible to both non-enzymatic as well as potential targeted enzymatic hydrolysis, and are more efficiently transported by amino acid or dipeptidyl transport systems in the gastrointestinal tract.

Examples of suitable amino acid residues include the following: Glycyl; aminopolycarboxylic acids, e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β,γ-dihydroxyglutamic acid, β-phenylglutamic acid, γ-methyleneglutamic acid, 3-aminoadipic acid, 2-aminopimelic acid, 2-aminosuberic acid and 2-aminosebacic acid residues; amino acid amides such as glutaminyl and asparaginyl; polyamino- or polybasic-monocarboxylic acids such as arginine, lysine, β-aminoalanine, γ-aminobutyrine, ornithine, citruline, homoarginine, homocitrulline, 5-hydroxy-2,6-diaminohexanoic acid (commonly, hydroxylysine, including allohydroxylysine) and diaminobutyric acid residues; other basic amino acid residues such as histidinyl; diaminodicarboxylic acids such as α,α'-diaminosuccinic acid, α,α'-diaminoglutaric acid, α,α'-diaminoadipic acid, α,α'-diaminopimelic acid, α,α'-diamino-β-hydroxypimelic acid, α,α'-diaminosuberic acid, α,α'-diaminoazelaic acid, and α,α'-diaminosebacic acid residues; imino acids such as proline, 4- or 3-hydroxy-2-pyrrolidinecarboxylic acid (commonly, hydroxyproline, including allohydroxyproline), γ-methylproline, pipecolic acid, 5-hydroxypipecolic acid, —N([CH$_2$]$_n$COOR$^{PR}$)$_2$, wherein n is 1, 2, 3, 4, 5 or 6 and R$^{PR}$ is —H or a protecting group, and azetidine-2-carboxylic acid residues; a mono- or di-alkyl (typically $C_1$-$C_8$ branched or normal) amino acid such as alanine, valine, leucine, allylglycine, butyrine, norvaline, norleucine, heptyline, α-methylserine, α-amino-α-methyl-γ-hydroxyvaleric acid, α-amino-α-methyl-δ-hydroxyvaleric acid, α-amino-α-methyl-ε-hydroxycaproic acid, isovaline, α-methylglutamic acid, α-aminoisobutyric acid, α-aminodiethylacetic acid, α-aminodiisopropylacetic acid, α-aminodi-n-propylacetic acid, α-aminodiisobutylacetic acid, α-aminodi-n-butylacetic acid, α-aminoethylisopropylacetic acid, α-amino-n-propylacetic acid, α-aminodiisoamyacetic acid, α-methylaspartic acid, α-methylglutamic acid, 1-aminocyclopropane-1-carboxylic acid; isoleucine, alloisoleucine, tert-leucine, β-methyltryptophan and α-amino-β-ethyl-β-phenylpropionic acid residues; β-phenylserinyl; aliphatic α-amino-β-hydroxy acids such as serine, β-hydroxyleucine, β-hydroxynorleucine, β-hydroxynorvaline, and α-amino-β-hydroxystearic acid residues; α-Amino, α-, γ-, δ- or ε-hydroxy acids such as homoserine, γ-hydroxynorvaline, δ-hydroxynorvaline and epsilon-hydroxynorleucine residues; canavinyl and canalinyl; γ-hydroxyornithinyl; 2-Hexosaminic acids such as D-glucosaminic acid or D-galactosaminic acid residues; α-amino-β-thiols such as penicillamine, β-thiolnorvaline or β-thiolbutyrine residues; other sulfur containing amino acid residues including cysteine; homocystine; β-phenylmethionine; methionine; S-allyl-L-cysteine sulfoxide; 2-thiolhistidine; cystathionine; and thiol ethers of cysteine or homocysteine; phenylalanine, tryptophan and ring-substituted α amino acids such as the phenyl- or cyclohexylamino acids α-aminophenylacetic acid, α-aminocyclohexylacetic acid and α-amino-β-cyclohexylpropionic acid; phenylalanine analogues and derivatives comprising aryl, lower alkyl, hydroxy, guanidino, oxyalkylether, nitro, sulfur or halo-substituted phenyl (e.g., tyrosine, methyltyrosine and o-chloro-, p-chloro-, 3,4-dichloro, o-, m- or p-methyl-, 2,4,6-trimethyl-, 2-ethoxy-5-nitro, 2-hydroxy-5-nitro and p-nitro-phenylalanine); furyl-, thienyl-, pyridyl-, pyrimidinyl-, purine or naphthylalanines; and tryptophan analogues and derivatives including kynurenine, 3-hydroxykynurenine, 2-hydroxytryptophan and 4-carboxytryptophan residues; α-amino substituted amino acid residues including sarcosine (N-methylglycine), N-benzylglycine, N-methylalanine, N-benzylalanine, N-methylphenylalanine, N-benzylphenylalanine, N-methylvaline and N-benzylvaline; and α-Hydroxy and substituted α-hydroxy amino acid residues including serine, threonine, allothreonine, phosphoserine and phosphothreonine residues.

Any one of the foregoing or other known amino acids are suitably employed in this invention. Typically amino acids are capable of autocatalytically hydrolyzing the amino acid-steroid bond. Thus, they typically contain, or upon being hydrolyzed in vivo, contain a free carboxyl group or amine group.

Also of interest are hydrophobic amino acids such as mono- or di-alkyl or aryl amino acids, cycloalkylamino acids and the like. These residues, together with $R^{29}$-$R^{34}$ ($R^{31}$-$R^{34}$ are defined below) can contribute to cell permeability by modulating the lipophilicity of a formula 1 or formula 2 compound. Typically, the residue does not contain a sulfhydryl or guanidino substituent.

Peptide. One, 2, 3 or more of $R^1$-$R^4$ can comprise a "peptide", i.e., two or more amino acids as defined above. Typically the amino acids are linked through normal peptide bonds, i.e., —CO—NH—, between adjacent amino acid residues. Peptides comprise dipeptides (dimers), tripeptides (trimers), short peptides of 4, 5, 6, 8, 10 or 15 residues, and longer peptides or proteins having about 100 or more residues. Invention compounds that comprise a peptide can be used as immunogens, prodrugs or as synthetic precursors for other steroid derivatives. In one embodiment, the peptide will contain a peptidolytic enzyme cleavage site at the peptide bond linking the first residue and the next residue distal to the steroid residue. Such cleavage sites are optionally flanked by enzymatic recognition structures, e.g. particular residues recognized by a hydrolytic enzyme, e.g., a peptidase located in the serum or in cells.

Peptidolytic enzymes are well known, and in particular include carboxypeptidases. Carboxypeptidases digest polypeptides by removing C-terminal residues, and are specific in many instances for particular C-terminal sequences. Such enzymes and their substrate requirements in general are well known. For example, a dipeptide having a given pair of residues and a free carboxyl terminus is covalently bonded through its α-amino group to the steroid nucleus. It is expected that the peptide will be cleaved by the appropriate dipeptidase, protease or by chemical hydrolysis, leaving the carboxyl of the proximal amino acid residue to autocatalytically cleave the amidate bond.

Examples of suitable dipeptidyl groups (designated by their single letter symbols) are shown in the table below.

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

| Dipeptides |
|---|
| AA, AR, AN, AD, AC, AE, AQ, AG, AH, AI, AL, AK, AM, AF, AP, AS, AT, AW, AY, AV, RA, RR, RN, RD, RC, RE, RQ, RG, RH, RI, RL, RK, RM, RF, RP, RS, RT, RW, RY, RV, NA, NR, NN, ND, NC, NE, NQ, NG, NH, NI, NL, NK, NM, NF, NP, NS, NT, NW, NY, NV, DA, DR, DN, DD, DC, DE, DQ, DG, DH, DI, DL, DK, DM, DF, DP, DS, DT, DW, DY, DV, CA, CR, CN, CD, CC, CE, CQ, CG, CH, CI, CL, CK, CM, CF, CP, CS, CT, CW, CY, CV, EA, ER, EN, ED, EC, EE, EQ, EG, EH, EI, EL, EK, EM, EF, EP, ES, ET, EW, EY, EV, QA, QR, QN, QD, QC, QE, QQ, QG, QH, QI, QL, QK, QM, QF, QP, QS, QT, QW, QY, QV, GA, GR, GN, GD, GC, GE, GQ, GG, GH, GI, GL, GK, GM, GF, GP, GS, GT, GW, GY, GV, HA, HR, HN, HD, HC, HE, HQ, HG, HH, HI, HL, HK, HM, HF, HP, HS, HT, HW, HY, HV, IA, IR, IN, ID, IC, IE, IQ, IG, IH, II, IL, IK, IM, IF, IP, IS, IT, IW, IY, IV, LA, LR, LN, LD, LC, LE, LQ, LG, LH, LI, LL, LK, LM, LF, LP, LS, LT, LW, LY, LV, KA, KR, KN, KD, KC, KE, KQ, KG, KH, KI, KL, KK, KM, KF, KP, KS, KT, KW, KY, KV, MA, MR, MN, MD, MC, ME, MQ, MG, MH, MI, ML, MK, MM, MF, MP, MS, MT, MW, MY, MV, FA, FR, FN, FD, FC, FE, FQ, FG, FH, FI, FL, FK, FM, FF, FP, FS, FT, FW, FY, FV, PA, PR, PN, PD, PC, PE, PQ, PG, PH, PI, PL, PK, PM, PF, PP, PS, PT, PW, PY, PV, SA, SR, SN, SD, SC, SE, SQ, SG, SH, SI, SL, SK, SM, SF, SP, SS, ST, SW, SY, SV, TA, TR, TN, TD, TC, TE, TQ, TG, TH, TI, TL, TK, TM, TF, TP, TS, TT, TW, TY, TV, WA, WR, WN, WD, WC, WE, WQ, WG, WH, WI, WL, WK, WM, WF, WP, WS, WT, WW, WY, WV, YA, YR, YN, YD, YC, YE, YQ, YG, YH, YI, YL, YK, YM, YF, YP, YS, YT, YW, YY, YV, VA, VR, VN, VD, VC, VE, VQ, VG, VH, VI, VL, VK, VM, VF, VP, VS, VT, VW, VY, VV |

Such dipeptides include species where both amino acids are in the L configuration, the D configuration or mixtures of configurations.

Tripeptides, i.e., 3 linked amino acid residues, are also useful embodiments. Tripeptides include those where A, C, D, E, F, G, H, I, K, L, M, N, P, Q, R, S, T, V, W or Y is linked by a standard peptide bond to the amino or the carboxyl terminus of any of the dipeptides listed above. The sequence -X1-pro-X2-(where X1 is any amino acid and X2 is hydrogen, any amino acid residue or a carboxyl ester of proline) will be cleaved by luminal carboxypeptidase to yield X1 with a free carboxyl, which in turn autocatalytically cleaves the amidate bond. X2 usually will be a benzyl ester of the carboxy group of X2. Other embodiments include tetrapeptides such as ones where any two of the dipeptides listed above, which may be the same or different dipeptides (e.g., AA and AA linked together or, e.g., AA and GI linked together), are linked to each other by a peptide bond through the amino terminus or carboxyl terminus. One, 2 or more tetrapeptides may bonded to the formula 1 or formula 2 compound through the tetrapeptide's amino or carboxyl terminus.

In some embodiments, the formula 1 or formula 2 compound comprises one or more amino acids or peptides having the structure (A), (B) or (C): (A) $R^{32}$—NH—{[C($R^{29}$)($R^{30}$)]$_b$—C(O)—N($R^{31}$)}$_f$—[C($R^{29}$)($R^{30}$)]$_a$—C(O)—O-steroid, (B) $R^{33}$—O—{C(O)—[C($R^{29}$)($R^{30}$)]$_d$—N($R^{31}$)}$_g$—C(O)—[C($R^{29}$)($R^{30}$)]$_c$—N($R^{31}$)—O-steroid, or (C) $R^{33}$—O—{C(O)—[C($R^{29}$)($R^{30}$)]$_d$—N($R^{31}$)}$_e$—C(O)—[C($R^{29}$)($R^{30}$)]$_c$—N($R^{31}$)—C(O)—O-steroid, wherein (A), (B) or (C) are independently selected and they are bonded to 1, 2, 3 or more of $R^1$ through $R^4$, where each $R^{29}$-$R^{31}$ is independently selected; $R^{29}$ independently are —H or a $C_{1-20}$ organic moiety (e.g., $C_{1-6}$ alkyl, e.g. —$CH_3$ or —$C_2H_5$); $R^{30}$ independently are the side chain of an amino acid, including the side chain of naturally occurring amino acids as described above, e.g., —H, —$CH_3$, —$CH_2C_6H_5$; $R^{31}$ is —H or a protecting group; $R^{32}$ and $R^{33}$ independently comprise —H, a protecting group, an ester or an amide where each atom or group is independently chosen; a, b, c and d independently are 1, 2, 3, 4 or 5, usually 1; e, f and g independently are an integer from 0 to about 1000, typically they independently are 0, 1, 2, 3, 4, 5, 6, 7 or 8; a, b, c and d independently are 1 or 2; e, f and g independently are 0, 1, 2, 3, 4 or 5.

If the amino acid(s) or residue(s) has 2 or more amine groups, e.g., a lysinyl or arginyl, or ornithinyl residue, then $R^{29}$ is usually —H and $R^{30}$ may comprise —[C($R^{34}$)$_2$]$_{n2}$N($R^{PR}$)— where n2 is 0, 1, 2, 3, 4, 5 or 6, $R^{PR}$ is —H or a protecting group and each $R^{34}$ independently is —H, $C_1$-$C_{20}$ optionally substituted alkyl, $C_6$-$C_{20}$ optionally substituted aryl, $C_7$-$C_{20}$ optionally substituted alkylaryl, $C_7$-$C_{20}$ optionally substituted arylalkyl, $C_1$-$C_{20}$ optionally substituted alkoxy, $C_6$-$C_{20}$ optionally substituted aryloxy or hydroxyl.

Such compounds will contain a plurality of steroid moieties. For example when both the epsilon (ε) or delta (δ) and alpha (α) amino groups of lysine or ornithine are substituted with steroid moieties the amidate is believed to be capable of releasing two molecules of active drug, each expected to emerge under different pharmacokinetics and therefore further sustaining the drug release.

Salt. Invention embodiments include salts and complexes of formula 1 compounds, including pharmaceutically acceptable or salts that are relatively non-toxic. Some of the compounds have one or more moieties that carry at least a partial positive or negative charge in aqueous solutions, typically at a pH of about 4-10, that can participate in forming a salt, a complex, a composition with partial salt and partial complex properties or other noncovalent interactions, all of which we refer to as a "salt(s)". Salts are usually biologically compatible or pharmaceutically acceptable or non-toxic, particularly for mammalian cells. Salts that are biologically toxic are optionally used with synthetic intermediates of invention compounds. When a water-soluble composition is desired, monovalent salts are usually preferred.

Metal salts typically are prepared by reacting the metal hydroxide with a compound of this invention. Examples of metal salts which are optionally prepared in this way are salts containing $Li^+$, $Na^+$, and $K^+$. A less soluble metal salt can be precipitated from the solution of a more soluble salt by adding a suitable metal compound. Invention salts may be formed from acid addition of certain organic acids, such as organic carboxylic acids, and inorganic acids, such as alkylsulfonic acids or hydrogen halide acids, to acidic or basic centers on invention compounds, such as basic centers on the invention pyrimidine base analogs. Metal salts include ones containing $Na^+$, $Li^+$, $K^+$, $Ca^{++}$ or $Mg^{++}$. Other metal salts may contain aluminum, barium, strontium, cadmium, bismuth, arsenic or zinc ion.

Salt(s) of compounds may comprise a combination of appropriate cations such as alkali and alkaline earth metal ions or ammonium and quaternary ammonium ions with the acid anion moiety of the phosphoric acid or phosphonic acid group, which may be present in invention polymers or monomers.

Salts are produced by standard methods, including dissolving free base in an aqueous, aqueous-alcohol or aqueous-organic solution containing the selected acid, optionally followed by evaporating the solution. The free base is reacted in an organic solution containing the acid, in which case the salt usually separates directly or one can concentrate the solution.

Suitable amine salts include amines having sufficient basicity to form a stable salt, preferably amines of low toxicity including trialkyl amines (tripropylamine, triethylamine, trimethylamine), procaine, dibenzylamine, N-benzyl-betaphenethylamine, ephenamine, N,N'-dibenzylethylenediamine, N-ethylpiperidine, benzylamine and dicyclohexylamine.

Salts include organic sulfonic acid or organic carboxylic acid salts, made for example by addition of the acids to basic centers, typically amines. Exemplary sulfonic acids include $C_{6-16}$ aryl sulfonic acids, $C_{6-16}$ heteroaryl sulfonic acids and $C_{1-16}$ alkyl sulfonic acids such as phenyl sulfonic acid, α-naphthalene sulfonic acid, β-naphthalene sulfonic acid, (S)-camphorsulfonic acid, methyl ($CH_3SO_3H$), ethyl ($C_2H_5SO_3H$), n-propyl, i-propyl, n-butyl, s-butyl, i-butyl, t-butyl, pentyl and hexyl sulfonic acids. Exemplary organic carboxylic acids include $C_{1-16}$ alkyl, $C_{6-16}$ aryl carboxylic acids and $C_{4-16}$ heteroaryl carboxylic acids such as acetic, glycolic, lactic, pyruvic, malonic, glutaric, tartaric, citric, fumaric, succinic, malic, maleic, oxalic, hydroxymaleic, benzoic, hydroxybenzoic, phenylacetic, cinnamic, salicylic, nicotinic and 2-phenoxybenzoic.

Invention salts include those made from inorganic acids, e.g., HF, HCl, HBr, Hl, $H_2SO_4$, $H_3PO_4$, $Na_2CO_3$, $K_2CO_3$, $CaCO_3$, $MgCO_3$ and $NaClO_3$. Suitable anions, which are optionally present with a cation such a $Ca^{++}$, $Mg^{++}$, $Li^+$, $Na^+$ or $K^+$, include formate, sorbate, glycodeoxycholate, cholate, deoxycholate, desoxycholate, taurocholate, taurodeoxycholate, taurolithocholate, tetraborate, nitrate, nitrite, sulfite, sulfamate, hyposulfite, bisulfite, metabisulfite, thiosulfate, silicate, metasilicate, gluconate, gulcuronate, hippurate, hydrosulfite, borate, metaborate and urate.

Salts also include the invention compound salts with one or more amino acids. Many amino acids are suitable, especially the naturally-occurring amino acids found as protein components, although the amino acid typically is one bearing a side chain with a basic or acidic group, e.g., lysine, arginine, histidine or glutamic acid, or a neutral group such as glycine, serine, threonine, alanine, isoleucine, or leucine.

The invention compositions include compounds in their un-ionized, as well as zwitterionic form, and combinations with stoiochimetric amounts of water as in hydrates.

Stereoisomers. The formula 1 compounds include enriched or resolved optical isomers at any or all asymmetric atoms as are apparent from the depictions. Both racemic and diasteromeric mixtures, as well as the individual optical isomers can be isolated or synthesized so as to be substantially free of their enantiomeric or diastereomeric partners, and these are all within the scope of the invention. Chiral centers may be found in invention compounds at, for example, $R^1$, $R^2$, $R^3$, $R^4$, $R^5$ or $R^6$.

One or more of the following methods are used to prepare the enantiomerically enriched or pure isomers herein. The methods are listed in approximately their order of preference, i.e., one ordinarily should employ stereospecific synthesis from chiral precursors before chromatographic resolution or before spontaneous crystallization.

Stereospecific synthesis is conveniently used when the appropriate chiral starting material is available and reaction steps are chosen that do not result in undesired racemization at chiral sites. One advantage of stereospecific synthesis is that it does not produce undesired enantiomers that must be removed from the final product, thereby lowering overall synthetic yield. In general, those skilled in the art would understand what starting materials and reaction conditions should be used to obtain the desired enantiomerically enriched or pure isomers by stereospecific synthesis.

Another synthesis method of general utility is chromatographic resolution of enantiomers on chiral chromatography resins. These resins are packed in columns, commonly called Pirkle columns, and are commercially available. The columns contain a chiral stationary phase. The racemate is placed in solution and loaded onto the column, and thereafter separated by HPLC. See for example, Proceedings Chromatographic Society—International Symposium on Chiral Separations, Sep. 3-4, 1987. Examples of chiral columns that could be used to screen for the optimal separation technique would include Diacel Chriacel OD, Regis Pirkle Covalent D-phenylglycine, Regis Pirkle Type 1A, Astec Cyclobond II, Astec Cyclobond III, Serva Chiral D-DL=Daltosil 100, Bakerbond DNBLeu, Sumipax OA-1000, Merck Cellulose Triacetate column, Astec Cyclobond I-Beta, or Regis Pirkle Covalent D-Naphthylalanine. Not all of these columns are likely to be effective with every racemic mixture. However, those skilled in the art understand that a certain amount of routine screening may be required to identify the most effective stationary phase. When using such columns it is desirable to employ embodiments of the compounds of this invention in which the charges are not neutralized, e.g., where acidic functionalities such as carboxyl are not esterified or amidated.

Another method entails converting the enantiomers in the mixture to diasteriomers with chiral auxiliaries and then separating the conjugates by ordinary column chromatography. This is a very suitable method, particularly when the embodiment contains free carboxyl, amino or hydroxyl that will form a salt or covalent bond to a chiral auxiliary. Chirally pure amino acids, organic acids or organosulfonic acids are all worthwhile exploring as chiral auxiliaries, all of which are well known in the art. Salts with such auxiliaries can be formed, or they can be covalently (but reversibly) bonded to the functional group. For example, pure D or L amino acids can be used to amidate the carboxyl group of invention embodiments that comprise a carboxyl group and then separated by chromatography.

Enzymatic resolution is another method of potential value. In such methods one prepares covalent derivatives of the enantiomers in the racemic mixture, generally lower alkyl esters (for example of carboxyl), and then exposes the derivative to enzymatic cleavage, generally hydrolysis. For this method to be successful an enzyme must be chosen that is capable of stereospecific cleavage, so it is frequently necessary to routinely screen several enzymes. If esters are to be cleaved, then one selects a group of esterases, phosphatases, and lipases and determines their activity on the derivative. Typical esterases are from liver, pancreas or other animal organs, and include porcine liver esterase.

If the enantiomeric mixture separates from solution or a melt as a conglomerate, i.e., a mixture of enantiomerically-pure crystals, then the crystals can be mechanically separated, thereby producing the enantiomerically enriched preparation. This method, however, is not practical for large scale preparations and is of limited value for true racemic compounds.

Asymmetric synthesis is another technique for achieving enantiomeric enrichment. For example, a chiral protecting group is reacted with the group to be protected and the reaction mixture allowed to equilibrate. If the reaction is enantiomerically specific then the product will be enriched in that enantiomer.

Further guidance in the separation of enantiomeric mixtures can be found, by way of example and not limitation, in "Enantiomers, Racemates, and resolutions", Jean Jacques, Andre Collet, and Samuel H. Wilen (Krieger Publishing Company, Malabar, Fla., 1991, ISBN 0-89464-618-4): Part 2, Resolution of Enantiomer Mixture, pages 217-435; more particularly, section 4, Resolution by Direct Crystallization, pages 217-251, section 5, Formation and Separation of Diastereomers, pages 251-369, section 6, Crystallization-Induced Asymmetric Transformations, pages 369-378, and section 7, Experimental Aspects and Art of Resolutions, pages 378-435; still more particularly, section 5.1.4, Resolution of Alcohols, Transformation of Alcohols into Salt-Forming Derivatives, pages 263-266, section 5.2.3, Covalent Derivatives of Alcohols, Thiols, and Phenols, pages 332-335, section 5.1.1, Resolution of Acids, pages 257-259, section 5.1.2, Resolution of Bases, pages 259-260, section 5.1.3, Resolution of Amino Acids, page 261-263, section 5.2.1, Covalent Derivatives of Acids, page 329, section 5.2.2, Covalent derivatives of Amines, pages 330-331, section 5.2.4, Covalent Derivatives of Aldehydes, Ketones, and Sulfoxides, pages 335-339, and section 5.2.7, Chromatographic Behavior of Covalent Diastereomers, pages 348-354.

The formula 1 and 2 compounds, e.g., EED, 17α-ethynyl-androst-5-ene-3β,17β-diol, 3β,17b-dihydroxy-androst-5-ene-16-one or an amino acid, peptide, carbonate, ester, thioester, monosaccharide or disaccharide derivative or prodrug of any of these compounds or 3β-methylcarbonate-androst-5-ene-7,17 dione, are useful to treat conditions that are associated with or that respond to modulation of AR activity, including prostate cancer, acne, male pattern baldness, hirsutism, hypogonadism and breast cancer. These compounds may be optionally be used in combination therapies to treat any of these diseases or conditions. The combinations include a formula 1 or 2 compound(s) combined with surgery, radiation therapy, cytotoxic agents, cytostatic agents or hormone therapies, including any of the therapies or treatments disclosed herein or in any of the references cited herein.

The formula 1 or 2 compounds are also useful to determine if the AR or another steroid receptor, e.g., an orphan receptor, are present in a cell population or cell extract. In these applications, the compounds will typically be labeled, e.g., radiolabels ($^{14}C$, $^{3}H$, $^{32}P$, $^{35}S$ or a radioactive iodine isotope) or labeled with a crosslinking moiety. In related applications, the compounds are useful as reference standards to compare their capacity to modulate AR activity with the capacity of known AR modulators, such as AED. In these applications, a formula 1 or 2 compound is used in a suitable assay system, e.g., one that comprises cells (in vitro or in vivo) that contain functional AR, an AR-responsive gene, e.g., ornithine carboxylase, that can be conveniently assayed, a formula 1 or 2 compound and a test compound. In such methods, the effect of the formula 1 or 2 compound on the capacity of the test compound to modulate the AR is examined, usually using a suitably controlled system, e.g., with varying concentrations of the formula 1 or 2 compound, or varying concentrations of the test compound. Assay systems, or components thereof that comprise the Ar have been described, see, e.g., U.S. Pat. Nos. 4,981,784 and 5,071,773, Evans, et al., *Science* 240: 889-895 1988, T. Berger et al., *J. Steriod Biochem. Molec. Biol.* 41:773-778 1992, J. Simenthal, et al., *J. Biol. Chem.* 266:510-514 1991, G. Scalabrino et al., *Mol. Cell. Endocrinol.* 77:1-35 1991, O. Janne, et al., *Ann. N.Y. Acad. Sci.* 438:72-84 1984, and R. Djurhuus, *Anal. Biochem.* 113:352-355 1981.

An effective dose of a formula 1 or formula 2 compound, or the "active ingredient", for use in therapeutic applications, e.g., prostate cancer treatment, will depend to a certain extent at least on factors such as the status of the condition being treated, whether the compound(s) is being used prophylactically (lower doses) or the severity of the malignancy, the method of delivery, and the pharmaceutical formulation. These factors will be determined by the clinician using conventional dose escalation studies. Typically the dose administered to the subject will be from about 0.03 to about 30 mg/kg body weight per day, generally about 0.1 to about 10 mg/kg body weight per day. For example, for topical delivery the daily candidate dose for an adult human of approximately 70 kg body weight will range from about 1 mg to about 750 mg, generally between about 5 mg and about 300 mg, usually between about 30 mg and about 250 mg. A daily dose may take the form of single or multiple doses or administration sites. For a formula 1 or 2 compound that is delivered parenterally, e.g., i.v., s.c. or i.m., the dose will generally be lower (e.g., about 0.02 to about 6 mg/kg) than a dose administered orally.

Pharmaceutical formulations that comprise a formula 1 or 2 compound will typically comprise one or more carriers or excipients and optionally other therapeutic ingredients. The carrier(s) will generally be "acceptable" in the sense of being compatible with the other ingredients of the formulation and physiologically innocuous to the recipient thereof. Such carriers or excipients are known, e.g., fillers, lubricants, binders and various liquid excipients for liquid formulations. Suitable carriers include those disclosed in the references cited herein.

Suitable formulations include aqueous or oily solutions of the active ingredient. Formulations suitable for parenteral delivery of the active ingredient include aqueous and non-aqueous compositions where the active ingredient is dissolved or suspended in solution. Such formulations will typically comprise about 25-300 mg/mL of the active ingredient, usually about 40-200 mg/mL. Formulations suitable for parenteral administration include aqueous and non-aqueous sterile injection solutions which may contain anti-oxidants, buffers, bacteriostats or solutes that render the formulation isotonic with the blood of the intended recipient. Other parenteral formulations may comprise aqueous and non-aqueous sterile suspensions which may include suspending agents and thickening agents.

Formulations suitable for topical administration include creams or ointments wherein the formula 1 or 2 compound is dissolved or suspended in a suitable carrier, especially a non-aqueous solvent or carrier for the active ingredient. The active ingredient is typically present in such formulations in a concentration of 0.5 to 20% w/w, often 0.5 to 10% w/w. Such formulations are suitable for use in applications such as treating male pattern baldness or acne.

Formulations suitable for buccal or sublingual administration include lozenges comprising the active ingredient, which is optionally present in a flavored basis such as sucrose and acacia or tragacanth. Pastilles may comprise the active ingredient in an inert basis such as gelatin and glycerin, or sucrose and acacia, and mouthwashes may comprise the active ingredient in a suitable liquid carrier.

Formulations for rectal administration may be presented as a suppository with a suitable base comprising for example cocoa butter or a salicylate.

Formulations suitable for intrapulmonary or nasal administration will have a particle size for example in the range of 0.01 to 200 microns (including particle sizes in a range between 0.01 and 500 microns in increments of 0.1 microns such as 0.1, 0.2, 0.3, 0.4, 0.5, 1, 2, 5, 30 microns, 35 microns, etc.), which is administered by inhalation through the nasal passage or by inhalation through the mouth so as to reach the various bronchi or alveolar sacs. Formulations suitable for aerosol or dry powder administration may be prepared according to conventional methods and may be delivered with other therapeutic agents such as compounds heretofore used in the treatment or prophylaxis of prostate cancer.

Formulations suitable for vaginal administration may be presented as pessaries, tampons, creams, gels, pastes, foams or spray formulations containing in addition to the active ingredient such carriers as are known in the art to be appropriate.

Formulations comprising an active ingredient are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as described herein, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring or coloring agents.

The invention further provides veterinary compositions comprising at least one active ingredient together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

The active ingredients may be used to provide controlled release pharmaceutical formulations containing an active ingredient ("controlled release formulations") in which the release of the active ingredient is controlled and regulated to allow less frequency dosing or to improve the pharmacokinetic or toxicity profile of a given active ingredient.

The formulations include those suitable for any of the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients or excipients. In general, the formulations are prepared by uniformly and intimately bringing into association the active ingredient with liquid carriers or finely divided solid carriers or both, and then, if necessary, shaping the product.

Formulations of the invention suitable for oral administration are prepared as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

If desired, the aqueous phase of a cream base may include, for example, polyhydric alcohol, i.e. an alcohol having two or more hydroxyl groups such as propylene glycol, butane 1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

In some embodiments, the methods or compositions described herein will utilize, in lieu of a formula 1 or 2 compound, one or more steroid or non-steroid compounds that are disclosed in U.S. Pat. No. 2,833,793, 2,911,418, 3,148,198, 3,471,480, 3,710,795, 3,711,606 3,976,691, 4,268,441, 4,427,649, 4,542,129, 4,666,898, 4,693,999, 4,978,532, 5,001,119, 5,043,165, 5,077,284, 5,028,631, 5,110,810, 5,157,031, 5,162,198, 5,175,154, 5,277,907, 5,292,730, 5,296,481, 5,372,996, 5,387,583, 5,407,684, 5,424,463, 5,461,042, 5,478,566, 5,506,223, 5,518,725, 5,527,788, 5,527,789, 5,532,230, 5,559,107, 5,562,910, 5,583,126, 5,585,371, 5,587,369, 5,591,736, 5,593,981, 5,610,150, 5,635,496, 5,641,766, 5,641,768, 5,656,621, 5,660,835, 5,677,336, 5,681,835, 5,686,438, 5,696,106, 5,696,127, 5,696,130, 5,700,793, 5,707,983, 5,709,878, 5,710,143, 5,714,481, 5,728,688, 5,736,537, 5,744,462, 5,753,237, 5,756,482, 5,776,921, 5,776,923, 5,780,460, 5,780,676, 5,795,880, 5,798,347, 5,798,348, 5,804,576, 5,807,848, 5,807,849, 5,811,418, 5,824,313, 5,824,668, 5,824,671, 5,827,841, 5,837,269, 5,837,700, 5,843,932, 5,846,963, 5,856,340, 5,859,000, 5,869,090, 5,863,910, 5,872,114, 5,872,147, 5,886,005, 5,889,042, 5,891,865, 5,892,069, 5,945,404 or 5,945,412 or in PCT publication number 97/49709.

The positions in the rings of formula 1 compounds are numbered as shown below.

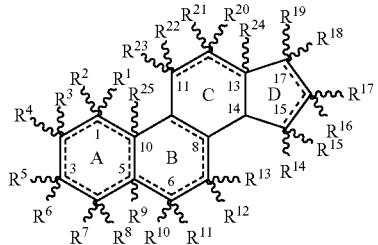

More than one double bond may be present in formula 1 compounds, but no carbon atom will carry a charge due to the presence of excess bonds or valences. Typically, 0, 1, 2, 3 or 4 double bonds will be present. Thus, if a double bond is present at the 5-6-positions, $R^9$ and one of $R^{10}$ and $R^{11}$ will be absent. Or, if one or both of the variable groups that are bonded to the ring atoms comprises a double bond, e.g., $=CH_2$, $=CHCH_3$, $=N-NH_2$, $=O$ or $=S$, there will be no double bond in the ring at those ring atom positions. The A ring may comprise 0, 1, 2 or 3 double bonds and that ring may thus be aromatic. The B and D rings may independently comprise 0, 1 or 2 double bonds and the C ring may comprise 1 double bond. When one or both of $R^{24}$ and $R^{25}$ are present, they independently are in the α- or β-configurations, and in some embodiments, they are independently $-CH_3$ or $-CH_2OH$ in the β-configuration.

Compounds of formula 2 have the structure

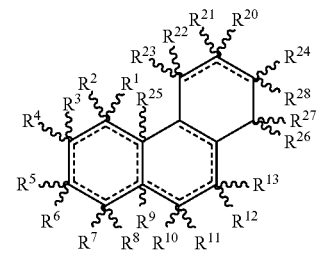

wherein $R^{26}$-$R^{28}$ independently comprise $-H$, $-OR^{PR}$, $-SR^{PR}$, $-N(R^{PR})_2$, $-O-Si-(R)_3$, $-CN$, $-NO_2$, an ester, a phosphoester, a phosphonoester, a sulfite ester, a sulfate ester, an amide, an amino acid, a peptide, an ether, a thioether, an acyl group, a carbonate, a carbamate, a carboxyl, a halogen, an optionally substituted alkyl group, an optionally substituted alkenyl group, an optionally substituted alkynyl group, an optionally substituted aryl moiety, an optionally substituted heteroaryl moiety, an optionally substituted monosaccharide, an optionally substituted oligosaccharide, a nucleoside, a nucleotide, an oligonucleotide, a polymer, or, $R^{26}$ and $R^{27}$ or $R^{24}$ and $R^{28}$ taken together independently comprise $=O$ or $=S$.

In some embodiments, one, two, three, four or more of $R^1$-$R^{28}$ independently comprise $-OH$, $=O$, $-SH$, $=S$, $-NH_2$, halogen, $=CH_2$, $=NOH$, $=NOC(O)CH_3$, $-O-C(O)-(CH_2)_m-(CF_2)_n-CH_3$, $-O-C(O)-(CH_2)_m-(CF_2)_n-CF_3$, $-O-C(O)-(CH_2)_m-(CF_2)_n-CH_2F$, $-O-C(O)-O-(CH_2)_m-(CF_2)_n-CH_3$, $-O-C(O)-O-(CH_2)_m-(CF_2)_n-CF_3$, $-O-C(O)-O-(CH_2)_m-(CF_2)_n-CH_2F$, $-O-C(O)-NH-(CH_2)_m-(CF_2)_n-CH_3$, $-O-C(O)-NH-(CH_2)_m-(CF_2)_n-CF_3$, $-O-C(O)-NH-(CH_2)_m-(CF_2)_n-CH_2F$ (where m is 1, 2, 3, 4, 5, 6, 7, 8, 9 or 10, n is 0, 1, 2, 3, 4, 5, 6, 7, 8, 9 or 10, usually n is 0), $-CH(CH_3)-(CH_2)_2-C(O)NH-CH_2COOH$, $-CH(CH_3)-(CH_2)_2-C(O)NH-CH_2SO_3H$, $-OSi(CH_3)_2 C(CH_3)_3$, $-C(OH)=CHCH_3$, $=CH(CH_2)_{0-15}CH_3$, $-(CH_2)_{0-14}-CH_2F$, $-(CH_2)_{0-14}-CH_2Cl$, $-(CH_2)_{0-14}-CH_2Br$, $-(CH_2)_{0-14}-CH_2I$, $-(CH_2)_{2-10}-O-(CH_2)_{0-4}CH_3$, $-(CH_2)_{2-10}-S-(CH_2)_{0-4}CH_3$, $-(CH_2)_{2-10}-NH-(CH_2)_{0-4}CH_3$, $-O-(CH_2)_{0-14}-CH_2F$, $-O-(CH_2)_{2-10}-CH_2Cl$, $-O-(CH_2)_{0-14}-CH_2Br$, $-O-(CH_2)_{0-14}-CH_2I$, $-O-(CH_2)_{2-10}-O-(CH_2)_{0-4}-CH_3$, $-O-(CH_2)_{2-10}-NH-(CH_2)_{0-4}-CH_3$, $-O-(CH_2)_{2-10}-NH-(CH_2)_{0-4}-CH_3$, $-O-C(O)-(CH_2)_{0-14}-CH_2F$, $-O-C(O)-(CH_2)_{0-14}-CH_2Cl$, $-O-C(O)-(CH_2)_{0-14}-CH_2Br$, $-O-C(O)-(CH_2)_{0-14}-CH_2I$, $-O-C(O)-(CH_2)_{2-10}-O-(CH_2)_{0-4}CH_3$, $-O-C(O)-(CH_2)_{2-10}-S-(CH_2)_{0-4}CH_3$, $-O-C(O)-(CH_2)_{2-10}-NH-(CH_2)_{0-4}-CH_3$, $-O-C(S)-(CH_2)_{0-14}-CH_2F$, $-O-C(S)-(CH_2)_{0-14}-$ CH$_2$Cl, —O—C(S)—(CH$_2$)$_{0-14}$—CH$_2$Br, —O—C(S)—(CH$_2$)$_{0-14}$—CH$_2$I, —O—C(S)—(CH$_2$)$_{2-10}$—O—(CH$_2$)$_{0-4}$—CH$_3$, —O—C(S)—(CH$_2$)$_{2-10}$—S—(CH$_2$)$_{0-4}$—CH$_3$, —O—C(S)—(CH$_2$)$_{2-10}$—NH—(CH$_2$)$_{0-4}$—CH$_3$, —(CH$_2$)$_{0-16}$NH$_2$, —(CH$_2$)$_{0-15}$CH$_3$, —(CH$_2$)$_{0-15}$CN, —(CH$_2$)$_{0-15}$CH=CH$_2$, —(CH$_2$)$_{0-15}$NHCH(O), —(CH$_2$)$_{0-16}$NH—(CH$_2$)$_{0-15}$CH$_3$, —(CH$_2$)$_{0-15}$CCH, —(CH$_2$)$_{0-15}$OC(O)CH$_3$, —(CH$_2$)$_{0-15}$OCH(OH)CH$_3$, —(CH$_2$)$_{0-15}$C(O)OCH$_3$, —(CH$_2$)$_{0-15}$C(O)OCH$_2$CH$_3$, —(CH$_2$)$_{0-15}$C(O)(CH$_2$)$_{0-15}$CH$_3$, —(CH$_2$)$_{0-15}$C(O)(CH$_2$)$_{0-15}$CH$_2$OH, —O(CH$_2$)$_{1-16}$NH$_2$, —O(CH$_2$)$_{1-15}$CH$_3$, —O(CH$_2$)$_{1-15}$CN, —O(CH$_2$)$_{1-15}$CH=CH$_2$, —O(CH$_2$)$_{1-15}$NHCH(O), —O(CH$_2$)$_{1-16}$NH—(CH$_2$)$_{1-15}$CH$_3$, —O(CH$_2$)$_{1-15}$CCH, —O(CH$_2$)$_{1-15}$OC(O)CH$_3$, —O(CH$_2$)$_{1-15}$OCH(OH)CH$_3$, —O(CH$_2$)$_{1-15}$C(O)OCH$_3$, —O(CH$_2$)$_{1-15}$C(O)OCH$_2$CH$_3$, —O(CH$_2$)$_{1-15}$C(O)(CH$_2$)$_{0-15}$CH$_3$, —O(CH$_2$)$_{1-5}$C(O)(CH$_2$)$_{0-15}$CH$_2$OH, —OC(O)(CH$_2$)$_{1-16}$NH$_2$, —OC(O)(CH$_2$)$_{1-15}$CH$_3$, —C(O)O(CH$_2$)$_{1-15}$CN, —C(O)O(CH$_2$)$_{1-15}$CH=CH$_2$, —OC(O)(CH$_2$)$_{1-15}$NHCH(O), —OC(O)(CH$_2$)$_{1-16}$NH—(CH$_2$)$_{1-15}$CH$_3$, —OC(O)(CH$_2$)$_{1-15}$CCH, —OC(O)(CH$_2$)$_{1-15}$OC(O)CH$_3$, —OC(O)(CH$_2$)$_{1-15}$OCH(OH)CH$_3$, —OC(O)(CH$_2$)$_{1-15}$C(O)OCH$_3$, —OC(O)(CH$_2$)$_{1-15}$C(O)OCH$_2$CH$_3$, —OC(O)(CH$_2$)$_{1-15}$C(O)(CH$_2$)$_{0-15}$CH$_3$, —OC(O)(CH$_2$)$_{1-15}$C(O)(CH$_2$)$_{0-15}$CH$_2$OH, —C(O)—O—(CH$_2$)$_m$CH$_3$ (where m is 1, 2, 3, 4, 5, 6, 7, 8, 9 or 10), —(CH$_2$)$_m$—C(O)OH (where m is 1, 2, 3, 4, 5, 6, 7, 8, 9 or 10), phosphoenolpyruvate, D-glucosamine, glucholic acid, glucuronic acid, pantothenic acid, pyruvic acid, glucose, fructose, mannose, sucrose, lactose, glycerol, 3-phosphoglycerate, a PEG (PEG 20, PEG 100, PEG 200, PEG 10000), a polyoxyalkylene polymer, glycine, alanine, phenylalanine, glutamic acid, lysine, threonine, proline and/or 4-hydroxyproline. Such substituents may be present in the α-configuration or the β-configuration.

Enumerated embodiments. By way of examples that further illustrate the formula 1 compounds, compounds or genera of compounds are named as described in the following groups of compounds.

Group 1 compounds. Compounds or genera of compounds are named in Table 2. Each named group 1 compound or genus is a compound or genus of formula 3

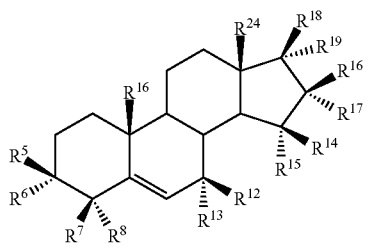

3 wherein $R^7$, $R^8$, $R^{14}$ and $R^{15}$ are all —H, and $R^{24}$ and $R^{25}$ are both —CH$_3$. The Table 2 compounds are named by numbers that specify the structures of the $R^5$, $R^6$, $R^{12}$, $R^{13}$, $R^{16}$, $R^{17}$, $R^{18}$ and $R^{19}$ variable groups in Table 1 as follows $R^5R^6.R^{12}R^{13}.R^{16}R^{17}.R^{18}R^{19}$. In some embodiments, 2 variable groups that are linked to the same carbon atom are taken together to form a double bonded moiety, e.g., =O, =CH$_2$.

Thus, based on the structures shown in Table 1, the compounds named 4.2.2.3, 4.3.2.3 and 8.1.6.10 in Table 2 have the structures

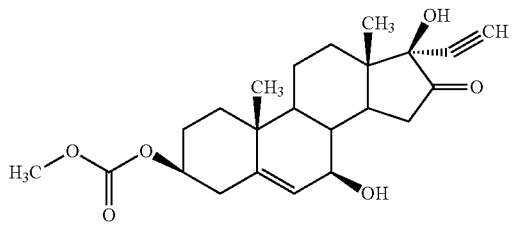

4.2.2.3 and

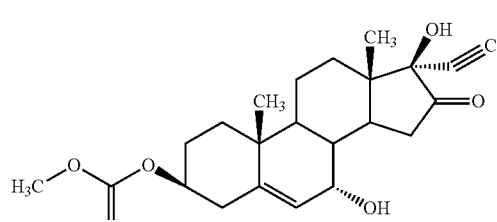

4.3.2.3

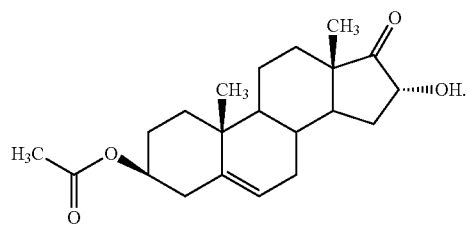

8.1.6.10

TABLE 1

| $R^5$, $R^6$ | | $R^{12}$, $R^{13}$ | |
|---|---|---|---|
| 1 | —OH, —H | 1 | —H, —H |
| 2 | —H, —OH | 2 | —OH, —H |
| 3 | —OH, —OH | 3 | —H, —OH |
| 4 | —O—C(O)—OCH$_3$, —H | 4 | —OH, —OH |
| 5 | —H, —O—C(O)—OCH$_3$ | 5 | —O—C(O)—OCH$_3$, —H |
| 6 | —O—CH$_2$—C$_6$H$_5$, —H | 6 | —H, —O—C(O)—OCH$_3$ |
| 7 | —H, —O—CH$_2$—C$_6$H$_5$ | 7 | =O |
| 8 | —O—C(O)—CH$_3$, —H | 8 | =S |
| 9 | —H, —O—C(O)—CH$_3$ | 9 | —SH, —H |
| 10 | =O | 10 | —H, —SH |

| $R^{16}$, $R^{17}$ | | $R^{18}$, $R^{19}$ | |
|---|---|---|---|
| 1 | —H, —H | 1 | —OH, —H |
| 2 | =O | 2 | —H, —OH |
| 3 | =CH$_2$ | 3 | —OH, —CCH |
| 4 | =S | 4 | —CCH, —OH |
| 5 | —OH, —H | 5 | —H, —CCH |
| 6 | —H, —OH | 6 | —CCH, —H |
| 7 | —O—C(O)—OCH$_3$, —H | 7 | —OH, —CCCH$_3$ |
| 8 | —H, —O—C(O)—OCH$_3$ | 8 | —O—C(O)—CH$_3$, —CCH |
| 9 | —O—C(O)—CH$_3$, —H | 9 | —O—C(O)—CH$_2$CH$_3$, —CCH |
| 10 | —H, —O—C(O)—CH$_3$ | 10 | =O |

TABLE 2

1.1.1.1, 1.1.1.2, 1.1.1.3, 1.1.1.4, 1.1.1.5, 1.1.1.6, 1.1.1.7, 1.1.1.8, 1.1.1.9, 1.1.1.10, 1.1.2.1, 1.1.2.2, 1.1.2.3, 1.1.2.4, 1.1.2.5, 1.1.2.6, 1.1.2.7, 1.1.2.8, 1.1.2.9, 1.1.2.10, 1.1.3.1, 1.1.3.2, 1.1.3.3, 1.1.3.4, 1.1.3.5, 1.1.3.6, 1.1.3.7, 1.1.3.8, 1.1.3.9, 1.1.3.10, 1.1.4.1, 1.1.4.2, 1.1.4.3, 1.1.4.4, 1.1.4.5, 1.1.4.6, 1.1.4.7, 1.1.4.8, 1.1.4.9, 1.1.4.10, 1.1.5.1, 1.1.5.2, 1.1.5.3, 1.1.5.4, 1.1.5.5, 1.1.5.6, 1.1.5.7, 1.1.5.8, 1.1.5.9, 1.1.5.10, 1.1.6.1, 1.1.6.2, 1.1.6.3, 1.1.6.4, 1.1.6.5, 1.1.6.6, 1.1.6.7, 1.1.6.8, 1.1.6.9, 1.1.6.10, 1.1.7.1, 1.1.7.2, 1.1.7.3, 1.1.7.4, 1.1.7.5, 1.1.7.6, 1.1.7.7, 1.1.7.8, 1.1.7.9, 1.1.7.10, 1.1.8.1, 1.1.8.2,

TABLE 2-continued 1.1.8.3, 1.1.8.4, 1.1.8.5, 1.1.8.6, 1.1.8.7, 1.1.8.8, 1.1.8.9, 1.1.8.10, 1.1.9.1, 1.1.9.2, 1.1.9.3, 1.1.9.4,
1.1.9.5, 1.1.9.6, 1.1.9.7, 1.1.9.8, 1.1.9.9, 1.1.9.10, 1.1.10.1, 1.1.10.2, 1.1.10.3, 1.1.10.4, 1.1.10.5,
1.1.10.6, 1.1.10.7, 1.1.10.8, 1.1.10.9, 1.1.10.10, 1.2.1.1, 1.2.1.2, 1.2.1.3, 1.2.1.4, 1.2.1.5, 1.2.1.6,
1.2.1.7, 1.2.1.8, 1.2.1.9, 1.2.1.10, 1.2.2.1, 1.2.2.2, 1.2.2.3, 1.2.2.4, 1.2.2.5, 1.2.2.6, 1.2.2.7, 1.2.2.8,
1.2.2.9, 1.2.2.10, 1.2.3.1, 1.2.3.2, 1.2.3.3, 1.2.3.4, 1.2.3.5, 1.2.3.6, 1.2.3.7, 1.2.3.8, 1.2.3.9, 1.2.3.10,
1.2.4.1, 1.2.4.2, 1.2.4.3, 1.2.4.4, 1.2.4.5, 1.2.4.6, 1.2.4.7, 1.2.4.8, 1.2.4.9, 1.2.4.10, 1.2.5.1, 1.2.5.2,
1.2.5.3, 1.2.5.4, 1.2.5.5, 1.2.5.6, 1.2.5.7, 1.2.5.8, 1.2.5.9, 1.2.5.10, 1.2.6.1, 1.2.6.2, 1.2.6.3, 1.2.6.4,
1.2.6.5, 1.2.6.6, 1.2.6.7, 1.2.6.8, 1.2.6.9, 1.2.6.10, 1.2.7.1, 1.2.7.2, 1.2.7.3, 1.2.7.4, 1.2.7.5, 1.2.7.6,
1.2.7.7, 1.2.7.8, 1.2.7.9, 1.2.7.10, 1.2.8.1, 1.2.8.2, 1.2.8.3, 1.2.8.4, 1.2.8.5, 1.2.8.6, 1.2.8.7, 1.2.8.8,
1.2.8.9, 1.2.8.10, 1.2.9.1, 1.2.9.2, 1.2.9.3, 1.2.9.4, 1.2.9.5, 1.2.9.6, 1.2.9.7, 1.2.9.8, 1.2.9.9, 1.2.9.10,
1.2.10.1, 1.2.10.2, 1.2.10.3, 1.2.10.4, 1.2.10.5, 1.2.10.6, 1.2.10.7, 1.2.10.8, 1.2.10.9, 1.2.10.10,
1.3.1.1, 1.3.1.2, 1.3.1.3, 1.3.1.4, 1.3.1.5, 1.3.1.6, 1.3.1.7, 1.3.1.8, 1.3.1.9, 1.3.1.10, 1.3.2.1, 1.3.2.2,
1.3.2.3, 1.3.2.4, 1.3.2.5, 1.3.2.6, 1.3.2.7, 1.3.2.8, 1.3.2.9, 1.3.2.10, 1.3.3.1, 1.3.3.2, 1.3.3.3, 1.3.3.4,
1.3.3.5, 1.3.3.6, 1.3.3.7, 1.3.3.8, 1.3.3.9, 1.3.3.10, 1.3.4.1, 1.3.4.2, 1.3.4.3, 1.3.4.4, 1.3.4.5, 1.3.4.6,
1.3.4.7, 1.3.4.8, 1.3.4.9, 1.3.4.10, 1.3.5.1, 1.3.5.2, 1.3.5.3, 1.3.5.4, 1.3.5.5, 1.3.5.6, 1.3.5.7, 1.3.5.8,
1.3.5.9, 1.3.5.10, 1.3.6.1, 1.3.6.2, 1.3.6.3, 1.3.6.4, 1.3.6.5, 1.3.6.6, 1.3.6.7, 1.3.6.8, 1.3.6.9, 1.3.6.10,
1.3.7.1, 1.3.7.2, 1.3.7.3, 1.3.7.4, 1.3.7.5, 1.3.7.6, 1.3.7.7, 1.3.7.8, 1.3.7.9, 1.3.7.10, 1.3.8.1, 1.3.8.2,
1.3.8.3, 1.3.8.4, 1.3.8.5, 1.3.8.6, 1.3.8.7, 1.3.8.8, 1.3.8.9, 1.3.8.10, 1.3.9.1, 1.3.9.2, 1.3.9.3, 1.3.9.4,
1.3.9.5, 1.3.9.6, 1.3.9.7, 1.3.9.8, 1.3.9.9, 1.3.9.10, 1.3.10.1, 1.3.10.2, 1.3.10.3, 1.3.10.4, 1.3.10.5,
1.3.10.6, 1.3.10.7, 1.3.10.8, 1.3.10.9, 1.3.10.10, 1.4.1.1, 1.4.1.2, 1.4.1.3, 1.4.1.4, 1.4.1.5, 1.4.1.6,
1.4.1.7, 1.4.1.8, 1.4.1.9, 1.4.1.10, 1.4.2.1, 1.4.2.2, 1.4.2.3, 1.4.2.4, 1.4.2.5, 1.4.2.6, 1.4.2.7, 1.4.2.8,
1.4.2.9, 1.4.2.10, 1.4.3.1, 1.4.3.2, 1.4.3.3, 1.4.3.4, 1.4.3.5, 1.4.3.6, 1.4.3.7, 1.4.3.8, 1.4.3.9, 1.4.3.10,
1.4.4.1, 1.4.4.2, 1.4.4.3, 1.4.4.4, 1.4.4.5, 1.4.4.6, 1.4.4.7, 1.4.4.8, 1.4.4.9, 1.4.4.10, 1.4.5.1, 1.4.5.2,
1.4.5.3, 1.4.5.4, 1.4.5.5, 1.4.5.6, 1.4.5.7, 1.4.5.8, 1.4.5.9, 1.4.5.10, 1.4.6.1, 1.4.6.2, 1.4.6.3, 1.4.6.4,
1.4.6.5, 1.4.6.6, 1.4.6.7, 1.4.6.8, 1.4.6.9, 1.4.6.10, 1.4.7.1, 1.4.7.2, 1.4.7.3, 1.4.7.4, 1.4.7.5, 1.4.7.6,
1.4.7.7, 1.4.7.8, 1.4.7.9, 1.4.7.10, 1.4.8.1, 1.4.8.2, 1.4.8.3, 1.4.8.4, 1.4.8.5, 1.4.8.6, 1.4.8.7, 1.4.8.8,
1.4.8.9, 1.4.8.10, 1.4.9.1, 1.4.9.2, 1.4.9.3, 1.4.9.4, 1.4.9.5, 1.4.9.6, 1.4.9.7, 1.4.9.8, 1.4.9.9, 1.4.9.10,
1.4.10.1, 1.4.10.2, 1.4.10.3, 1.4.10.4, 1.4.10.5, 1.4.10.6, 1.4.10.7, 1.4.10.8, 1.4.10.9, 1.4.10.10,
1.5.1.1, 1.5.1.2, 1.5.1.3, 1.5.1.4, 1.5.1.5, 1.5.1.6, 1.5.1.7, 1.5.1.8, 1.5.1.9, 1.5.1.10, 1.5.2.1, 1.5.2.2,
1.5.2.3, 1.5.2.4, 1.5.2.5, 1.5.2.6, 1.5.2.7, 1.5.2.8, 1.5.2.9, 1.5.2.10, 1.5.3.1, 1.5.3.2, 1.5.3.3, 1.5.3.4,
1.5.3.5, 1.5.3.6, 1.5.3.7, 1.5.3.8, 1.5.3.9, 1.5.3.10, 1.5.4.1, 1.5.4.2, 1.5.4.3, 1.5.4.4, 1.5.4.5, 1.5.4.6,
1.5.4.7, 1.5.4.8, 1.5.4.9, 1.5.4.10, 1.5.5.1, 1.5.5.2, 1.5.5.3, 1.5.5.4, 1.5.5.5, 1.5.5.6, 1.5.5.7, 1.5.5.8,
1.5.5.9, 1.5.5.10, 1.5.6.1, 1.5.6.2, 1.5.6.3, 1.5.6.4, 1.5.6.5, 1.5.6.6, 1.5.6.7, 1.5.6.8, 1.5.6.9, 1.5.6.10,
1.5.7.1, 1.5.7.2, 1.5.7.3, 1.5.7.4, 1.5.7.5, 1.5.7.6, 1.5.7.7, 1.5.7.8, 1.5.7.9, 1.5.7.10, 1.5.8.1, 1.5.8.2,
1.5.8.3, 1.5.8.4, 1.5.8.5, 1.5.8.6, 1.5.8.7, 1.5.8.8, 1.5.8.9, 1.5.8.10, 1.5.9.1, 1.5.9.2, 1.5.9.3, 1.5.9.4,
1.5.9.5, 1.5.9.6, 1.5.9.7, 1.5.9.8, 1.5.9.9, 1.5.9.10, 1.5.10.1, 1.5.10.2, 1.5.10.3, 1.5.10.4, 1.5.10.5,
1.5.10.6, 1.5.10.7, 1.5.10.8, 1.5.10.9, 1.5.10.10, 1.6.1.1, 1.6.1.2, 1.6.1.3, 1.6.1.4, 1.6.1.5, 1.6.1.6,
1.6.1.7, 1.6.1.8, 1.6.1.9, 1.6.1.10, 1.6.2.1, 1.6.2.2, 1.6.2.3, 1.6.2.4, 1.6.2.5, 1.6.2.6, 1.6.2.7, 1.6.2.8,
1.6.2.9, 1.6.2.10, 1.6.3.1, 1.6.3.2, 1.6.3.3, 1.6.3.4, 1.6.3.5, 1.6.3.6, 1.6.3.7, 1.6.3.8, 1.6.3.9, 1.6.3.10,
1.6.4.1, 1.6.4.2, 1.6.4.3, 1.6.4.4, 1.6.4.5, 1.6.4.6, 1.6.4.7, 1.6.4.8, 1.6.4.9, 1.6.4.10, 1.6.5.1, 1.6.5.2,
1.6.5.3, 1.6.5.4, 1.6.5.5, 1.6.5.6, 1.6.5.7, 1.6.5.8, 1.6.5.9, 1.6.5.10, 1.6.6.1, 1.6.6.2, 1.6.6.3, 1.6.6.4,
1.6.6.5, 1.6.6.6, 1.6.6.7, 1.6.6.8, 1.6.6.9, 1.6.6.10, 1.6.7.1, 1.6.7.2, 1.6.7.3, 1.6.7.4, 1.6.7.5, 1.6.7.6,
1.6.7.7, 1.6.7.8, 1.6.7.9, 1.6.7.10, 1.6.8.1, 1.6.8.2, 1.6.8.3, 1.6.8.4, 1.6.8.5, 1.6.8.6, 1.6.8.7, 1.6.8.8,
1.6.8.9, 1.6.8.10, 1.6.9.1, 1.6.9.2, 1.6.9.3, 1.6.9.4, 1.6.9.5, 1.6.9.6, 1.6.9.7, 1.6.9.8, 1.6.9.9, 1.6.9.10,
1.6.10.1, 1.6.10.2, 1.6.10.3, 1.6.10.4, 1.6.10.5, 1.6.10.6, 1.6.10.7, 1.6.10.8, 1.6.10.9, 1.6.10.10,
1.7.1.1, 1.7.1.2, 1.7.1.3, 1.7.1.4, 1.7.1.5, 1.7.1.6, 1.7.1.7, 1.7.1.8, 1.7.1.9, 1.7.1.10, 1.7.2.1, 1.7.2.2,
1.7.2.3, 1.7.2.4, 1.7.2.5, 1.7.2.6, 1.7.2.7, 1.7.2.8, 1.7.2.9, 1.7.2.10, 1.7.3.1, 1.7.3.2, 1.7.3.3, 1.7.3.4,
1.7.3.5, 1.7.3.6, 1.7.3.7, 1.7.3.8, 1.7.3.9, 1.7.3.10, 1.7.4.1, 1.7.4.2, 1.7.4.3, 1.7.4.4, 1.7.4.5, 1.7.4.6,
1.7.4.7, 1.7.4.8, 1.7.4.9, 1.7.4.10, 1.7.5.1, 1.7.5.2, 1.7.5.3, 1.7.5.4, 1.7.5.5, 1.7.5.6, 1.7.5.7, 1.7.5.8,
1.7.5.9, 1.7.5.10, 1.7.6.1, 1.7.6.2, 1.7.6.3, 1.7.6.4, 1.7.6.5, 1.7.6.6, 1.7.6.7, 1.7.6.8, 1.7.6.9, 1.7.6.10,
1.7.7.1, 1.7.7.2, 1.7.7.3, 1.7.7.4, 1.7.7.5, 1.7.7.6, 1.7.7.7, 1.7.7.8, 1.7.7.9, 1.7.7.10, 1.7.8.1, 1.7.8.2,
1.7.8.3, 1.7.8.4, 1.7.8.5, 1.7.8.6, 1.7.8.7, 1.7.8.8, 1.7.8.9, 1.7.8.10, 1.7.9.1, 1.7.9.2, 1.7.9.3, 1.7.9.4,
1.7.9.5, 1.7.9.6, 1.7.9.7, 1.7.9.8, 1.7.9.9, 1.7.9.10, 1.7.10.1, 1.7.10.2, 1.7.10.3, 1.7.10.4, 1.7.10.5,
1.7.10.6, 1.7.10.7, 1.7.10.8, 1.7.10.9, 1.7.10.10, 1.8.1.1, 1.8.1.2, 1.8.1.3, 1.8.1.4, 1.8.1.5, 1.8.1.6,
1.8.1.7, 1.8.1.8, 1.8.1.9, 1.8.1.10, 1.8.2.1, 1.8.2.2, 1.8.2.3, 1.8.2.4, 1.8.2.5, 1.8.2.6, 1.8.2.7, 1.8.2.8,
1.8.2.9, 1.8.2.10, 1.8.3.1, 1.8.3.2, 1.8.3.3, 1.8.3.4, 1.8.3.5, 1.8.3.6, 1.8.3.7, 1.8.3.8, 1.8.3.9, 1.8.3.10,
1.8.4.1, 1.8.4.2, 1.8.4.3, 1.8.4.4, 1.8.4.5, 1.8.4.6, 1.8.4.7, 1.8.4.8, 1.8.4.9, 1.8.4.10, 1.8.5.1, 1.8.5.2,
1.8.5.3, 1.8.5.4, 1.8.5.5, 1.8.5.6, 1.8.5.7, 1.8.5.8, 1.8.5.9, 1.8.5.10, 1.8.6.1, 1.8.6.2, 1.8.6.3, 1.8.6.4,
1.8.6.5, 1.8.6.6, 1.8.6.7, 1.8.6.8, 1.8.6.9, 1.8.6.10, 1.8.7.1, 1.8.7.2, 1.8.7.3, 1.8.7.4, 1.8.7.5, 1.8.7.6,
1.8.7.7, 1.8.7.8, 1.8.7.9, 1.8.7.10, 1.8.8.1, 1.8.8.2, 1.8.8.3, 1.8.8.4, 1.8.8.5, 1.8.8.6, 1.8.8.7, 1.8.8.8,
1.8.8.9, 1.8.8.10, 1.8.9.1, 1.8.9.2, 1.8.9.3, 1.8.9.4, 1.8.9.5, 1.8.9.6, 1.8.9.7, 1.8.9.8, 1.8.9.9, 1.8.9.10,
1.8.10.1, 1.8.10.2, 1.8.10.3, 1.8.10.4, 1.8.10.5, 1.8.10.6, 1.8.10.7, 1.8.10.8, 1.8.10.9, 1.8.10.10,
1.9.1.1, 1.9.1.2, 1.9.1.3, 1.9.1.4, 1.9.1.5, 1.9.1.6, 1.9.1.7, 1.9.1.8, 1.9.1.9, 1.9.1.10, 1.9.2.1, 1.9.2.2,
1.9.2.3, 1.9.2.4, 1.9.2.5, 1.9.2.6, 1.9.2.7, 1.9.2.8, 1.9.2.9, 1.9.2.10, 1.9.3.1, 1.9.3.2, 1.9.3.3, 1.9.3.4,
1.9.3.5, 1.9.3.6, 1.9.3.7, 1.9.3.8, 1.9.3.9, 1.9.3.10, 1.9.4.1, 1.9.4.2, 1.9.4.3, 1.9.4.4, 1.9.4.5, 1.9.4.6,
1.9.4.7, 1.9.4.8, 1.9.4.9, 1.9.4.10, 1.9.5.1, 1.9.5.2, 1.9.5.3, 1.9.5.4, 1.9.5.5, 1.9.5.6, 1.9.5.7, 1.9.5.8,
1.9.5.9, 1.9.5.10, 1.9.6.1, 1.9.6.2, 1.9.6.3, 1.9.6.4, 1.9.6.5, 1.9.6.6, 1.9.6.7, 1.9.6.8, 1.9.6.9, 1.9.6.10,
1.9.7.1, 1.9.7.2, 1.9.7.3, 1.9.7.4, 1.9.7.5, 1.9.7.6, 1.9.7.7, 1.9.7.8, 1.9.7.9, 1.9.7.10, 1.9.8.1, 1.9.8.2,
1.9.8.3, 1.9.8.4, 1.9.8.5, 1.9.8.6, 1.9.8.7, 1.9.8.8, 1.9.8.9, 1.9.8.10, 1.9.9.1, 1.9.9.2, 1.9.9.3, 1.9.9.4,
1.9.9.5, 1.9.9.6, 1.9.9.7, 1.9.9.8, 1.9.9.9, 1.9.9.10, 1.9.10.1, 1.9.10.2, 1.9.10.3, 1.9.10.4, 1.9.10.5,
1.9.10.6, 1.9.10.7, 1.9.10.8, 1.9.10.9, 1.9.10.10, 1.10.1.1, 1.10.1.2, 1.10.1.3, 1.10.1.4, 1.10.1.5,
1.10.1.6, 1.10.1.7, 1.10.1.8, 1.10.1.9, 1.10.1.10, 1.10.2.1, 1.10.2.2, 1.10.2.3, 1.10.2.4, 1.10.2.5,
1.10.2.6, 1.10.2.7, 1.10.2.8, 1.10.2.9, 1.10.2.10, 1.10.3.1, 1.10.3.2, 1.10.3.3, 1.10.3.4, 1.10.3.5,
1.10.3.6, 1.10.3.7, 1.10.3.8, 1.10.3.9, 1.10.3.10, 1.10.4.1, 1.10.4.2, 1.10.4.3, 1.10.4.4, 1.10.4.5,
1.10.4.6, 1.10.4.7, 1.10.4.8, 1.10.4.9, 1.10.4.10, 1.10.5.1, 1.10.5.2, 1.10.5.3, 1.10.5.4, 1.10.5.5,
1.10.5.6, 1.10.5.7, 1.10.5.8, 1.10.5.9, 1.10.5.10, 1.10.6.1, 1.10.6.2, 1.10.6.3, 1.10.6.4, 1.10.6.5,
1.10.6.6, 1.10.6.7, 1.10.6.8, 1.10.6.9, 1.10.6.10, 1.10.7.1, 1.10.7.2, 1.10.7.3, 1.10.7.4, 1.10.7.5,
1.10.7.6, 1.10.7.7, 1.10.7.8, 1.10.7.9, 1.10.7.10, 1.10.8.1, 1.10.8.2, 1.10.8.3, 1.10.8.4, 1.10.8.5,
1.10.8.6, 1.10.8.7, 1.10.8.8, 1.10.8.9, 1.10.8.10, 1.10.9.1, 1.10.9.2, 1.10.9.3, 1.10.9.4, 1.10.9.5,
1.10.9.6, 1.10.9.7, 1.10.9.8, 1.10.9.9, 1.10.9.10, 1.10.10.1, 1.10.10.2, 1.10.10.3, 1.10.10.4, 1.10.10.5, TABLE 2-continued 1.10.10.6, 1.10.10.7, 1.10.10.8, 1.10.10.9, 1.10.10.10, 2.1.1.1, 2.1.1.2, 2.1.1.3, 2.1.1.4, 2.1.1.5, 2.1.1.6, 2.1.1.7, 2.1.1.8, 2.1.1.9, 2.1.1.10, 2.1.2.1, 2.1.2.2, 2.1.2.3, 2.1.2.4, 2.1.2.5, 2.1.2.6, 2.1.2.7, 2.1.2.8, 2.1.2.9, 2.1.2.10, 2.1.3.1, 2.1.3.2, 2.1.3.3, 2.1.3.4, 2.1.3.5, 2.1.3.6, 2.1.3.7, 2.1.3.8, 2.1.3.9, 2.1.3.10, 2.1.4.1, 2.1.4.2, 2.1.4.3, 2.1.4.4, 2.1.4.5, 2.1.4.6, 2.1.4.7, 2.1.4.8, 2.1.4.9, 2.1.4.10, 2.1.5.1, 2.1.5.2, 2.1.5.3, 2.1.5.4, 2.1.5.5, 2.1.5.6, 2.1.5.7, 2.1.5.8, 2.1.5.9, 2.1.5.10, 2.1.6.1, 2.1.6.2, 2.1.6.3, 2.1.6.4, 2.1.6.5, 2.1.6.6, 2.1.6.7, 2.1.6.8, 2.1.6.9, 2.1.6.10, 2.1.7.1, 2.1.7.2, 2.1.7.3, 2.1.7.4, 2.1.7.5, 2.1.7.6, 2.1.7.7, 2.1.7.8, 2.1.7.9, 2.1.7.10, 2.1.8.1, 2.1.8.2, 2.1.8.3, 2.1.8.4, 2.1.8.5, 2.1.8.6, 2.1.8.7, 2.1.8.8, 2.1.8.9, 2.1.8.10, 2.1.9.1, 2.1.9.2, 2.1.9.3, 2.1.9.4, 2.1.9.5, 2.1.9.6, 2.1.9.7, 2.1.9.8, 2.1.9.9, 2.1.9.10, 2.1.10.1, 2.1.10.2, 2.1.10.3, 2.1.10.4, 2.1.10.5, 2.1.10.6, 2.1.10.7, 2.1.10.8, 2.1.10.9, 2.1.10.10, 2.2.1.1, 2.2.1.2, 2.2.1.3, 2.2.1.4, 2.2.1.5, 2.2.1.6, 2.2.1.7, 2.2.1.8, 2.2.1.9, 2.2.1.10, 2.2.2.1, 2.2.2.2, 2.2.2.3, 2.2.2.4, 2.2.2.5, 2.2.2.6, 2.2.2.7, 2.2.2.8, 2.2.2.9, 2.2.2.10, 2.2.3.1, 2.2.3.2, 2.2.3.3, 2.2.3.4, 2.2.3.5, 2.2.3.6, 2.2.3.7, 2.2.3.8, 2.2.3.9, 2.2.3.10, 2.2.4.1, 2.2.4.2, 2.2.4.3, 2.2.4.4, 2.2.4.5, 2.2.4.6, 2.2.4.7, 2.2.4.8, 2.2.4.9, 2.2.4.10, 2.2.5.1, 2.2.5.2, 2.2.5.3, 2.2.5.4, 2.2.5.5, 2.2.5.6, 2.2.5.7, 2.2.5.8, 2.2.5.9, 2.2.5.10, 2.2.6.1, 2.2.6.2, 2.2.6.3, 2.2.6.4, 2.2.6.5, 2.2.6.6, 2.2.6.7, 2.2.6.8, 2.2.6.9, 2.2.6.10, 2.2.7.1, 2.2.7.2, 2.2.7.3, 2.2.7.4, 2.2.7.5, 2.2.7.6, 2.2.7.7, 2.2.7.8, 2.2.7.9, 2.2.7.10, 2.2.8.1, 2.2.8.2, 2.2.8.3, 2.2.8.4, 2.2.8.5, 2.2.8.6, 2.2.8.7, 2.2.8.8, 2.2.8.9, 2.2.8.10, 2.2.9.1, 2.2.9.2, 2.2.9.3, 2.2.9.4, 2.2.9.5, 2.2.9.6, 2.2.9.7, 2.2.9.8, 2.2.9.9, 2.2.9.10, 2.2.10.1, 2.2.10.2, 2.2.10.3, 2.2.10.4, 2.2.10.5, 2.2.10.6, 2.2.10.7, 2.2.10.8, 2.2.10.9, 2.2.10.10, 2.3.1.1, 2.3.1.2, 2.3.1.3, 2.3.1.4, 2.3.1.5, 2.3.1.6, 2.3.1.7, 2.3.1.8, 2.3.1.9, 2.3.1.10, 2.3.2.1, 2.3.2.2, 2.3.2.3, 2.3.2.4, 2.3.2.5, 2.3.2.6, 2.3.2.7, 2.3.2.8, 2.3.2.9, 2.3.2.10, 2.3.3.1, 2.3.3.2, 2.3.3.3, 2.3.3.4, 2.3.3.5, 2.3.3.6, 2.3.3.7, 2.3.3.8, 2.3.3.9, 2.3.3.10, 2.3.4.1, 2.3.4.2, 2.3.4.3, 2.3.4.4, 2.3.4.5, 2.3.4.6, 2.3.4.7, 2.3.4.8, 2.3.4.9, 2.3.4.10, 2.3.5.1, 2.3.5.2, 2.3.5.3, 2.3.5.4, 2.3.5.5, 2.3.5.6, 2.3.5.7, 2.3.5.8, 2.3.5.9, 2.3.5.10, 2.3.6.1, 2.3.6.2, 2.3.6.3, 2.3.6.4, 2.3.6.5, 2.3.6.6, 2.3.6.7, 2.3.6.8, 2.3.6.9, 2.3.6.10, 2.3.7.1, 2.3.7.2, 2.3.7.3, 2.3.7.4, 2.3.7.5, 2.3.7.6, 2.3.7.7, 2.3.7.8, 2.3.7.9, 2.3.7.10, 2.3.8.1, 2.3.8.2, 2.3.8.3, 2.3.8.4, 2.3.8.5, 2.3.8.6, 2.3.8.7, 2.3.8.8, 2.3.8.9, 2.3.8.10, 2.3.9.1, 2.3.9.2, 2.3.9.3, 2.3.9.4, 2.3.9.5, 2.3.9.6, 2.3.9.7, 2.3.9.8, 2.3.9.9, 2.3.9.10, 2.3.10.1, 2.3.10.2, 2.3.10.3, 2.3.10.4, 2.3.10.5, 2.3.10.6, 2.3.10.7, 2.3.10.8, 2.3.10.9, 2.3.10.10, 2.4.1.1, 2.4.1.2, 2.4.1.3, 2.4.1.4, 2.4.1.5, 2.4.1.6, 2.4.1.7, 2.4.1.8, 2.4.1.9, 2.4.1.10, 2.4.2.1, 2.4.2.2, 2.4.2.3, 2.4.2.4, 2.4.2.5, 2.4.2.6, 2.4.2.7, 2.4.2.8, 2.4.2.9, 2.4.2.10, 2.4.3.1, 2.4.3.2, 2.4.3.3, 2.4.3.4, 2.4.3.5, 2.4.3.6, 2.4.3.7, 2.4.3.8, 2.4.3.9, 2.4.3.10, 2.4.4.1, 2.4.4.2, 2.4.4.3, 2.4.4.4, 2.4.4.5, 2.4.4.6, 2.4.4.7, 2.4.4.8, 2.4.4.9, 2.4.4.10, 2.4.5.1, 2.4.5.2, 2.4.5.3, 2.4.5.4, 2.4.5.5, 2.4.5.6, 2.4.5.7, 2.4.5.8, 2.4.5.9, 2.4.5.10, 2.4.6.1, 2.4.6.2, 2.4.6.3, 2.4.6.4, 2.4.6.5, 2.4.6.6, 2.4.6.7, 2.4.6.8, 2.4.6.9, 2.4.6.10, 2.4.7.1, 2.4.7.2, 2.4.7.3, 2.4.7.4, 2.4.7.5, 2.4.7.6, 2.4.7.7, 2.4.7.8, 2.4.7.9, 2.4.7.10, 2.4.8.1, 2.4.8.2, 2.4.8.3, 2.4.8.4, 2.4.8.5, 2.4.8.6, 2.4.8.7, 2.4.8.8, 2.4.8.9, 2.4.8.10, 2.4.9.1, 2.4.9.2, 2.4.9.3, 2.4.9.4, 2.4.9.5, 2.4.9.6, 2.4.9.7, 2.4.9.8, 2.4.9.9, 2.4.9.10, 2.4.10.1, 2.4.10.2, 2.4.10.3, 2.4.10.4, 2.4.10.5, 2.4.10.6, 2.4.10.7, 2.4.10.8, 2.4.10.9, 2.4.10.10, 2.5.1.1, 2.5.1.2, 2.5.1.3, 2.5.1.4, 2.5.1.5, 2.5.1.6, 2.5.1.7, 2.5.1.8, 2.5.1.9, 2.5.1.10, 2.5.2.1, 2.5.2.2, 2.5.2.3, 2.5.2.4, 2.5.2.5, 2.5.2.6, 2.5.2.7, 2.5.2.8, 2.5.2.9, 2.5.2.10, 2.5.3.1, 2.5.3.2, 2.5.3.3, 2.5.3.4, 2.5.3.5, 2.5.3.6, 2.5.3.7, 2.5.3.8, 2.5.3.9, 2.5.3.10, 2.5.4.1, 2.5.4.2, 2.5.4.3, 2.5.4.4, 2.5.4.5, 2.5.4.6, 2.5.4.7, 2.5.4.8, 2.5.4.9, 2.5.4.10, 2.5.5.1, 2.5.5.2, 2.5.5.3, 2.5.5.4, 2.5.5.5, 2.5.5.6, 2.5.5.7, 2.5.5.8, 2.5.5.9, 2.5.5.10, 2.5.6.1, 2.5.6.2, 2.5.6.3, 2.5.6.4, 2.5.6.5, 2.5.6.6, 2.5.6.7, 2.5.6.8, 2.5.6.9, 2.5.6.10, 2.5.7.1, 2.5.7.2, 2.5.7.3, 2.5.7.4, 2.5.7.5, 2.5.7.6, 2.5.7.7, 2.5.7.8, 2.5.7.9, 2.5.7.10, 2.5.8.1, 2.5.8.2, 2.5.8.3, 2.5.8.4, 2.5.8.5, 2.5.8.6, 2.5.8.7, 2.5.8.8, 2.5.8.9, 2.5.8.10, 2.5.9.1, 2.5.9.2, 2.5.9.3, 2.5.9.4, 2.5.9.5, 2.5.9.6, 2.5.9.7, 2.5.9.8, 2.5.9.9, 2.5.9.10, 2.5.10.1, 2.5.10.2, 2.5.10.3, 2.5.10.4, 2.5.10.5, 2.5.10.6, 2.5.10.7, 2.5.10.8, 2.5.10.9, 2.5.10.10, 2.6.1.1, 2.6.1.2, 2.6.1.3, 2.6.1.4, 2.6.1.5, 2.6.1.6, 2.6.1.7, 2.6.1.8, 2.6.1.9, 2.6.1.10, 2.6.2.1, 2.6.2.2, 2.6.2.3, 2.6.2.4, 2.6.2.5, 2.6.2.6, 2.6.2.7, 2.6.2.8, 2.6.2.9, 2.6.2.10, 2.6.3.1, 2.6.3.2, 2.6.3.3, 2.6.3.4, 2.6.3.5, 2.6.3.6, 2.6.3.7, 2.6.3.8, 2.6.3.9, 2.6.3.10, 2.6.4.1, 2.6.4.2, 2.6.4.3, 2.6.4.4, 2.6.4.5, 2.6.4.6, 2.6.4.7, 2.6.4.8, 2.6.4.9, 2.6.4.10, 2.6.5.1, 2.6.5.2, 2.6.5.3, 2.6.5.4, 2.6.5.5, 2.6.5.6, 2.6.5.7, 2.6.5.8, 2.6.5.9, 2.6.5.10, 2.6.6.1, 2.6.6.2, 2.6.6.3, 2.6.6.4, 2.6.6.5, 2.6.6.6, 2.6.6.7, 2.6.6.8, 2.6.6.9, 2.6.6.10, 2.6.7.1, 2.6.7.2, 2.6.7.3, 2.6.7.4, 2.6.7.5, 2.6.7.6, 2.6.7.7, 2.6.7.8, 2.6.7.9, 2.6.7.10, 2.6.8.1, 2.6.8.2, 2.6.8.3, 2.6.8.4, 2.6.8.5, 2.6.8.6, 2.6.8.7, 2.6.8.8, 2.6.8.9, 2.6.8.10, 2.6.9.1, 2.6.9.2, 2.6.9.3, 2.6.9.4, 2.6.9.5, 2.6.9.6, 2.6.9.7, 2.6.9.8, 2.6.9.9, 2.6.9.10, 2.6.10.1, 2.6.10.2, 2.6.10.3, 2.6.10.4, 2.6.10.5, 2.6.10.6, 2.6.10.7, 2.6.10.8, 2.6.10.9, 2.6.10.10, 2.7.1.1, 2.7.1.2, 2.7.1.3, 2.7.1.4, 2.7.1.5, 2.7.1.6, 2.7.1.7, 2.7.1.8, 2.7.1.9, 2.7.1.10, 2.7.2.1, 2.7.2.2, 2.7.2.3, 2.7.2.4, 2.7.2.5, 2.7.2.6, 2.7.2.7, 2.7.2.8, 2.7.2.9, 2.7.2.10, 2.7.3.1, 2.7.3.2, 2.7.3.3, 2.7.3.4, 2.7.3.5, 2.7.3.6, 2.7.3.7, 2.7.3.8, 2.7.3.9, 2.7.3.10, 2.7.4.1, 2.7.4.2, 2.7.4.3, 2.7.4.4, 2.7.4.5, 2.7.4.6, 2.7.4.7, 2.7.4.8, 2.7.4.9, 2.7.4.10, 2.7.5.1, 2.7.5.2, 2.7.5.3, 2.7.5.4, 2.7.5.5, 2.7.5.6, 2.7.5.7, 2.7.5.8, 2.7.5.9, 2.7.5.10, 2.7.6.1, 2.7.6.2, 2.7.6.3, 2.7.6.4, 2.7.6.5, 2.7.6.6, 2.7.6.7, 2.7.6.8, 2.7.6.9, 2.7.6.10, 2.7.7.1, 2.7.7.2, 2.7.7.3, 2.7.7.4, 2.7.7.5, 2.7.7.6, 2.7.7.7, 2.7.7.8, 2.7.7.9, 2.7.7.10, 2.7.8.1, 2.7.8.2, 2.7.8.3, 2.7.8.4, 2.7.8.5, 2.7.8.6, 2.7.8.7, 2.7.8.8, 2.7.8.9, 2.7.8.10, 2.7.9.1, 2.7.9.2, 2.7.9.3, 2.7.9.4, 2.7.9.5, 2.7.9.6, 2.7.9.7, 2.7.9.8, 2.7.9.9, 2.7.9.10, 2.7.10.1, 2.7.10.2, 2.7.10.3, 2.7.10.4, 2.7.10.5, 2.7.10.6, 2.7.10.7, 2.7.10.8, 2.7.10.9, 2.7.10.10, 2.8.1.1, 2.8.1.2, 2.8.1.3, 2.8.1.4, 2.8.1.5, 2.8.1.6, 2.8.1.7, 2.8.1.8, 2.8.1.9, 2.8.1.10, 2.8.2.1, 2.8.2.2, 2.8.2.3, 2.8.2.4, 2.8.2.5, 2.8.2.6, 2.8.2.7, 2.8.2.8, 2.8.2.9, 2.8.2.10, 2.8.3.1, 2.8.3.2, 2.8.3.3, 2.8.3.4, 2.8.3.5, 2.8.3.6, 2.8.3.7, 2.8.3.8, 2.8.3.9, 2.8.3.10, 2.8.4.1, 2.8.4.2, 2.8.4.3, 2.8.4.4, 2.8.4.5, 2.8.4.6, 2.8.4.7, 2.8.4.8, 2.8.4.9, 2.8.4.10, 2.8.5.1, 2.8.5.2, 2.8.5.3, 2.8.5.4, 2.8.5.5, 2.8.5.6, 2.8.5.7, 2.8.5.8, 2.8.5.9, 2.8.5.10, 2.8.6.1, 2.8.6.2, 2.8.6.3, 2.8.6.4, 2.8.6.5, 2.8.6.6, 2.8.6.7, 2.8.6.8, 2.8.6.9, 2.8.6.10, 2.8.7.1, 2.8.7.2, 2.8.7.3, 2.8.7.4, 2.8.7.5, 2.8.7.6, 2.8.7.7, 2.8.7.8, 2.8.7.9, 2.8.7.10, 2.8.8.1, 2.8.8.2, 2.8.8.3, 2.8.8.4, 2.8.8.5, 2.8.8.6, 2.8.8.7, 2.8.8.8, 2.8.8.9, 2.8.8.10, 2.8.9.1, 2.8.9.2, 2.8.9.3, 2.8.9.4, 2.8.9.5, 2.8.9.6, 2.8.9.7, 2.8.9.8, 2.8.9.9, 2.8.9.10, 2.8.10.1, 2.8.10.2, 2.8.10.3, 2.8.10.4, 2.8.10.5, 2.8.10.6, 2.8.10.7, 2.8.10.8, 2.8.10.9, 2.8.10.10, 2.9.1.1, 2.9.1.2, 2.9.1.3, 2.9.1.4, 2.9.1.5, 2.9.1.6, 2.9.1.7, 2.9.1.8, 2.9.1.9, 2.9.1.10, 2.9.2.1, 2.9.2.2, 2.9.2.3, 2.9.2.4, 2.9.2.5, 2.9.2.6, 2.9.2.7, 2.9.2.8, 2.9.2.9, 2.9.2.10, 2.9.3.1, 2.9.3.2, 2.9.3.3, 2.9.3.4, 2.9.3.5, 2.9.3.6, 2.9.3.7, 2.9.3.8, 2.9.3.9, 2.9.3.10, 2.9.4.1, 2.9.4.2, 2.9.4.3, 2.9.4.4, 2.9.4.5, 2.9.4.6, 2.9.4.7, 2.9.4.8, 2.9.4.9, 2.9.4.10, 2.9.5.1, 2.9.5.2, 2.9.5.3, 2.9.5.4, 2.9.5.5, 2.9.5.6, 2.9.5.7, 2.9.5.8, 2.9.5.9, 2.9.5.10, 2.9.6.1, 2.9.6.2, 2.9.6.3, 2.9.6.4, 2.9.6.5, 2.9.6.6, 2.9.6.7, 2.9.6.8, 2.9.6.9, 2.9.6.10, 2.9.7.1, 2.9.7.2, 2.9.7.3, 2.9.7.4, 2.9.7.5, 2.9.7.6, 2.9.7.7, 2.9.7.8, 2.9.7.9, 2.9.7.10, 2.9.8.1, 2.9.8.2, 2.9.8.3, 2.9.8.4, 2.9.8.5, 2.9.8.6, 2.9.8.7, 2.9.8.8, 2.9.8.9, 2.9.8.10, 2.9.9.1, 2.9.9.2, 2.9.9.3, 2.9.9.4, 2.9.9.5, 2.9.9.6, 2.9.9.7, 2.9.9.8, 2.9.9.9, 2.9.9.10, 2.9.10.1, 2.9.10.2, 2.9.10.3, 2.9.10.4, 2.9.10.5, 2.9.10.6, 2.9.10.7, 2.9.10.8, 2.9.10.9, 2.9.10.10, 2.10.1.1, 2.10.1.2, 2.10.1.3, 2.10.1.4, 2.10.1.5, 2.10.1.6, 2.10.1.7, 2.10.1.8, 2.10.1.9, 2.10.1.10, 2.10.2.1, 2.10.2.2, 2.10.2.3, 2.10.2.4, 2.10.2.5, 2.10.2.6, 2.10.2.7, 2.10.2.8, 2.10.2.9, 2.10.2.10, 2.10.3.1, 2.10.3.2, 2.10.3.3, 2.10.3.4, 2.10.3.5, 2.10.3.6, 2.10.3.7, 2.10.3.8, 2.10.3.9, TABLE 2-continued 2.10.3.10, 2.10.4.1, 2.10.4.2, 2.10.4.3, 2.10.4.4, 2.10.4.5, 2.10.4.6, 2.10.4.7, 2.10.4.8, 2.10.4.9,
2.10.4.10, 2.10.5.1, 2.10.5.2, 2.10.5.3, 2.10.5.4, 2.10.5.5, 2.10.5.6, 2.10.5.7, 2.10.5.8, 2.10.5.9,
2.10.5.10, 2.10.6.1, 2.10.6.2, 2.10.6.3, 2.10.6.4, 2.10.6.5, 2.10.6.6, 2.10.6.7, 2.10.6.8, 2.10.6.9,
2.10.6.10, 2.10.7.1, 2.10.7.2, 2.10.7.3, 2.10.7.4, 2.10.7.5, 2.10.7.6, 2.10.7.7, 2.10.7.8, 2.10.7.9,
2.10.7.10, 2.10.8.1, 2.10.8.2, 2.10.8.3, 2.10.8.4, 2.10.8.5, 2.10.8.6, 2.10.8.7, 2.10.8.8, 2.10.8.9,
2.10.8.10, 2.10.9.1, 2.10.9.2, 2.10.9.3, 2.10.9.4, 2.10.9.5, 2.10.9.6, 2.10.9.7, 2.10.9.8, 2.10.9.9,
2.10.9.10, 2.10.10.1, 2.10.10.2, 2.10.10.3, 2.10.10.4, 2.10.10.5, 2.10.10.6, 2.10.10.7, 2.10.10.8,
2.10.10.9, 2.10.10.10, 3.1.1.1, 3.1.1.2, 3.1.1.3, 3.1.1.4, 3.1.1.5, 3.1.1.6, 3.1.1.7, 3.1.1.8, 3.1.1.9,
3.1.1.10, 3.1.2.1, 3.1.2.2, 3.1.2.3, 3.1.2.4, 3.1.2.5, 3.1.2.6, 3.1.2.7, 3.1.2.8, 3.1.2.9, 3.1.2.10, 3.1.3.1,
3.1.3.2, 3.1.3.3, 3.1.3.4, 3.1.3.5, 3.1.3.6, 3.1.3.7, 3.1.3.8, 3.1.3.9, 3.1.3.10, 3.1.4.1, 3.1.4.2, 3.1.4.3,
3.1.4.4, 3.1.4.5, 3.1.4.6, 3.1.4.7, 3.1.4.8, 3.1.4.9, 3.1.4.10, 3.1.5.1, 3.1.5.2, 3.1.5.3, 3.1.5.4, 3.1.5.5,
3.1.5.6, 3.1.5.7, 3.1.5.8, 3.1.5.9, 3.1.5.10, 3.1.6.1, 3.1.6.2, 3.1.6.3, 3.1.6.4, 3.1.6.5, 3.1.6.6, 3.1.6.7,
3.1.6.8, 3.1.6.9, 3.1.6.10, 3.1.7.1, 3.1.7.2, 3.1.7.3, 3.1.7.4, 3.1.7.5, 3.1.7.6, 3.1.7.7, 3.1.7.8, 3.1.7.9,
3.1.7.10, 3.1.8.1, 3.1.8.2, 3.1.8.3, 3.1.8.4, 3.1.8.5, 3.1.8.6, 3.1.8.7, 3.1.8.8, 3.1.8.9, 3.1.8.10, 3.1.9.1,
3.1.9.2, 3.1.9.3, 3.1.9.4, 3.1.9.5, 3.1.9.6, 3.1.9.7, 3.1.9.8, 3.1.9.9, 3.1.9.10, 3.1.10.1, 3.1.10.2,
3.1.10.3, 3.1.10.4, 3.1.10.5, 3.1.10.6, 3.1.10.7, 3.1.10.8, 3.1.10.9, 3.1.10.10, 3.2.1.1, 3.2.1.2, 3.2.1.3,
3.2.1.4, 3.2.1.5, 3.2.1.6, 3.2.1.7, 3.2.1.8, 3.2.1.9, 3.2.1.10, 3.2.2.1, 3.2.2.2, 3.2.2.3, 3.2.2.4, 3.2.2.5,
3.2.2.6, 3.2.2.7, 3.2.2.8, 3.2.2.9, 3.2.2.10, 3.2.3.1, 3.2.3.2, 3.2.3.3, 3.2.3.4, 3.2.3.5, 3.2.3.6, 3.2.3.7,
3.2.3.8, 3.2.3.9, 3.2.3.10, 3.2.4.1, 3.2.4.2, 3.2.4.3, 3.2.4.4, 3.2.4.5, 3.2.4.6, 3.2.4.7, 3.2.4.8, 3.2.4.9,
3.2.4.10, 3.2.5.1, 3.2.5.2, 3.2.5.3, 3.2.5.4, 3.2.5.5, 3.2.5.6, 3.2.5.7, 3.2.5.8, 3.2.5.9, 3.2.5.10, 3.2.6.1,
3.2.6.2, 3.2.6.3, 3.2.6.4, 3.2.6.5, 3.2.6.6, 3.2.6.7, 3.2.6.8, 3.2.6.9, 3.2.6.10, 3.2.7.1, 3.2.7.2, 3.2.7.3,
3.2.7.4, 3.2.7.5, 3.2.7.6, 3.2.7.7, 3.2.7.8, 3.2.7.9, 3.2.7.10, 3.2.8.1, 3.2.8.2, 3.2.8.3, 3.2.8.4, 3.2.8.5,
3.2.8.6, 3.2.8.7, 3.2.8.8, 3.2.8.9, 3.2.8.10, 3.2.9.1, 3.2.9.2, 3.2.9.3, 3.2.9.4, 3.2.9.5, 3.2.9.6, 3.2.9.7,
3.2.9.8, 3.2.9.9, 3.2.9.10, 3.2.10.1, 3.2.10.2, 3.2.10.3, 3.2.10.4, 3.2.10.5, 3.2.10.6, 3.2.10.7, 3.2.10.8,
3.2.10.9, 3.2.10.10, 3.3.1.1, 3.3.1.2, 3.3.1.3, 3.3.1.4, 3.3.1.5, 3.3.1.6, 3.3.1.7, 3.3.1.8, 3.3.1.9,
3.3.1.10, 3.3.2.1, 3.3.2.2, 3.3.2.3, 3.3.2.4, 3.3.2.5, 3.3.2.6, 3.3.2.7, 3.3.2.8, 3.3.2.9, 3.3.2.10, 3.3.3.1,
3.3.3.2, 3.3.3.3, 3.3.3.4, 3.3.3.5, 3.3.3.6, 3.3.3.7, 3.3.3.8, 3.3.3.9, 3.3.3.10, 3.3.4.1, 3.3.4.2, 3.3.4.3,
3.3.4.4, 3.3.4.5, 3.3.4.6, 3.3.4.7, 3.3.4.8, 3.3.4.9, 3.3.4.10, 3.3.5.1, 3.3.5.2, 3.3.5.3, 3.3.5.4, 3.3.5.5,
3.3.5.6, 3.3.5.7, 3.3.5.8, 3.3.5.9, 3.3.5.10, 3.3.6.1, 3.3.6.2, 3.3.6.3, 3.3.6.4, 3.3.6.5, 3.3.6.6, 3.3.6.7,
3.3.6.8, 3.3.6.9, 3.3.6.10, 3.3.7.1, 3.3.7.2, 3.3.7.3, 3.3.7.4, 3.3.7.5, 3.3.7.6, 3.3.7.7, 3.3.7.8, 3.3.7.9,
3.3.7.10, 3.3.8.1, 3.3.8.2, 3.3.8.3, 3.3.8.4, 3.3.8.5, 3.3.8.6, 3.3.8.7, 3.3.8.8, 3.3.8.9, 3.3.8.10, 3.3.9.1,
3.3.9.2, 3.3.9.3, 3.3.9.4, 3.3.9.5, 3.3.9.6, 3.3.9.7, 3.3.9.8, 3.3.9.9, 3.3.9.10, 3.3.10.1, 3.3.10.2,
3.3.10.3, 3.3.10.4, 3.3.10.5, 3.3.10.6, 3.3.10.7, 3.3.10.8, 3.3.10.9, 3.3.10.10, 3.4.1.1, 3.4.1.2, 3.4.1.3,
3.4.1.4, 3.4.1.5, 3.4.1.6, 3.4.1.7, 3.4.1.8, 3.4.1.9, 3.4.1.10, 3.4.2.1, 3.4.2.2, 3.4.2.3, 3.4.2.4, 3.4.2.5,
3.4.2.6, 3.4.2.7, 3.4.2.8, 3.4.2.9, 3.4.2.10, 3.4.3.1, 3.4.3.2, 3.4.3.3, 3.4.3.4, 3.4.3.5, 3.4.3.6, 3.4.3.7,
3.4.3.8, 3.4.3.9, 3.4.3.10, 3.4.4.1, 3.4.4.2, 3.4.4.3, 3.4.4.4, 3.4.4.5, 3.4.4.6, 3.4.4.7, 3.4.4.8, 3.4.4.9,
3.4.4.10, 3.4.5.1, 3.4.5.2, 3.4.5.3, 3.4.5.4, 3.4.5.5, 3.4.5.6, 3.4.5.7, 3.4.5.8, 3.4.5.9, 3.4.5.10, 3.4.6.1,
3.4.6.2, 3.4.6.3, 3.4.6.4, 3.4.6.5, 3.4.6.6, 3.4.6.7, 3.4.6.8, 3.4.6.9, 3.4.6.10, 3.4.7.1, 3.4.7.2, 3.4.7.3,
3.4.7.4, 3.4.7.5, 3.4.7.6, 3.4.7.7, 3.4.7.8, 3.4.7.9, 3.4.7.10, 3.4.8.1, 3.4.8.2, 3.4.8.3, 3.4.8.4, 3.4.8.5,
3.4.8.6, 3.4.8.7, 3.4.8.8, 3.4.8.9, 3.4.8.10, 3.4.9.1, 3.4.9.2, 3.4.9.3, 3.4.9.4, 3.4.9.5, 3.4.9.6, 3.4.9.7,
3.4.9.8, 3.4.9.9, 3.4.9.10, 3.4.10.1, 3.4.10.2, 3.4.10.3, 3.4.10.4, 3.4.10.5, 3.4.10.6, 3.4.10.7, 3.4.10.8,
3.4.10.9, 3.4.10.10, 3.5.1.1, 3.5.1.2, 3.5.1.3, 3.5.1.4, 3.5.1.5, 3.5.1.6, 3.5.1.7, 3.5.1.8, 3.5.1.9,
3.5.1.10, 3.5.2.1, 3.5.2.2, 3.5.2.3, 3.5.2.4, 3.5.2.5, 3.5.2.6, 3.5.2.7, 3.5.2.8, 3.5.2.9, 3.5.2.10, 3.5.3.1,
3.5.3.2, 3.5.3.3, 3.5.3.4, 3.5.3.5, 3.5.3.6, 3.5.3.7, 3.5.3.8, 3.5.3.9, 3.5.3.10, 3.5.4.1, 3.5.4.2, 3.5.4.3,
3.5.4.4, 3.5.4.5, 3.5.4.6, 3.5.4.7, 3.5.4.8, 3.5.4.9, 3.5.4.10, 3.5.5.1, 3.5.5.2, 3.5.5.3, 3.5.5.4, 3.5.5.5,
3.5.5.6, 3.5.5.7, 3.5.5.8, 3.5.5.9, 3.5.5.10, 3.5.6.1, 3.5.6.2, 3.5.6.3, 3.5.6.4, 3.5.6.5, 3.5.6.6, 3.5.6.7,
3.5.6.8, 3.5.6.9, 3.5.6.10, 3.5.7.1, 3.5.7.2, 3.5.7.3, 3.5.7.4, 3.5.7.5, 3.5.7.6, 3.5.7.7, 3.5.7.8, 3.5.7.9,
3.5.7.10, 3.5.8.1, 3.5.8.2, 3.5.8.3, 3.5.8.4, 3.5.8.5, 3.5.8.6, 3.5.8.7, 3.5.8.8, 3.5.8.9, 3.5.8.10, 3.5.9.1,
3.5.9.2, 3.5.9.3, 3.5.9.4, 3.5.9.5, 3.5.9.6, 3.5.9.7, 3.5.9.8, 3.5.9.9, 3.5.9.10, 3.5.10.1, 3.5.10.2,
3.5.10.3, 3.5.10.4, 3.5.10.5, 3.5.10.6, 3.5.10.7, 3.5.10.8, 3.5.10.9, 3.5.10.10, 3.6.1.1, 3.6.1.2, 3.6.1.3,
3.6.1.4, 3.6.1.5, 3.6.1.6, 3.6.1.7, 3.6.1.8, 3.6.1.9, 3.6.1.10, 3.6.2.1, 3.6.2.2, 3.6.2.3, 3.6.2.4, 3.6.2.5,
3.6.2.6, 3.6.2.7, 3.6.2.8, 3.6.2.9, 3.6.2.10, 3.6.3.1, 3.6.3.2, 3.6.3.3, 3.6.3.4, 3.6.3.5, 3.6.3.6, 3.6.3.7,
3.6.3.8, 3.6.3.9, 3.6.3.10, 3.6.4.1, 3.6.4.2, 3.6.4.3, 3.6.4.4, 3.6.4.5, 3.6.4.6, 3.6.4.7, 3.6.4.8, 3.6.4.9,
3.6.4.10, 3.6.5.1, 3.6.5.2, 3.6.5.3, 3.6.5.4, 3.6.5.5, 3.6.5.6, 3.6.5.7, 3.6.5.8, 3.6.5.9, 3.6.5.10, 3.6.6.1,
3.6.6.2, 3.6.6.3, 3.6.6.4, 3.6.6.5, 3.6.6.6, 3.6.6.7, 3.6.6.8, 3.6.6.9, 3.6.6.10, 3.6.7.1, 3.6.7.2, 3.6.7.3,
3.6.7.4, 3.6.7.5, 3.6.7.6, 3.6.7.7, 3.6.7.8, 3.6.7.9, 3.6.7.10, 3.6.8.1, 3.6.8.2, 3.6.8.3, 3.6.8.4, 3.6.8.5,
3.6.8.6, 3.6.8.7, 3.6.8.8, 3.6.8.9, 3.6.8.10, 3.6.9.1, 3.6.9.2, 3.6.9.3, 3.6.9.4, 3.6.9.5, 3.6.9.6, 3.6.9.7,
3.6.9.8, 3.6.9.9, 3.6.9.10, 3.6.10.1, 3.6.10.2, 3.6.10.3, 3.6.10.4, 3.6.10.5, 3.6.10.6, 3.6.10.7, 3.6.10.8,
3.6.10.9, 3.6.10.10, 3.7.1.1, 3.7.1.2, 3.7.1.3, 3.7.1.4, 3.7.1.5, 3.7.1.6, 3.7.1.7, 3.7.1.8, 3.7.1.9,
3.7.1.10, 3.7.2.1, 3.7.2.2, 3.7.2.3, 3.7.2.4, 3.7.2.5, 3.7.2.6, 3.7.2.7, 3.7.2.8, 3.7.2.9, 3.7.2.10, 3.7.3.1,
3.7.3.2, 3.7.3.3, 3.7.3.4, 3.7.3.5, 3.7.3.6, 3.7.3.7, 3.7.3.8, 3.7.3.9, 3.7.3.10, 3.7.4.1, 3.7.4.2, 3.7.4.3,
3.7.4.4, 3.7.4.5, 3.7.4.6, 3.7.4.7, 3.7.4.8, 3.7.4.9, 3.7.4.10, 3.7.5.1, 3.7.5.2, 3.7.5.3, 3.7.5.4, 3.7.5.5,
3.7.5.6, 3.7.5.7, 3.7.5.8, 3.7.5.9, 3.7.5.10, 3.7.6.1, 3.7.6.2, 3.7.6.3, 3.7.6.4, 3.7.6.5, 3.7.6.6, 3.7.6.7,
3.7.6.8, 3.7.6.9, 3.7.6.10, 3.7.7.1, 3.7.7.2, 3.7.7.3, 3.7.7.4, 3.7.7.5, 3.7.7.6, 3.7.7.7, 3.7.7.8, 3.7.7.9,
3.7.7.10, 3.7.8.1, 3.7.8.2, 3.7.8.3, 3.7.8.4, 3.7.8.5, 3.7.8.6, 3.7.8.7, 3.7.8.8, 3.7.8.9, 3.7.8.10, 3.7.9.1,
3.7.9.2, 3.7.9.3, 3.7.9.4, 3.7.9.5, 3.7.9.6, 3.7.9.7, 3.7.9.8, 3.7.9.9, 3.7.9.10, 3.7.10.1, 3.7.10.2,
3.7.10.3, 3.7.10.4, 3.7.10.5, 3.7.10.6, 3.7.10.7, 3.7.10.8, 3.7.10.9, 3.7.10.10, 3.8.1.1, 3.8.1.2, 3.8.1.3,
3.8.1.4, 3.8.1.5, 3.8.1.6, 3.8.1.7, 3.8.1.8, 3.8.1.9, 3.8.1.10, 3.8.2.1, 3.8.2.2, 3.8.2.3, 3.8.2.4, 3.8.2.5,
3.8.2.6, 3.8.2.7, 3.8.2.8, 3.8.2.9, 3.8.2.10, 3.8.3.1, 3.8.3.2, 3.8.3.3, 3.8.3.4, 3.8.3.5, 3.8.3.6, 3.8.3.7,
3.8.3.8, 3.8.3.9, 3.8.3.10, 3.8.4.1, 3.8.4.2, 3.8.4.3, 3.8.4.4, 3.8.4.5, 3.8.4.6, 3.8.4.7, 3.8.4.8, 3.8.4.9,
3.8.4.10, 3.8.5.1, 3.8.5.2, 3.8.5.3, 3.8.5.4, 3.8.5.5, 3.8.5.6, 3.8.5.7, 3.8.5.8, 3.8.5.9, 3.8.5.10, 3.8.6.1,
3.8.6.2, 3.8.6.3, 3.8.6.4, 3.8.6.5, 3.8.6.6, 3.8.6.7, 3.8.6.8, 3.8.6.9, 3.8.6.10, 3.8.7.1, 3.8.7.2, 3.8.7.3,
3.8.7.4, 3.8.7.5, 3.8.7.6, 3.8.7.7, 3.8.7.8, 3.8.7.9, 3.8.7.10, 3.8.8.1, 3.8.8.2, 3.8.8.3, 3.8.8.4, 3.8.8.5,
3.8.8.6, 3.8.8.7, 3.8.8.8, 3.8.8.9, 3.8.8.10, 3.8.9.1, 3.8.9.2, 3.8.9.3, 3.8.9.4, 3.8.9.5, 3.8.9.6, 3.8.9.7,
3.8.9.8, 3.8.9.9, 3.8.9.10, 3.8.10.1, 3.8.10.2, 3.8.10.3, 3.8.10.4, 3.8.10.5, 3.8.10.6, 3.8.10.7, 3.8.10.8,
3.8.10.9, 3.8.10.10, 3.9.1.1, 3.9.1.2, 3.9.1.3, 3.9.1.4, 3.9.1.5, 3.9.1.6, 3.9.1.7, 3.9.1.8, 3.9.1.9,
3.9.1.10, 3.9.2.1, 3.9.2.2, 3.9.2.3, 3.9.2.4, 3.9.2.5, 3.9.2.6, 3.9.2.7, 3.9.2.8, 3.9.2.9, 3.9.2.10, 3.9.3.1,
3.9.3.2, 3.9.3.3, 3.9.3.4, 3.9.3.5, 3.9.3.6, 3.9.3.7, 3.9.3.8, 3.9.3.9, 3.9.3.10, 3.9.4.1, 3.9.4.2, 3.9.4.3,
3.9.4.4, 3.9.4.5, 3.9.4.6, 3.9.4.7, 3.9.4.8, 3.9.4.9, 3.9.4.10, 3.9.5.1, 3.9.5.2, 3.9.5.3, 3.9.5.4, 3.9.5.5,
3.9.5.6, 3.9.5.7, 3.9.5.8, 3.9.5.9, 3.9.5.10, 3.9.6.1, 3.9.6.2, 3.9.6.3, 3.9.6.4, 3.9.6.5, 3.9.6.6, 3.9.6.7, TABLE 2-continued 3.9.6.8, 3.9.6.9, 3.9.6.10, 3.9.7.1, 3.9.7.2, 3.9.7.3, 3.9.7.4, 3.9.7.5, 3.9.7.6, 3.9.7.7, 3.9.7.8, 3.9.7.9, 3.9.7.10, 3.9.8.1, 3.9.8.2, 3.9.8.3, 3.9.8.4, 3.9.8.5, 3.9.8.6, 3.9.8.7, 3.9.8.8, 3.9.8.9, 3.9.8.10, 3.9.9.1, 3.9.9.2, 3.9.9.3, 3.9.9.4, 3.9.9.5, 3.9.9.6, 3.9.9.7, 3.9.9.8, 3.9.9.9, 3.9.9.10, 3.9.10.1, 3.9.10.2, 3.9.10.3, 3.9.10.4, 3.9.10.5, 3.9.10.6, 3.9.10.7, 3.9.10.8, 3.9.10.9, 3.9.10.10, 3.10.1.1, 3.10.1.2, 3.10.1.3, 3.10.1.4, 3.10.1.5, 3.10.1.6, 3.10.1.7, 3.10.1.8, 3.10.1.9, 3.10.1.10, 3.10.2.1, 3.10.2.2, 3.10.2.3, 3.10.2.4, 3.10.2.5, 3.10.2.6, 3.10.2.7, 3.10.2.8, 3.10.2.9, 3.10.2.10, 3.10.3.1, 3.10.3.2, 3.10.3.3, 3.10.3.4, 3.10.3.5, 3.10.3.6, 3.10.3.7, 3.10.3.8, 3.10.3.9, 3.10.3.10, 3.10.4.1, 3.10.4.2, 3.10.4.3, 3.10.4.4, 3.10.4.5, 3.10.4.6, 3.10.4.7, 3.10.4.8, 3.10.4.9, 3.10.4.10, 3.10.5.1, 3.10.5.2, 3.10.5.3, 3.10.5.4, 3.10.5.5, 3.10.5.6, 3.10.5.7, 3.10.5.8, 3.10.5.9, 3.10.5.10, 3.10.6.1, 3.10.6.2, 3.10.6.3, 3.10.6.4, 3.10.6.5, 3.10.6.6, 3.10.6.7, 3.10.6.8, 3.10.6.9, 3.10.6.10, 3.10.7.1, 3.10.7.2, 3.10.7.3, 3.10.7.4, 3.10.7.5, 3.10.7.6, 3.10.7.7, 3.10.7.8, 3.10.7.9, 3.10.7.10, 3.10.8.1, 3.10.8.2, 3.10.8.3, 3.10.8.4, 3.10.8.5, 3.10.8.6, 3.10.8.7, 3.10.8.8, 3.10.8.9, 3.10.8.10, 3.10.9.1, 3.10.9.2, 3.10.9.3, 3.10.9.4, 3.10.9.5, 3.10.9.6, 3.10.9.7, 3.10.9.8, 3.10.9.9, 3.10.9.10, 3.10.10.1, 3.10.10.2, 3.10.10.3, 3.10.10.4, 3.10.10.5, 3.10.10.6, 3.10.10.7, 3.10.10.8, 3.10.10.9, 3.10.10.10, 4.1.1.1, 4.1.1.2, 4.1.1.3, 4.1.1.4, 4.1.1.5, 4.1.1.6, 4.1.1.7, 4.1.1.8, 4.1.1.9, 4.1.1.10, 4.1.2.1, 4.1.2.2, 4.1.2.3, 4.1.2.4, 4.1.2.5, 4.1.2.6, 4.1.2.7, 4.1.2.8, 4.1.2.9, 4.1.2.10, 4.1.3.1, 4.1.3.2, 4.1.3.3, 4.1.3.4, 4.1.3.5, 4.1.3.6, 4.1.3.7, 4.1.3.8, 4.1.3.9, 4.1.3.10, 4.1.4.1, 4.1.4.2, 4.1.4.3, 4.1.4.4, 4.1.4.5, 4.1.4.6, 4.1.4.7, 4.1.4.8, 4.1.4.9, 4.1.4.10, 4.1.5.1, 4.1.5.2, 4.1.5.3, 4.1.5.4, 4.1.5.5, 4.1.5.6, 4.1.5.7, 4.1.5.8, 4.1.5.9, 4.1.5.10, 4.1.6.1, 4.1.6.2, 4.1.6.3, 4.1.6.4, 4.1.6.5, 4.1.6.6, 4.1.6.7, 4.1.6.8, 4.1.6.9, 4.1.6.10, 4.1.7.1, 4.1.7.2, 4.1.7.3, 4.1.7.4, 4.1.7.5, 4.1.7.6, 4.1.7.7, 4.1.7.8, 4.1.7.9, 4.1.7.10, 4.1.8.1, 4.1.8.2, 4.1.8.3, 4.1.8.4, 4.1.8.5, 4.1.8.6, 4.1.8.7, 4.1.8.8, 4.1.8.9, 4.1.8.10, 4.1.9.1, 4.1.9.2, 4.1.9.3, 4.1.9.4, 4.1.9.5, 4.1.9.6, 4.1.9.7, 4.1.9.8, 4.1.9.9, 4.1.9.10, 4.1.10.1, 4.1.10.2, 4.1.10.3, 4.1.10.4, 4.1.10.5, 4.1.10.6, 4.1.10.7, 4.1.10.8, 4.1.10.9, 4.1.10.10, 4.2.1.1, 4.2.1.2, 4.2.1.3, 4.2.1.4, 4.2.1.5, 4.2.1.6, 4.2.1.7, 4.2.1.8, 4.2.1.9, 4.2.1.10, 4.2.2.1, 4.2.2.2, 4.2.2.3, 4.2.2.4, 4.2.2.5, 4.2.2.6, 4.2.2.7, 4.2.2.8, 4.2.2.9, 4.2.2.10, 4.2.3.1, 4.2.3.2, 4.2.3.3, 4.2.3.4, 4.2.3.5, 4.2.3.6, 4.2.3.7, 4.2.3.8, 4.2.3.9, 4.2.3.10, 4.2.4.1, 4.2.4.2, 4.2.4.3, 4.2.4.4, 4.2.4.5, 4.2.4.6, 4.2.4.7, 4.2.4.8, 4.2.4.9, 4.2.4.10, 4.2.5.1, 4.2.5.2, 4.2.5.3, 4.2.5.4, 4.2.5.5, 4.2.5.6, 4.2.5.7, 4.2.5.8, 4.2.5.9, 4.2.5.10, 4.2.6.1, 4.2.6.2, 4.2.6.3, 4.2.6.4, 4.2.6.5, 4.2.6.6, 4.2.6.7, 4.2.6.8, 4.2.6.9, 4.2.6.10, 4.2.7.1, 4.2.7.2, 4.2.7.3, 4.2.7.4, 4.2.7.5, 4.2.7.6, 4.2.7.7, 4.2.7.8, 4.2.7.9, 4.2.7.10, 4.2.8.1, 4.2.8.2, 4.2.8.3, 4.2.8.4, 4.2.8.5, 4.2.8.6, 4.2.8.7, 4.2.8.8, 4.2.8.9, 4.2.8.10, 4.2.9.1, 4.2.9.2, 4.2.9.3, 4.2.9.4, 4.2.9.5, 4.2.9.6, 4.2.9.7, 4.2.9.8, 4.2.9.9, 4.2.9.10, 4.2.10.1, 4.2.10.2, 4.2.10.3, 4.2.10.4, 4.2.10.5, 4.2.10.6, 4.2.10.7, 4.2.10.8, 4.2.10.9, 4.2.10.10, 4.3.1.1, 4.3.1.2, 4.3.1.3, 4.3.1.4, 4.3.1.5, 4.3.1.6, 4.3.1.7, 4.3.1.8, 4.3.1.9, 4.3.1.10, 4.3.2.1, 4.3.2.2, 4.3.2.3, 4.3.2.4, 4.3.2.5, 4.3.2.6, 4.3.2.7, 4.3.2.8, 4.3.2.9, 4.3.2.10, 4.3.3.1, 4.3.3.2, 4.3.3.3, 4.3.3.4, 4.3.3.5, 4.3.3.6, 4.3.3.7, 4.3.3.8, 4.3.3.9, 4.3.3.10, 4.3.4.1, 4.3.4.2, 4.3.4.3, 4.3.4.4, 4.3.4.5, 4.3.4.6, 4.3.4.7, 4.3.4.8, 4.3.4.9, 4.3.4.10, 4.3.5.1, 4.3.5.2, 4.3.5.3, 4.3.5.4, 4.3.5.5, 4.3.5.6, 4.3.5.7, 4.3.5.8, 4.3.5.9, 4.3.5.10, 4.3.6.1, 4.3.6.2, 4.3.6.3, 4.3.6.4, 4.3.6.5, 4.3.6.6, 4.3.6.7, 4.3.6.8, 4.3.6.9, 4.3.6.10, 4.3.7.1, 4.3.7.2, 4.3.7.3, 4.3.7.4, 4.3.7.5, 4.3.7.6, 4.3.7.7, 4.3.7.8, 4.3.7.9, 4.3.7.10, 4.3.8.1, 4.3.8.2, 4.3.8.3, 4.3.8.4, 4.3.8.5, 4.3.8.6, 4.3.8.7, 4.3.8.8, 4.3.8.9, 4.3.8.10, 4.3.9.1, 4.3.9.2, 4.3.9.3, 4.3.9.4, 4.3.9.5, 4.3.9.6, 4.3.9.7, 4.3.9.8, 4.3.9.9, 4.3.9.10, 4.3.10.1, 4.3.10.2, 4.3.10.3, 4.3.10.4, 4.3.10.5, 4.3.10.6, 4.3.10.7, 4.3.10.8, 4.3.10.9, 4.3.10.10, 4.4.1.1, 4.4.1.2, 4.4.1.3, 4.4.1.4, 4.4.1.5, 4.4.1.6, 4.4.1.7, 4.4.1.8, 4.4.1.9, 4.4.1.10, 4.4.2.1, 4.4.2.2, 4.4.2.3, 4.4.2.4, 4.4.2.5, 4.4.2.6, 4.4.2.7, 4.4.2.8, 4.4.2.9, 4.4.2.10, 4.4.3.1, 4.4.3.2, 4.4.3.3, 4.4.3.4, 4.4.3.5, 4.4.3.6, 4.4.3.7, 4.4.3.8, 4.4.3.9, 4.4.3.10, 4.4.4.1, 4.4.4.2, 4.4.4.3, 4.4.4.4, 4.4.4.5, 4.4.4.6, 4.4.4.7, 4.4.4.8, 4.4.4.9, 4.4.4.10, 4.4.5.1, 4.4.5.2, 4.4.5.3, 4.4.5.4, 4.4.5.5, 4.4.5.6, 4.4.5.7, 4.4.5.8, 4.4.5.9, 4.4.5.10, 4.4.6.1, 4.4.6.2, 4.4.6.3, 4.4.6.4, 4.4.6.5, 4.4.6.6, 4.4.6.7, 4.4.6.8, 4.4.6.9, 4.4.6.10, 4.4.7.1, 4.4.7.2, 4.4.7.3, 4.4.7.4, 4.4.7.5, 4.4.7.6, 4.4.7.7, 4.4.7.8, 4.4.7.9, 4.4.7.10, 4.4.8.1, 4.4.8.2, 4.4.8.3, 4.4.8.4, 4.4.8.5, 4.4.8.6, 4.4.8.7, 4.4.8.8, 4.4.8.9, 4.4.8.10, 4.4.9.1, 4.4.9.2, 4.4.9.3, 4.4.9.4, 4.4.9.5, 4.4.9.6, 4.4.9.7, 4.4.9.8, 4.4.9.9, 4.4.9.10, 4.4.10.1, 4.4.10.2, 4.4.10.3, 4.4.10.4, 4.4.10.5, 4.4.10.6, 4.4.10.7, 4.4.10.8, 4.4.10.9, 4.4.10.10, 4.5.1.1, 4.5.1.2, 4.5.1.3, 4.5.1.4, 4.5.1.5, 4.5.1.6, 4.5.1.7, 4.5.1.8, 4.5.1.9, 4.5.1.10, 4.5.2.1, 4.5.2.2, 4.5.2.3, 4.5.2.4, 4.5.2.5, 4.5.2.6, 4.5.2.7, 4.5.2.8, 4.5.2.9, 4.5.2.10, 4.5.3.1, 4.5.3.2, 4.5.3.3, 4.5.3.4, 4.5.3.5, 4.5.3.6, 4.5.3.7, 4.5.3.8, 4.5.3.9, 4.5.3.10, 4.5.4.1, 4.5.4.2, 4.5.4.3, 4.5.4.4, 4.5.4.5, 4.5.4.6, 4.5.4.7, 4.5.4.8, 4.5.4.9, 4.5.4.10, 4.5.5.1, 4.5.5.2, 4.5.5.3, 4.5.5.4, 4.5.5.5, 4.5.5.6, 4.5.5.7, 4.5.5.8, 4.5.5.9, 4.5.5.10, 4.5.6.1, 4.5.6.2, 4.5.6.3, 4.5.6.4, 4.5.6.5, 4.5.6.6, 4.5.6.7, 4.5.6.8, 4.5.6.9, 4.5.6.10, 4.5.7.1, 4.5.7.2, 4.5.7.3, 4.5.7.4, 4.5.7.5, 4.5.7.6, 4.5.7.7, 4.5.7.8, 4.5.7.9, 4.5.7.10, 4.5.8.1, 4.5.8.2, 4.5.8.3, 4.5.8.4, 4.5.8.5, 4.5.8.6, 4.5.8.7, 4.5.8.8, 4.5.8.9, 4.5.8.10, 4.5.9.1, 4.5.9.2, 4.5.9.3, 4.5.9.4, 4.5.9.5, 4.5.9.6, 4.5.9.7, 4.5.9.8, 4.5.9.9, 4.5.9.10, 4.5.10.1, 4.5.10.2, 4.5.10.3, 4.5.10.4, 4.5.10.5, 4.5.10.6, 4.5.10.7, 4.5.10.8, 4.5.10.9, 4.5.10.10, 4.6.1.1, 4.6.1.2, 4.6.1.3, 4.6.1.4, 4.6.1.5, 4.6.1.6, 4.6.1.7, 4.6.1.8, 4.6.1.9, 4.6.1.10, 4.6.2.1, 4.6.2.2, 4.6.2.3, 4.6.2.4, 4.6.2.5, 4.6.2.6, 4.6.2.7, 4.6.2.8, 4.6.2.9, 4.6.2.10, 4.6.3.1, 4.6.3.2, 4.6.3.3, 4.6.3.4, 4.6.3.5, 4.6.3.6, 4.6.3.7, 4.6.3.8, 4.6.3.9, 4.6.3.10, 4.6.4.1, 4.6.4.2, 4.6.4.3, 4.6.4.4, 4.6.4.5, 4.6.4.6, 4.6.4.7, 4.6.4.8, 4.6.4.9, 4.6.4.10, 4.6.5.1, 4.6.5.2, 4.6.5.3, 4.6.5.4, 4.6.5.5, 4.6.5.6, 4.6.5.7, 4.6.5.8, 4.6.5.9, 4.6.5.10, 4.6.6.1, 4.6.6.2, 4.6.6.3, 4.6.6.4, 4.6.6.5, 4.6.6.6, 4.6.6.7, 4.6.6.8, 4.6.6.9, 4.6.6.10, 4.6.7.1, 4.6.7.2, 4.6.7.3, 4.6.7.4, 4.6.7.5, 4.6.7.6, 4.6.7.7, 4.6.7.8, 4.6.7.9, 4.6.7.10, 4.6.8.1, 4.6.8.2, 4.6.8.3, 4.6.8.4, 4.6.8.5, 4.6.8.6, 4.6.8.7, 4.6.8.8, 4.6.8.9, 4.6.8.10, 4.6.9.1, 4.6.9.2, 4.6.9.3, 4.6.9.4, 4.6.9.5, 4.6.9.6, 4.6.9.7, 4.6.9.8, 4.6.9.9, 4.6.9.10, 4.6.10.1, 4.6.10.2, 4.6.10.3, 4.6.10.4, 4.6.10.5, 4.6.10.6, 4.6.10.7, 4.6.10.8, 4.6.10.9, 4.6.10.10, 4.7.1.1, 4.7.1.2, 4.7.1.3, 4.7.1.4, 4.7.1.5, 4.7.1.6, 4.7.1.7, 4.7.1.8, 4.7.1.9, 4.7.1.10, 4.7.2.1, 4.7.2.2, 4.7.2.3, 4.7.2.4, 4.7.2.5, 4.7.2.6, 4.7.2.7, 4.7.2.8, 4.7.2.9, 4.7.2.10, 4.7.3.1, 4.7.3.2, 4.7.3.3, 4.7.3.4, 4.7.3.5, 4.7.3.6, 4.7.3.7, 4.7.3.8, 4.7.3.9, 4.7.3.10, 4.7.4.1, 4.7.4.2, 4.7.4.3, 4.7.4.4, 4.7.4.5, 4.7.4.6, 4.7.4.7, 4.7.4.8, 4.7.4.9, 4.7.4.10, 4.7.5.1, 4.7.5.2, 4.7.5.3, 4.7.5.4, 4.7.5.5, 4.7.5.6, 4.7.5.7, 4.7.5.8, 4.7.5.9, 4.7.5.10, 4.7.6.1, 4.7.6.2, 4.7.6.3, 4.7.6.4, 4.7.6.5, 4.7.6.6, 4.7.6.7, 4.7.6.8, 4.7.6.9, 4.7.6.10, 4.7.7.1, 4.7.7.2, 4.7.7.3, 4.7.7.4, 4.7.7.5, 4.7.7.6, 4.7.7.7, 4.7.7.8, 4.7.7.9, 4.7.7.10, 4.7.8.1, 4.7.8.2, 4.7.8.3, 4.7.8.4, 4.7.8.5, 4.7.8.6, 4.7.8.7, 4.7.8.8, 4.7.8.9, 4.7.8.10, 4.7.9.1, 4.7.9.2, 4.7.9.3, 4.7.9.4, 4.7.9.5, 4.7.9.6, 4.7.9.7, 4.7.9.8, 4.7.9.9, 4.7.9.10, 4.7.10.1, 4.7.10.2, 4.7.10.3, 4.7.10.4, 4.7.10.5, 4.7.10.6, 4.7.10.7, 4.7.10.8, 4.7.10.9, 4.7.10.10, 4.8.1.1, 4.8.1.2, 4.8.1.3, 4.8.1.4, 4.8.1.5, 4.8.1.6, 4.8.1.7, 4.8.1.8, 4.8.1.9, 4.8.1.10, 4.8.2.1, 4.8.2.2, 4.8.2.3, 4.8.2.4, 4.8.2.5, 4.8.2.6, 4.8.2.7, 4.8.2.8, 4.8.2.9, 4.8.2.10, 4.8.3.1, 4.8.3.2, 4.8.3.3, 4.8.3.4, 4.8.3.5, 4.8.3.6, 4.8.3.7, 4.8.3.8, 4.8.3.9, 4.8.3.10, 4.8.4.1, 4.8.4.2, 4.8.4.3, 4.8.4.4, 4.8.4.5, 4.8.4.6, 4.8.4.7, 4.8.4.8, 4.8.4.9, 4.8.4.10, 4.8.5.1, 4.8.5.2, 4.8.5.3, 4.8.5.4, 4.8.5.5, 4.8.5.6, 4.8.5.7, 4.8.5.8, 4.8.5.9, 4.8.5.10, 4.8.6.1, 4.8.6.2, 4.8.6.3, 4.8.6.4, 4.8.6.5, 4.8.6.6, 4.8.6.7, 4.8.6.8, 4.8.6.9, 4.8.6.10, 4.8.7.1, 4.8.7.2, 4.8.7.3, 4.8.7.4, 4.8.7.5, 4.8.7.6, 4.8.7.7, 4.8.7.8, 4.8.7.9, 4.8.7.10, 4.8.8.1, 4.8.8.2, 4.8.8.3, 4.8.8.4, 4.8.8.5, 4.8.8.6, 4.8.8.7, 4.8.8.8, 4.8.8.9, TABLE 2-continued 4.8.8.10, 4.8.9.1, 4.8.9.2, 4.8.9.3, 4.8.9.4, 4.8.9.5, 4.8.9.6, 4.8.9.7, 4.8.9.8, 4.8.9.9, 4.8.9.10, 4.8.10.1,
4.8.10.2, 4.8.10.3, 4.8.10.4, 4.8.10.5, 4.8.10.6, 4.8.10.7, 4.8.10.8, 4.8.10.9, 4.8.10.10, 4.9.1.1,
4.9.1.2, 4.9.1.3, 4.9.1.4, 4.9.1.5, 4.9.1.6, 4.9.1.7, 4.9.1.8, 4.9.1.9, 4.9.1.10, 4.9.2.1, 4.9.2.2, 4.9.2.3,
4.9.2.4, 4.9.2.5, 4.9.2.6, 4.9.2.7, 4.9.2.8, 4.9.2.9, 4.9.2.10, 4.9.3.1, 4.9.3.2, 4.9.3.3, 4.9.3.4, 4.9.3.5,
4.9.3.6, 4.9.3.7, 4.9.3.8, 4.9.3.9, 4.9.3.10, 4.9.4.1, 4.9.4.2, 4.9.4.3, 4.9.4.4, 4.9.4.5, 4.9.4.6, 4.9.4.7,
4.9.4.8, 4.9.4.9, 4.9.4.10, 4.9.5.1, 4.9.5.2, 4.9.5.3, 4.9.5.4, 4.9.5.5, 4.9.5.6, 4.9.5.7, 4.9.5.8, 4.9.5.9,
4.9.5.10, 4.9.6.1, 4.9.6.2, 4.9.6.3, 4.9.6.4, 4.9.6.5, 4.9.6.6, 4.9.6.7, 4.9.6.8, 4.9.6.9, 4.9.6.10, 4.9.7.1,
4.9.7.2, 4.9.7.3, 4.9.7.4, 4.9.7.5, 4.9.7.6, 4.9.7.7, 4.9.7.8, 4.9.7.9, 4.9.7.10, 4.9.8.1, 4.9.8.2, 4.9.8.3,
4.9.8.4, 4.9.8.5, 4.9.8.6, 4.9.8.7, 4.9.8.8, 4.9.8.9, 4.9.8.10, 4.9.9.1, 4.9.9.2, 4.9.9.3, 4.9.9.4, 4.9.9.5,
4.9.9.6, 4.9.9.7, 4.9.9.8, 4.9.9.9, 4.9.9.10, 4.9.10.1, 4.9.10.2, 4.9.10.3, 4.9.10.4, 4.9.10.5, 4.9.10.6,
4.9.10.7, 4.9.10.8, 4.9.10.9, 4.9.10.10, 4.10.1.1, 4.10.1.2, 4.10.1.3, 4.10.1.4, 4.10.1.5, 4.10.1.6,
4.10.1.7, 4.10.1.8, 4.10.1.9, 4.10.1.10, 4.10.2.1, 4.10.2.2, 4.10.2.3, 4.10.2.4, 4.10.2.5, 4.10.2.6,
4.10.2.7, 4.10.2.8, 4.10.2.9, 4.10.2.10, 4.10.3.1, 4.10.3.2, 4.10.3.3, 4.10.3.4, 4.10.3.5, 4.10.3.6,
4.10.3.7, 4.10.3.8, 4.10.3.9, 4.10.3.10, 4.10.4.1, 4.10.4.2, 4.10.4.3, 4.10.4.4, 4.10.4.5, 4.10.4.6,
4.10.4.7, 4.10.4.8, 4.10.4.9, 4.10.4.10, 4.10.5.1, 4.10.5.2, 4.10.5.3, 4.10.5.4, 4.10.5.5, 4.10.5.6,
4.10.5.7, 4.10.5.8, 4.10.5.9, 4.10.5.10, 4.10.6.1, 4.10.6.2, 4.10.6.3, 4.10.6.4, 4.10.6.5, 4.10.6.6,
4.10.6.7, 4.10.6.8, 4.10.6.9, 4.10.6.10, 4.10.7.1, 4.10.7.2, 4.10.7.3, 4.10.7.4, 4.10.7.5, 4.10.7.6,
4.10.7.7, 4.10.7.8, 4.10.7.9, 4.10.7.10, 4.10.8.1, 4.10.8.2, 4.10.8.3, 4.10.8.4, 4.10.8.5, 4.10.8.6,
4.10.8.7, 4.10.8.8, 4.10.8.9, 4.10.8.10, 4.10.9.1, 4.10.9.2, 4.10.9.3, 4.10.9.4, 4.10.9.5, 4.10.9.6,
4.10.9.7, 4.10.9.8, 4.10.9.9, 4.10.9.10, 4.10.10.1, 4.10.10.2, 4.10.10.3, 4.10.10.4, 4.10.10.5,
4.10.10.6, 4.10.10.7, 4.10.10.8, 4.10.10.9, 4.10.10.10, 5.1.1.1, 5.1.1.2, 5.1.1.3, 5.1.1.4, 5.1.1.5,
5.1.1.6, 5.1.1.7, 5.1.1.8, 5.1.1.9, 5.1.1.10, 5.1.2.1, 5.1.2.2, 5.1.2.3, 5.1.2.4, 5.1.2.5, 5.1.2.6, 5.1.2.7,
5.1.2.8, 5.1.2.9, 5.1.2.10, 5.1.3.1, 5.1.3.2, 5.1.3.3, 5.1.3.4, 5.1.3.5, 5.1.3.6, 5.1.3.7, 5.1.3.8, 5.1.3.9,
5.1.3.10, 5.1.4.1, 5.1.4.2, 5.1.4.3, 5.1.4.4, 5.1.4.5, 5.1.4.6, 5.1.4.7, 5.1.4.8, 5.1.4.9, 5.1.4.10, 5.1.5.1,
5.1.5.2, 5.1.5.3, 5.1.5.4, 5.1.5.5, 5.1.5.6, 5.1.5.7, 5.1.5.8, 5.1.5.9, 5.1.5.10, 5.1.6.1, 5.1.6.2, 5.1.6.3,
5.1.6.4, 5.1.6.5, 5.1.6.6, 5.1.6.7, 5.1.6.8, 5.1.6.9, 5.1.6.10, 5.1.7.1, 5.1.7.2, 5.1.7.3, 5.1.7.4, 5.1.7.5,
5.1.7.6, 5.1.7.7, 5.1.7.8, 5.1.7.9, 5.1.7.10, 5.1.8.1, 5.1.8.2, 5.1.8.3, 5.1.8.4, 5.1.8.5, 5.1.8.6, 5.1.8.7,
5.1.8.8, 5.1.8.9, 5.1.8.10, 5.1.9.1, 5.1.9.2, 5.1.9.3, 5.1.9.4, 5.1.9.5, 5.1.9.6, 5.1.9.7, 5.1.9.8, 5.1.9.9,
5.1.9.10, 5.1.10.1, 5.1.10.2, 5.1.10.3, 5.1.10.4, 5.1.10.5, 5.1.10.6, 5.1.10.7, 5.1.10.8, 5.1.10.9,
5.1.10.10, 5.2.1.1, 5.2.1.2, 5.2.1.3, 5.2.1.4, 5.2.1.5, 5.2.1.6, 5.2.1.7, 5.2.1.8, 5.2.1.9, 5.2.1.10, 5.2.2.1,
5.2.2.2, 5.2.2.3, 5.2.2.4, 5.2.2.5, 5.2.2.6, 5.2.2.7, 5.2.2.8, 5.2.2.9, 5.2.2.10, 5.2.3.1, 5.2.3.2, 5.2.3.3,
5.2.3.4, 5.2.3.5, 5.2.3.6, 5.2.3.7, 5.2.3.8, 5.2.3.9, 5.2.3.10, 5.2.4.1, 5.2.4.2, 5.2.4.3, 5.2.4.4, 5.2.4.5,
5.2.4.6, 5.2.4.7, 5.2.4.8, 5.2.4.9, 5.2.4.10, 5.2.5.1, 5.2.5.2, 5.2.5.3, 5.2.5.4, 5.2.5.5, 5.2.5.6, 5.2.5.7,
5.2.5.8, 5.2.5.9, 5.2.5.10, 5.2.6.1, 5.2.6.2, 5.2.6.3, 5.2.6.4, 5.2.6.5, 5.2.6.6, 5.2.6.7, 5.2.6.8, 5.2.6.9,
5.2.6.10, 5.2.7.1, 5.2.7.2, 5.2.7.3, 5.2.7.4, 5.2.7.5, 5.2.7.6, 5.2.7.7, 5.2.7.8, 5.2.7.9, 5.2.7.10, 5.2.8.1,
5.2.8.2, 5.2.8.3, 5.2.8.4, 5.2.8.5, 5.2.8.6, 5.2.8.7, 5.2.8.8, 5.2.8.9, 5.2.8.10, 5.2.9.1, 5.2.9.2, 5.2.9.3,
5.2.9.4, 5.2.9.5, 5.2.9.6, 5.2.9.7, 5.2.9.8, 5.2.9.9, 5.2.9.10, 5.2.10.1, 5.2.10.2, 5.2.10.3, 5.2.10.4,
5.2.10.5, 5.2.10.6, 5.2.10.7, 5.2.10.8, 5.2.10.9, 5.2.10.10, 5.3.1.1, 5.3.1.2, 5.3.1.3, 5.3.1.4, 5.3.1.5,
5.3.1.6, 5.3.1.7, 5.3.1.8, 5.3.1.9, 5.3.1.10, 5.3.2.1, 5.3.2.2, 5.3.2.3, 5.3.2.4, 5.3.2.5, 5.3.2.6, 5.3.2.7,
5.3.2.8, 5.3.2.9, 5.3.2.10, 5.3.3.1, 5.3.3.2, 5.3.3.3, 5.3.3.4, 5.3.3.5, 5.3.3.6, 5.3.3.7, 5.3.3.8, 5.3.3.9,
5.3.3.10, 5.3.4.1, 5.3.4.2, 5.3.4.3, 5.3.4.4, 5.3.4.5, 5.3.4.6, 5.3.4.7, 5.3.4.8, 5.3.4.9, 5.3.4.10, 5.3.5.1,
5.3.5.2, 5.3.5.3, 5.3.5.4, 5.3.5.5, 5.3.5.6, 5.3.5.7, 5.3.5.8, 5.3.5.9, 5.3.5.10, 5.3.6.1, 5.3.6.2, 5.3.6.3,
5.3.6.4, 5.3.6.5, 5.3.6.6, 5.3.6.7, 5.3.6.8, 5.3.6.9, 5.3.6.10, 5.3.7.1, 5.3.7.2, 5.3.7.3, 5.3.7.4, 5.3.7.5,
5.3.7.6, 5.3.7.7, 5.3.7.8, 5.3.7.9, 5.3.7.10, 5.3.8.1, 5.3.8.2, 5.3.8.3, 5.3.8.4, 5.3.8.5, 5.3.8.6, 5.3.8.7,
5.3.8.8, 5.3.8.9, 5.3.8.10, 5.3.9.1, 5.3.9.2, 5.3.9.3, 5.3.9.4, 5.3.9.5, 5.3.9.6, 5.3.9.7, 5.3.9.8, 5.3.9.9,
5.3.9.10, 5.3.10.1, 5.3.10.2, 5.3.10.3, 5.3.10.4, 5.3.10.5, 5.3.10.6, 5.3.10.7, 5.3.10.8, 5.3.10.9,
5.3.10.10, 5.4.1.1, 5.4.1.2, 5.4.1.3, 5.4.1.4, 5.4.1.5, 5.4.1.6, 5.4.1.7, 5.4.1.8, 5.4.1.9, 5.4.1.10, 5.4.2.1,
5.4.2.2, 5.4.2.3, 5.4.2.4, 5.4.2.5, 5.4.2.6, 5.4.2.7, 5.4.2.8, 5.4.2.9, 5.4.2.10, 5.4.3.1, 5.4.3.2, 5.4.3.3,
5.4.3.4, 5.4.3.5, 5.4.3.6, 5.4.3.7, 5.4.3.8, 5.4.3.9, 5.4.3.10, 5.4.4.1, 5.4.4.2, 5.4.4.3, 5.4.4.4, 5.4.4.5,
5.4.4.6, 5.4.4.7, 5.4.4.8, 5.4.4.9, 5.4.4.10, 5.4.5.1, 5.4.5.2, 5.4.5.3, 5.4.5.4, 5.4.5.5, 5.4.5.6, 5.4.5.7,
5.4.5.8, 5.4.5.9, 5.4.5.10, 5.4.6.1, 5.4.6.2, 5.4.6.3, 5.4.6.4, 5.4.6.5, 5.4.6.6, 5.4.6.7, 5.4.6.8, 5.4.6.9,
5.4.6.10, 5.4.7.1, 5.4.7.2, 5.4.7.3, 5.4.7.4, 5.4.7.5, 5.4.7.6, 5.4.7.7, 5.4.7.8, 5.4.7.9, 5.4.7.10, 5.4.8.1,
5.4.8.2, 5.4.8.3, 5.4.8.4, 5.4.8.5, 5.4.8.6, 5.4.8.7, 5.4.8.8, 5.4.8.9, 5.4.8.10, 5.4.9.1, 5.4.9.2, 5.4.9.3,
5.4.9.4, 5.4.9.5, 5.4.9.6, 5.4.9.7, 5.4.9.8, 5.4.9.9, 5.4.9.10, 5.4.10.1, 5.4.10.2, 5.4.10.3, 5.4.10.4,
5.4.10.5, 5.4.10.6, 5.4.10.7, 5.4.10.8, 5.4.10.9, 5.4.10.10, 5.5.1.1, 5.5.1.2, 5.5.1.3, 5.5.1.4, 5.5.1.5,
5.5.1.6, 5.5.1.7, 5.5.1.8, 5.5.1.9, 5.5.1.10, 5.5.2.1, 5.5.2.2, 5.5.2.3, 5.5.2.4, 5.5.2.5, 5.5.2.6, 5.5.2.7,
5.5.2.8, 5.5.2.9, 5.5.2.10, 5.5.3.1, 5.5.3.2, 5.5.3.3, 5.5.3.4, 5.5.3.5, 5.5.3.6, 5.5.3.7, 5.5.3.8, 5.5.3.9,
5.5.3.10, 5.5.4.1, 5.5.4.2, 5.5.4.3, 5.5.4.4, 5.5.4.5, 5.5.4.6, 5.5.4.7, 5.5.4.8, 5.5.4.9, 5.5.4.10, 5.5.5.1,
5.5.5.2, 5.5.5.3, 5.5.5.4, 5.5.5.5, 5.5.5.6, 5.5.5.7, 5.5.5.8, 5.5.5.9, 5.5.5.10, 5.5.6.1, 5.5.6.2, 5.5.6.3,
5.5.6.4, 5.5.6.5, 5.5.6.6, 5.5.6.7, 5.5.6.8, 5.5.6.9, 5.5.6.10, 5.5.7.1, 5.5.7.2, 5.5.7.3, 5.5.7.4, 5.5.7.5,
5.5.7.6, 5.5.7.7, 5.5.7.8, 5.5.7.9, 5.5.7.10, 5.5.8.1, 5.5.8.2, 5.5.8.3, 5.5.8.4, 5.5.8.5, 5.5.8.6, 5.5.8.7,
5.5.8.8, 5.5.8.9, 5.5.8.10, 5.5.9.1, 5.5.9.2, 5.5.9.3, 5.5.9.4, 5.5.9.5, 5.5.9.6, 5.5.9.7, 5.5.9.8, 5.5.9.9,
5.5.9.10, 5.5.10.1, 5.5.10.2, 5.5.10.3, 5.5.10.4, 5.5.10.5, 5.5.10.6, 5.5.10.7, 5.5.10.8, 5.5.10.9,
5.5.10.10, 5.6.1.1, 5.6.1.2, 5.6.1.3, 5.6.1.4, 5.6.1.5, 5.6.1.6, 5.6.1.7, 5.6.1.8, 5.6.1.9, 5.6.1.10, 5.6.2.1,
5.6.2.2, 5.6.2.3, 5.6.2.4, 5.6.2.5, 5.6.2.6, 5.6.2.7, 5.6.2.8, 5.6.2.9, 5.6.2.10, 5.6.3.1, 5.6.3.2, 5.6.3.3,
5.6.3.4, 5.6.3.5, 5.6.3.6, 5.6.3.7, 5.6.3.8, 5.6.3.9, 5.6.3.10, 5.6.4.1, 5.6.4.2, 5.6.4.3, 5.6.4.4, 5.6.4.5,
5.6.4.6, 5.6.4.7, 5.6.4.8, 5.6.4.9, 5.6.4.10, 5.6.5.1, 5.6.5.2, 5.6.5.3, 5.6.5.4, 5.6.5.5, 5.6.5.6, 5.6.5.7,
5.6.5.8, 5.6.5.9, 5.6.5.10, 5.6.6.1, 5.6.6.2, 5.6.6.3, 5.6.6.4, 5.6.6.5, 5.6.6.6, 5.6.6.7, 5.6.6.8, 5.6.6.9,
5.6.6.10, 5.6.7.1, 5.6.7.2, 5.6.7.3, 5.6.7.4, 5.6.7.5, 5.6.7.6, 5.6.7.7, 5.6.7.8, 5.6.7.9, 5.6.7.10, 5.6.8.1,
5.6.8.2, 5.6.8.3, 5.6.8.4, 5.6.8.5, 5.6.8.6, 5.6.8.7, 5.6.8.8, 5.6.8.9, 5.6.8.10, 5.6.9.1, 5.6.9.2, 5.6.9.3,
5.6.9.4, 5.6.9.5, 5.6.9.6, 5.6.9.7, 5.6.9.8, 5.6.9.9, 5.6.9.10, 5.6.10.1, 5.6.10.2, 5.6.10.3, 5.6.10.4,
5.6.10.5, 5.6.10.6, 5.6.10.7, 5.6.10.8, 5.6.10.9, 5.6.10.10, 5.7.1.1, 5.7.1.2, 5.7.1.3, 5.7.1.4, 5.7.1.5,
5.7.1.6, 5.7.1.7, 5.7.1.8, 5.7.1.9, 5.7.1.10, 5.7.2.1, 5.7.2.2, 5.7.2.3, 5.7.2.4, 5.7.2.5, 5.7.2.6, 5.7.2.7,
5.7.2.8, 5.7.2.9, 5.7.2.10, 5.7.3.1, 5.7.3.2, 5.7.3.3, 5.7.3.4, 5.7.3.5, 5.7.3.6, 5.7.3.7, 5.7.3.8, 5.7.3.9,
5.7.3.10, 5.7.4.1, 5.7.4.2, 5.7.4.3, 5.7.4.4, 5.7.4.5, 5.7.4.6, 5.7.4.7, 5.7.4.8, 5.7.4.9, 5.7.4.10, 5.7.5.1,
5.7.5.2, 5.7.5.3, 5.7.5.4, 5.7.5.5, 5.7.5.6, 5.7.5.7, 5.7.5.8, 5.7.5.9, 5.7.5.10, 5.7.6.1, 5.7.6.2, 5.7.6.3,
5.7.6.4, 5.7.6.5, 5.7.6.6, 5.7.6.7, 5.7.6.8, 5.7.6.9, 5.7.6.10, 5.7.7.1, 5.7.7.2, 5.7.7.3, 5.7.7.4, 5.7.7.5,
5.7.7.6, 5.7.7.7, 5.7.7.8, 5.7.7.9, 5.7.7.10, 5.7.8.1, 5.7.8.2, 5.7.8.3, 5.7.8.4, 5.7.8.5, 5.7.8.6, 5.7.8.7,
5.7.8.8, 5.7.8.9, 5.7.8.10, 5.7.9.1, 5.7.9.2, 5.7.9.3, 5.7.9.4, 5.7.9.5, 5.7.9.6, 5.7.9.7, 5.7.9.8, 5.7.9.9,
5.7.9.10, 5.7.10.1, 5.7.10.2, 5.7.10.3, 5.7.10.4, 5.7.10.5, 5.7.10.6, 5.7.10.7, 5.7.10.8, 5.7.10.9, TABLE 2-continued 5.7.10.10, 5.8.1.1, 5.8.1.2, 5.8.1.3, 5.8.1.4, 5.8.1.5, 5.8.1.6, 5.8.1.7, 5.8.1.8, 5.8.1.9, 5.8.1.10, 5.8.2.1, 5.8.2.2, 5.8.2.3, 5.8.2.4, 5.8.2.5, 5.8.2.6, 5.8.2.7, 5.8.2.8, 5.8.2.9, 5.8.2.10, 5.8.3.1, 5.8.3.2, 5.8.3.3, 5.8.3.4, 5.8.3.5, 5.8.3.6, 5.8.3.7, 5.8.3.8, 5.8.3.9, 5.8.3.10, 5.8.4.1, 5.8.4.2, 5.8.4.3, 5.8.4.4, 5.8.4.5, 5.8.4.6, 5.8.4.7, 5.8.4.8, 5.8.4.9, 5.8.4.10, 5.8.5.1, 5.8.5.2, 5.8.5.3, 5.8.5.4, 5.8.5.5, 5.8.5.6, 5.8.5.7, 5.8.5.8, 5.8.5.9, 5.8.5.10, 5.8.6.1, 5.8.6.2, 5.8.6.3, 5.8.6.4, 5.8.6.5, 5.8.6.6, 5.8.6.7, 5.8.6.8, 5.8.6.9, 5.8.6.10, 5.8.7.1, 5.8.7.2, 5.8.7.3, 5.8.7.4, 5.8.7.5, 5.8.7.6, 5.8.7.7, 5.8.7.8, 5.8.7.9, 5.8.7.10, 5.8.8.1, 5.8.8.2, 5.8.8.3, 5.8.8.4, 5.8.8.5, 5.8.8.6, 5.8.8.7, 5.8.8.8, 5.8.8.9, 5.8.8.10, 5.8.9.1, 5.8.9.2, 5.8.9.3, 5.8.9.4, 5.8.9.5, 5.8.9.6, 5.8.9.7, 5.8.9.8, 5.8.9.9, 5.8.9.10, 5.8.10.1, 5.8.10.2, 5.8.10.3, 5.8.10.4, 5.8.10.5, 5.8.10.6, 5.8.10.7, 5.8.10.8, 5.8.10.9, 5.8.10.10, 5.9.1.1, 5.9.1.2, 5.9.1.3, 5.9.1.4, 5.9.1.5, 5.9.1.6, 5.9.1.7, 5.9.1.8, 5.9.1.9, 5.9.1.10, 5.9.2.1, 5.9.2.2, 5.9.2.3, 5.9.2.4, 5.9.2.5, 5.9.2.6, 5.9.2.7, 5.9.2.8, 5.9.2.9, 5.9.2.10, 5.9.3.1, 5.9.3.2, 5.9.3.3, 5.9.3.4, 5.9.3.5, 5.9.3.6, 5.9.3.7, 5.9.3.8, 5.9.3.9, 5.9.3.10, 5.9.4.1, 5.9.4.2, 5.9.4.3, 5.9.4.4, 5.9.4.5, 5.9.4.6, 5.9.4.7, 5.9.4.8, 5.9.4.9, 5.9.4.10, 5.9.5.1, 5.9.5.2, 5.9.5.3, 5.9.5.4, 5.9.5.5, 5.9.5.6, 5.9.5.7, 5.9.5.8, 5.9.5.9, 5.9.5.10, 5.9.6.1, 5.9.6.2, 5.9.6.3, 5.9.6.4, 5.9.6.5, 5.9.6.6, 5.9.6.7, 5.9.6.8, 5.9.6.9, 5.9.6.10, 5.9.7.1, 5.9.7.2, 5.9.7.3, 5.9.7.4, 5.9.7.5, 5.9.7.6, 5.9.7.7, 5.9.7.8, 5.9.7.9, 5.9.7.10, 5.9.8.1, 5.9.8.2, 5.9.8.3, 5.9.8.4, 5.9.8.5, 5.9.8.6, 5.9.8.7, 5.9.8.8, 5.9.8.9, 5.9.8.10, 5.9.9.1, 5.9.9.2, 5.9.9.3, 5.9.9.4, 5.9.9.5, 5.9.9.6, 5.9.9.7, 5.9.9.8, 5.9.9.9, 5.9.9.10, 5.9.10.1, 5.9.10.2, 5.9.10.3, 5.9.10.4, 5.9.10.5, 5.9.10.6, 5.9.10.7, 5.9.10.8, 5.9.10.9, 5.9.10.10, 5.10.1.1, 5.10.1.2, 5.10.1.3, 5.10.1.4, 5.10.1.5, 5.10.1.6, 5.10.1.7, 5.10.1.8, 5.10.1.9, 5.10.1.10, 5.10.2.1, 5.10.2.2, 5.10.2.3, 5.10.2.4, 5.10.2.5, 5.10.2.6, 5.10.2.7, 5.10.2.8, 5.10.2.9, 5.10.2.10, 5.10.3.1, 5.10.3.2, 5.10.3.3, 5.10.3.4, 5.10.3.5, 5.10.3.6, 5.10.3.7, 5.10.3.8, 5.10.3.9, 5.10.3.10, 5.10.4.1, 5.10.4.2, 5.10.4.3, 5.10.4.4, 5.10.4.5, 5.10.4.6, 5.10.4.7, 5.10.4.8, 5.10.4.9, 5.10.4.10, 5.10.5.1, 5.10.5.2, 5.10.5.3, 5.10.5.4, 5.10.5.5, 5.10.5.6, 5.10.5.7, 5.10.5.8, 5.10.5.9, 5.10.5.10, 5.10.6.1, 5.10.6.2, 5.10.6.3, 5.10.6.4, 5.10.6.5, 5.10.6.6, 5.10.6.7, 5.10.6.8, 5.10.6.9, 5.10.6.10, 5.10.7.1, 5.10.7.2, 5.10.7.3, 5.10.7.4, 5.10.7.5, 5.10.7.6, 5.10.7.7, 5.10.7.8, 5.10.7.9, 5.10.7.10, 5.10.8.1, 5.10.8.2, 5.10.8.3, 5.10.8.4, 5.10.8.5, 5.10.8.6, 5.10.8.7, 5.10.8.8, 5.10.8.9, 5.10.8.10, 5.10.9.1, 5.10.9.2, 5.10.9.3, 5.10.9.4, 5.10.9.5, 5.10.9.6, 5.10.9.7, 5.10.9.8, 5.10.9.9, 5.10.9.10, 5.10.10.1, 5.10.10.2, 5.10.10.3, 5.10.10.4, 5.10.10.5, 5.10.10.6, 5.10.10.7, 5.10.10.8, 5.10.10.9, 5.10.10.10, 6.1.1.1, 6.1.1.2, 6.1.1.3, 6.1.1.4, 6.1.1.5, 6.1.1.6, 6.1.1.7, 6.1.1.8, 6.1.1.9, 6.1.1.10, 6.1.2.1, 6.1.2.2, 6.1.2.3, 6.1.2.4, 6.1.2.5, 6.1.2.6, 6.1.2.7, 6.1.2.8, 6.1.2.9, 6.1.2.10, 6.1.3.1, 6.1.3.2, 6.1.3.3, 6.1.3.4, 6.1.3.5, 6.1.3.6, 6.1.3.7, 6.1.3.8, 6.1.3.9, 6.1.3.10, 6.1.4.1, 6.1.4.2, 6.1.4.3, 6.1.4.4, 6.1.4.5, 6.1.4.6, 6.1.4.7, 6.1.4.8, 6.1.4.9, 6.1.4.10, 6.1.5.1, 6.1.5.2, 6.1.5.3, 6.1.5.4, 6.1.5.5, 6.1.5.6, 6.1.5.7, 6.1.5.8, 6.1.5.9, 6.1.5.10, 6.1.6.1, 6.1.6.2, 6.1.6.3, 6.1.6.4, 6.1.6.5, 6.1.6.6, 6.1.6.7, 6.1.6.8, 6.1.6.9, 6.1.6.10, 6.1.7.1, 6.1.7.2, 6.1.7.3, 6.1.7.4, 6.1.7.5, 6.1.7.6, 6.1.7.7, 6.1.7.8, 6.1.7.9, 6.1.7.10, 6.1.8.1, 6.1.8.2, 6.1.8.3, 6.1.8.4, 6.1.8.5, 6.1.8.6, 6.1.8.7, 6.1.8.8, 6.1.8.9, 6.1.8.10, 6.1.9.1, 6.1.9.2, 6.1.9.3, 6.1.9.4, 6.1.9.5, 6.1.9.6, 6.1.9.7, 6.1.9.8, 6.1.9.9, 6.1.9.10, 6.1.10.1, 6.1.10.2, 6.1.10.3, 6.1.10.4, 6.1.10.5, 6.1.10.6, 6.1.10.7, 6.1.10.8, 6.1.10.9, 6.1.10.10, 6.2.1.1, 6.2.1.2, 6.2.1.3, 6.2.1.4, 6.2.1.5, 6.2.1.6, 6.2.1.7, 6.2.1.8, 6.2.1.9, 6.2.1.10, 6.2.2.1, 6.2.2.2, 6.2.2.3, 6.2.2.4, 6.2.2.5, 6.2.2.6, 6.2.2.7, 6.2.2.8, 6.2.2.9, 6.2.2.10, 6.2.3.1, 6.2.3.2, 6.2.3.3, 6.2.3.4, 6.2.3.5, 6.2.3.6, 6.2.3.7, 6.2.3.8, 6.2.3.9, 6.2.3.10, 6.2.4.1, 6.2.4.2, 6.2.4.3, 6.2.4.4, 6.2.4.5, 6.2.4.6, 6.2.4.7, 6.2.4.8, 6.2.4.9, 6.2.4.10, 6.2.5.1, 6.2.5.2, 6.2.5.3, 6.2.5.4, 6.2.5.5, 6.2.5.6, 6.2.5.7, 6.2.5.8, 6.2.5.9, 6.2.5.10, 6.2.6.1, 6.2.6.2, 6.2.6.3, 6.2.6.4, 6.2.6.5, 6.2.6.6, 6.2.6.7, 6.2.6.8, 6.2.6.9, 6.2.6.10, 6.2.7.1, 6.2.7.2, 6.2.7.3, 6.2.7.4, 6.2.7.5, 6.2.7.6, 6.2.7.7, 6.2.7.8, 6.2.7.9, 6.2.7.10, 6.2.8.1, 6.2.8.2, 6.2.8.3, 6.2.8.4, 6.2.8.5, 6.2.8.6, 6.2.8.7, 6.2.8.8, 6.2.8.9, 6.2.8.10, 6.2.9.1, 6.2.9.2, 6.2.9.3, 6.2.9.4, 6.2.9.5, 6.2.9.6, 6.2.9.7, 6.2.9.8, 6.2.9.9, 6.2.9.10, 6.2.10.1, 6.2.10.2, 6.2.10.3, 6.2.10.4, 6.2.10.5, 6.2.10.6, 6.2.10.7, 6.2.10.8, 6.2.10.9, 6.2.10.10, 6.3.1.1, 6.3.1.2, 6.3.1.3, 6.3.1.4, 6.3.1.5, 6.3.1.6, 6.3.1.7, 6.3.1.8, 6.3.1.9, 6.3.1.10, 6.3.2.1, 6.3.2.2, 6.3.2.3, 6.3.2.4, 6.3.2.5, 6.3.2.6, 6.3.2.7, 6.3.2.8, 6.3.2.9, 6.3.2.10, 6.3.3.1, 6.3.3.2, 6.3.3.3, 6.3.3.4, 6.3.3.5, 6.3.3.6, 6.3.3.7, 6.3.3.8, 6.3.3.9, 6.3.3.10, 6.3.4.1, 6.3.4.2, 6.3.4.3, 6.3.4.4, 6.3.4.5, 6.3.4.6, 6.3.4.7, 6.3.4.8, 6.3.4.9, 6.3.4.10, 6.3.5.1, 6.3.5.2, 6.3.5.3, 6.3.5.4, 6.3.5.5, 6.3.5.6, 6.3.5.7, 6.3.5.8, 6.3.5.9, 6.3.5.10, 6.3.6.1, 6.3.6.2, 6.3.6.3, 6.3.6.4, 6.3.6.5, 6.3.6.6, 6.3.6.7, 6.3.6.8, 6.3.6.9, 6.3.6.10, 6.3.7.1, 6.3.7.2, 6.3.7.3, 6.3.7.4, 6.3.7.5, 6.3.7.6, 6.3.7.7, 6.3.7.8, 6.3.7.9, 6.3.7.10, 6.3.8.1, 6.3.8.2, 6.3.8.3, 6.3.8.4, 6.3.8.5, 6.3.8.6, 6.3.8.7, 6.3.8.8, 6.3.8.9, 6.3.8.10, 6.3.9.1, 6.3.9.2, 6.3.9.3, 6.3.9.4, 6.3.9.5, 6.3.9.6, 6.3.9.7, 6.3.9.8, 6.3.9.9, 6.3.9.10, 6.3.10.1, 6.3.10.2, 6.3.10.3, 6.3.10.4, 6.3.10.5, 6.3.10.6, 6.3.10.7, 6.3.10.8, 6.3.10.9, 6.3.10.10, 6.4.1.1, 6.4.1.2, 6.4.1.3, 6.4.1.4, 6.4.1.5, 6.4.1.6, 6.4.1.7, 6.4.1.8, 6.4.1.9, 6.4.1.10, 6.4.2.1, 6.4.2.2, 6.4.2.3, 6.4.2.4, 6.4.2.5, 6.4.2.6, 6.4.2.7, 6.4.2.8, 6.4.2.9, 6.4.2.10, 6.4.3.1, 6.4.3.2, 6.4.3.3, 6.4.3.4, 6.4.3.5, 6.4.3.6, 6.4.3.7, 6.4.3.8, 6.4.3.9, 6.4.3.10, 6.4.4.1, 6.4.4.2, 6.4.4.3, 6.4.4.4, 6.4.4.5, 6.4.4.6, 6.4.4.7, 6.4.4.8, 6.4.4.9, 6.4.4.10, 6.4.5.1, 6.4.5.2, 6.4.5.3, 6.4.5.4, 6.4.5.5, 6.4.5.6, 6.4.5.7, 6.4.5.8, 6.4.5.9, 6.4.5.10, 6.4.6.1, 6.4.6.2, 6.4.6.3, 6.4.6.4, 6.4.6.5, 6.4.6.6, 6.4.6.7, 6.4.6.8, 6.4.6.9, 6.4.6.10, 6.4.7.1, 6.4.7.2, 6.4.7.3, 6.4.7.4, 6.4.7.5, 6.4.7.6, 6.4.7.7, 6.4.7.8, 6.4.7.9, 6.4.7.10, 6.4.8.1, 6.4.8.2, 6.4.8.3, 6.4.8.4, 6.4.8.5, 6.4.8.6, 6.4.8.7, 6.4.8.8, 6.4.8.9, 6.4.8.10, 6.4.9.1, 6.4.9.2, 6.4.9.3, 6.4.9.4, 6.4.9.5, 6.4.9.6, 6.4.9.7, 6.4.9.8, 6.4.9.9, 6.4.9.10, 6.4.10.1, 6.4.10.2, 6.4.10.3, 6.4.10.4, 6.4.10.5, 6.4.10.6, 6.4.10.7, 6.4.10.8, 6.4.10.9, 6.4.10.10, 6.5.1.1, 6.5.1.2, 6.5.1.3, 6.5.1.4, 6.5.1.5, 6.5.1.6, 6.5.1.7, 6.5.1.8, 6.5.1.9, 6.5.1.10, 6.5.2.1, 6.5.2.2, 6.5.2.3, 6.5.2.4, 6.5.2.5, 6.5.2.6, 6.5.2.7, 6.5.2.8, 6.5.2.9, 6.5.2.10, 6.5.3.1, 6.5.3.2, 6.5.3.3, 6.5.3.4, 6.5.3.5, 6.5.3.6, 6.5.3.7, 6.5.3.8, 6.5.3.9, 6.5.3.10, 6.5.4.1, 6.5.4.2, 6.5.4.3, 6.5.4.4, 6.5.4.5, 6.5.4.6, 6.5.4.7, 6.5.4.8, 6.5.4.9, 6.5.4.10, 6.5.5.1, 6.5.5.2, 6.5.5.3, 6.5.5.4, 6.5.5.5, 6.5.5.6, 6.5.5.7, 6.5.5.8, 6.5.5.9, 6.5.5.10, 6.5.6.1, 6.5.6.2, 6.5.6.3, 6.5.6.4, 6.5.6.5, 6.5.6.6, 6.5.6.7, 6.5.6.8, 6.5.6.9, 6.5.6.10, 6.5.7.1, 6.5.7.2, 6.5.7.3, 6.5.7.4, 6.5.7.5, 6.5.7.6, 6.5.7.7, 6.5.7.8, 6.5.7.9, 6.5.7.10, 6.5.8.1, 6.5.8.2, 6.5.8.3, 6.5.8.4, 6.5.8.5, 6.5.8.6, 6.5.8.7, 6.5.8.8, 6.5.8.9, 6.5.8.10, 6.5.9.1, 6.5.9.2, 6.5.9.3, 6.5.9.4, 6.5.9.5, 6.5.9.6, 6.5.9.7, 6.5.9.8, 6.5.9.9, 6.5.9.10, 6.5.10.1, 6.5.10.2, 6.5.10.3, 6.5.10.4, 6.5.10.5, 6.5.10.6, 6.5.10.7, 6.5.10.8, 6.5.10.9, 6.5.10.10, 6.6.1.1, 6.6.1.2, 6.6.1.3, 6.6.1.4, 6.6.1.5, 6.6.1.6, 6.6.1.7, 6.6.1.8, 6.6.1.9, 6.6.1.10, 6.6.2.1, 6.6.2.2, 6.6.2.3, 6.6.2.4, 6.6.2.5, 6.6.2.6, 6.6.2.7, 6.6.2.8, 6.6.2.9, 6.6.2.10, 6.6.3.1, 6.6.3.2, 6.6.3.3, 6.6.3.4, 6.6.3.5, 6.6.3.6, 6.6.3.7, 6.6.3.8, 6.6.3.9, 6.6.3.10, 6.6.4.1, 6.6.4.2, 6.6.4.3, 6.6.4.4, 6.6.4.5, 6.6.4.6, 6.6.4.7, 6.6.4.8, 6.6.4.9, 6.6.4.10, 6.6.5.1, 6.6.5.2, 6.6.5.3, 6.6.5.4, 6.6.5.5, 6.6.5.6, 6.6.5.7, 6.6.5.8, 6.6.5.9, 6.6.5.10, 6.6.6.1, 6.6.6.2, 6.6.6.3, 6.6.6.4, 6.6.6.5, 6.6.6.6, 6.6.6.7, 6.6.6.8, 6.6.6.9, 6.6.6.10, 6.6.7.1, 6.6.7.2, 6.6.7.3, 6.6.7.4, 6.6.7.5, 6.6.7.6, 6.6.7.7, 6.6.7.8, 6.6.7.9, 6.6.7.10, 6.6.8.1, 6.6.8.2, 6.6.8.3, 6.6.8.4, 6.6.8.5, 6.6.8.6, 6.6.8.7, 6.6.8.8, 6.6.8.9, 6.6.8.10, 6.6.9.1, 6.6.9.2, 6.6.9.3, 6.6.9.4, 6.6.9.5, 6.6.9.6, 6.6.9.7, 6.6.9.8, 6.6.9.9, 6.6.9.10, 6.6.10.1, 6.6.10.2, 6.6.10.3, 6.6.10.4, 6.6.10.5, 6.6.10.6, 6.6.10.7, 6.6.10.8, 6.6.10.9, 6.6.10.10, 6.7.1.1, 6.7.1.2, 6.7.1.3, 6.7.1.4, 6.7.1.5, 6.7.1.6, 6.7.1.7, 6.7.1.8, 6.7.1.9, 6.7.1.10, 6.7.2.1, 6.7.2.2, 6.7.2.3, 6.7.2.4, 6.7.2.5, 6.7.2.6, 6.7.2.7, 6.7.2.8, 6.7.2.9, 6.7.2.10, 6.7.3.1, TABLE 2-continued 6.7.3.2, 6.7.3.3, 6.7.3.4, 6.7.3.5, 6.7.3.6, 6.7.3.7, 6.7.3.8, 6.7.3.9, 6.7.3.10, 6.7.4.1, 6.7.4.2, 6.7.4.3, 6.7.4.4, 6.7.4.5, 6.7.4.6, 6.7.4.7, 6.7.4.8, 6.7.4.9, 6.7.4.10, 6.7.5.1, 6.7.5.2, 6.7.5.3, 6.7.5.4, 6.7.5.5, 6.7.5.6, 6.7.5.7, 6.7.5.8, 6.7.5.9, 6.7.5.10, 6.7.6.1, 6.7.6.2, 6.7.6.3, 6.7.6.4, 6.7.6.5, 6.7.6.6, 6.7.6.7, 6.7.6.8, 6.7.6.9, 6.7.6.10, 6.7.7.1, 6.7.7.2, 6.7.7.3, 6.7.7.4, 6.7.7.5, 6.7.7.6, 6.7.7.7, 6.7.7.8, 6.7.7.9, 6.7.7.10, 6.7.8.1, 6.7.8.2, 6.7.8.3, 6.7.8.4, 6.7.8.5, 6.7.8.6, 6.7.8.7, 6.7.8.8, 6.7.8.9, 6.7.8.10, 6.7.9.1, 6.7.9.2, 6.7.9.3, 6.7.9.4, 6.7.9.5, 6.7.9.6, 6.7.9.7, 6.7.9.8, 6.7.9.9, 6.7.9.10, 6.7.10.1, 6.7.10.2, 6.7.10.3, 6.7.10.4, 6.7.10.5, 6.7.10.6, 6.7.10.7, 6.7.10.8, 6.7.10.9, 6.7.10.10, 6.8.1.1, 6.8.1.2, 6.8.1.3, 6.8.1.4, 6.8.1.5, 6.8.1.6, 6.8.1.7, 6.8.1.8, 6.8.1.9, 6.8.1.10, 6.8.2.1, 6.8.2.2, 6.8.2.3, 6.8.2.4, 6.8.2.5, 6.8.2.6, 6.8.2.7, 6.8.2.8, 6.8.2.9, 6.8.2.10, 6.8.3.1, 6.8.3.2, 6.8.3.3, 6.8.3.4, 6.8.3.5, 6.8.3.6, 6.8.3.7, 6.8.3.8, 6.8.3.9, 6.8.3.10, 6.8.4.1, 6.8.4.2, 6.8.4.3, 6.8.4.4, 6.8.4.5, 6.8.4.6, 6.8.4.7, 6.8.4.8, 6.8.4.9, 6.8.4.10, 6.8.5.1, 6.8.5.2, 6.8.5.3, 6.8.5.4, 6.8.5.5, 6.8.5.6, 6.8.5.7, 6.8.5.8, 6.8.5.9, 6.8.5.10, 6.8.6.1, 6.8.6.2, 6.8.6.3, 6.8.6.4, 6.8.6.5, 6.8.6.6, 6.8.6.7, 6.8.6.8, 6.8.6.9, 6.8.6.10, 6.8.7.1, 6.8.7.2, 6.8.7.3, 6.8.7.4, 6.8.7.5, 6.8.7.6, 6.8.7.7, 6.8.7.8, 6.8.7.9, 6.8.7.10, 6.8.8.1, 6.8.8.2, 6.8.8.3, 6.8.8.4, 6.8.8.5, 6.8.8.6, 6.8.8.7, 6.8.8.8, 6.8.8.9, 6.8.8.10, 6.8.9.1, 6.8.9.2, 6.8.9.3, 6.8.9.4, 6.8.9.5, 6.8.9.6, 6.8.9.7, 6.8.9.8, 6.8.9.9, 6.8.9.10, 6.8.10.1, 6.8.10.2, 6.8.10.3, 6.8.10.4, 6.8.10.5, 6.8.10.6, 6.8.10.7, 6.8.10.8, 6.8.10.9, 6.8.10.10, 6.9.1.1, 6.9.1.2, 6.9.1.3, 6.9.1.4, 6.9.1.5, 6.9.1.6, 6.9.1.7, 6.9.1.8, 6.9.1.9, 6.9.1.10, 6.9.2.1, 6.9.2.2, 6.9.2.3, 6.9.2.4, 6.9.2.5, 6.9.2.6, 6.9.2.7, 6.9.2.8, 6.9.2.9, 6.9.2.10, 6.9.3.1, 6.9.3.2, 6.9.3.3, 6.9.3.4, 6.9.3.5, 6.9.3.6, 6.9.3.7, 6.9.3.8, 6.9.3.9, 6.9.3.10, 6.9.4.1, 6.9.4.2, 6.9.4.3, 6.9.4.4, 6.9.4.5, 6.9.4.6, 6.9.4.7, 6.9.4.8, 6.9.4.9, 6.9.4.10, 6.9.5.1, 6.9.5.2, 6.9.5.3, 6.9.5.4, 6.9.5.5, 6.9.5.6, 6.9.5.7, 6.9.5.8, 6.9.5.9, 6.9.5.10, 6.9.6.1, 6.9.6.2, 6.9.6.3, 6.9.6.4, 6.9.6.5, 6.9.6.6, 6.9.6.7, 6.9.6.8, 6.9.6.9, 6.9.6.10, 6.9.7.1, 6.9.7.2, 6.9.7.3, 6.9.7.4, 6.9.7.5, 6.9.7.6, 6.9.7.7, 6.9.7.8, 6.9.7.9, 6.9.7.10, 6.9.8.1, 6.9.8.2, 6.9.8.3, 6.9.8.4, 6.9.8.5, 6.9.8.6, 6.9.8.7, 6.9.8.8, 6.9.8.9, 6.9.8.10, 6.9.9.1, 6.9.9.2, 6.9.9.3, 6.9.9.4, 6.9.9.5, 6.9.9.6, 6.9.9.7, 6.9.9.8, 6.9.9.9, 6.9.9.10, 6.9.10.1, 6.9.10.2, 6.9.10.3, 6.9.10.4, 6.9.10.5, 6.9.10.6, 6.9.10.7, 6.9.10.8, 6.9.10.9, 6.9.10.10, 6.10.1.1, 6.10.1.2, 6.10.1.3, 6.10.1.4, 6.10.1.5, 6.10.1.6, 6.10.1.7, 6.10.1.8, 6.10.1.9, 6.10.1.10, 6.10.2.1, 6.10.2.2, 6.10.2.3, 6.10.2.4, 6.10.2.5, 6.10.2.6, 6.10.2.7, 6.10.2.8, 6.10.2.9, 6.10.2.10, 6.10.3.1, 6.10.3.2, 6.10.3.3, 6.10.3.4, 6.10.3.5, 6.10.3.6, 6.10.3.7, 6.10.3.8, 6.10.3.9, 6.10.3.10, 6.10.4.1, 6.10.4.2, 6.10.4.3, 6.10.4.4, 6.10.4.5, 6.10.4.6, 6.10.4.7, 6.10.4.8, 6.10.4.9, 6.10.4.10, 6.10.5.1, 6.10.5.2, 6.10.5.3, 6.10.5.4, 6.10.5.5, 6.10.5.6, 6.10.5.7, 6.10.5.8, 6.10.5.9, 6.10.5.10, 6.10.6.1, 6.10.6.2, 6.10.6.3, 6.10.6.4, 6.10.6.5, 6.10.6.6, 6.10.6.7, 6.10.6.8, 6.10.6.9, 6.10.6.10, 6.10.7.1, 6.10.7.2, 6.10.7.3, 6.10.7.4, 6.10.7.5, 6.10.7.6, 6.10.7.7, 6.10.7.8, 6.10.7.9, 6.10.7.10, 6.10.8.1, 6.10.8.2, 6.10.8.3, 6.10.8.4, 6.10.8.5, 6.10.8.6, 6.10.8.7, 6.10.8.8, 6.10.8.9, 6.10.8.10, 6.10.9.1, 6.10.9.2, 6.10.9.3, 6.10.9.4, 6.10.9.5, 6.10.9.6, 6.10.9.7, 6.10.9.8, 6.10.9.9, 6.10.9.10, 6.10.10.1, 6.10.10.2, 6.10.10.3, 6.10.10.4, 6.10.10.5, 6.10.10.6, 6.10.10.7, 6.10.10.8, 6.10.10.9, 6.10.10.10, 7.1.1.1, 7.1.1.2, 7.1.1.3, 7.1.1.4, 7.1.1.5, 7.1.1.6, 7.1.1.7, 7.1.1.8, 7.1.1.9, 7.1.1.10, 7.1.2.1, 7.1.2.2, 7.1.2.3, 7.1.2.4, 7.1.2.5, 7.1.2.6, 7.1.2.7, 7.1.2.8, 7.1.2.9, 7.1.2.10, 7.1.3.1, 7.1.3.2, 7.1.3.3, 7.1.3.4, 7.1.3.5, 7.1.3.6, 7.1.3.7, 7.1.3.8, 7.1.3.9, 7.1.3.10, 7.1.4.1, 7.1.4.2, 7.1.4.3, 7.1.4.4, 7.1.4.5, 7.1.4.6, 7.1.4.7, 7.1.4.8, 7.1.4.9, 7.1.4.10, 7.1.5.1, 7.1.5.2, 7.1.5.3, 7.1.5.4, 7.1.5.5, 7.1.5.6, 7.1.5.7, 7.1.5.8, 7.1.5.9, 7.1.5.10, 7.1.6.1, 7.1.6.2, 7.1.6.3, 7.1.6.4, 7.1.6.5, 7.1.6.6, 7.1.6.7, 7.1.6.8, 7.1.6.9, 7.1.6.10, 7.1.7.1, 7.1.7.2, 7.1.7.3, 7.1.7.4, 7.1.7.5, 7.1.7.6, 7.1.7.7, 7.1.7.8, 7.1.7.9, 7.1.7.10, 7.1.8.1, 7.1.8.2, 7.1.8.3, 7.1.8.4, 7.1.8.5, 7.1.8.6, 7.1.8.7, 7.1.8.8, 7.1.8.9, 7.1.8.10, 7.1.9.1, 7.1.9.2, 7.1.9.3, 7.1.9.4, 7.1.9.5, 7.1.9.6, 7.1.9.7, 7.1.9.8, 7.1.9.9, 7.1.9.10, 7.1.10.1, 7.1.10.2, 7.1.10.3, 7.1.10.4, 7.1.10.5, 7.1.10.6, 7.1.10.7, 7.1.10.8, 7.1.10.9, 7.1.10.10, 7.2.1.1, 7.2.1.2, 7.2.1.3, 7.2.1.4, 7.2.1.5, 7.2.1.6, 7.2.1.7, 7.2.1.8, 7.2.1.9, 7.2.1.10, 7.2.2.1, 7.2.2.2, 7.2.2.3, 7.2.2.4, 7.2.2.5, 7.2.2.6, 7.2.2.7, 7.2.2.8, 7.2.2.9, 7.2.2.10, 7.2.3.1, 7.2.3.2, 7.2.3.3, 7.2.3.4, 7.2.3.5, 7.2.3.6, 7.2.3.7, 7.2.3.8, 7.2.3.9, 7.2.3.10, 7.2.4.1, 7.2.4.2, 7.2.4.3, 7.2.4.4, 7.2.4.5, 7.2.4.6, 7.2.4.7, 7.2.4.8, 7.2.4.9, 7.2.4.10, 7.2.5.1, 7.2.5.2, 7.2.5.3, 7.2.5.4, 7.2.5.5, 7.2.5.6, 7.2.5.7, 7.2.5.8, 7.2.5.9, 7.2.5.10, 7.2.6.1, 7.2.6.2, 7.2.6.3, 7.2.6.4, 7.2.6.5, 7.2.6.6, 7.2.6.7, 7.2.6.8, 7.2.6.9, 7.2.6.10, 7.2.7.1, 7.2.7.2, 7.2.7.3, 7.2.7.4, 7.2.7.5, 7.2.7.6, 7.2.7.7, 7.2.7.8, 7.2.7.9, 7.2.7.10, 7.2.8.1, 7.2.8.2, 7.2.8.3, 7.2.8.4, 7.2.8.5, 7.2.8.6, 7.2.8.7, 7.2.8.8, 7.2.8.9, 7.2.8.10, 7.2.9.1, 7.2.9.2, 7.2.9.3, 7.2.9.4, 7.2.9.5, 7.2.9.6, 7.2.9.7, 7.2.9.8, 7.2.9.9, 7.2.9.10, 7.2.10.1, 7.2.10.2, 7.2.10.3, 7.2.10.4, 7.2.10.5, 7.2.10.6, 7.2.10.7, 7.2.10.8, 7.2.10.9, 7.2.10.10, 7.3.1.1, 7.3.1.2, 7.3.1.3, 7.3.1.4, 7.3.1.5, 7.3.1.6, 7.3.1.7, 7.3.1.8, 7.3.1.9, 7.3.1.10, 7.3.2.1, 7.3.2.2, 7.3.2.3, 7.3.2.4, 7.3.2.5, 7.3.2.6, 7.3.2.7, 7.3.2.8, 7.3.2.9, 7.3.2.10, 7.3.3.1, 7.3.3.2, 7.3.3.3, 7.3.3.4, 7.3.3.5, 7.3.3.6, 7.3.3.7, 7.3.3.8, 7.3.3.9, 7.3.3.10, 7.3.4.1, 7.3.4.2, 7.3.4.3, 7.3.4.4, 7.3.4.5, 7.3.4.6, 7.3.4.7, 7.3.4.8, 7.3.4.9, 7.3.4.10, 7.3.5.1, 7.3.5.2, 7.3.5.3, 7.3.5.4, 7.3.5.5, 7.3.5.6, 7.3.5.7, 7.3.5.8, 7.3.5.9, 7.3.5.10, 7.3.6.1, 7.3.6.2, 7.3.6.3, 7.3.6.4, 7.3.6.5, 7.3.6.6, 7.3.6.7, 7.3.6.8, 7.3.6.9, 7.3.6.10, 7.3.7.1, 7.3.7.2, 7.3.7.3, 7.3.7.4, 7.3.7.5, 7.3.7.6, 7.3.7.7, 7.3.7.8, 7.3.7.9, 7.3.7.10, 7.3.8.1, 7.3.8.2, 7.3.8.3, 7.3.8.4, 7.3.8.5, 7.3.8.6, 7.3.8.7, 7.3.8.8, 7.3.8.9, 7.3.8.10, 7.3.9.1, 7.3.9.2, 7.3.9.3, 7.3.9.4, 7.3.9.5, 7.3.9.6, 7.3.9.7, 7.3.9.8, 7.3.9.9, 7.3.9.10, 7.3.10.1, 7.3.10.2, 7.3.10.3, 7.3.10.4, 7.3.10.5, 7.3.10.6, 7.3.10.7, 7.3.10.8, 7.3.10.9, 7.3.10.10, 7.4.1.1, 7.4.1.2, 7.4.1.3, 7.4.1.4, 7.4.1.5, 7.4.1.6, 7.4.1.7, 7.4.1.8, 7.4.1.9, 7.4.1.10, 7.4.2.1, 7.4.2.2, 7.4.2.3, 7.4.2.4, 7.4.2.5, 7.4.2.6, 7.4.2.7, 7.4.2.8, 7.4.2.9, 7.4.2.10, 7.4.3.1, 7.4.3.2, 7.4.3.3, 7.4.3.4, 7.4.3.5, 7.4.3.6, 7.4.3.7, 7.4.3.8, 7.4.3.9, 7.4.3.10, 7.4.4.1, 7.4.4.2, 7.4.4.3, 7.4.4.4, 7.4.4.5, 7.4.4.6, 7.4.4.7, 7.4.4.8, 7.4.4.9, 7.4.4.10, 7.4.5.1, 7.4.5.2, 7.4.5.3, 7.4.5.4, 7.4.5.5, 7.4.5.6, 7.4.5.7, 7.4.5.8, 7.4.5.9, 7.4.5.10, 7.4.6.1, 7.4.6.2, 7.4.6.3, 7.4.6.4, 7.4.6.5, 7.4.6.6, 7.4.6.7, 7.4.6.8, 7.4.6.9, 7.4.6.10, 7.4.7.1, 7.4.7.2, 7.4.7.3, 7.4.7.4, 7.4.7.5, 7.4.7.6, 7.4.7.7, 7.4.7.8, 7.4.7.9, 7.4.7.10, 7.4.8.1, 7.4.8.2, 7.4.8.3, 7.4.8.4, 7.4.8.5, 7.4.8.6, 7.4.8.7, 7.4.8.8, 7.4.8.9, 7.4.8.10, 7.4.9.1, 7.4.9.2, 7.4.9.3, 7.4.9.4, 7.4.9.5, 7.4.9.6, 7.4.9.7, 7.4.9.8, 7.4.9.9, 7.4.9.10, 7.4.10.1, 7.4.10.2, 7.4.10.3, 7.4.10.4, 7.4.10.5, 7.4.10.6, 7.4.10.7, 7.4.10.8, 7.4.10.9, 7.4.10.10, 7.5.1.1, 7.5.1.2, 7.5.1.3, 7.5.1.4, 7.5.1.5, 7.5.1.6, 7.5.1.7, 7.5.1.8, 7.5.1.9, 7.5.1.10, 7.5.2.1, 7.5.2.2, 7.5.2.3, 7.5.2.4, 7.5.2.5, 7.5.2.6, 7.5.2.7, 7.5.2.8, 7.5.2.9, 7.5.2.10, 7.5.3.1, 7.5.3.2, 7.5.3.3, 7.5.3.4, 7.5.3.5, 7.5.3.6, 7.5.3.7, 7.5.3.8, 7.5.3.9, 7.5.3.10, 7.5.4.1, 7.5.4.2, 7.5.4.3, 7.5.4.4, 7.5.4.5, 7.5.4.6, 7.5.4.7, 7.5.4.8, 7.5.4.9, 7.5.4.10, 7.5.5.1, 7.5.5.2, 7.5.5.3, 7.5.5.4, 7.5.5.5, 7.5.5.6, 7.5.5.7, 7.5.5.8, 7.5.5.9, 7.5.5.10, 7.5.6.1, 7.5.6.2, 7.5.6.3, 7.5.6.4, 7.5.6.5, 7.5.6.6, 7.5.6.7, 7.5.6.8, 7.5.6.9, 7.5.6.10, 7.5.7.1, 7.5.7.2, 7.5.7.3, 7.5.7.4, 7.5.7.5, 7.5.7.6, 7.5.7.7, 7.5.7.8, 7.5.7.9, 7.5.7.10, 7.5.8.1, 7.5.8.2, 7.5.8.3, 7.5.8.4, 7.5.8.5, 7.5.8.6, 7.5.8.7, 7.5.8.8, 7.5.8.9, 7.5.8.10, 7.5.9.1, 7.5.9.2, 7.5.9.3, 7.5.9.4, 7.5.9.5, 7.5.9.6, 7.5.9.7, 7.5.9.8, 7.5.9.9, 7.5.9.10, 7.5.10.1, 7.5.10.2, 7.5.10.3, 7.5.10.4, 7.5.10.5, 7.5.10.6, 7.5.10.7, 7.5.10.8, 7.5.10.9, 7.5.10.10, 7.6.1.1, 7.6.1.2, 7.6.1.3, 7.6.1.4, 7.6.1.5, 7.6.1.6, 7.6.1.7, 7.6.1.8, 7.6.1.9, 7.6.1.10, 7.6.2.1, 7.6.2.2, 7.6.2.3, 7.6.2.4, 7.6.2.5, 7.6.2.6, 7.6.2.7, 7.6.2.8, 7.6.2.9, 7.6.2.10, 7.6.3.1, 7.6.3.2, 7.6.3.3, 7.6.3.4, 7.6.3.5, 7.6.3.6, 7.6.3.7, 7.6.3.8, 7.6.3.9, 7.6.3.10, 7.6.4.1, 7.6.4.2, 7.6.4.3, 7.6.4.4, 7.6.4.5, 7.6.4.6, 7.6.4.7, 7.6.4.8, 7.6.4.9, 7.6.4.10, 7.6.5.1, 7.6.5.2, 7.6.5.3, TABLE 2-continued 7.6.5.4, 7.6.5.5, 7.6.5.6, 7.6.5.7, 7.6.5.8, 7.6.5.9, 7.6.5.10, 7.6.6.1, 7.6.6.2, 7.6.6.3, 7.6.6.4, 7.6.6.5, 7.6.6.6, 7.6.6.7, 7.6.6.8, 7.6.6.9, 7.6.6.10, 7.6.7.1, 7.6.7.2, 7.6.7.3, 7.6.7.4, 7.6.7.5, 7.6.7.6, 7.6.7.7, 7.6.7.8, 7.6.7.9, 7.6.7.10, 7.6.8.1, 7.6.8.2, 7.6.8.3, 7.6.8.4, 7.6.8.5, 7.6.8.6, 7.6.8.7, 7.6.8.8, 7.6.8.9, 7.6.8.10, 7.6.9.1, 7.6.9.2, 7.6.9.3, 7.6.9.4, 7.6.9.5, 7.6.9.6, 7.6.9.7, 7.6.9.8, 7.6.9.9, 7.6.10.1, 7.6.10.2, 7.6.10.3, 7.6.10.4, 7.6.10.5, 7.6.10.6, 7.6.10.7, 7.6.10.8, 7.6.10.9, 7.6.10.10, 7.7.1.1, 7.7.1.2, 7.7.1.3, 7.7.1.4, 7.7.1.5, 7.7.1.6, 7.7.1.7, 7.7.1.8, 7.7.1.9, 7.7.1.10, 7.7.2.1, 7.7.2.2, 7.7.2.3, 7.7.2.4, 7.7.2.5, 7.7.2.6, 7.7.2.7, 7.7.2.8, 7.7.2.9, 7.7.2.10, 7.7.3.1, 7.7.3.2, 7.7.3.3, 7.7.3.4, 7.7.3.5, 7.7.3.6, 7.7.3.7, 7.7.3.8, 7.7.3.9, 7.7.3.10, 7.7.4.1, 7.7.4.2, 7.7.4.3, 7.7.4.4, 7.7.4.5, 7.7.4.6, 7.7.4.7, 7.7.4.8, 7.7.4.9, 7.7.4.10, 7.7.5.1, 7.7.5.2, 7.7.5.3, 7.7.5.4, 7.7.5.5, 7.7.5.6, 7.7.5.7, 7.7.5.8, 7.7.5.9, 7.7.5.10, 7.7.6.1, 7.7.6.2, 7.7.6.3, 7.7.6.4, 7.7.6.5, 7.7.6.6, 7.7.6.7, 7.7.6.8, 7.7.6.9, 7.7.6.10, 7.7.7.1, 7.7.7.2, 7.7.7.3, 7.7.7.4, 7.7.7.5, 7.7.7.6, 7.7.7.7, 7.7.7.8, 7.7.7.9, 7.7.7.10, 7.7.8.1, 7.7.8.2, 7.7.8.3, 7.7.8.4, 7.7.8.5, 7.7.8.6, 7.7.8.7, 7.7.8.8, 7.7.8.9, 7.7.8.10, 7.7.9.1, 7.7.9.2, 7.7.9.3, 7.7.9.4, 7.7.9.5, 7.7.9.6, 7.7.9.7, 7.7.9.8, 7.7.9.9, 7.7.9.10, 7.7.10.1, 7.7.10.2, 7.7.10.3, 7.7.10.4, 7.7.10.5, 7.7.10.6, 7.7.10.7, 7.7.10.8, 7.7.10.9, 7.7.10.10, 7.8.1.1, 7.8.1.2, 7.8.1.3, 7.8.1.4, 7.8.1.5, 7.8.1.6, 7.8.1.7, 7.8.1.8, 7.8.1.9, 7.8.1.10, 7.8.2.1, 7.8.2.2, 7.8.2.3, 7.8.2.4, 7.8.2.5, 7.8.2.6, 7.8.2.7, 7.8.2.8, 7.8.2.9, 7.8.2.10, 7.8.3.1, 7.8.3.2, 7.8.3.3, 7.8.3.4, 7.8.3.5, 7.8.3.6, 7.8.3.7, 7.8.3.8, 7.8.3.9, 7.8.3.10, 7.8.4.1, 7.8.4.2, 7.8.4.3, 7.8.4.4, 7.8.4.5, 7.8.4.6, 7.8.4.7, 7.8.4.8, 7.8.4.9, 7.8.4.10, 7.8.5.1, 7.8.5.2, 7.8.5.3, 7.8.5.4, 7.8.5.5, 7.8.5.6, 7.8.5.7, 7.8.5.8, 7.8.5.9, 7.8.5.10, 7.8.6.1, 7.8.6.2, 7.8.6.3, 7.8.6.4, 7.8.6.5, 7.8.6.6, 7.8.6.7, 7.8.6.8, 7.8.6.9, 7.8.6.10, 7.8.7.1, 7.8.7.2, 7.8.7.3, 7.8.7.4, 7.8.7.5, 7.8.7.6, 7.8.7.7, 7.8.7.8, 7.8.7.9, 7.8.7.10, 7.8.8.1, 7.8.8.2, 7.8.8.3, 7.8.8.4, 7.8.8.5, 7.8.8.6, 7.8.8.7, 7.8.8.8, 7.8.8.9, 7.8.8.10, 7.8.9.1, 7.8.9.2, 7.8.9.3, 7.8.9.4, 7.8.9.5, 7.8.9.6, 7.8.9.7, 7.8.9.8, 7.8.9.9, 7.8.9.10, 7.8.10.1, 7.8.10.2, 7.8.10.3, 7.8.10.4, 7.8.10.5, 7.8.10.6, 7.8.10.7, 7.8.10.8, 7.8.10.9, 7.8.10.10, 7.9.1.1, 7.9.1.2, 7.9.1.3, 7.9.1.4, 7.9.1.5, 7.9.1.6, 7.9.1.7, 7.9.1.8, 7.9.1.9, 7.9.1.10, 7.9.2.1, 7.9.2.2, 7.9.2.3, 7.9.2.4, 7.9.2.5, 7.9.2.6, 7.9.2.7, 7.9.2.8, 7.9.2.9, 7.9.2.10, 7.9.3.1, 7.9.3.2, 7.9.3.3, 7.9.3.4, 7.9.3.5, 7.9.3.7, 7.9.3.8, 7.9.3.9, 7.9.3.10, 7.9.4.1, 7.9.4.2, 7.9.4.3, 7.9.4.4, 7.9.4.5, 7.9.4.6, 7.9.4.7, 7.9.4.8, 7.9.4.9, 7.9.4.10, 7.9.5.1, 7.9.5.2, 7.9.5.3, 7.9.5.4, 7.9.5.5, 7.9.5.6, 7.9.5.7, 7.9.5.8, 7.9.5.9, 7.9.5.10, 7.9.6.1, 7.9.6.2, 7.9.6.3, 7.9.6.4, 7.9.6.5, 7.9.6.6, 7.9.6.7, 7.9.6.8, 7.9.6.9, 7.9.6.10, 7.9.7.1, 7.9.7.2, 7.9.7.3, 7.9.7.4, 7.9.7.5, 7.9.7.6, 7.9.7.7, 7.9.7.8, 7.9.7.9, 7.9.7.10, 7.9.8.1, 7.9.8.2, 7.9.8.3, 7.9.8.4, 7.9.8.5, 7.9.8.6, 7.9.8.7, 7.9.8.8, 7.9.8.9, 7.9.8.10, 7.9.9.1, 7.9.9.2, 7.9.9.3, 7.9.9.4, 7.9.9.5, 7.9.9.6, 7.9.9.7, 7.9.9.8, 7.9.9.9, 7.9.9.10, 7.9.10.1, 7.9.10.2, 7.9.10.3, 7.9.10.4, 7.9.10.5, 7.9.10.6, 7.9.10.7, 7.9.10.8, 7.9.10.9, 7.9.10.10, 7.10.1.1, 7.10.1.2, 7.10.1.3, 7.10.1.4, 7.10.1.5, 7.10.1.6, 7.10.1.7, 7.10.1.8, 7.10.1.9, 7.10.1.10, 7.10.2.1, 7.10.2.2, 7.10.2.3, 7.10.2.4, 7.10.2.5, 7.10.2.6, 7.10.2.7, 7.10.2.8, 7.10.2.9, 7.10.2.10, 7.10.3.1, 7.10.3.2, 7.10.3.3, 7.10.3.4, 7.10.3.5, 7.10.3.6, 7.10.3.7, 7.10.3.8, 7.10.3.9, 7.10.3.10, 7.10.4.1, 7.10.4.2, 7.10.4.3, 7.10.4.4, 7.10.4.5, 7.10.4.6, 7.10.4.7, 7.10.4.8, 7.10.4.9, 7.10.4.10, 7.10.5.1, 7.10.5.2, 7.10.5.3, 7.10.5.4, 7.10.5.5, 7.10.5.6, 7.10.5.7, 7.10.5.8, 7.10.5.9, 7.10.5.10, 7.10.6.1, 7.10.6.2, 7.10.6.3, 7.10.6.4, 7.10.6.5, 7.10.6.6, 7.10.6.7, 7.10.6.8, 7.10.6.9, 7.10.6.10, 7.10.7.1, 7.10.7.2, 7.10.7.3, 7.10.7.4, 7.10.7.5, 7.10.7.6, 7.10.7.7, 7.10.7.8, 7.10.7.9, 7.10.7.10, 7.10.8.1, 7.10.8.2, 7.10.8.3, 7.10.8.4, 7.10.8.5, 7.10.8.6, 7.10.8.7, 7.10.8.8, 7.10.8.9, 7.10.8.10, 7.10.9.1, 7.10.9.2, 7.10.9.3, 7.10.9.4, 7.10.9.5, 7.10.9.6, 7.10.9.7, 7.10.9.8, 7.10.9.9, 7.10.9.10, 7.10.10.1, 7.10.10.2, 7.10.10.3, 7.10.10.4, 7.10.10.5, 7.10.10.6, 7.10.10.7, 7.10.10.8, 7.10.10.9, 7.10.10.10, 8.1.1.1, 8.1.1.2, 8.1.1.3, 8.1.1.4, 8.1.1.5, 8.1.1.6, 8.1.1.7, 8.1.1.8, 8.1.1.9, 8.1.1.10, 8.1.2.1, 8.1.2.2, 8.1.2.3, 8.1.2.4, 8.1.2.5, 8.1.2.6, 8.1.2.7, 8.1.2.8, 8.1.2.9, 8.1.2.10, 8.1.3.1, 8.1.3.2, 8.1.3.3, 8.1.3.4, 8.1.3.5, 8.1.3.6, 8.1.3.7, 8.1.3.8, 8.1.3.9, 8.1.3.10, 8.1.4.1, 8.1.4.2, 8.1.4.3, 8.1.4.4, 8.1.4.5, 8.1.4.6, 8.1.4.7, 8.1.4.8, 8.1.4.9, 8.1.4.10, 8.1.5.1, 8.1.5.2, 8.1.5.3, 8.1.5.4, 8.1.5.5, 8.1.5.6, 8.1.5.7, 8.1.5.8, 8.1.5.9, 8.1.5.10, 8.1.6.1, 8.1.6.2, 8.1.6.3, 8.1.6.4, 8.1.6.5, 8.1.6.6, 8.1.6.7, 8.1.6.8, 8.1.6.9, 8.1.6.10, 8.1.7.1, 8.1.7.2, 8.1.7.3, 8.1.7.4, 8.1.7.5, 8.1.7.6, 8.1.7.7, 8.1.7.8, 8.1.7.9, 8.1.7.10, 8.1.8.1, 8.1.8.2, 8.1.8.3, 8.1.8.4, 8.1.8.5, 8.1.8.6, 8.1.8.7, 8.1.8.8, 8.1.8.9, 8.1.8.10, 8.1.9.1, 8.1.9.2, 8.1.9.3, 8.1.9.4, 8.1.9.5, 8.1.9.6, 8.1.9.7, 8.1.9.8, 8.1.9.9, 8.1.9.10, 8.1.10.1, 8.1.10.2, 8.1.10.3, 8.1.10.4, 8.1.10.5, 8.1.10.6, 8.1.10.7, 8.1.10.8, 8.1.10.9, 8.1.10.10, 8.2.1.1, 8.2.1.2, 8.2.1.3, 8.2.1.4, 8.2.1.5, 8.2.1.6, 8.2.1.7, 8.2.1.8, 8.2.1.9, 8.2.1.10, 8.2.2.1, 8.2.2.2, 8.2.2.3, 8.2.2.4, 8.2.2.5, 8.2.2.6, 8.2.2.7, 8.2.2.8, 8.2.2.9, 8.2.2.10, 8.2.3.1, 8.2.3.2, 8.2.3.3, 8.2.3.4, 8.2.3.5, 8.2.3.6, 8.2.3.7, 8.2.3.8, 8.2.3.9, 8.2.3.10, 8.2.4.1, 8.2.4.2, 8.2.4.3, 8.2.4.4, 8.2.4.5, 8.2.4.6, 8.2.4.7, 8.2.4.8, 8.2.4.9, 8.2.4.10, 8.2.5.1, 8.2.5.2, 8.2.5.3, 8.2.5.4, 8.2.5.5, 8.2.5.6, 8.2.5.7, 8.2.5.8, 8.2.5.9, 8.2.5.10, 8.2.6.1, 8.2.6.2, 8.2.6.3, 8.2.6.4, 8.2.6.5, 8.2.6.6, 8.2.6.7, 8.2.6.8, 8.2.6.9, 8.2.6.10, 8.2.7.1, 8.2.7.2, 8.2.7.3, 8.2.7.4, 8.2.7.5, 8.2.7.6, 8.2.7.7, 8.2.7.8, 8.2.7.9, 8.2.7.10, 8.2.8.1, 8.2.8.2, 8.2.8.3, 8.2.8.4, 8.2.8.5, 8.2.8.6, 8.2.8.7, 8.2.8.8, 8.2.8.9, 8.2.8.10, 8.2.9.1, 8.2.9.2, 8.2.9.3, 8.2.9.4, 8.2.9.5, 8.2.9.6, 8.2.9.7, 8.2.9.8, 8.2.9.9, 8.2.9.10, 8.2.10.1, 8.2.10.2, 8.2.10.3, 8.2.10.4, 8.2.10.5, 8.2.10.6, 8.2.10.7, 8.2.10.8, 8.2.10.9, 8.2.10.10, 8.3.1.1, 8.3.1.2, 8.3.1.3, 8.3.1.4, 8.3.1.5, 8.3.1.6, 8.3.1.7, 8.3.1.8, 8.3.1.9, 8.3.1.10, 8.3.2.1, 8.3.2.2, 8.3.2.3, 8.3.2.4, 8.3.2.5, 8.3.2.6, 8.3.2.7, 8.3.2.8, 8.3.2.9, 8.3.2.10, 8.3.3.1, 8.3.3.2, 8.3.3.3, 8.3.3.4, 8.3.3.5, 8.3.3.6, 8.3.3.7, 8.3.3.8, 8.3.3.9, 8.3.3.10, 8.3.4.1, 8.3.4.2, 8.3.4.3, 8.3.4.4, 8.3.4.5, 8.3.4.6, 8.3.4.7, 8.3.4.8, 8.3.4.9, 8.3.4.10, 8.3.5.1, 8.3.5.2, 8.3.5.3, 8.3.5.4, 8.3.5.5, 8.3.5.6, 8.3.5.7, 8.3.5.8, 8.3.5.9, 8.3.5.10, 8.3.6.1, 8.3.6.2, 8.3.6.3, 8.3.6.4, 8.3.6.5, 8.3.6.6, 8.3.6.7, 8.3.6.8, 8.3.6.9, 8.3.6.10, 8.3.7.1, 8.3.7.2, 8.3.7.3, 8.3.7.4, 8.3.7.5, 8.3.7.6, 8.3.7.7, 8.3.7.8, 8.3.7.9, 8.3.7.10, 8.3.8.1, 8.3.8.2, 8.3.8.3, 8.3.8.4, 8.3.8.5, 8.3.8.6, 8.3.8.7, 8.3.8.8, 8.3.8.9, 8.3.8.10, 8.3.9.1, 8.3.9.2, 8.3.9.3, 8.3.9.4, 8.3.9.5, 8.3.9.6, 8.3.9.7, 8.3.9.8, 8.3.9.9, 8.3.9.10, 8.3.10.1, 8.3.10.2, 8.3.10.3, 8.3.10.4, 8.3.10.5, 8.3.10.6, 8.3.10.7, 8.3.10.8, 8.3.10.9, 8.3.10.10, 8.4.1.1, 8.4.1.2, 8.4.1.3, 8.4.1.4, 8.4.1.5, 8.4.1.6, 8.4.1.7, 8.4.1.8, 8.4.1.9, 8.4.1.10, 8.4.2.1, 8.4.2.2, 8.4.2.3, 8.4.2.4, 8.4.2.5, 8.4.2.6, 8.4.2.7, 8.4.2.8, 8.4.2.9, 8.4.2.10, 8.4.3.1, 8.4.3.2, 8.4.3.3, 8.4.3.4, 8.4.3.5, 8.4.3.6, 8.4.3.7, 8.4.3.8, 8.4.3.9, 8.4.3.10, 8.4.4.1, 8.4.4.2, 8.4.4.3, 8.4.4.4, 8.4.4.5, 8.4.4.6, 8.4.4.7, 8.4.4.8, 8.4.4.9, 8.4.4.10, 8.4.5.1, 8.4.5.2, 8.4.5.3, 8.4.5.4, 8.4.5.5, 8.4.5.6, 8.4.5.7, 8.4.5.8, 8.4.5.9, 8.4.5.10, 8.4.6.1, 8.4.6.2, 8.4.6.3, 8.4.6.4, 8.4.6.5, 8.4.6.6, 8.4.6.7, 8.4.6.8, 8.4.6.9, 8.4.6.10, 8.4.7.1, 8.4.7.2, 8.4.7.3, 8.4.7.4, 8.4.7.5, 8.4.7.6, 8.4.7.7, 8.4.7.8, 8.4.7.9, 8.4.7.10, 8.4.8.1, 8.4.8.2, 8.4.8.3, 8.4.8.4, 8.4.8.5, 8.4.8.6, 8.4.8.7, 8.4.8.8, 8.4.8.9, 8.4.8.10, 8.4.9.1, 8.4.9.2, 8.4.9.3, 8.4.9.4, 8.4.9.5, 8.4.9.6, 8.4.9.7, 8.4.9.8, 8.4.9.9, 8.4.9.10, 8.4.10.1, 8.4.10.2, 8.4.10.3, 8.4.10.4, 8.4.10.5, 8.4.10.6, 8.4.10.7, 8.4.10.8, 8.4.10.9, 8.4.10.10, 8.5.1.1, 8.5.1.2, 8.5.1.3, 8.5.1.4, 8.5.1.5, 8.5.1.6, 8.5.1.7, 8.5.1.8, 8.5.1.9, 8.5.1.10, 8.5.2.1, 8.5.2.2, 8.5.2.3, 8.5.2.4, 8.5.2.5, 8.5.2.6, 8.5.2.7, 8.5.2.8, 8.5.2.9, 8.5.2.10, 8.5.3.1, 8.5.3.2, 8.5.3.3, 8.5.3.4, 8.5.3.5, 8.5.3.6, 8.5.3.7, 8.5.3.8, 8.5.3.9, 8.5.3.10, 8.5.4.1, 8.5.4.2, 8.5.4.3, 8.5.4.4, 8.5.4.5, 8.5.4.6, 8.5.4.7, 8.5.4.8, 8.5.4.9, 8.5.4.10, 8.5.5.1, 8.5.5.2, 8.5.5.3, 8.5.5.4, 8.5.5.5, 8.5.5.6, 8.5.5.7, 8.5.5.8, 8.5.5.9, 8.5.5.10, 8.5.6.1, 8.5.6.2, 8.5.6.3, 8.5.6.4, 8.5.6.5, 8.5.6.6, 8.5.6.7, 8.5.6.8, 8.5.6.9, 8.5.6.10, 8.5.7.1, 8.5.7.2, 8.5.7.3, 8.5.7.4, 8.5.7.5, TABLE 2-continued 8.5.7.6, 8.5.7.7, 8.5.7.8, 8.5.7.9, 8.5.7.10, 8.5.8.1, 8.5.8.2, 8.5.8.3, 8.5.8.4, 8.5.8.5, 8.5.8.6, 8.5.8.7, 8.5.8.8, 8.5.8.9, 8.5.8.10, 8.5.9.1, 8.5.9.2, 8.5.9.3, 8.5.9.4, 8.5.9.5, 8.5.9.6, 8.5.9.7, 8.5.9.8, 8.5.9.9, 8.5.9.10, 8.5.10.1, 8.5.10.2, 8.5.10.3, 8.5.10.4, 8.5.10.5, 8.5.10.6, 8.5.10.7, 8.5.10.8, 8.5.10.9, 8.5.10.10, 8.6.1.1, 8.6.1.2, 8.6.1.3, 8.6.1.4, 8.6.1.5, 8.6.1.6, 8.6.1.7, 8.6.1.8, 8.6.1.9, 8.6.1.10, 8.6.2.1, 8.6.2.2, 8.6.2.3, 8.6.2.4, 8.6.2.5, 8.6.2.6, 8.6.2.7, 8.6.2.8, 8.6.2.9, 8.6.2.10, 8.6.3.1, 8.6.3.2, 8.6.3.3, 8.6.3.4, 8.6.3.5, 8.6.3.6, 8.6.3.7, 8.6.3.8, 8.6.3.9, 8.6.3.10, 8.6.4.1, 8.6.4.2, 8.6.4.3, 8.6.4.4, 8.6.4.5, 8.6.4.6, 8.6.4.7, 8.6.4.8, 8.6.4.9, 8.6.4.10, 8.6.5.1, 8.6.5.2, 8.6.5.3, 8.6.5.4, 8.6.5.5, 8.6.5.6, 8.6.5.7, 8.6.5.8, 8.6.5.9, 8.6.5.10, 8.6.6.1, 8.6.6.2, 8.6.6.3, 8.6.6.4, 8.6.6.5, 8.6.6.6, 8.6.6.7, 8.6.6.8, 8.6.6.9, 8.6.6.10, 8.6.7.1, 8.6.7.2, 8.6.7.3, 8.6.7.4, 8.6.7.5, 8.6.7.6, 8.6.7.7, 8.6.7.8, 8.6.7.9, 8.6.7.10, 8.6.8.1, 8.6.8.2, 8.6.8.3, 8.6.8.4, 8.6.8.5, 8.6.8.6, 8.6.8.7, 8.6.8.8, 8.6.8.9, 8.6.8.10, 8.6.9.1, 8.6.9.2, 8.6.9.3, 8.6.9.4, 8.6.9.5, 8.6.9.6, 8.6.9.7, 8.6.9.8, 8.6.9.9, 8.6.9.10, 8.6.10.1, 8.6.10.2, 8.6.10.3, 8.6.10.4, 8.6.10.5, 8.6.10.6, 8.6.10.7, 8.6.10.8, 8.6.10.9, 8.6.10.10, 8.7.1.1, 8.7.1.2, 8.7.1.3, 8.7.1.4, 8.7.1.5, 8.7.1.6, 8.7.1.7, 8.7.1.8, 8.7.1.9, 8.7.1.10, 8.7.2.1, 8.7.2.2, 8.7.2.3, 8.7.2.4, 8.7.2.5, 8.7.2.6, 8.7.2.7, 8.7.2.8, 8.7.2.9, 8.7.2.10, 8.7.3.1, 8.7.3.2, 8.7.3.3, 8.7.3.4, 8.7.3.5, 8.7.3.6, 8.7.3.7, 8.7.3.8, 8.7.3.9, 8.7.3.10, 8.7.4.1, 8.7.4.2, 8.7.4.3, 8.7.4.4, 8.7.4.5, 8.7.4.6, 8.7.4.7, 8.7.4.8, 8.7.4.9, 8.7.4.10, 8.7.5.1, 8.7.5.2, 8.7.5.3, 8.7.5.4, 8.7.5.5, 8.7.5.6, 8.7.5.7, 8.7.5.8, 8.7.5.9, 8.7.5.10, 8.7.6.1, 8.7.6.2, 8.7.6.3, 8.7.6.4, 8.7.6.5, 8.7.6.6, 8.7.6.7, 8.7.6.8, 8.7.6.9, 8.7.6.10, 8.7.7.1, 8.7.7.2, 8.7.7.3, 8.7.7.4, 8.7.7.5, 8.7.7.6, 8.7.7.7, 8.7.7.8, 8.7.7.9, 8.7.7.10, 8.7.8.1, 8.7.8.2, 8.7.8.3, 8.7.8.4, 8.7.8.5, 8.7.8.6, 8.7.8.7, 8.7.8.8, 8.7.8.9, 8.7.8.10, 8.7.9.1, 8.7.9.2, 8.7.9.3, 8.7.9.4, 8.7.9.5, 8.7.9.6, 8.7.9.7, 8.7.9.8, 8.7.9.9, 8.7.9.10, 8.7.10.1, 8.7.10.2, 8.7.10.3, 8.7.10.4, 8.7.10.5, 8.7.10.6, 8.7.10.7, 8.7.10.8, 8.7.10.9, 8.7.10.10, 8.8.1.1, 8.8.1.2, 8.8.1.3, 8.8.1.4, 8.8.1.5, 8.8.1.6, 8.8.1.7, 8.8.1.8, 8.8.1.9, 8.8.1.10, 8.8.2.1, 8.8.2.2, 8.8.2.3, 8.8.2.4, 8.8.2.5, 8.8.2.6, 8.8.2.7, 8.8.2.8, 8.8.2.9, 8.8.2.10, 8.8.3.1, 8.8.3.2, 8.8.3.3, 8.8.3.4, 8.8.3.5, 8.8.3.6, 8.8.3.7, 8.8.3.8, 8.8.3.9, 8.8.3.10, 8.8.4.1, 8.8.4.2, 8.8.4.3, 8.8.4.4, 8.8.4.5, 8.8.4.6, 8.8.4.7, 8.8.4.8, 8.8.4.9, 8.8.4.10, 8.8.5.1, 8.8.5.2, 8.8.5.3, 8.8.5.4, 8.8.5.5, 8.8.5.6, 8.8.5.7, 8.8.5.8, 8.8.5.9, 8.8.5.10, 8.8.6.1, 8.8.6.2, 8.8.6.3, 8.8.6.4, 8.8.6.5, 8.8.6.6, 8.8.6.8, 8.8.6.9, 8.8.6.10, 8.8.7.1, 8.8.7.2, 8.8.7.3, 8.8.7.4, 8.8.7.5, 8.8.7.6, 8.8.7.7, 8.8.7.8, 8.8.7.9, 8.8.7.10, 8.8.8.1, 8.8.8.2, 8.8.8.3, 8.8.8.4, 8.8.8.5, 8.8.8.6, 8.8.8.7, 8.8.8.8, 8.8.8.9, 8.8.8.10, 8.8.9.1, 8.8.9.2, 8.8.9.3, 8.8.9.4, 8.8.9.5, 8.8.9.6, 8.8.9.7, 8.8.9.8, 8.8.9.9, 8.8.9.10, 8.8.10.1, 8.8.10.2, 8.8.10.3, 8.8.10.4, 8.8.10.5, 8.8.10.6, 8.8.10.7, 8.8.10.8, 8.8.10.9, 8.8.10.10, 8.9.1.1, 8.9.1.2, 8.9.1.3, 8.9.1.4, 8.9.1.5, 8.9.1.6, 8.9.1.7, 8.9.1.8, 8.9.1.9, 8.9.1.10, 8.9.2.1, 8.9.2.2, 8.9.2.3, 8.9.2.4, 8.9.2.5, 8.9.2.6, 8.9.2.7, 8.9.2.8, 8.9.2.9, 8.9.2.10, 8.9.3.1, 8.9.3.2, 8.9.3.3, 8.9.3.4, 8.9.3.5, 8.9.3.6, 8.9.3.7, 8.9.3.8, 8.9.3.9, 8.9.3.10, 8.9.4.1, 8.9.4.2, 8.9.4.3, 8.9.4.4, 8.9.4.5, 8.9.4.6, 8.9.4.7, 8.9.4.8, 8.9.4.9, 8.9.4.10, 8.9.5.1, 8.9.5.2, 8.9.5.3, 8.9.5.4, 8.9.5.5, 8.9.5.6, 8.9.5.7, 8.9.5.8, 8.9.5.9, 8.9.5.10, 8.9.6.1, 8.9.6.2, 8.9.6.3, 8.9.6.4, 8.9.6.5, 8.9.6.6, 8.9.6.7, 8.9.6.8, 8.9.6.9, 8.9.6.10, 8.9.7.1, 8.9.7.2, 8.9.7.3, 8.9.7.4, 8.9.7.5, 8.9.7.6, 8.9.7.7, 8.9.7.8, 8.9.7.9, 8.9.7.10, 8.9.8.1, 8.9.8.2, 8.9.8.3, 8.9.8.4, 8.9.8.5, 8.9.8.6, 8.9.8.7, 8.9.8.8, 8.9.8.9, 8.9.8.10, 8.9.9.1, 8.9.9.2, 8.9.9.3, 8.9.9.4, 8.9.9.5, 8.9.9.6, 8.9.9.7, 8.9.9.8, 8.9.9.9, 8.9.9.10, 8.9.10.1, 8.9.10.2, 8.9.10.3, 8.9.10.4, 8.9.10.5, 8.9.10.6, 8.9.10.7, 8.9.10.8, 8.9.10.9, 8.9.10.10, 8.10.1.1, 8.10.1.2, 8.10.1.3, 8.10.1.4, 8.10.1.5, 8.10.1.6, 8.10.1.7, 8.10.1.8, 8.10.1.9, 8.10.1.10, 8.10.2.1, 8.10.2.2, 8.10.2.3, 8.10.2.4, 8.10.2.5, 8.10.2.6, 8.10.2.7, 8.10.2.8, 8.10.2.9, 8.10.2.10, 8.10.3.1, 8.10.3.2, 8.10.3.3, 8.10.3.4, 8.10.3.5, 8.10.3.6, 8.10.3.7, 8.10.3.8, 8.10.3.9, 8.10.3.10, 8.10.4.1, 8.10.4.2, 8.10.4.3, 8.10.4.4, 8.10.4.5, 8.10.4.6, 8.10.4.7, 8.10.4.8, 8.10.4.9, 8.10.4.10, 8.10.5.1, 8.10.5.2, 8.10.5.3, 8.10.5.4, 8.10.5.5, 8.10.5.6, 8.10.5.7, 8.10.5.8, 8.10.5.9, 8.10.5.10, 8.10.6.1, 8.10.6.2, 8.10.6.3, 8.10.6.4, 8.10.6.5, 8.10.6.6, 8.10.6.7, 8.10.6.8, 8.10.6.9, 8.10.6.10, 8.10.7.1, 8.10.7.2, 8.10.7.3, 8.10.7.4, 8.10.7.5, 8.10.7.6, 8.10.7.7, 8.10.7.8, 8.10.7.9, 8.10.7.10, 8.10.8.1, 8.10.8.2, 8.10.8.3, 8.10.8.4, 8.10.8.5, 8.10.8.6, 8.10.8.7, 8.10.8.8, 8.10.8.9, 8.10.8.10, 8.10.9.1, 8.10.9.2, 8.10.9.3, 8.10.9.4, 8.10.9.5, 8.10.9.6, 8.10.9.7, 8.10.9.8, 8.10.9.9, 8.10.9.10, 8.10.10.1, 8.10.10.2, 8.10.10.3, 8.10.10.4, 8.10.10.5, 8.10.10.6, 8.10.10.7, 8.10.10.8, 8.10.10.9, 8.10.10.10, 9.1.1.1, 9.1.1.2, 9.1.1.3, 9.1.1.4, 9.1.1.5, 9.1.1.6, 9.1.1.7, 9.1.1.8, 9.1.1.9, 9.1.1.10, 9.1.2.1, 9.1.2.2, 9.1.2.3, 9.1.2.4, 9.1.2.5, 9.1.2.6, 9.1.2.7, 9.1.2.8, 9.1.2.9, 9.1.2.10, 9.1.3.1, 9.1.3.2, 9.1.3.3, 9.1.3.4, 9.1.3.5, 9.1.3.6, 9.1.3.7, 9.1.3.8, 9.1.3.9, 9.1.3.10, 9.1.4.1, 9.1.4.2, 9.1.4.3, 9.1.4.4, 9.1.4.5, 9.1.4.6, 9.1.4.7, 9.1.4.8, 9.1.4.9, 9.1.4.10, 9.1.5.1, 9.1.5.2, 9.1.5.3, 9.1.5.4, 9.1.5.5, 9.1.5.6, 9.1.5.7, 9.1.5.8, 9.1.5.9, 9.1.5.10, 9.1.6.1, 9.1.6.2, 9.1.6.3, 9.1.6.4, 9.1.6.5, 9.1.6.6, 9.1.6.7, 9.1.6.8, 9.1.6.9, 9.1.6.10, 9.1.7.1, 9.1.7.2, 9.1.7.3, 9.1.7.4, 9.1.7.5, 9.1.7.6, 9.1.7.7, 9.1.7.8, 9.1.7.9, 9.1.7.10, 9.1.8.1, 9.1.8.2, 9.1.8.3, 9.1.8.4, 9.1.8.5, 9.1.8.6, 9.1.8.7, 9.1.8.8, 9.1.8.9, 9.1.8.10, 9.1.9.1, 9.1.9.2, 9.1.9.3, 9.1.9.4, 9.1.9.5, 9.1.9.6, 9.1.9.7, 9.1.9.8, 9.1.9.9, 9.1.9.10, 9.1.10.1, 9.1.10.2, 9.1.10.3, 9.1.10.4, 9.1.10.5, 9.1.10.6, 9.1.10.7, 9.1.10.8, 9.1.10.9, 9.1.10.10, 9.2.1.1, 9.2.1.2, 9.2.1.3, 9.2.1.4, 9.2.1.5, 9.2.1.6, 9.2.1.7, 9.2.1.8, 9.2.1.9, 9.2.1.10, 9.2.2.1, 9.2.2.2, 9.2.2.3, 9.2.2.4, 9.2.2.5, 9.2.2.6, 9.2.2.7, 9.2.2.8, 9.2.2.9, 9.2.2.10, 9.2.3.1, 9.2.3.2, 9.2.3.3, 9.2.3.4, 9.2.3.5, 9.2.3.6, 9.2.3.7, 9.2.3.8, 9.2.3.9, 9.2.3.10, 9.2.4.1, 9.2.4.2, 9.2.4.3, 9.2.4.4, 9.2.4.5, 9.2.4.6, 9.2.4.7, 9.2.4.8, 9.2.4.9, 9.2.4.10, 9.2.5.1, 9.2.5.2, 9.2.5.3, 9.2.5.4, 9.2.5.5, 9.2.5.6, 9.2.5.7, 9.2.5.8, 9.2.5.9, 9.2.5.10, 9.2.6.1, 9.2.6.2, 9.2.6.3, 9.2.6.4, 9.2.6.5, 9.2.6.6, 9.2.6.7, 9.2.6.8, 9.2.6.9, 9.2.6.10, 9.2.7.1, 9.2.7.2, 9.2.7.3, 9.2.7.4, 9.2.7.5, 9.2.7.6, 9.2.7.7, 9.2.7.8, 9.2.7.9, 9.2.7.10, 9.2.8.1, 9.2.8.2, 9.2.8.3, 9.2.8.4, 9.2.8.5, 9.2.8.6, 9.2.8.7, 9.2.8.8, 9.2.8.9, 9.2.8.10, 9.2.9.1, 9.2.9.2, 9.2.9.3, 9.2.9.4, 9.2.9.5, 9.2.9.6, 9.2.9.7, 9.2.9.8, 9.2.9.9, 9.2.9.10, 9.2.10.1, 9.2.10.2, 9.2.10.3, 9.2.10.4, 9.2.10.5, 9.2.10.6, 9.2.10.7, 9.2.10.8, 9.2.10.9, 9.2.10.10, 9.3.1.1, 9.3.1.2, 9.3.1.3, 9.3.1.4, 9.3.1.5, 9.3.1.6, 9.3.1.7, 9.3.1.8, 9.3.1.9, 9.3.1.10, 9.3.2.1, 9.3.2.2, 9.3.2.3, 9.3.2.4, 9.3.2.5, 9.3.2.6, 9.3.2.7, 9.3.2.8, 9.3.2.9, 9.3.2.10, 9.3.3.1, 9.3.3.2, 9.3.3.3, 9.3.3.4, 9.3.3.5, 9.3.3.6, 9.3.3.7, 9.3.3.8, 9.3.3.9, 9.3.3.10, 9.3.4.1, 9.3.4.2, 9.3.4.3, 9.3.4.4, 9.3.4.5, 9.3.4.6, 9.3.4.7, 9.3.4.8, 9.3.4.9, 9.3.4.10, 9.3.5.1, 9.3.5.2, 9.3.5.3, 9.3.5.4, 9.3.5.5, 9.3.5.6, 9.3.5.7, 9.3.5.8, 9.3.5.9, 9.3.5.10, 9.3.6.1, 9.3.6.2, 9.3.6.3, 9.3.6.4, 9.3.6.5, 9.3.6.6, 9.3.6.7, 9.3.6.8, 9.3.6.9, 9.3.6.10, 9.3.7.1, 9.3.7.2, 9.3.7.3, 9.3.7.4, 9.3.7.5, 9.3.7.6, 9.3.7.7, 9.3.7.8, 9.3.7.9, 9.3.7.10, 9.3.8.1, 9.3.8.2, 9.3.8.3, 9.3.8.4, 9.3.8.5, 9.3.8.6, 9.3.8.7, 9.3.8.8, 9.3.8.9, 9.3.8.10, 9.3.9.1, 9.3.9.2, 9.3.9.3, 9.3.9.4, 9.3.9.5, 9.3.9.6, 9.3.9.7, 9.3.9.8, 9.3.9.9, 9.3.9.10, 9.3.10.1, 9.3.10.2, 9.3.10.3, 9.3.10.4, 9.3.10.5, 9.3.10.6, 9.3.10.7, 9.3.10.8, 9.3.10.9, 9.3.10.10, 9.4.1.1, 9.4.1.2, 9.4.1.3, 9.4.1.4, 9.4.1.5, 9.4.1.6, 9.4.1.7, 9.4.1.8, 9.4.1.9, 9.4.1.10, 9.4.2.1, 9.4.2.2, 9.4.2.3, 9.4.2.4, 9.4.2.5, 9.4.2.6, 9.4.2.7, 9.4.2.8, 9.4.2.9, 9.4.2.10, 9.4.3.1, 9.4.3.2, 9.4.3.3, 9.4.3.4, 9.4.3.5, 9.4.3.6, 9.4.3.7, 9.4.3.8, 9.4.3.9, 9.4.3.10, 9.4.4.1, 9.4.4.2, 9.4.4.3, 9.4.4.4, 9.4.4.5, 9.4.4.6, 9.4.4.7, 9.4.4.8, 9.4.4.9, 9.4.4.10, 9.4.5.1, 9.4.5.2, 9.4.5.3, 9.4.5.4, 9.4.5.5, 9.4.5.6, 9.4.5.7, 9.4.5.8, 9.4.5.9, 9.4.5.10, 9.4.6.1, 9.4.6.2, 9.4.6.3, 9.4.6.4, 9.4.6.5, 9.4.6.6, 9.4.6.7, 9.4.6.8, 9.4.6.9, 9.4.6.10, 9.4.7.1, 9.4.7.2, 9.4.7.3, 9.4.7.4, 9.4.7.5, 9.4.7.6, 9.4.7.7, 9.4.7.8, 9.4.7.9, 9.4.7.10, 9.4.8.1, 9.4.8.2, 9.4.8.3, 9.4.8.4, 9.4.8.5, 9.4.8.6, 9.4.8.7, 9.4.8.8, 9.4.8.9, 9.4.8.10, 9.4.9.1, 9.4.9.2, 9.4.9.3, 9.4.9.4, 9.4.9.5, 9.4.9.6, 9.4.9.7,

TABLE 2-continued 9.4.9.8, 9.4.9.9, 9.4.9.10, 9.4.10.1, 9.4.10.2, 9.4.10.3, 9.4.10.4, 9.4.10.5, 9.4.10.6, 9.4.10.7, 9.4.10.8, 9.4.10.9, 9.4.10.10, 9.5.1.1, 9.5.1.2, 9.5.1.3, 9.5.1.4, 9.5.1.5, 9.5.1.6, 9.5.1.7, 9.5.1.8, 9.5.1.9, 9.5.1.10, 9.5.2.1, 9.5.2.2, 9.5.2.3, 9.5.2.4, 9.5.2.5, 9.5.2.6, 9.5.2.7, 9.5.2.8, 9.5.2.9, 9.5.2.10, 9.5.3.1, 9.5.3.2, 9.5.3.3, 9.5.3.4, 9.5.3.5, 9.5.3.6, 9.5.3.7, 9.5.3.8, 9.5.3.9, 9.5.3.10, 9.5.4.1, 9.5.4.2, 9.5.4.3, 9.5.4.4, 9.5.4.5, 9.5.4.6, 9.5.4.7, 9.5.4.8, 9.5.4.9, 9.5.4.10, 9.5.5.1, 9.5.5.2, 9.5.5.3, 9.5.5.4, 9.5.5.5, 9.5.5.6, 9.5.5.7, 9.5.5.8, 9.5.5.9, 9.5.5.10, 9.5.6.1, 9.5.6.2, 9.5.6.3, 9.5.6.4, 9.5.6.5, 9.5.6.6, 9.5.6.7, 9.5.6.8, 9.5.6.9, 9.5.6.10, 9.5.7.1, 9.5.7.2, 9.5.7.3, 9.5.7.4, 9.5.7.5, 9.5.7.6, 9.5.7.7, 9.5.7.8, 9.5.7.9, 9.5.7.10, 9.5.8.1, 9.5.8.2, 9.5.8.3, 9.5.8.4, 9.5.8.5, 9.5.8.6, 9.5.8.7, 9.5.8.8, 9.5.8.9, 9.5.8.10, 9.5.9.1, 9.5.9.2, 9.5.9.3, 9.5.9.4, 9.5.9.5, 9.5.9.6, 9.5.9.7, 9.5.9.8, 9.5.9.9, 9.5.9.10, 9.5.10.1, 9.5.10.2, 9.5.10.3, 9.5.10.4, 9.5.10.5, 9.5.10.6, 9.5.10.7, 9.5.10.8, 9.5.10.9, 9.5.10.10, 9.6.1.1, 9.6.1.2, 9.6.1.3, 9.6.1.4, 9.6.1.5, 9.6.1.6, 9.6.1.7, 9.6.1.8, 9.6.1.9, 9.6.1.10, 9.6.2.1, 9.6.2.2, 9.6.2.3, 9.6.2.4, 9.6.2.5, 9.6.2.6, 9.6.2.7, 9.6.2.8, 9.6.2.9, 9.6.2.10, 9.6.3.1, 9.6.3.2, 9.6.3.3, 9.6.3.4, 9.6.3.5, 9.6.3.6, 9.6.3.7, 9.6.3.8, 9.6.3.9, 9.6.3.10, 9.6.4.1, 9.6.4.2, 9.6.4.3, 9.6.4.4, 9.6.4.5, 9.6.4.6, 9.6.4.7, 9.6.4.8, 9.6.4.9, 9.6.4.10, 9.6.5.1, 9.6.5.2, 9.6.5.3, 9.6.5.4, 9.6.5.5, 9.6.5.6, 9.6.5.7, 9.6.5.8, 9.6.5.9, 9.6.5.10, 9.6.6.1, 9.6.6.2, 9.6.6.3, 9.6.6.4, 9.6.6.5, 9.6.6.6, 9.6.6.7, 9.6.6.8, 9.6.6.9, 9.6.6.10, 9.6.7.1, 9.6.7.2, 9.6.7.3, 9.6.7.4, 9.6.7.5, 9.6.7.6, 9.6.7.7, 9.6.7.8, 9.6.7.9, 9.6.7.10, 9.6.8.1, 9.6.8.2, 9.6.8.3, 9.6.8.4, 9.6.8.5, 9.6.8.6, 9.6.8.7, 9.6.8.8, 9.6.8.9, 9.6.8.10, 9.6.9.1, 9.6.9.2, 9.6.9.3, 9.6.9.4, 9.6.9.5, 9.6.9.6, 9.6.9.7, 9.6.9.8, 9.6.9.9, 9.6.9.10, 9.6.10.1, 9.6.10.2, 9.6.10.3, 9.6.10.4, 9.6.10.5, 9.6.10.6, 9.6.10.7, 9.6.10.8, 9.6.10.9, 9.6.10.10, 9.7.1.1, 9.7.1.2, 9.7.1.3, 9.7.1.4, 9.7.1.5, 9.7.1.6, 9.7.1.7, 9.7.1.8, 9.7.1.9, 9.7.1.10, 9.7.2.1, 9.7.2.2, 9.7.2.3, 9.7.2.4, 9.7.2.5, 9.7.2.6, 9.7.2.7, 9.7.2.8, 9.7.2.9, 9.7.2.10, 9.7.3.1, 9.7.3.2, 9.7.3.3, 9.7.3.4, 9.7.3.5, 9.7.3.6, 9.7.3.7, 9.7.3.8, 9.7.3.9, 9.7.3.10, 9.7.4.1, 9.7.4.2, 9.7.4.3, 9.7.4.4, 9.7.4.5, 9.7.4.6, 9.7.4.7, 9.7.4.8, 9.7.4.9, 9.7.4.10, 9.7.5.1, 9.7.5.2, 9.7.5.3, 9.7.5.4, 9.7.5.5, 9.7.5.6, 9.7.5.7, 9.7.5.8, 9.7.5.9, 9.7.5.10, 9.7.6.1, 9.7.6.2, 9.7.6.3, 9.7.6.4, 9.7.6.5, 9.7.6.6, 9.7.6.7, 9.7.6.8, 9.7.6.9, 9.7.6.10, 9.7.7.1, 9.7.7.2, 9.7.7.3, 9.7.7.4, 9.7.7.5, 9.7.7.6, 9.7.7.7, 9.7.7.8, 9.7.7.9, 9.7.7.10, 9.7.8.1, 9.7.8.2, 9.7.8.3, 9.7.8.4, 9.7.8.5, 9.7.8.6, 9.7.8.7, 9.7.8.8, 9.7.8.9, 9.7.8.10, 9.7.9.1, 9.7.9.2, 9.7.9.3, 9.7.9.4, 9.7.9.5, 9.7.9.6, 9.7.9.7, 9.7.9.8, 9.7.9.9, 9.7.9.10, 9.7.10.1, 9.7.10.2, 9.7.10.3, 9.7.10.4, 9.7.10.5, 9.7.10.6, 9.7.10.7, 9.7.10.8, 9.7.10.9, 9.7.10.10, 9.8.1.1, 9.8.1.2, 9.8.1.3, 9.8.1.4, 9.8.1.5, 9.8.1.6, 9.8.1.7, 9.8.1.8, 9.8.1.9, 9.8.1.10, 9.8.2.1, 9.8.2.2, 9.8.2.3, 9.8.2.4, 9.8.2.5, 9.8.2.6, 9.8.2.7, 9.8.2.8, 9.8.2.9, 9.8.2.10, 9.8.3.1, 9.8.3.2, 9.8.3.3, 9.8.3.4, 9.8.3.5, 9.8.3.6, 9.8.3.7, 9.8.3.8, 9.8.3.9, 9.8.3.10, 9.8.4.1, 9.8.4.2, 9.8.4.3, 9.8.4.4, 9.8.4.5, 9.8.4.6, 9.8.4.7, 9.8.4.8, 9.8.4.9, 9.8.4.10, 9.8.5.1, 9.8.5.2, 9.8.5.3, 9.8.5.4, 9.8.5.5, 9.8.5.6, 9.8.5.7, 9.8.5.8, 9.8.5.9, 9.8.5.10, 9.8.6.1, 9.8.6.2, 9.8.6.3, 9.8.6.4, 9.8.6.5, 9.8.6.6, 9.8.6.7, 9.8.6.8, 9.8.6.9, 9.8.6.10, 9.8.7.1, 9.8.7.2, 9.8.7.3, 9.8.7.4, 9.8.7.5, 9.8.7.6, 9.8.7.7, 9.8.7.8, 9.8.7.9, 9.8.7.10, 9.8.8.1, 9.8.8.2, 9.8.8.3, 9.8.8.4, 9.8.8.5, 9.8.8.6, 9.8.8.7, 9.8.8.8, 9.8.8.9, 9.8.8.10, 9.8.9.1, 9.8.9.2, 9.8.9.3, 9.8.9.4, 9.8.9.5, 9.8.9.6, 9.8.9.7, 9.8.9.8, 9.8.9.9, 9.8.9.10, 9.8.10.1, 9.8.10.2, 9.8.10.3, 9.8.10.4, 9.8.10.5, 9.8.10.6, 9.8.10.7, 9.8.10.8, 9.8.10.9, 9.8.10.10, 9.9.1.1, 9.9.1.2, 9.9.1.3, 9.9.1.4, 9.9.1.5, 9.9.1.6, 9.9.1.7, 9.9.1.8, 9.9.1.9, 9.9.1.10, 9.9.2.1, 9.9.2.2, 9.9.2.3, 9.9.2.4, 9.9.2.5, 9.9.2.6, 9.9.2.7, 9.9.2.8, 9.9.2.9, 9.9.2.10, 9.9.3.1, 9.9.3.2, 9.9.3.3, 9.9.3.4, 9.9.3.5, 9.9.3.6, 9.9.3.7, 9.9.3.8, 9.9.3.9, 9.9.3.10, 9.9.4.1, 9.9.4.2, 9.9.4.3, 9.9.4.4, 9.9.4.5, 9.9.4.6, 9.9.4.7, 9.9.4.8, 9.9.4.9, 9.9.4.10, 9.9.5.1, 9.9.5.2, 9.9.5.3, 9.9.5.4, 9.9.5.5, 9.9.5.6, 9.9.5.7, 9.9.5.8, 9.9.5.9, 9.9.5.10, 9.9.6.1, 9.9.6.2, 9.9.6.3, 9.9.6.4, 9.9.6.5, 9.9.6.6, 9.9.6.7, 9.9.6.8, 9.9.6.9, 9.9.6.10, 9.9.7.1, 9.9.7.2, 9.9.7.3, 9.9.7.4, 9.9.7.5, 9.9.7.6, 9.9.7.7, 9.9.7.8, 9.9.7.9, 9.9.7.10, 9.9.8.1, 9.9.8.2, 9.9.8.3, 9.9.8.4, 9.9.8.5, 9.9.8.6, 9.9.8.7, 9.9.8.8, 9.9.8.9, 9.9.8.10, 9.9.9.1, 9.9.9.2, 9.9.9.3, 9.9.9.4, 9.9.9.5, 9.9.9.6, 9.9.9.7, 9.9.9.8, 9.9.9.9, 9.9.9.10, 9.9.10.1, 9.9.10.2, 9.9.10.3, 9.9.10.4, 9.9.10.5, 9.9.10.6, 9.9.10.7, 9.9.10.8, 9.9.10.9, 9.9.10.10, 9.10.1.1, 9.10.1.2, 9.10.1.3, 9.10.1.4, 9.10.1.5, 9.10.1.6, 9.10.1.7, 9.10.1.8, 9.10.1.9, 9.10.1.10, 9.10.2.1, 9.10.2.2, 9.10.2.3, 9.10.2.4, 9.10.2.5, 9.10.2.6, 9.10.2.7, 9.10.2.8, 9.10.2.9, 9.10.2.10, 9.10.3.1, 9.10.3.2, 9.10.3.3, 9.10.3.4, 9.10.3.5, 9.10.3.6, 9.10.3.7, 9.10.3.8, 9.10.3.9, 9.10.3.10, 9.10.4.1, 9.10.4.2, 9.10.4.3, 9.10.4.4, 9.10.4.5, 9.10.4.6, 9.10.4.7, 9.10.4.8, 9.10.4.9, 9.10.4.10, 9.10.5.1, 9.10.5.2, 9.10.5.3, 9.10.5.4, 9.10.5.5, 9.10.5.6, 9.10.5.7, 9.10.5.8, 9.10.5.9, 9.10.5.10, 9.10.6.1, 9.10.6.2, 9.10.6.3, 9.10.6.4, 9.10.6.5, 9.10.6.6, 9.10.6.7, 9.10.6.8, 9.10.6.9, 9.10.6.10, 9.10.7.1, 9.10.7.2, 9.10.7.3, 9.10.7.4, 9.10.7.5, 9.10.7.6, 9.10.7.7, 9.10.7.8, 9.10.7.9, 9.10.7.10, 9.10.8.1, 9.10.8.2, 9.10.8.3, 9.10.8.4, 9.10.8.5, 9.10.8.6, 9.10.8.7, 9.10.8.8, 9.10.8.9, 9.10.8.10, 9.10.9.1, 9.10.9.2, 9.10.9.3, 9.10.9.4, 9.10.9.5, 9.10.9.6, 9.10.9.7, 9.10.9.8, 9.10.9.9, 9.10.9.10, 9.10.10.1, 9.10.10.2, 9.10.10.3, 9.10.10.4, 9.10.10.5, 9.10.10.6, 9.10.10.7, 9.10.10.8, 9.10.10.9, 9.10.10.10, 10.1.1.1, 10.1.1.2, 10.1.1.3, 10.1.1.4, 10.1.1.5, 10.1.1.6, 10.1.1.7, 10.1.1.8, 10.1.1.9, 10.1.1.10, 10.1.2.1, 10.1.2.2, 10.1.2.3, 10.1.2.4, 10.1.2.5, 10.1.2.6, 10.1.2.7, 10.1.2.8, 10.1.2.9, 10.1.2.10, 10.1.3.1, 10.1.3.2, 10.1.3.3, 10.1.3.4, 10.1.3.5, 10.1.3.6, 10.1.3.7, 10.1.3.8, 10.1.3.9, 10.1.3.10, 10.1.4.1, 10.1.4.2, 10.1.4.3, 10.1.4.4, 10.1.4.5, 10.1.4.6, 10.1.4.7, 10.1.4.8, 10.1.4.9, 10.1.4.10, 10.1.5.1, 10.1.5.2, 10.1.5.3, 10.1.5.4, 10.1.5.5, 10.1.5.6, 10.1.5.7, 10.1.5.8, 10.1.5.9, 10.1.5.10, 10.1.6.1, 10.1.6.2, 10.1.6.3, 10.1.6.4, 10.1.6.5, 10.1.6.6, 10.1.6.7, 10.1.6.8, 10.1.6.9, 10.1.6.10, 10.1.7.1, 10.1.7.2, 10.1.7.3, 10.1.7.4, 10.1.7.5, 10.1.7.6, 10.1.7.7, 10.1.7.8, 10.1.7.9, 10.1.7.10, 10.1.8.1, 10.1.8.2, 10.1.8.3, 10.1.8.4, 10.1.8.5, 10.1.8.6, 10.1.8.7, 10.1.8.8, 10.1.8.9, 10.1.8.10, 10.1.9.1, 10.1.9.2, 10.1.9.3, 10.1.9.4, 10.1.9.5, 10.1.9.6, 10.1.9.7, 10.1.9.8, 10.1.9.9, 10.1.9.10, 10.1.10.1, 10.1.10.2, 10.1.10.3, 10.1.10.4, 10.1.10.5, 10.1.10.6, 10.1.10.7, 10.1.10.8, 10.1.10.9, 10.1.10.10, 10.2.1.1, 10.2.1.2, 10.2.1.3, 10.2.1.4, 10.2.1.5, 10.2.1.6, 10.2.1.7, 10.2.1.8, 10.2.1.9, 10.2.1.10, 10.2.2.1, 10.2.2.2, 10.2.2.3, 10.2.2.4, 10.2.2.5, 10.2.2.6, 10.2.2.7, 10.2.2.8, 10.2.2.9, 10.2.2.10, 10.2.3.1, 10.2.3.2, 10.2.3.3, 10.2.3.4, 10.2.3.5, 10.2.3.6, 10.2.3.7, 10.2.3.8, 10.2.3.9, 10.2.3.10, 10.2.4.1, 10.2.4.2, 10.2.4.3, 10.2.4.4, 10.2.4.5, 10.2.4.6, 10.2.4.7, 10.2.4.8, 10.2.4.9, 10.2.4.10, 10.2.5.1, 10.2.5.2, 10.2.5.3, 10.2.5.4, 10.2.5.5, 10.2.5.6, 10.2.5.7, 10.2.5.8, 10.2.5.9, 10.2.5.10, 10.2.6.1, 10.2.6.2, 10.2.6.3, 10.2.6.4, 10.2.6.5, 10.2.6.6, 10.2.6.7, 10.2.6.8, 10.2.6.9, 10.2.6.10, 10.2.7.1, 10.2.7.2, 10.2.7.3, 10.2.7.4, 10.2.7.5, 10.2.7.6, 10.2.7.7, 10.2.7.8, 10.2.7.9, 10.2.7.10, 10.2.8.1, 10.2.8.2, 10.2.8.3, 10.2.8.4, 10.2.8.5, 10.2.8.6, 10.2.8.7, 10.2.8.8, 10.2.8.9, 10.2.8.10, 10.2.9.1, 10.2.9.2, 10.2.9.3, 10.2.9.4, 10.2.9.5, 10.2.9.6, 10.2.9.7, 10.2.9.8, 10.2.9.9, 10.2.9.10, 10.2.10.1, 10.2.10.2, 10.2.10.3, 10.2.10.4, 10.2.10.5, 10.2.10.6, 10.2.10.7, 10.2.10.8, 10.2.10.9, 10.2.10.10, 10.3.1.1, 10.3.1.2, 10.3.1.3, 10.3.1.4, 10.3.1.5, 10.3.1.6, 10.3.1.7, 10.3.1.8, 10.3.1.9, 10.3.1.10, 10.3.2.1, 10.3.2.2, 10.3.2.3, 10.3.2.4, 10.3.2.5, 10.3.2.6, 10.3.2.7, 10.3.2.8, 10.3.2.9, 10.3.2.10, 10.3.3.1, 10.3.3.2, 10.3.3.3, 10.3.3.4, 10.3.3.5, 10.3.3.6, 10.3.3.7, 10.3.3.8, 10.3.3.9, 10.3.3.10, 10.3.4.1, 10.3.4.2, 10.3.4.3, 10.3.4.4, 10.3.4.5, 10.3.4.6, 10.3.4.7, 10.3.4.8, 10.3.4.9, 10.3.4.10, 10.3.5.1, 10.3.5.2, 10.3.5.3, 10.3.5.4, 10.3.5.5, 10.3.5.6, 10.3.5.7, 10.3.5.8, 10.3.5.9, 10.3.5.10, 10.3.6.1, 10.3.6.2, 10.3.6.3, 10.3.6.4, 10.3.6.5, 10.3.6.6, 10.3.6.7, 10.3.6.8, 10.3.6.9,

TABLE 2-continued 10.3.6.10, 10.3.7.1, 10.3.7.2, 10.3.7.3, 10.3.7.4, 10.3.7.5, 10.3.7.6, 10.3.7.7, 10.3.7.8, 10.3.7.9,
10.3.7.10, 10.3.8.1, 10.3.8.2, 10.3.8.3, 10.3.8.4, 10.3.8.5, 10.3.8.6, 10.3.8.7, 10.3.8.8, 10.3.8.9,
10.3.8.10, 10.3.9.1, 10.3.9.2, 10.3.9.3, 10.3.9.4, 10.3.9.5, 10.3.9.6, 10.3.9.7, 10.3.9.8, 10.3.9.9,
10.3.9.10, 10.3.10.1, 10.3.10.2, 10.3.10.3, 10.3.10.4, 10.3.10.5, 10.3.10.6, 10.3.10.7, 10.3.10.8,
10.3.10.9, 10.3.10.10, 10.4.1.1, 10.4.1.2, 10.4.1.3, 10.4.1.4, 10.4.1.5, 10.4.1.6, 10.4.1.7, 10.4.1.8,
10.4.1.9, 10.4.1.10, 10.4.2.1, 10.4.2.2, 10.4.2.3, 10.4.2.4, 10.4.2.5, 10.4.2.6, 10.4.2.7, 10.4.2.8,
10.4.2.9, 10.4.2.10, 10.4.3.1, 10.4.3.2, 10.4.3.3, 10.4.3.4, 10.4.3.5, 10.4.3.6, 10.4.3.7, 10.4.3.8,
10.4.3.9, 10.4.3.10, 10.4.4.1, 10.4.4.2, 10.4.4.3, 10.4.4.4, 10.4.4.5, 10.4.4.6, 10.4.4.7, 10.4.4.8,
10.4.4.9, 10.4.4.10, 10.4.5.1, 10.4.5.2, 10.4.5.3, 10.4.5.4, 10.4.5.5, 10.4.5.6, 10.4.5.7, 10.4.5.8,
10.4.5.9, 10.4.5.10, 10.4.6.1, 10.4.6.2, 10.4.6.3, 10.4.6.4, 10.4.6.5, 10.4.6.6, 10.4.6.7, 10.4.6.8,
10.4.6.9, 10.4.6.10, 10.4.7.1, 10.4.7.2, 10.4.7.3, 10.4.7.4, 10.4.7.5, 10.4.7.6, 10.4.7.7, 10.4.7.8,
10.4.7.9, 10.4.7.10, 10.4.8.1, 10.4.8.2, 10.4.8.3, 10.4.8.4, 10.4.8.5, 10.4.8.6, 10.4.8.7, 10.4.8.8,
10.4.8.9, 10.4.8.10, 10.4.9.1, 10.4.9.2, 10.4.9.3, 10.4.9.4, 10.4.9.5, 10.4.9.6, 10.4.9.7, 10.4.9.8,
10.4.9.9, 10.4.9.10, 10.4.10.1, 10.4.10.2, 10.4.10.3, 10.4.10.4, 10.4.10.5, 10.4.10.6, 10.4.10.7,
10.4.10.8, 10.4.10.9, 10.4.10.10, 10.5.1.1, 10.5.1.2, 10.5.1.3, 10.5.1.4, 10.5.1.5, 10.5.1.6, 10.5.1.7,
10.5.1.8, 10.5.1.9, 10.5.1.10, 10.5.2.1, 10.5.2.2, 10.5.2.3, 10.5.2.4, 10.5.2.5, 10.5.2.6, 10.5.2.7,
10.5.2.8, 10.5.2.9, 10.5.2.10, 10.5.3.1, 10.5.3.2, 10.5.3.3, 10.5.3.4, 10.5.3.5, 10.5.3.6, 10.5.3.7,
10.5.3.8, 10.5.3.9, 10.5.3.10, 10.5.4.1, 10.5.4.2, 10.5.4.3, 10.5.4.4, 10.5.4.5, 10.5.4.6, 10.5.4.7,
10.5.4.8, 10.5.4.9, 10.5.4.10, 10.5.5.1, 10.5.5.2, 10.5.5.3, 10.5.5.4, 10.5.5.5, 10.5.5.6, 10.5.5.7,
10.5.5.8, 10.5.5.9, 10.5.5.10, 10.5.6.1, 10.5.6.2, 10.5.6.3, 10.5.6.4, 10.5.6.5, 10.5.6.6, 10.5.6.7,
10.5.6.8, 10.5.6.9, 10.5.6.10, 10.5.7.1, 10.5.7.2, 10.5.7.3, 10.5.7.4, 10.5.7.5, 10.5.7.6, 10.5.7.7,
10.5.7.8, 10.5.7.9, 10.5.7.10, 10.5.8.1, 10.5.8.2, 10.5.8.3, 10.5.8.4, 10.5.8.5, 10.5.8.6, 10.5.8.7,
10.5.8.8, 10.5.8.9, 10.5.8.10, 10.5.9.1, 10.5.9.2, 10.5.9.3, 10.5.9.4, 10.5.9.5, 10.5.9.6, 10.5.9.7,
10.5.9.8, 10.5.9.9, 10.5.9.10, 10.5.10.1, 10.5.10.2, 10.5.10.3, 10.5.10.4, 10.5.10.5, 10.5.10.6,
10.5.10.7, 10.5.10.8, 10.5.10.9, 10.5.10.10, 10.6.1.1, 10.6.1.2, 10.6.1.3, 10.6.1.4, 10.6.1.5, 10.6.1.6,
10.6.1.7, 10.6.1.8, 10.6.1.9, 10.6.1.10, 10.6.2.1, 10.6.2.2, 10.6.2.3, 10.6.2.4, 10.6.2.5, 10.6.2.6,
10.6.2.7, 10.6.2.8, 10.6.2.9, 10.6.2.10, 10.6.3.1, 10.6.3.2, 10.6.3.3, 10.6.3.4, 10.6.3.5, 10.6.3.6,
10.6.3.7, 10.6.3.8, 10.6.3.9, 10.6.3.10, 10.6.4.1, 10.6.4.2, 10.6.4.3, 10.6.4.4, 10.6.4.5, 10.6.4.6,
10.6.4.7, 10.6.4.8, 10.6.4.9, 10.6.4.10, 10.6.5.1, 10.6.5.2, 10.6.5.3, 10.6.5.4, 10.6.5.5, 10.6.5.6,
10.6.5.7, 10.6.5.8, 10.6.5.9, 10.6.5.10, 10.6.6.1, 10.6.6.2, 10.6.6.3, 10.6.6.4, 10.6.6.5, 10.6.6.6,
10.6.6.7, 10.6.6.8, 10.6.6.9, 10.6.6.10, 10.6.7.1, 10.6.7.2, 10.6.7.3, 10.6.7.4, 10.6.7.5, 10.6.7.6,
10.6.7.7, 10.6.7.8, 10.6.7.9, 10.6.7.10, 10.6.8.1, 10.6.8.2, 10.6.8.3, 10.6.8.4, 10.6.8.5, 10.6.8.6,
10.6.8.7, 10.6.8.8, 10.6.8.9, 10.6.8.10, 10.6.9.1, 10.6.9.2, 10.6.9.3, 10.6.9.4, 10.6.9.5, 10.6.9.6,
10.6.9.7, 10.6.9.8, 10.6.9.9, 10.6.9.10, 10.6.10.1, 10.6.10.2, 10.6.10.3, 10.6.10.4, 10.6.10.5,
10.6.10.6, 10.6.10.7, 10.6.10.8, 10.6.10.9, 10.6.10.10, 10.7.1.1, 10.7.1.2, 10.7.1.3, 10.7.1.4, 10.7.1.5,
10.7.1.6, 10.7.1.7, 10.7.1.8, 10.7.1.9, 10.7.1.10, 10.7.2.1, 10.7.2.2, 10.7.2.3, 10.7.2.4, 10.7.2.5,
10.7.2.6, 10.7.2.7, 10.7.2.8, 10.7.2.9, 10.7.2.10, 10.7.3.1, 10.7.3.2, 10.7.3.3, 10.7.3.4, 10.7.3.5,
10.7.3.6, 10.7.3.7, 10.7.3.8, 10.7.3.9, 10.7.3.10, 10.7.4.1, 10.7.4.2, 10.7.4.3, 10.7.4.4, 10.7.4.5,
10.7.4.6, 10.7.4.7, 10.7.4.8, 10.7.4.9, 10.7.4.10, 10.7.5.1, 10.7.5.2, 10.7.5.3, 10.7.5.4, 10.7.5.5,
10.7.5.6, 10.7.5.7, 10.7.5.8, 10.7.5.9, 10.7.5.10, 10.7.6.1, 10.7.6.2, 10.7.6.3, 10.7.6.4, 10.7.6.5,
10.7.6.6, 10.7.6.7, 10.7.6.8, 10.7.6.9, 10.7.6.10, 10.7.7.1, 10.7.7.2, 10.7.7.3, 10.7.7.4, 10.7.7.5,
10.7.7.6, 10.7.7.7, 10.7.7.8, 10.7.7.9, 10.7.7.10, 10.7.8.1, 10.7.8.2, 10.7.8.3, 10.7.8.4, 10.7.8.5,
10.7.8.6, 10.7.8.7, 10.7.8.8, 10.7.8.9, 10.7.8.10, 10.7.9.1, 10.7.9.2, 10.7.9.3, 10.7.9.4, 10.7.9.5,
10.7.9.6, 10.7.9.7, 10.7.9.8, 10.7.9.9, 10.7.9.10, 10.7.10.1, 10.7.10.2, 10.7.10.3, 10.7.10.4, 10.7.10.5,
10.7.10.6, 10.7.10.7, 10.7.10.8, 10.7.10.9, 10.7.10.10, 10.8.1.1, 10.8.1.2, 10.8.1.3, 10.8.1.4, 10.8.1.5,
10.8.1.6, 10.8.1.7, 10.8.1.8, 10.8.1.9, 10.8.1.10, 10.8.2.1, 10.8.2.2, 10.8.2.3, 10.8.2.4, 10.8.2.5,
10.8.2.6, 10.8.2.7, 10.8.2.8, 10.8.2.9, 10.8.2.10, 10.8.3.1, 10.8.3.2, 10.8.3.3, 10.8.3.4, 10.8.3.5,
10.8.3.6, 10.8.3.7, 10.8.3.8, 10.8.3.9, 10.8.3.10, 10.8.4.1, 10.8.4.2, 10.8.4.3, 10.8.4.4, 10.8.4.5,
10.8.4.6, 10.8.4.7, 10.8.4.8, 10.8.4.9, 10.8.4.10, 10.8.5.1, 10.8.5.2, 10.8.5.3, 10.8.5.4, 10.8.5.5,
10.8.5.6, 10.8.5.7, 10.8.5.8, 10.8.5.9, 10.8.5.10, 10.8.6.1, 10.8.6.2, 10.8.6.3, 10.8.6.4, 10.8.6.5,
10.8.6.6, 10.8.6.7, 10.8.6.8, 10.8.6.9, 10.8.6.10, 10.8.7.1, 10.8.7.2, 10.8.7.3, 10.8.7.4, 10.8.7.5,
10.8.7.6, 10.8.7.7, 10.8.7.8, 10.8.7.9, 10.8.7.10, 10.8.8.1, 10.8.8.2, 10.8.8.3, 10.8.8.4, 10.8.8.5,
10.8.8.6, 10.8.8.7, 10.8.8.8, 10.8.8.9, 10.8.8.10, 10.8.9.1, 10.8.9.2, 10.8.9.3, 10.8.9.4, 10.8.9.5,
10.8.9.6, 10.8.9.7, 10.8.9.8, 10.8.9.9, 10.8.9.10, 10.8.10.1, 10.8.10.2, 10.8.10.3, 10.8.10.4, 10.8.10.5,
10.8.10.6, 10.8.10.7, 10.8.10.8, 10.8.10.9, 10.8.10.10, 10.9.1.1, 10.9.1.2, 10.9.1.3, 10.9.1.4, 10.9.1.5,
10.9.1.6, 10.9.1.7, 10.9.1.8, 10.9.1.9, 10.9.1.10, 10.9.2.1, 10.9.2.2, 10.9.2.3, 10.9.2.4, 10.9.2.5,
10.9.2.6, 10.9.2.7, 10.9.2.8, 10.9.2.9, 10.9.2.10, 10.9.3.1, 10.9.3.2, 10.9.3.3, 10.9.3.4, 10.9.3.5,
10.9.3.6, 10.9.3.7, 10.9.3.8, 10.9.3.9, 10.9.3.10, 10.9.4.1, 10.9.4.2, 10.9.4.3, 10.9.4.4, 10.9.4.5,
10.9.4.6, 10.9.4.7, 10.9.4.8, 10.9.4.9, 10.9.4.10, 10.9.5.1, 10.9.5.2, 10.9.5.3, 10.9.5.4, 10.9.5.5,
10.9.5.6, 10.9.5.7, 10.9.5.8, 10.9.5.9, 10.9.5.10, 10.9.6.1, 10.9.6.2, 10.9.6.3, 10.9.6.4, 10.9.6.5,
10.9.6.6, 10.9.6.7, 10.9.6.8, 10.9.6.9, 10.9.6.10, 10.9.7.1, 10.9.7.2, 10.9.7.3, 10.9.7.4, 10.9.7.5,
10.9.7.6, 10.9.7.7, 10.9.7.8, 10.9.7.9, 10.9.7.10, 10.9.8.1, 10.9.8.2, 10.9.8.3, 10.9.8.4, 10.9.8.5,
10.9.8.6, 10.9.8.7, 10.9.8.8, 10.9.8.9, 10.9.8.10, 10.9.9.1, 10.9.9.2, 10.9.9.3, 10.9.9.4, 10.9.9.5,
10.9.9.6, 10.9.9.7, 10.9.9.8, 10.9.9.9, 10.9.9.10, 10.9.10.1, 10.9.10.2, 10.9.10.3, 10.9.10.4, 10.9.10.5,
10.9.10.6, 10.9.10.7, 10.9.10.8, 10.9.10.9, 10.9.10.10, 10.10.1.1, 10.10.1.2, 10.10.1.3, 10.10.1.4,
10.10.1.5, 10.10.1.6, 10.10.1.7, 10.10.1.8, 10.10.1.9, 10.10.1.10, 10.10.2.1, 10.10.2.2, 10.10.2.3,
10.10.2.4, 10.10.2.5, 10.10.2.6, 10.10.2.7, 10.10.2.8, 10.10.2.9, 10.10.2.10, 10.10.3.1, 10.10.3.2,
10.10.3.3, 10.10.3.4, 10.10.3.5, 10.10.3.6, 10.10.3.7, 10.10.3.8, 10.10.3.9, 10.10.3.10, 10.10.4.1,
10.10.4.2, 10.10.4.3, 10.10.4.4, 10.10.4.5, 10.10.4.6, 10.10.4.7, 10.10.4.8, 10.10.4.9, 10.10.4.10,
10.10.5.1, 10.10.5.2, 10.10.5.3, 10.10.5.4, 10.10.5.5, 10.10.5.6, 10.10.5.7, 10.10.5.8, 10.10.5.9,
10.10.5.10, 10.10.6.1, 10.10.6.2, 10.10.6.3, 10.10.6.4, 10.10.6.5, 10.10.6.6, 10.10.6.7, 10.10.6.8,
10.10.6.9, 10.10.6.10, 10.10.7.1, 10.10.7.2, 10.10.7.3, 10.10.7.4, 10.10.7.5, 10.10.7.6, 10.10.7.7,
10.10.7.8, 10.10.7.9, 10.10.7.10, 10.10.8.1, 10.10.8.2, 10.10.8.3, 10.10.8.4, 10.10.8.5, 10.10.8.6,
10.10.8.7, 10.10.8.8, 10.10.8.9, 10.10.8.10, 10.10.9.1, 10.10.9.2, 10.10.9.3, 10.10.9.4, 10.10.9.5,
10.10.9.6, 10.10.9.7, 10.10.9.8, 10.10.9.9, 10.10.9.10, 10.10.10.1, 10.10.10.2, 10.10.10.3,
10.10.10.4, 10.10.10.5, 10.10.10.6, 10.10.10.7, 10.10.10.8, 10.10.10.9, 10.10.10.10

Additional exemplary formula 1 compound groups include compounds or genera of compounds named in the groups disclosed below. The configurations of all hydrogen atoms for the following groups are as defined for the group 1 compounds above.

Group 2 compounds. These compounds are named as defined for group 1 compounds, except that $R^{14}$ in formula 3 is —OH and $R^{15}$ is —H. Thus, the group 2 compound named 4.2.2.3 has the structure

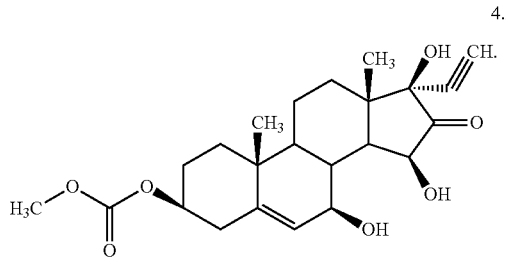
4.2.2.3

Group 3 compounds. These compounds are named as defined for group 1 compounds, except that $R^{14}$ in formula 3 is —H and $R^{15}$ is —OH. Thus, the group 3 compound named 4.2.2.3 has the structure

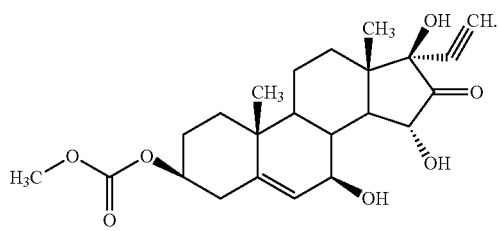
4.2.2.3

Group 4 compounds. These compounds are named as defined for group 1 compounds, except that $R^{14}$ and $R^{15}$ in formula 3 are both —OH. Thus, the group 4 compound named 4.2.2.3 has the structure

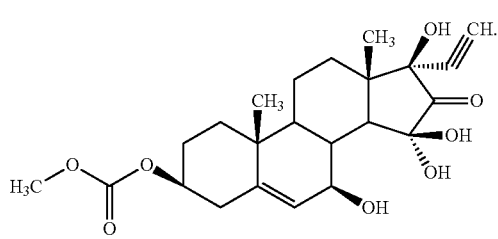
4.2.2.3

Group 5 compounds. These compounds are named as defined for group 1 compounds, except that $R^{14}$ and $R^{15}$ in formula 3 together comprise =O. Thus, the group 5 compound named 4.2.2.3 has the structure

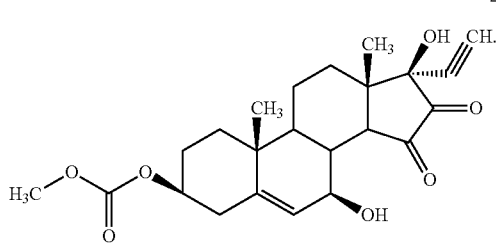
4.2.2.3

Group 6 compounds. These compounds are named as defined for group 1 compounds, except that $R^{24}$ in formula 3 is —H, —CH$_2$OH, —CH$_2$OC(O)CH$_3$, —OC(O)CH$_3$ or —CH$_2$OC(O)OCH$_3$. Thus, the group 6 compound named 4.2.2.3 has the structure

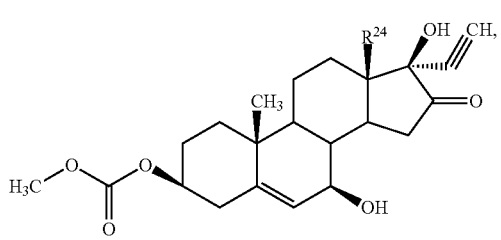
4.2.2.3 where $R^{24}$ is —H, —CH$_2$OH, —CH$_2$OC(O)CH$_3$, —OC(O)CH$_3$ or —CH$_2$OC(O)OCH$_3$.

Group 7 compounds. These compounds are named as defined for group 1 compounds, except that $R^{25}$ in formula 3 is —H, —CH$_2$OH, —CH$_2$OC(O)CH$_3$, —OC(O)CH$_3$ or —CH$_2$OC(O)OCH$_3$. Thus, the group 7 compound named 4.2.2.3 has the structure

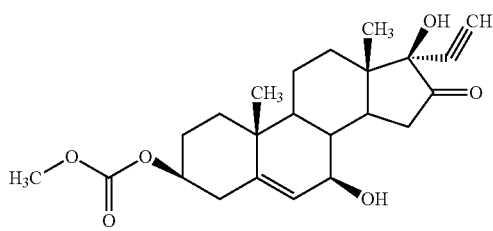
4.2.2.3 where $R^{25}$ is —H, —CH$_2$OH, —CH$_2$OC(O)CH$_3$, —OC(O)CH$_3$ or —CH$_2$OC(O)OCH$_3$.

Group 8 compounds. These compounds are named as defined for group 1 compounds, except that the double bond at the 5-6 position is absent, $R^9$, $R^{19}$ and $R^{11}$ (as defined for formula 1) are present and are all hydrogen, and $R^9$ is in the α-configuration. Thus, the group 8 compound named 4.2.2.3 has the structure 4.2.2.3

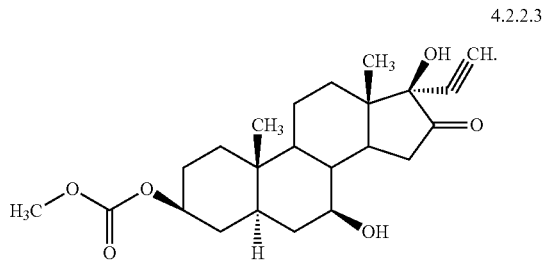

Group 9 compounds. These compounds are named as defined for group 1 compounds, except that the double bond at the 5-6 position is absent, $R^9$, $R^{19}$ and $R^{11}$ (as defined for formula 1) are present and are all hydrogen, and $R^9$ is in the β-configuration. Thus, the group 9 compound named 4.2.2.3 has the structure 4.2.2.3

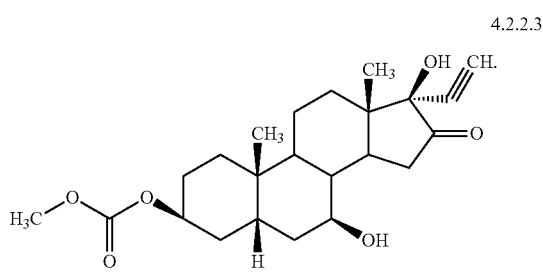

Group 10 compounds. These compounds are named as defined for group 1 compounds, except that $R^{14}$ is —O—C(O)—CH$_2$NH$_2$, —O—C(O)—O—CH$_3$, —O—C(O)—CH$_3$ or —SH. Thus, the group 10 compound named 4.2.2.3 has the structure 4.2.2.3

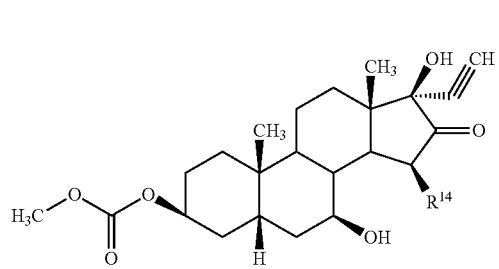

where $R^{14}$ is —O—C(O)—CH$_2$NH$_2$, —O—C(O)—O—CH$_3$, —O—C(O)—CH$_3$ or —SH.

Group 11 compounds. These compounds are named as defined for group 1 compounds, except that $R^{15}$ is —OH, —O—C(O)—O—CH$_3$, —O—C(O)—CH$_3$ or —SH. Thus, the group 11 compound named 4.2.2.3 has the structure 4.2.2.3

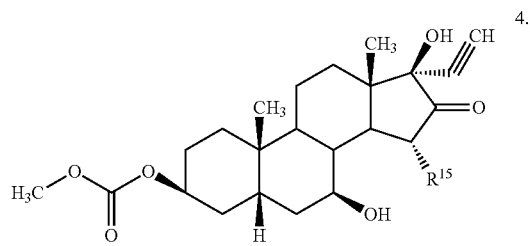

where $R^{15}$ is —O—C(O)—CH$_2$NH$_2$, —O—C(O)—O—CH$_3$, —O—C(O)—CH$_3$ or —SH.

Group 12 compounds. Group 12 comprises 11 subgroups of compounds, subgroups 12-1 through group 12-11. These compounds are named as defined for any compound or genus in any of group 1 through group 11 compounds, except that the $R^5$ and $R^6$ structures in Table 1 have the following structures. 1 —Cl, —H; 2 —H, —Cl; 3 —H, —Br; 4 —Br, —H; 5 —O—CH$_2$—C$_6$H$_4$—OCH$_3$, —H; 6 —H, —O—CH$_2$—C$_6$H$_4$—OCH$_3$; 7 —O—CH$_2$—C$_6$H$_4$—F, —H; 8 —H, —O—CH$_2$—C$_6$H$_4$—F; 9 —O—C(O)—CH$_2$—C$_6$H$_5$, —OH; 10 —OH, —O—C(O)—CH$_2$—C$_6$H$_5$. Thus, the subgroup 12-1 and 12-2 compounds named 4.2.2.3 have the structure subgroup 12-1, compound 4.2.2.3

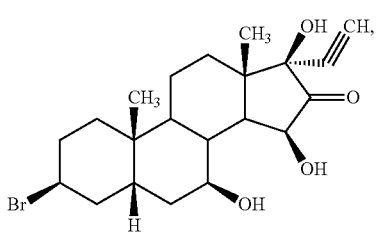

subgroup 12-2, compound 4.2.2.3

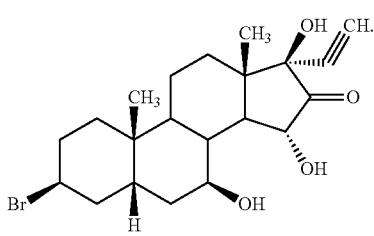

Group 13 compounds. Group 13 comprises 11 subgroups of compounds, subgroups 13-1 through group 13-11. These compounds are named as defined for any compound or genus in any of group 1 through group 11 compounds, except that the $R^5$ and $R^6$ structures in Table 1 have the following structures. 1 —H, —H; 2 —, —CCH$_3$; 3 —CCH$_3$, —H; 4 —OH, —CCH$_3$; 5 —CCH$_3$, —OH; 6 —H, —CH$_3$; 7 —CH$_3$, —H; 8 —CH$_3$, —CH$_3$; 9 —C$_2$H$_5$, —C$_2$H$_5$; 10 —C$_2$H$_5$, —H. Thus, the group 13-1 and 13-2 compounds named 4.2.2.3 have the structure subgroup 13-1, compound 4.2.2.3

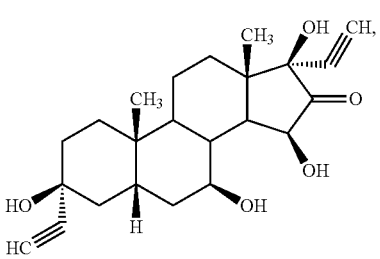

subgroup 13-2, compound 4.2.2.3

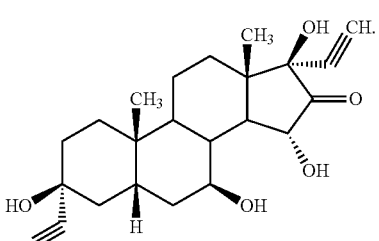

Other embodiments of the formula 1 and 2 compounds include compounds having the formulas 3 and 4

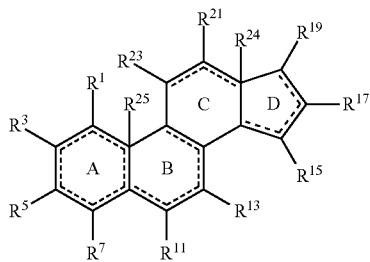

3

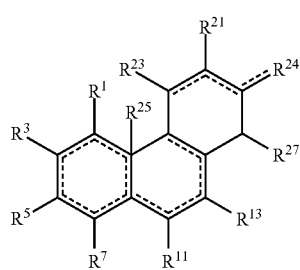

4 wherein, $R^1$-$R^{27}$ are independently chosen and have the definitions given herein. Exemplary formula 3 and 4 compounds have 0, 1, 2 or 3 double bonds and a non-hydrogen hydrogen substituent at 2, 3, 4 or more of $R^1$, $R^3$, $R^5$, $R^{11}$, $R^{13}$, $R^{17}$, $R^{19}$, $R^{24}$ and $R^{25}$. When three double bonds are present in the A ring, then $R^{25}$ is absent. Such embodiments include each of the compounds groups described above wherein the A ring is aromatic and in such compounds, only one variable group is present at each carbon atom in the A ring, and the $R^1$, $R^3$, $R^5$ and $R^7$ variable groups are as defined in the compound groups given above. Substituents include methyl at $R^{24}$ and $R^{25}$ and independently selected —$OR^{PR}$ (e.g., —OH), =O, —$SR^{PR}$ (e.g., —SH) or halogen at 2, 3 or more of $R^3$, $R^5$, $R^{11}$, $R^{17}$ and $R^{19}$, with remaining positions being hydrogen.

In other embodiments the formula 3 compound shown in compound group 1 comprises (1) a double bond at the 16-17 position and only $R^{17}$ and $R^{18}$ are present at 16 and 17, (2) a double bond at the 16-17 position and only $R^{16}$ and $R^{18}$ are present at 16 and 17, (3) a double bond at the 16-17 position and only $R^{17}$ and $R^{19}$ are present at 16 and 17, (4) a double bond at the 16-17 position and only $R^{16}$ and $R^{19}$ are present at 16 and 17, (5) a double bond at the 5-6 and 16-17 positions and only $R^{17}$ and $R^{18}$ are present at 16 and 17, (6) a double bond at the 5-6 and 16-17 positions and only $R^{16}$ and $R^{18}$ are present at 16 and 17, (7) a double bond at the 5-6 and 16-17 positions 5-6 and 16-17 positions and only $R^{17}$ and $R^{19}$ are present at 16 and 17, (8) a double bond at the 5-6 and 16-17 positions and only $R^{16}$ and $R^{19}$ are present at 16 and 17, (9) a double bond at the 4-5 and 16-17 positions and only $R^{17}$ and $R^{18}$ are present at 16 and 17, (10) a double bond at the 4-5 and 16-17 positions and only $R^{16}$ and $R^{18}$ are present at 16 and 17, (11) a double bond at the 4-5 and 16-17 positions 4-5 and 16-17 positions and only $R^{17}$ and $R^{19}$ are present at 16 and 17, (12) a double bond at the 5-6 and 16-17 positions and only $R^{16}$ and $R^{19}$ are present at 16 and 17, (13) a double bond at the 1-2 and 16-17 positions and only $R^{17}$ and $R^{18}$ are present at 16 and 17, (14) a double bond at the 1-2 and 16-17 positions and only $R^{16}$ and $R^{18}$ are present at 16 and 17, (15) a double bond at the 1-2 and 16-17 positions 5-6 and 16-17 positions and only $R^{17}$ and $R^{19}$ are present at 16 and 17, or (16) a double bond at the 1-2 and 16-17 positions and only $R^{16}$ and $R^{19}$ are present at 16 and 17. In any of these embodiments, a single variable group is bonded to ring carbon atoms and the variable group can be as described in any of the compound groups described above. For these compounds, the variable groups at the 1, 2, 4, 6, 11 and 12 positions may comprise one, two or three moieties other than hydrogen, e.g., optionally substituted alkyl, optionally substituted alkoxy, optionally substituted alkylaryl, an ester, an ether, a thioether, a thioester, an optionally substituted heterocycle, or an optionally substituted monosaccharide, while the remainder of the variable groups at the 1, 2, 4, 6, 11 and 12 positions are hydrogen.

In some embodiments, when one or more of $R^1$-$R^{28}$ is a protected moiety, e.g., —$OR^{PR}$, —$SR^{PR}$, —$N(R^{PR})_2$, the $R^{PR}$ protecting group, together with the atom to which it is linked, comprises an ester, a thioester, a phosphoester, a phosphonoester, a sulfite ester, a sulfate ester, an amide, an amino acid, a peptide, an ether, a thioether, an acyl group, a carbonate, a carbamate, a slufonamide, an optionally substituted alkyl group, an optionally substituted alkenyl group, an optionally substituted alkynyl group, an optionally substituted aryl moiety, an optionally substituted heteroaryl moiety, an optionally substituted monosaccharide, an optionally substituted oligosaccharide, a nucleoside, a nucleotide, an oligonucleotide or a polymer.

In all of the embodiments of the formula 1 or formula 2 compounds described herein, the variable groups are in the α, β or αβ configuration, unless otherwise specified. Esters and thioesters at one, two or more variable groups, e.g., at 1, 3, 6, 7 or 17, may comprise a saturated or unsaturated, normal or branched fatty acid, typically comprising about 4 to about 20 carbon atoms. Such fatty acids, if unsaturated may comprise one, two or more double bonds or one or two triple bonds. Exemplary fatty acids include one having the structure $CH_3$—$(CH_2)_{3\text{-}18}$—COOH, $CH_3$—$(CH_2)_{1\text{-}8}$—CH=CH—$(CH_2)_{1\text{-}8}$—COOH, $CH_3$—$(CH_2)_{2\text{-}6}$—CH=CH—$(CH_2)_{2\text{-}6}$—COOH and $CH_3$—$(CH_2)_{1\text{-}5}$—CH=CH—$(CH_2)_{2\text{-}4}$—CH=CH—$(CH_2)_{1\text{-}5}$—COOH. The double bond in the fatty acids can be in the cis, trans or cis and trans configurations and they are optionally substituted with one, two or more substituents as described for esters, e.g., with —O—, —OH, —S— or —SH.

Exemplary synthesis methods. By way of exemplification and not limitation, the following methods are used to prepare the one or more of the compounds disclosed herein. Starting materials or straightforward variations of the schemes are found, e.g., in the following citations, which are all incorporated herein by reference:

U.S. Pat. Nos. 4,602,008, 4,989,694, 5,001,119, 5,175,154, 5,571,795, 5,627,270, 5,681,964, 5,714,481, 5,744,453, 5,939,545, 5,939,570, 5,962,442, 5,962,443, 5,994,568; international publication numbers WO 9408588, WO 9508558, WO 9508559, WO 9638466, WO 9809450; and European patent applications EP 232788, EP 430078.

Scheme 1. Exemplary formula 1 compounds are prepared as shown in the schemes below. For the structures shown in scheme 1, $R^5$-$R^9$ are as defined for formula 1 compounds. Thus, when $R^{24}$ and $R^{25}$ are both —$CH_3$ in the β-configuration, H at the 9 and 14 positions are in the α-configuration, acetate at the 3-position is in the β-configuration, and H at the 8 position is in the β-configuration, the first compound in scheme 1 is DHEA acetate. The acetate groups at the 3, 7, 16, 17 or other positions in this scheme and in other schemes disclosed herein may independently be other ester moieties as described herein, e.g., $C_{2-50}$ esters including —C(O)—$(CH_2)_{0-4}$—$(CF_2)_{0-4}$—$CF_3$, including —C(O)—$CF_3$, —C(O)—$C_{2-29}$ optionally substituted alkyl, —C(O)—$CH_2$—$C_{2-28}$ optionally substituted alkenyl, —C(O)—$CH_2$—$C_{2-28}$ optionally substituted alkynyl, —C(O)—$(CH_2)_{0-6}$-optionally substituted phenyl, or —C(O)—$(CH_2)_{0-6}$-optionally substituted heterocycle or other organic moieties as disclosed herein or in the cited references.

Typical substituents for these organic moieties are as described herein, e.g., one, two, three or more independently selected —O—, =O, optionally protected hydroxyl, —S—, optionally protected thiol, —NH—, optionally protected —$NH_2$, optionally protected —C(O)OH, —C(O)—NH—, —C(O)—$NH_2$, —$NH_2$—C(O)—H, —$NH_2$—C(O)—$C_{0-4}H_{1-9}$, —$NH_2$—C(O)—O—$C_{0-4}H_{1-9}$, —CN, —$NO_2$, —$N_3$ or halogen. Reactive groups are protected as needed, e.g., =O would usually be protected in the LiCR reaction that is used to generate compound I in scheme 1 below.

Scheme 1

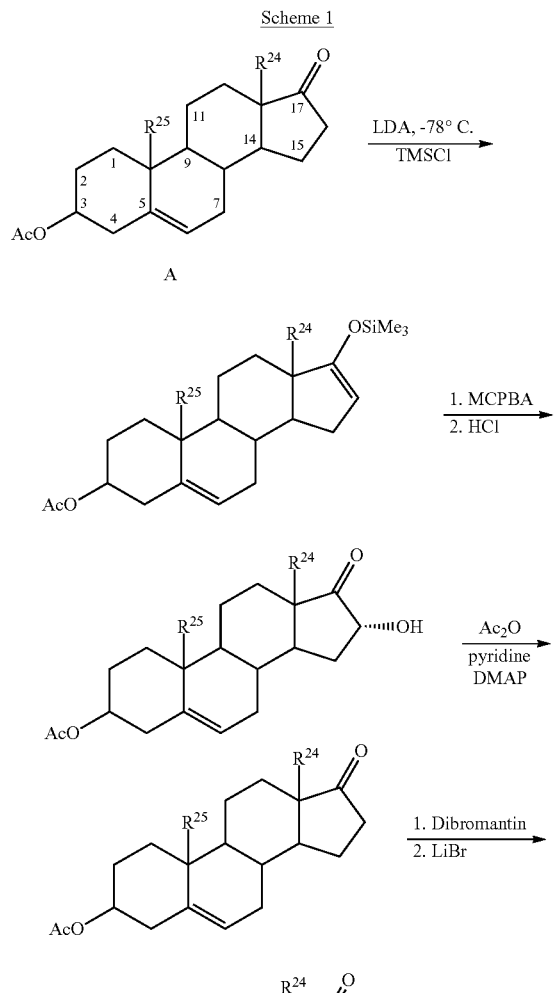

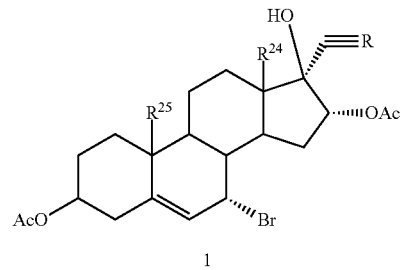

Abbreviations:
LDA = lithium diisopropyl amide; MCPBA = m-chloroperbenzoic acid;
TMSCl = trimethychlorosilane; DMAP = 4- dimethylaminopyridne;
Dibromantin = 1,3-dibromo-4,4-dimethylhydantoin.
R = $CR^A$; $R^A$ = —H or a C1-C50 organic moiety as described herein, e.g., —H, —$C_{1-20}$ optionally substituted alkyl, —$C_{1-20}$ optionally substituted alkenyl, —$C_{1-20}$ optionally substituted alkynyl, —$(CH_2)_{0-6}$-optionally substituted phenyl or —$(CH_2)_{0-6}$-optionally substituted heterocycle.

Scheme 2. Compounds of formula 2A are prepared from structure A compounds shown in scheme 1 using the last two steps of Scheme 1: (1) dibromantin, (2) LiBr, (3) Li—C—R, where R is $CR^A$ and $R^A$ is —H or —$C_{1-12}$ optionally substituted alkyl. When H at the 9 and 14 positions are in the α-configuration and H at the 8 position is in the β-configuration the first compound in scheme 1 is DHEA acetate. Typical substituents for the $R^A$ alkyl moiety includes one, two or more independently selected —O—, optionally protected =O, optionally protected hydroxyl, —S—, optionally protected thiol, —NH—, optionally protected —$NH_2$, optionally protected —C(O)OH, —C(O)—NH—, —C(O)—$NH_2$, —$NH_2$—C(O)—H, —$NH_2$—C(O)—$C_{0-4}H_{1-9}$, —$NH_2$—C(O)—O—$C_{0-4}H_{1-9}$, —CN, —$NO_2$, —$N_3$ or halogen.

Scheme 2

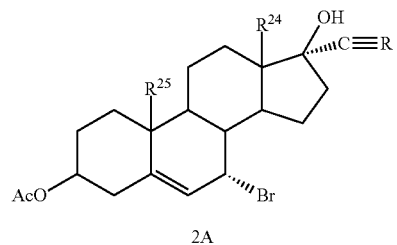

2A

Scheme 3. The allylic bromination at C-7 is accomplished essentially as shown in Scheme 1. R and $R^A$ are as defined in Schemes 1 and 2.

Scheme 3

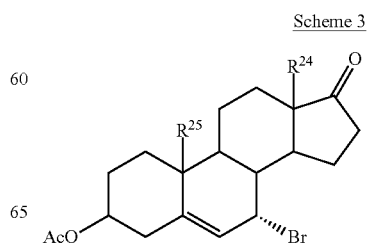

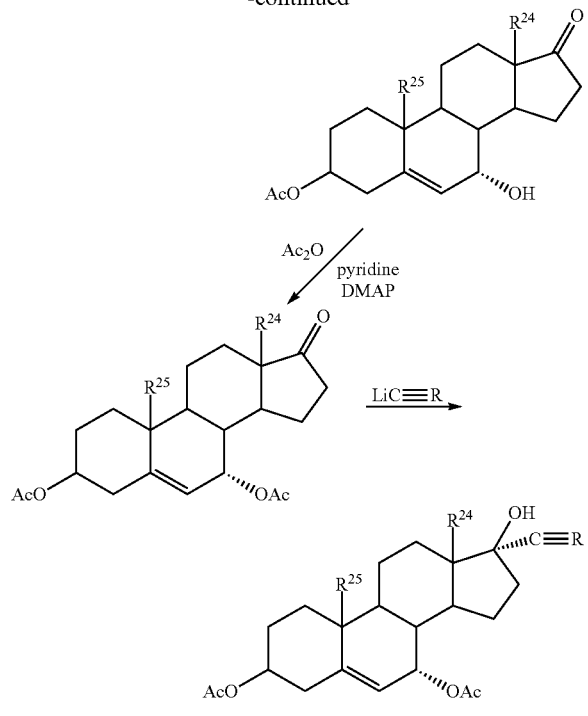

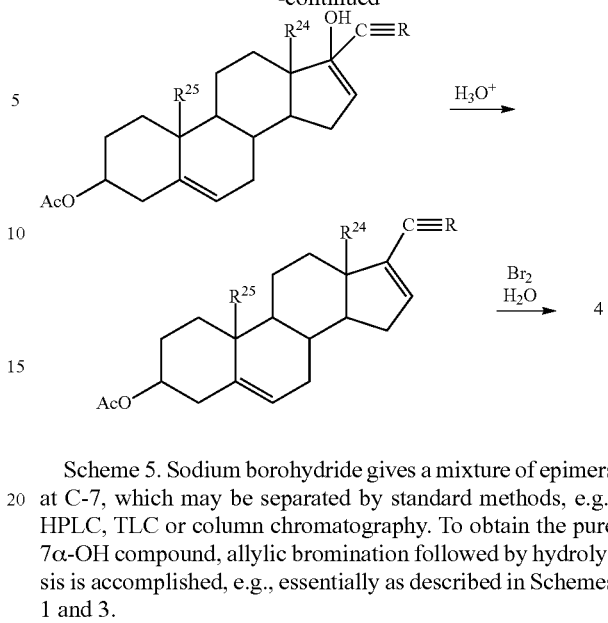

Scheme 4. The addition of lithium reagent (lithium acetylide when R is —CH) to the 17-position >C=O in the presence of the bromide at C-16 results in epoxide formation or in a pinacol rearrangement. Alternatively, compounds without of structure 3 can be dehydrated by mild acid catalysis to form compounds of formula 4 by treatment of the alkene with $Br_2$, $H_2O$. R and $R^4$ are as defined in Schemes 1 and 2.

Scheme 5. Sodium borohydride gives a mixture of epimers at C-7, which may be separated by standard methods, e.g., HPLC, TLC or column chromatography. To obtain the pure 7α-OH compound, allylic bromination followed by hydrolysis is accomplished, e.g., essentially as described in Schemes 1 and 3.

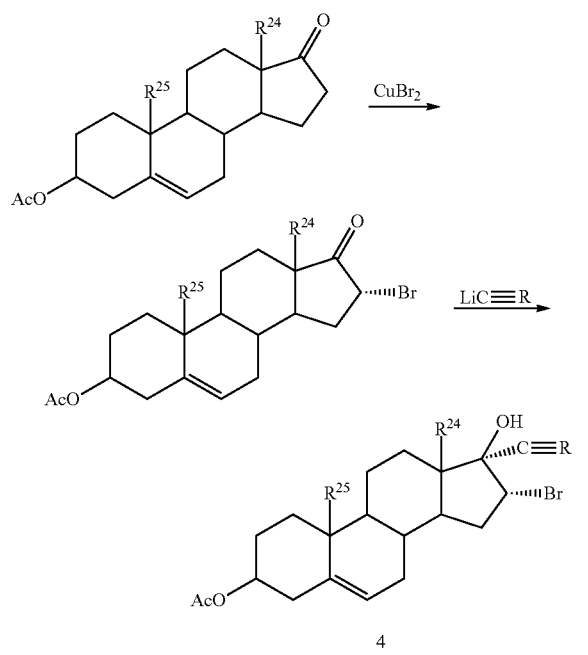

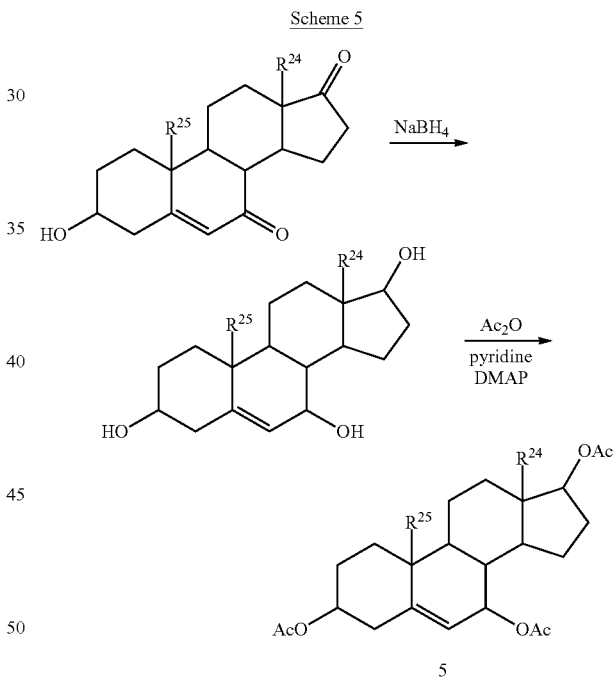

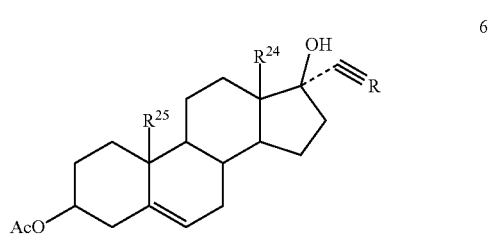

Scheme 6. Formula 6 compounds are prepared by treatment of the acetate with lithium acetylide as in Schemes 1, 2, 3 or 4. R and $R^4$ are as defined in Schemes 1 and 2.

Scheme 7. Formula 7 compounds are prepared from the 3-acetate with reagents described in Schemes 1 and 4. R and $R^4$ are as defined in Schemes 1 and 2.

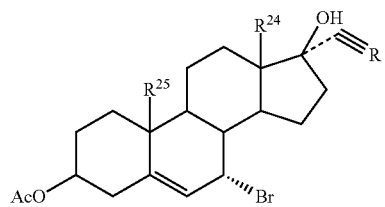

7

Scheme 8. Formula 8 compounds are prepared from the formula A compounds by sodium borohydride reduction at C-17 followed by acetylation.

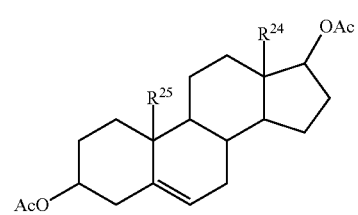

8

Scheme 9. The starting material is made using reactions described in Schemes 1 and 3.

Scheme 9

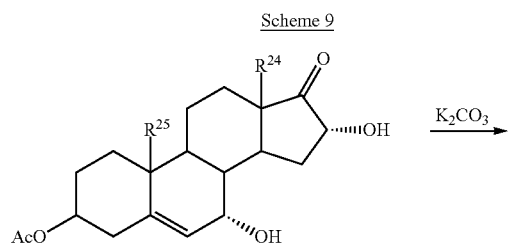

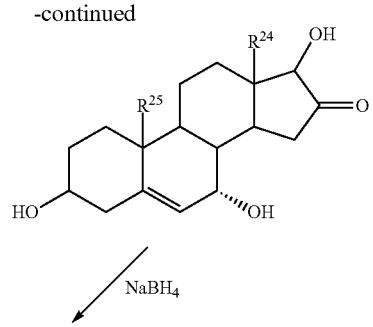

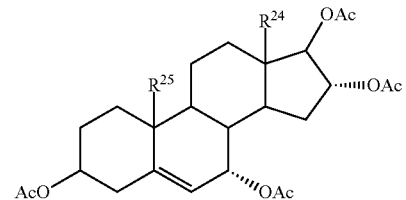

9

Scheme 10. Reduction and acetylation at C-3 and hydrolysis and oxidation at C-17 will allow formula 10a and 10b compounds to undergo functionalization as shown in Schemes 1-9 at C-3, C-16 and C-17. The 7-oxo acetate can be substituted for the formula A compound 3-acetate and functionalization at C-3, C-16 and C-17 is achieved similarly for 7-oxo compounds using the reactions shown in schemes 1-9.

Treatment of 10a with LDA, followed by alkylation of the enolate allows introduction of side chains, which may be, e.g., C1-C20 alkyl (methyl, ethyl), C1-C20 alkenyl ($CH_2$=CH—$(CH_2)_{0-6}$—), benzyl, —$(CH_2)_{1-4}$—O—$(CH_2)_{0-4}$—$CH_3$.

Scheme 10

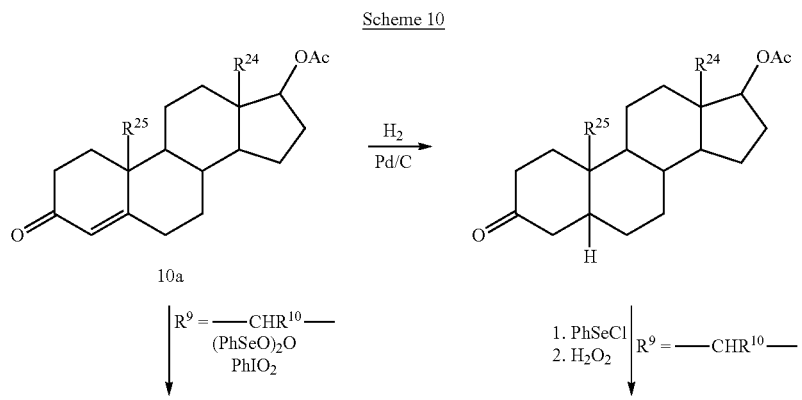

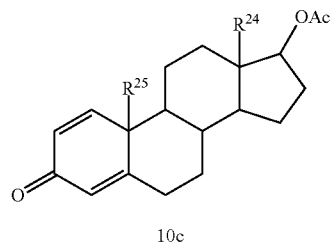

10c

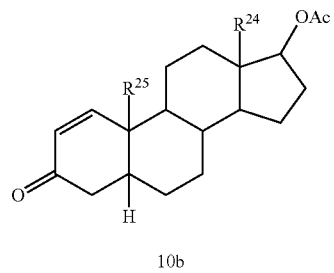

10b

Schemes 1-9 show the introduction of the hydroxyl function at the positions shown. Methods to convert hydroxyl to other functional groups are accomplished essentially as described, e.g., in the references cited herein. For example, esters, of formula 1-10c compounds, such as —O—C(O)—$R^B$ where $R^B$ is a $C_{1-50}$ organic moiety, are prepared from the steroid alcohol by treatment with the appropriate acid anhydride or acid chloride ($R^B$—C(O)—Cl) to form any desired ester. Ethers, such as —O—$R^B$, are prepared from alcohols by formation of the alkaline metal alkoxide (Na$^+$ or K$^+$) followed by treatment with a primary or secondary iodide ($R^B$—I). Thionoesters, $R^B$—C(S)—O—, are prepared by treating the $R^B$—C(O)—O— ester with Lawesson's reagent.

Sulfates, NaO—S(O)(O)—O—, $R^B$—O—S(O)(O)—O—, e.g., $CH_3(CH_2)_{0-18}$—S(O)(O)—O—, are prepared by treatment of alcohols with chlorosulfonic acid followed by NaOH or alternatively by oxidation of sulfites using $KMnO_4$. If the alkyl (e.g., methyl) ester is desired alkylchloro-sulfonate (methylchloro-sulfonate) can be used. Sulfites HO—S(O)—O— and ammonium salts $NH_4O$—S(O)—O, or $R^BO$—S(O)—O— esters (e.g., $CH_3O$—S(O)—O—) are prepared by standard methods. The ammonium salts are prepared by treatment of alcohols with ammonia and sulfur dioxide. The esters such as alkyl, alkenyl and alkynyl esters (e.g., methyl ester) are obtained when alcohols are treated with alkylchlorosulfite (e.g., methycholorosulfite), alkenylchlorosulfite or alkynylchlorosulfite in the presence of a suitable base such as triethylamine. Phosphoesters, $R^BO$—P(OR$^{PR}$)(O)—O— are prepared by treating the alcohol with diethylchlorophosphate in the presence of $Na_2CO_3$. Alternatively, if the alcohol is treated with phosphoric acid diesters in the presence of triphenylphospine (PPh$_3$) and diethylazodicarboxylate (DEAD) the corresponding triesters are formed with inversion (Mitsunobu reaction).

Phosphothioesters, $R^BO$—P(SR$^{PR}$)(O)—O— are generated by treatment of alcohols with the monothio analog of diethylchlorophosphate as described for phosphoesters yielding the phosphothioesters. Carbonates, $R^BO$—C(O)—O— are generated from the corresponding steroid alcohol using the chloroformate ($R^B$—C(O)—Cl), e.g., $C_{1-20}$ alkyl, alkenyl or alkynyl chloroformates (e.g. $CH_3(CH_2)_{0-5}$—C(O)Cl). Carbamates, $R^B$—NH—C(O)—O— are made from steroid alcohols by treatment with isocyanates ($R^B$N=C=O) or NaOCN in the presence of trifluororoacetic acid. Aminoacid esters, ZNX—CHY—C(O)—O— are generated by coupling the steroid alcohol with the acid chloride of the N-protected amino acid.

Oxidation of hydroxyl groups that are linked to the steroid nucleus is used to obtain ketones and related functionalities. For example, conversion of alcohols to ketones can be achieved using a variety of oxidizing agents such as $CrO_3$ in AcOH, or pyridinium cholorchromate, pyridinium dichromate or oxalyl chloride with triethylamine (Swern oxidation). Thioketones (=S) are prepared by treating ketones with Lawesson's reagent (2,4-bis(4-methoxyphenyl)-1,3,2,4-dithiadiphosphetane-2,4-disulfide; commercially available from Aldrich). Thioacetals, —C(SR$^B$)(SR$^B$)—, are prepared from ketones (—C(O)—) by treatment with $R^B$—SH thiols under acid catalysis conditions (e.g., HCl). Phosphonoesters, $R^B$—P(OR$^{PR}$)(O)—, are generated by addition of the phosphorus acid diester to ketones in the presence of KF to yield hydroxy phosphonoesters. One may optionally remove the hydroxy group using a dehydration and hydrogenation sequence.

Substitution of hydroxyl groups is used to generate a number of functionalities. For example, thiols, —SH, are prepared from alcohols by conversion of the alcohol with inversion to the bromide using PBr$_3$. Treatment of the bromide with thiourea followed by NaOH gives the thiol. Thioethers, $R^B$—S—, are prepared from thiols by treatment with NaOH and the required halide, e.g., alkyl halide. Alternatively, alcohol derivatives like tosylates or mesylates can be displaced by thiolate anions, $R^B$—S$^-$, to yield the thioether. Thioesters, R—C(O)—S—, are prepared by treating the tosylate (mesylate) of the alcohol with the sodium salt of the thioacid.

Substitution of hydroxyl groups can be used to generate both esters, $R^BO$—C(O)—, and amides, NHR$^B$—C(O)—, linked to the steroid at carbon atoms. For amides and amines, $R^B$ is —H, a protecting group or a $C_{1-50}$ organic moiety. These are synthesized from the steroid bromide with inversion by displacement with NaCN. The cyanide group can be hydrolyzed to the amide or the acid. The acid is esterified or treated by standard peptide coupling reactions with an O-protected amino acid in the presence of a suitable carboxyl activating agents such as dicyclohexylcarbodiimide (DCC) to form steroid —C(O)—NH—CHY—C(O)—OR, where Y is the side chain of an amino acid or a C1-C10 organic moiety and R is a protecting group (or hydrogen when deprotected).

Amines and derivatives of amines, e.g., $R^B$NH—, $R^B$—C(O)NH—, $R^B$—OC(O)—NH— or $R^BO$—C(O)—CHR$^B$—NH— linked to steroid carbon atoms, are typically prepared by standard methods. For example, amines (NH$_2$-steroid) are generally prepared using the Hoffmann rearrangement (Br$_2$, NaOH) from the amide (NH$_2$—C(O)-steroid) or the Curtius rearrangement (NaN$_3$) from the acid chloride of the steroid. The $R^B$ substituent can subsequently be introduced by alkylation. Steroid alcohols can be used as starting materials under standard Mitsunobu conditions (PPh$_3$, DEAD) to yield N-Boc sulfonamides using N-(t-butoxycarbonyl)-p-toluenesulfonamide. One can selectively remove either protecting group. Treatment with trifluoroacetic acid affords the sulfonamide ($R^B$—S(O)(O)—NH-steroid). Alternatively, sodium napthalenide deprotects to give the N-Boc compound. Amines ($NH_2$-steroid) can be converted to amides ($R^B$NH—C(O)-steroid) using acyl chlorides ($R^B$—C(O)—Cl). Treatment with ethyl chloroformate gives the N-carbamate ($R^B$O—C(O)—NH-steroid). The amine ($NH_2$-steroid) can be alkylated with an α-bromoester ($R^B$—C(O)—CHY—$NH_2$) to yield the amino acid substituted steroid ($R^B$—O—C(O)—CHY—NH-steroid).

Where reactions such as substitutions give a product mixture, the desired intermediate is optionally separated from other products or at least partially enriched (e.g., enriched at least about 10-fold, usually at least about 50-100-fold) from other products before subsequent reactions are conducted. Substitution at steroid carbon atoms will generally proceed with greatest efficiency at the 3-position, which is relatively sterically unhindered and C-17 is generally somewhat less accessible than the C-3 position. The relative reactivities of the C-3, C-7, C-17 and C-16 positions allows one to use their reactivities to control the sequential introduction of different functional groups into the same steroid molecule. Also, groups, such as hydroxyl at more reactive positions, C-3 or C-17, may be sequentially protected or deprotected to allow introduction of functional groups at other positions, such as C-7 or C-16.

Polymers such as PEG are linked to the compounds essentially as described above. For example, PEG 200 or PEG 300 is linked to the steroid at the 3, 7, 16, 17 or other positions by an ether linkage (PEG-O-steroid) using a PEG alkoxide (PEG-ONa), to displace the steroid bromide. Alternatively, PEG-Br can be treated with the steroid alkoxide. Polyethylene glycol esters such as those described in U.S. Pat. No. 5,681,964 can also be prepared using a suitable formula 1 compound and the methods described therein. Monosaccharides or polysaccharides and oligonucleotides are linked to steroid hydroxyl groups using known methods, see e.g., U.S. Pat. No. 5,627,270.

Scheme 11. Formula 1 or 2 compounds that contain an organic moiety that is linked to the 1 position are prepared essentially as follows. The allylic bromination reaction to generate 11 may utilize any suitable reagent, e.g., N-bromosuccinimide ("NBS") to yield the 1-bromo derivative. This intermediate is treated with zinc to yield the alkylated derivative 12. Organic moieties are introduced into the 1 position using a corresponding reagent, e.g., $(R^{35})_2$CuLi, where $R^{35}$ is a C1-C25 organic moiety that may comprise 1, 2, 3, 4 or more substituents, e.g., —O—, —S—, —NH—, —$OR^{PR}$, protected ketone (e.g., ethylene ketal), —$SR^{PR}$ or —$N(R^{PR})_2$. In other embodiments, $R^{35}$ is $R^1$. Thus, when $R^{35}$ is methyl, a methyl group is introduced into the 1 position, or when $R^{35}$ is —$CH_2$—$OR^{PR}$, the —$CH_2$—$OR^{PR}$ group is introduced into the 1 position. Compound 12 is converted to the 17 hydroxyl derivative 13 by hydrolysis using standard methods, e.g., treatment with sodium carbonate in methanol. The compound 15 is converted to the 17-hydroxy derivative by reduction of the ketone, e.g., using $LiBH_4$ or $NaBH_4$ in ethanol or by catalytic hydrogenation with $H_2/N_1$, $H_2/Pt$ or $H_2/Pd$. Catalytic hydrogenation will also result in reduction of the double bond in 12, 13, 14 or 15. Alternatively, a hydroxyl at both the 3 and 17 positions is obtained by reducing the ketone in compound 12 and removing the acetate group or by directly reducing the 3 ketone in compound 13.

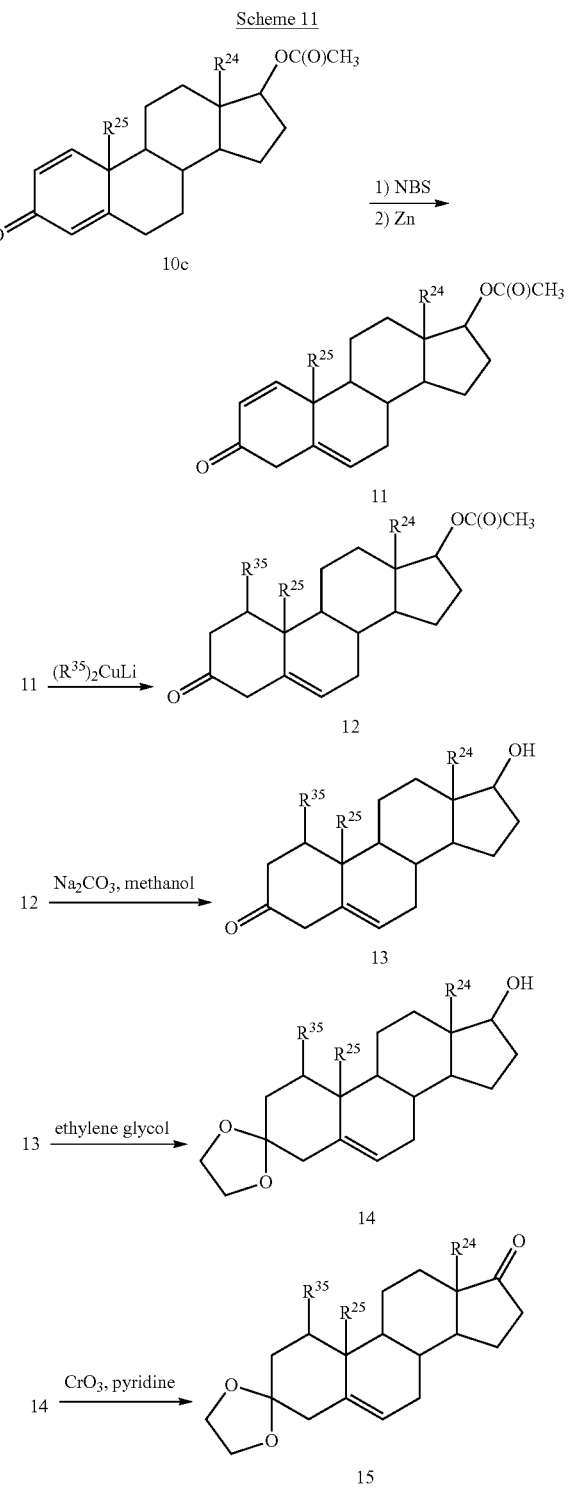

Scheme 12. Formula 1 or 2 compounds that contain a hydroxyl or ether that is linked to the 1 position are prepared essentially as follows. A hydroxyl is introduced into the 1 position by oxidation of a suitable starting material using alkaline hydrogen peroxide to obtain the epoxide 16. The compound 16 is converted to the 1-hydroxyl derivative by treatment, e.g., with excess lithium metal and excess ammonium chloride in $NH_4$-THF (1:1) at reflux to give 17. The ketal group is hydrolyzed to give the 17 ketone. The hydroxyl group at 1 is optionally further converted to other moieties essentially as described above.

Scheme 12

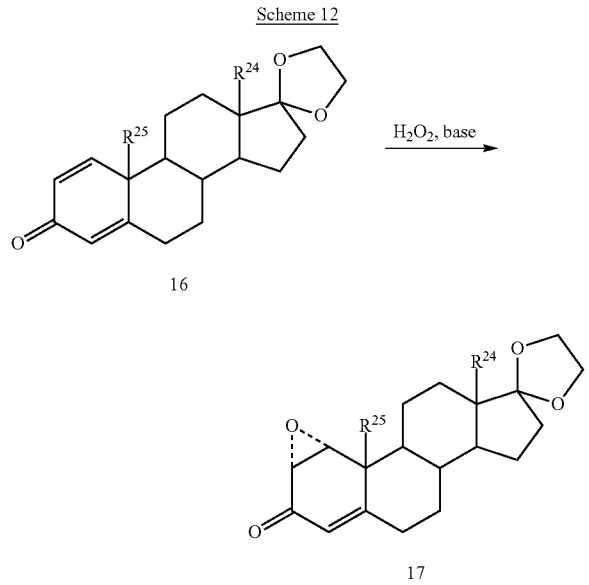

Scheme 13. Formula 1 or 2 compounds that contain an organic moiety that is linked to the 2 position are prepared essentially as follows. Organic moieties are introduced into the 2 position using a corresponding reagent, e.g., $(R^{35})_2$CuLi, where $R^{36}$ is a C1-C25 organic moiety that may comprise 1, 2, 3, 4 or more substituents, e.g., —O—, —S—, —NH—, —$OR^{PR}$, protected ketone (e.g., ethylene ketal), —$SR^{PR}$ or —$N(R^{PR})_2$. In other embodiments, $R^{36}$ is $R^3$. Thus, when $R^{36}$ is methyl, a methyl group is introduced into the 2 position, or when $R^{36}$ is —$CH_2$—$OR^{PR}$, the —$CH_2$—$OR^{PR}$ group is introduced into the 2 position. The starting material 18 is testosterone when $R^{24}$ and $R^{25}$ are both methyl. The compound 18 is alkylated using an alkylating agent such as the iodide $R^{36}$I in the presence of a strong base such as lithium diisopropylamide ("LDA"), n-butyllithium sodium t-pentoxide or $(C_2H_5)_2$Ni to give $R^{36}$ bonded to the steroid in the α and β configurations. The 2β-$R^{36}$ group is epimerized to the 2α configuration using a strong base, e.g., a sodium alkoxide such as sodium methoxide in an alcohol such as methanol. Alternatively the two epimers are at least substantially separated by routine methods.

Scheme 13

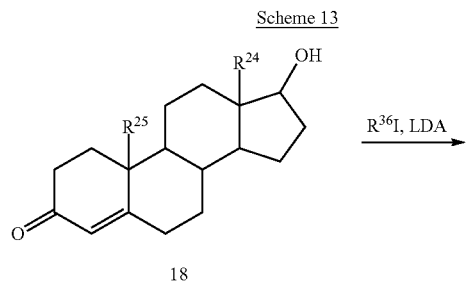

-continued

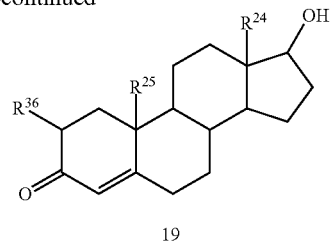

Other formula 1 and 2 compounds are prepared using methods similar to e.g., those described herein or in the cited references.

The following numbered embodiments further exemplify the invention and some of its aspects and related subject matter.

1. A method to treat or prevent an androgen responsive disease, e.g., prostate cancer or breast cancer in a subject comprising administering to a subject an effective amount of a compound of formula 1 or formula 2.

2. The method of embodiment 1 wherein the subject is a human.

3. The method of embodiments 1 or 2 wherein the formula 1 compound is a derivative of 1, 3, 5(10)-estratriene-17α-ethynyl-3β,17β-diol, 17α-ethynyl-androstene-3β,17β-diol, 3β,17β-dihydroxy-androst-5-en-16-one, 3β,-methylcarbonate-androst-5-en-7,17-dione, wherein the derivative comprises 1, 2, 3, 4, 5 or 6 independently selected moieties selected from an a thioester, a thioether, a carbonate, a carbamate, a sulfonamide, halogen, a monosaccharide, a disaccharide, an oligosaccharide, an amino acid or a peptide.

4. The method of any of embodiments 1-3 wherein the formula 1 or formula 2 compound is present in a composition that comprises a pharmaceutically acceptable carrier.

5. The method of any of embodiments 1-4 wherein a therapeutic agent (or a therapeutic treatment) is present in the assay system or in the subject, wherein the agent is optionally selected from an effective amount of one or more of the group consisting of hydroxyflutamide, leuprolide, megesterol, diethylstilbesterol, aminoglutethimide, spironolactone, tamoxifen, cyproterone acetate, bicalutamide doxorubicin, cisplatin, estramustine phosphate, hydroxyurea, cyclophosphamide, cyclophosphamide dacarbazine (DITC), procarbazine, semustine (methyl-CCNU), methotrexate, 5-fluorouracil or streptozocin or radiation therapy.

6. The method of embodiment 5 wherein the therapeutic agent is hydroxyflutamide, cyproterone acetate or bicalutamide.

7. The method of any of embodiments 1-6 wherein the formula 1 or formula 2 compound comprises 1, 2, 3 or 4 moieties independently selected from —OH, =O, —SH, =S, —$NH_2$, halogen, =$CH_2$, =NOH, =$NOC(O)CH_3$, —O—C(O)—$(CH_2)_m$—$(CF_2)_n$—$CH_3$, —O—C(O)—$(CH_2)_m$—$(CF_2)_n$—$CF_3$, —O—C(O)—$(CH_2)_m$—$(CF_2)_n$—$CH_2F$, —O—C(O)—O—$(CH_2)_m$—$(CF_2)_n$—$CH_3$, —O—C(O)—O—$(CH_2)_m$—$(CF_2)_n$—$CF_3$, —O—C(O)—O—$(CH_2)_m$—$(CF_2)_n$—$CH_2F$, —O—C(O)—NH—$(CH_2)_m$—$(CF_2)_n$—$CH_3$, —O—C(O)—NH—$(CH_2)_m$—$(CF_2)_n$—$CF_3$, —O—C(O)—NH—$(CH_2)_m$—$(CF_2)_n$—$CH_2F$ (where m is 1, 2, 3, 4, 5, 6, 7, 8, 9 or 10, n is 0, 1, 2, 3, 4, 5, 6, 7, 8, 9 or 10, usually n is 0), —CH($CH_3$)—$(CH_2)_2$—C(O)NH—$CH_2$COOH, —CH($CH_3$)—$(CH_2)_2$—C(O)NH—$CH_2SO_3H$, —OSi($CH_3$)$_2$C($CH_3$)$_3$, —C(OH)=$CHCH_3$, =CH$(CH_2)_{0-15}CH_3$, —$(CH_2)_{0-14}$—$CH_2F$, —$(CH_2)_{0-14}$—$CH_2Cl$, —$(CH_2)_{0-14}$—$CH_2Br$, —$(CH_2)_{0-14}$—$CH_2I$, —$(CH_2)_{2-10}$—

O—(CH$_2$)$_{0-4}$—CH$_3$, —(CH$_2$)$_{2-10}$—S—(CH$_2$)$_{0-4}$—CH$_3$, —(CH$_2$)$_{2-10}$—NH—(CH$_2$)$_{0-4}$—CH$_3$, —O—(CH$_2$)$_{0-14}$—CH$_2$F, —O—(CH$_2$)$_{0-14}$—CH$_2$Cl, —O—(CH$_2$)$_{0-14}$—CH$_2$Br, —O—(CH$_2$)$_{0-14}$CH$_2$I, —O—(CH$_2$)$_{2-10}$—O—(CH$_2$)$_{0-4}$CH$_3$, —O—(CH$_2$)$_{2-10}$—S—(CH$_2$)$_{0-4}$CH$_3$, —O—(CH$_2$)$_{2-10}$—NH—(CH$_2$)$_{0-4}$—CH$_3$, —O—C(O)—(CH$_2$)$_{0-14}$CH$_2$F, —O—C(O)—(CH$_2$)$_{0-14}$—CH$_2$Cl, —O—C(O)—(CH$_2$)$_{0-14}$—CH$_2$Br, —O—C(O)—(CH$_2$)$_{0-14}$—CH$_2$I, —O—C(O)—(CH$_2$)$_{2-10}$—(CH$_2$)$_{0-4}$—CH$_3$, —O—C(O)—(CH$_2$)$_{2-10}$—S—(CH$_2$)$_{0-4}$—CH$_3$, —O—C(O)—(CH$_2$)$_{2-10}$—NH—(CH$_2$)$_{0-4}$—CH$_3$, —O—C(S)—(CH$_2$)$_{0-14}$—CH$_2$F, —O—C(S)—(CH$_2$)$_{0-14}$—CH$_2$Cl, —O—C(S)—(CH$_2$)$_{0-14}$—CH$_2$Br, —O—C(S)—(CH$_2$)$_{0-14}$—CH$_2$I, —O—C(S)—(CH$_2$)$_{2-10}$—S—(CH$_2$)$_{0-4}$—CH$_3$, —O—C(S)—(CH$_2$)$_{2-10}$—S—(CH$_2$)$_{0-4}$—CH$_3$, —O—C(S)—(CH$_2$)$_{2-10}$—NH—(CH$_2$)$_{0-4}$—CH$_3$, —(CH$_2$)$_{0-16}$NH$_2$, —(CH$_2$)$_{0-15}$CH$_3$, —(CH$_2$)$_{0-15}$CN, —(CH$_2$)$_{0-15}$CH=CH$_2$, —(CH$_2$)$_{0-15}$NHCH(O), —(CH$_2$)$_{0-16}$NH—(CH$_2$)$_{0-15}$CH$_3$, —(CH$_2$)$_{0-15}$CCH, —(CH$_2$)$_{0-15}$OC(O)CH$_3$, —(CH$_2$)$_{0-15}$OCH(OH)CH$_3$, —(CH$_2$)$_{0-15}$C(O)OCH$_3$, —(CH$_2$)$_{0-15}$C(O)OCH$_2$CH$_3$, —(CH$_2$)$_{0-15}$C(O)(CH$_2$)$_{1-15}$CH$_3$, —(CH$_2$)$_{0-15}$C(O)(CH$_2$)$_{0-15}$CH$_2$OH, —O(CH$_2$)$_{1-16}$NH$_2$, —O(CH$_2$)$_{1-15}$CH$_3$, —O(CH$_2$)$_{1-15}$CN, —O(CH$_2$)$_{1-15}$CH=CH$_2$, —O(CH$_2$)$_{1-15}$NHCH(O), —O(CH$_2$)$_{1-16}$NH—(CH$_2$)$_{1-15}$CH$_3$, —O(CH$_2$)$_{1-15}$CCH, —O(CH$_2$)$_{1-15}$OC(O)CH$_3$, —O(CH$_2$)$_{1-15}$OCH(OH)CH$_3$, —O(CH$_2$)$_{1-15}$C(O)OCH$_3$, —O(CH$_2$)$_{1-15}$C(O)OCH$_2$CH$_3$, —O(CH$_2$)$_{1-15}$C(O)(CH$_2$)$_{0-15}$CH$_3$, —O(CH$_2$)$_{1-15}$C(O)(CH$_2$)$_{1-15}$CH$_2$OH, —OC(O)(CH$_2$)$_{1-16}$NH$_2$, —OC(O)(CH$_2$)$_{1-15}$CH$_3$, —C(O)O(CH$_2$)$_{1-15}$CN, —C(O)O(CH$_2$)$_{1-15}$CH=CH$_2$, —OC(O)(CH$_2$)$_{1-15}$NHCH(O), —OC(O)(CH$_2$)$_{1-16}$NH—(CH$_2$)$_{1-15}$CH$_3$, —OC(O)(CH$_2$)$_{1-15}$CCH, —OC(O)(CH$_2$)$_{1-15}$OC(O)CH$_3$, —OC(O)(CH$_2$)$_{1-15}$OCH(OH)CH$_3$, —OC(O)(CH$_2$)$_{1-15}$C(O)OCH$_3$, —OC(O)(CH$_2$)$_{1-15}$C(O)OCH$_2$CH$_3$, —OC(O)(CH$_2$)$_{1-15}$C(O)(CH$_2$)$_{0-15}$CH$_3$, —OC(O)(CH$_2$)$_{1-15}$C(O)(CH$_2$)$_{0-15}$CH$_2$OH, —C(O)—O—(CH$_2$)$_m$CH$_3$ (where m is 1, 2, 3, 4, 5, 6, 7, 8, 9 or 10), —(CH$_2$)$_m$—C(O)OH (where m is 1, 2, 3, 4, 5, 6, 7, 8, 9 or 10), phosphoenolpyruvate, D-glucosamine, glucholic acid, glucuronic acid, pantothenic acid, pyruvic acid, glucose, fructose, mannose, rhamnose, fucose, sucrose, lactose, glycerol, 3-phosphoglycerate, glycine, alanine, phenylalanine, glutamic acid, lysine, threonine, proline and/or 4-hydroxyproline 8. The method of embodiment 7 wherein (a) $R^{24}$ is —CH$_2$OH, —CH$_2$—O—C(O)(CH$_2$)$_{1-16}$NH$_{23}$—OC(O)(CH$_2$)$_{1-15}$CH$_3$ or —OC(O)(CH$_2$)$_{1-15}$CH$_2$OH, or (b) $R^{25}$ is —CH$_2$OH, —CH$_2$—O—C(O)(CH$_2$)$_{1-16}$NH$_{23}$—OC(O)(CH$_2$)$_{1-15}$CH$_3$ or —OC(O)(CH$_2$)$_{1-15}$CH$_2$OH, or (c) $R^1$ is —OH, —SH, —NH$_2$, a halogen, —O—C(O)—CH$_3$, or —O—C(O)—C$_2$H$_5$, or (d) $R^1$ and $R^2$ together are =O, =S, =CH$_2$, =CHCH$_3$, =NOH, =NOC(O)CH$_3$, or they are both —OH, or a halogen, or (e) $R^3$ is —OH, —SH, —NH$_2$, a halogen, —O—C(O)—CH$_3$, or —O—C(O)—C$_2$H$_5$, or (f) $R^3$ and $R^4$ together are =O, =S, =CH$_2$, =CHCH$_3$, =NOH, =NOC(O)CH$_3$, or they are both —OH, or a halogen, or (g) $R^7$ is —OH, —SH, —NH$_2$, a halogen, —O—C(O)—CH$_3$, or —O—C(O)—C$_2$H$_5$, or (h) $R^7$ and $R^8$ together are =O, =S, =CH$_2$, =CHCH$_3$, =NOH, =NOC(O)CH$_3$, or they are both —OH, or a halogen, or (i) $R^{15}$ is —OH, —SH, —NH$_2$, a halogen, —O—C(O)—CH$_3$, or —O—C(O)—C$_2$H$_5$, or (j) $R^{15}$ and $R^{11}$ together are =O, =S, =CH$_2$, =CHCH$_3$, =NOH, =NOC(O)CH$_3$, or they are both —OH, or a halogen, or (k) $R^{14}$ is —OH, —SH, —NH$_2$, a halogen, —O—C(O)—CH$_3$, or —O—C(O)—C$_2$H$_5$, or (l) $R^{14}$ and $R^{15}$ together are =O, =S, =CH$_2$, =CHCH$_3$, =NOH, =NOC(O)CH$_3$, or they are both —OH, or a halogen, or (m) $R^{16}$ is —OH, —SH, —NH$_2$, a halogen, —O—C(O)—CH$_3$, or —O—C(O)—C$_2$H$_5$, or (n) $R^{16}$ and $R^{17}$ together are =O, =S, =CH$_2$, =CHCH$_3$, =NOH, =NOC(O)CH$_3$, or they are both —OH, or a halogen, or (O)$R^{25}$ is —OH, —SH, —NH$_2$, a halogen, —O—C(O)—CH$_3$, or —O—C(O)—C$_2$H$_5$, or (p) $R^{20}$ and $R^{21}$ together are =O, =S, =CH$_2$, =CHCH$_3$, =NOH, =NOC(O)CH$_3$, or they are both —OH, or a halogen, or (q) $R^{22}$ is —OH, —SH, —NH$_2$, a halogen, —O—C(O)—CH$_3$, or —O—C(O)—C$_2$H$_5$, or (r) $R^{22}$ and $R^{23}$ together are =O, =S, =CH$_2$, =CHCH$_3$, =NOH, =NOC(O)CH$_3$, or they are both —OH, or a halogen, or (s) $R^{24}$ is —OH, —SH, —NH$_2$, a halogen, —O—C(O)—CH$_3$, or —O—C(O)—C$_2$H$_5$, or (t) $R^{24}$ and $R^{28}$ together are =O, =S, =CH$_2$, =CHCH$_3$, =NOH, =NOC(O)CH$_3$, or they are both —OH, or a halogen, or (u) $R^{26}$ is —OH, —SH, —NH$_2$, a halogen, —O—C(O)—CH$_3$, or —O—C(O)—C$_2$H$_5$, or (v) $R^{26}$ and $R^{27}$ together are =O, =S, =CH$_2$, =CHCH$_3$, =NOH, =NOC(O)CH$_3$, or they are both —OH, or a halogen.

9. A product produced by the process of contacting a formula 1 or a formula 2 compound with one or more carriers and storing the product for at least about 3 months under ambient conditions in a sealed container.

10. A kit comprising a formula 1 or a formula 2 compound, a container comprising unit dosage or multiple dosage forms of the formula 1 or 2 compound and a label comprising one or more of (1) directions for therapeutic use of the formula 1 or 2 compound, (2) counterindications or toxicities for the formula 1 or 2 compound and (3) information about the formula 1 or 2 compound's structure or the formulation that contains the formula 1 or 2 compound.

11. A method comprising administering to a subject having an androgen responsive condition such as benign prostatic hyperplasia, prostate cancer or breast cancer an effective amount of a compound selected from the compounds or groups of compounds selected from compounds named in any compound groups described herein.

12. The method of embodiment 11, wherein one or more of the symptoms of benign prostatic hyperplasia, prostate cancer or breast cancer are ameliorated or wherein any undesired cell proliferation or disease progression associated with benign prostatic hyperplasia, prostate cancer or breast cancer is reduced or delayed.

13. A compound having formula 1 or formula 2.

14. A composition comprising a formula 1 or formula 2 compound and a pharmaceutically acceptable carrier.

15. Use of a compound of formula 1 or 2 for the manufacture of a medicament for use to treat or prevent an androgen responsive disease in a subject, or to ameliorate one or more symptoms thereof, e.g., in a mmal or a human.

16. The method of embodiment 15 wherein the androgen responsive disease is prostate cancer, benign prostatic hyperplasia or breast cancer.

17. A kit comprising a formulation that comprises a unit dosage or a multiple dosage comprising a formula 1 or a formula 2 compound, e.g., a compound in any compound group or embodiment disclosed herein, and one or more excipients wherein the formulation is dispensed in a suitable container, wherein the kit further comprises a label that provides information about one or more of (1) the formula 1 or 2 compound's chemical structure, (2) any recommended dosing regimen, (3) any adverse effects of administering the formula 1 or 2 compound to a subject that are required to be disclosed and (4) the amount of the formula 1 or 2 compound that is present in each unit dose or in the entire container.

18. A product produced by the process of contacting a formula 1 compound, e.g., a compound in any compound group or embodiment disclosed herein, and an excipient.

19. The method of embodiment 1 wherein the compound of formula 1 or 2 is administered to the subject on an intermittent basis, e.g., dosing for 1, 2, 4, 5, 7, 10 or more consecutive days, followed by no dosing for at least about 5-180 days, followed by dosing again.

20. The method of embodiment 20 herein the compound of formula 1 or 2 is administered every other day for at least about 3-45 days, followed by at least about 3-180 days of not dosing the subject, optionally followed by another course of administration.

All references cited herein are incorporated herein by reference in their entirety.

The following examples further illustrate the invention and are not intended to limit it in any manner.

Example 1

AR activity assay. One biological function of the AR is to act as a transcription factor, which can modulate transcription of target genes. AED, 5α-dihydrotestosterone (DHT), 17β-estradiol (E2), and progesterone were purchased from Sigma. Ethynyl derivatized steroids were purchased from Steraloids. The plasmid pSG5-wild-type AR (pSG5) and mouse mammalian tumor virus (MMTV)-chloramphenicol acetyltransferase (CAT) were constructed as described (6). The numbers in parentheses, e.g., (6) in the preceding sentence, refer to the references listed in the reference section below. Other steroid compounds, were synthesized using routine protocols and others have been described (19, 20). The human prostate cancer cell line, PC-3, and human breast cancer cell line, MCF-7, were maintained in Dulbecco's modified eagles medium (DMEM) containing 10% fetal calf serum. DNA transfection and CAT assays were performed essentially as described (4, 6, 7). Briefly, 4×10$^5$ cells were plated on 60 mm dishes 24 h before transfection, and the medium was changed to DMEM (without phenol red) with 10% charcoal-stripped fetal calf serum 1 hour before transfection. The cells were transfected using the calcium phosphate precipitation method. The total amount of DNA was adjusted to 8.5 µg with pSG5 in each transfection assay. After transfecting the cells for 24 hours, the transfection medium was removed, fresh DMEM was added and steroids were added. The cells were then incubated in DMEM with steroids for 24 hours. After incubation, the cells were harvested and whole cell extracts were used for CAT assay. Transfection efficiency was normalized by cotransfection with a β-galactosidase vector, which acted as an internal control. The CAT enzyme activity was quantitated by phosphor imager according to the manufacturer's instructions (Molecular Dynamics).

| compound number | compound name |
|---|---|
| 0 | 7-oxo-dehydroepiandrosterone |
| 1 | 17α-ethynyl-17β-hydroxy-4-estrene-3-one |
| 2 | 17α-ethynyl-17β-hydroxy-4-estrene-3-one |
| 3 | 17α-ethynyl-17β-hydroxy-5(10)-estrene-3-one |
| 4 | 1,3,5(10)-estratriene-17a-ethynyl-3β,17β-diol |
| 5 | androst-5-ene-3β,11β,17β-triol |
| 6 | 17α-ethynyl-androst-5-ene-3β,17β-diol |
| 7 | 17α-ethynyl-17β-hydroxy-4-androsten-3-one |
| 8 | 3β,17β-dihydroxy-androst-5-en-16-one |
| 9 | 3β,17β-dihydroxy-androst-4-en |
| 10 | 3β,-methylcarbonate-androst-5-en-7,17-dione |
| 11 | 3β,17β-dihydroxy-androst-5-en-11-one |
| 13 | 3β,17β-diacetoxy-androst-5-ene-7α,17β-diol |
| 14 | 3β,17β-diacetoxy-androst-5-ene-7-one |

-continued

| compound number | compound name |
|---|---|
| 15 | 3β-methoxy-17β-hydroxy-androst-5-ene-7-one |
| 16 | 3β-methoxy-androst-5-ene-?,17β-diol |
| 17 | 17β-methoxy-androst-3,5-diene-7-one |
| 18 | 17-methyl-marrianolic acid |
| 19 | 17β-hydroxy-androst-3,5-diene-7-one |
| 21 | 5α-androstane-3α,17β-diol |
| 22 | 7-oxo-androstene-3β,17β-diol |

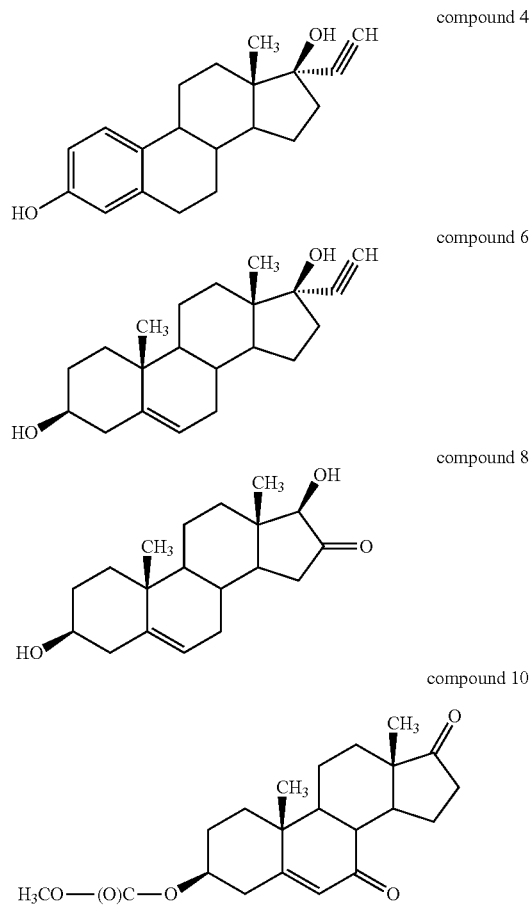

Example 2

Induction of AR-mediated transcriptional activity. Steroid compounds were screened for their ability to induce AR transcriptional activity in the AR-negative PC-3 cell line. The results of the CAT assay were obtained by transient co-transfection of AR plasmid and a reporter plasmid (MMTVCAT) containing the CAT gene linked to the androgen response element (ARE). After transfection, the cells were treated with various DHEA derivatives at 1000, 10, and 0.1 nM. As shown in FIG. 1, compounds 0, 4, 5, 6, 8, 10, 13, 15, 16, 18, and 22 had little androgenic activity but they did induce a low level of AR-mediated CAT gene transactivation. AED (compound 21) had about the same capacity as DHT to stimulate AR-mediated CAT gene transcription.

Example 3

Figure 2A:
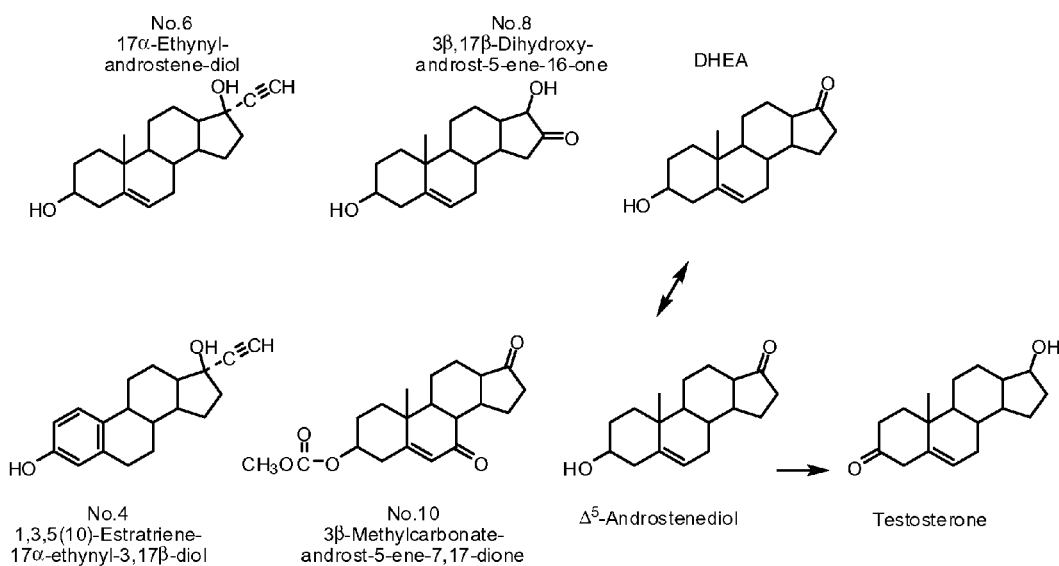
FIG. 2A shows the structures of compounds 4, 6, 8 and 10 and DHEA, Adiol and testosterone.
Figure 2B:
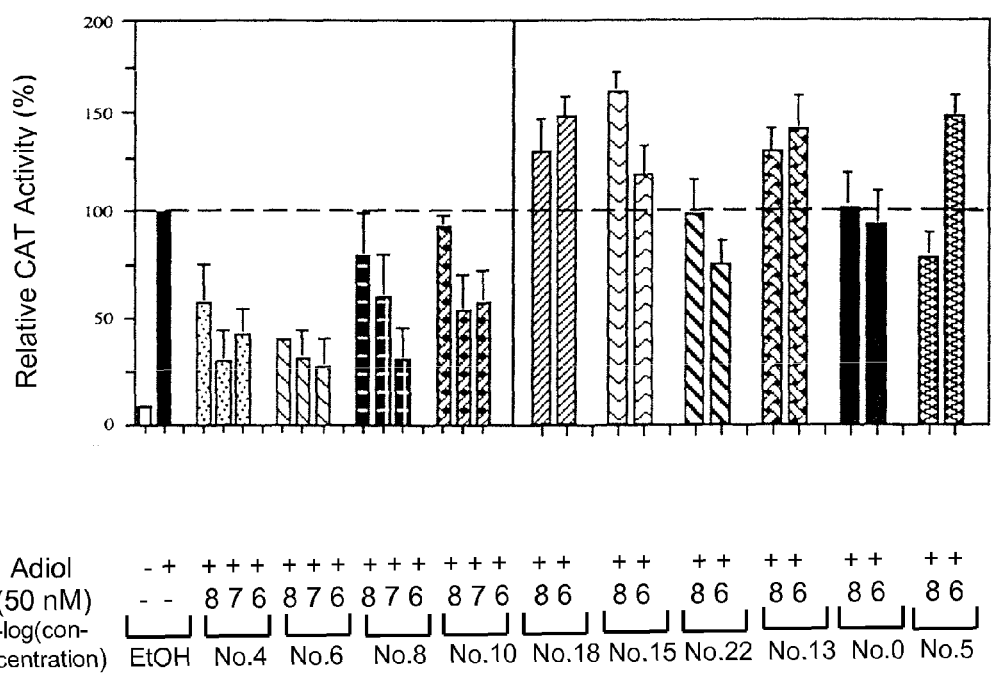
FIG. 2B shows effects of some tested compounds on CAT activity.

Identification of anti-adiol activity of steroids with low androgenic effects. Several compounds were screened for their capacity to modulate AED's effects on AR-mediated activation of gene transcription in PC-3 cells. The chemical structures of compounds 4, 6, 8 and 10 are shown in FIG. 2A. The PC-3 cells were co-transfected with pSG5 and the MMTV-CAT reporter vector in the presence of 50 nM AED and each compound at a concentration of 10, 100, or 1000 nM. As shown in FIG. 2B, compounds 4, 6, 8 and 10 antagonized AED-mediated AR transcriptional activity. At concentrations of 0.1 µM and 1 µM, compounds 4 and 6 suppressed the AED-induced AR transactivation to less than 30%. Compounds 0, 5, 13, 15, 18 and 22 show either activation of AED-mediated AR transcriptional activity or they have no effect.

Example 4

Figure 3:
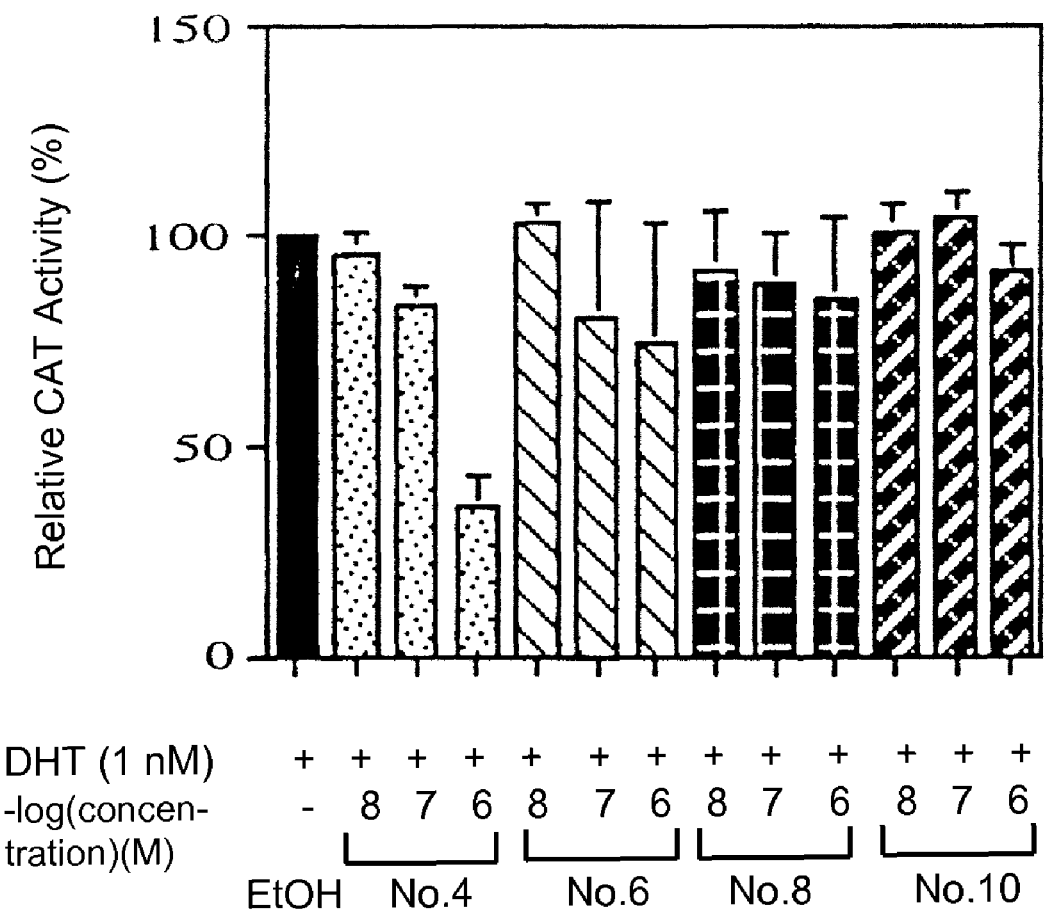
FIG. 3 shows the effects of compounds 4, 6, 8 and 10 on DHT-induced androgen receptor transcriptional activity.

Identification of anti-DHT effects of steroids. Compounds 4, 6, 8 and 10 were examined to determine whether these AED antagonists had the ability to repress DHT-induced AR transactivation. PC-3 cells were co-transfected with pSG5 and the MMTV-CAT reporter plasmid in the presence of 1 nM DHT and each compound at 10, 100, or 1000 nM. Compound 4 repressed the DHT-induced AR transactivation to less than 40% at 1 µM (FIG. 3).

Example 5

Figure 4:
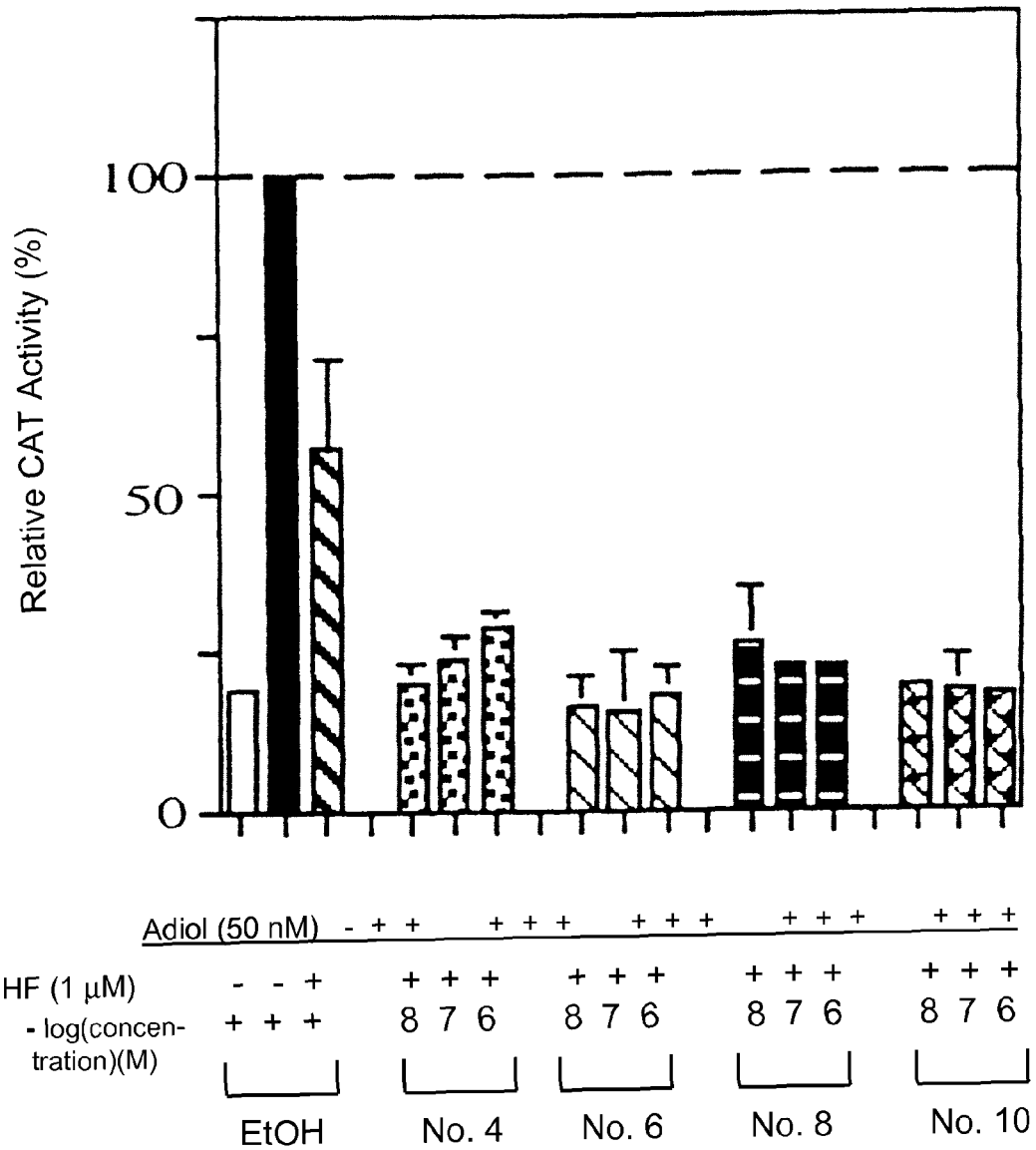
FIG. 4 shows the effects of compounds 4, 6, 8 and 10 on Adiol-induced and hydroxyflutamide (HF) blocked androgen receptor transcriptional activity.
Figure 5:
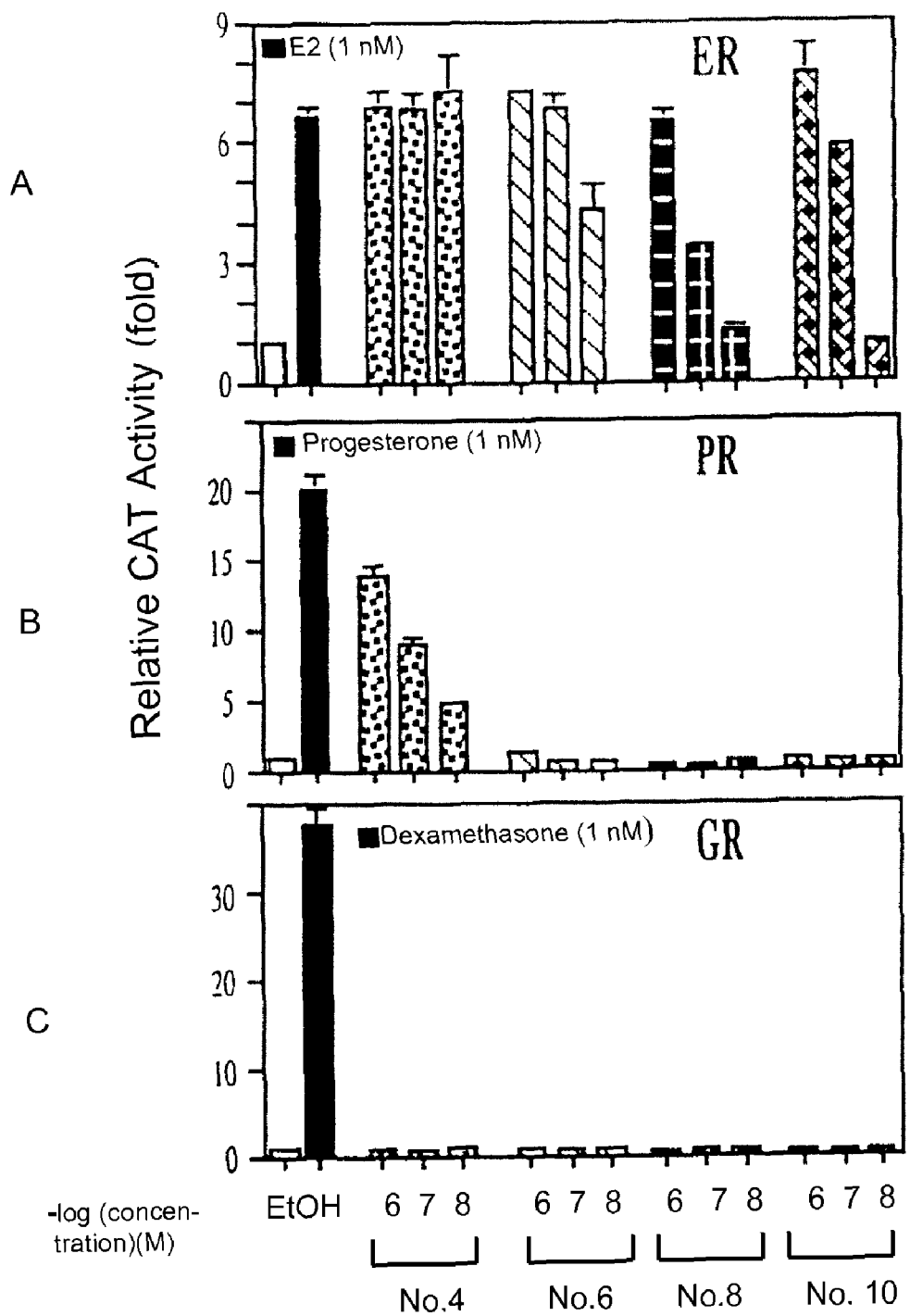
FIG. 5 shows the effects of compounds 4, 6, 8 and 10 on the estrogen receptor (ER), progesterone receptor (PR) and glucocorticoid receptor (GR) as discussed in example 6.

Suppression of the AED-induced AR transcriptional activity in the presence of HF. To mimic the in vivo condition of total androgen blockage in prostate cancer patients, compounds 4, 6, 8 and 10 were examined for their capacity to antagonize AED-induced AR transactivation in the presence of HF. In the presence of 1 µM HF, 50 nM AED, and each compound at 0.01, 0.1 or 1 µM, PC-3 cells were transiently transfected with pSG5 and the MMTV-CAT reporter plasmid. As shown in FIG. 4, HF suppressed AED-mediated AR transcription activity by about 40%. The compounds tested decreased AED-mediated AR transcription activity by about 75%.

Example 6

Steroid Hormone Specificity of DHEA Metabolites (No. 4, 6, 8, & 10). The estrogen receptor (ER)-positive MCF-7 cell line was transfected with a CAT reporter plasmid containing an estrogen response element linked to the CAT gene. PC-3 cells were transfected with MMTV-CAT reporter and progesterone receptor (PR) or glucocorticoid receptor (GR) to test the steroid hormone specificity of compounds 4, 6, 8 and 10. All 4 compounds have some estrogenic activity and only compound 4, which has a 17α-ethynyl group, shows some weak PR activity. None of these four compounds showed any GR activity.

REFERENCES

The following citations describe various aspects of prostate cancer and related subject matter. 1. Landis, S. H., Murray, T., Bolden, S. & Wingo, P. A. (1999) Canadian Cancer J. Clin. 49:8-31; 2. Garnick, M. B. (1997) Urology 49:5-15; 3. Gaddipati, J. P., McLeod, D. G., Heidenberg, H. B., Sesterhenn, I. A., Finger, M. J., Moul, J. W. & Srivastava, S. (1994) Cancer Res. 54:2861-2864; 4. Miyamoto, H., Yeh, S., Lardy, H., Messing, E. & Chang, C, (1998) Proc. Nad. Acad. Sci. USA 95:11083-11088; 5. Adams, J. B. (1985) Mol. Cell. Endocrinol. 41:1-17; 6. Yeh, S. & Chang, C. (1996) Proc. Natl. Acad. Sci. USA 93:5517-5521; 7. Yeh, S., Miyamoto, H., Shima, H. & Chang, C. (1998) Proc. Natl. Acad. Sci. USA 95:5527-5532; 8. Kang, H.-Y., Yeh, S., Fujimoto, N., & Chang, C. (1999) J. Biol. Chem. 274:8570-8576; 9. Fujimoto, N., Yeh, S., Kang, H.-Y., Inui, S., Chang, H.-C., Mizokami, A., & Chang, C. (1999) J. Biol. Chem. 274:8316-8321; 10. Yeh, S., Miyamoto, H., Nishimura, K., Kang, H., Ludlow, J., Hsiao, P., Wang, C., Su, C., & Chang, C. (1998) Biochem. Biophys. Res. Commun. 248:361-367; 11. Hsiao, P-W, Lin, D-L., Nakao, R. & Chang, C, (1999) J. Biol. Chem. 274: 20229-20234; 12. Hsiao, P.-W. & Chang, C. (1999) J. Biol. Chem. 274:22373-22379; 13. Belanger, A., Brochu, M. & Cliche, J. (1986) J. Clin. Endocrinol. Metab. 62:812-815; 14. Hirschmann, H., de Courcy, C., Levy, R. P. & Miller, K. L. (1960) J. Biol. Chem. 235:PC48-PC49; 15. Kirshner, M. A., Sinhamahapatra, S., Zucker, 1. R., Lorlaux, L. & Nieschiag, E. (1973) J. Clin. Endocrinol. Metab. 37:183-189; 16. Bonney, R. C., Scanlon, M. J., Jones, D. L., Beranek, P. A., Reed, M. J. & James, V. H (1984) J. Steroid Biochem. 20:1353-1355; 17. Mills, 1. H. (1967) Proc. Royal Soc. Med. 60:905-906; 18. Labrie, F., Dupont, A., Giguere, M., Borsanyi, J. P., Lacourclere, Y., Monfette, G., Emond, J. & Bergeron, N. (1988) Br. J. Urol. 61:341-346; 19. Lardy, H., Kneer, N., Wei, Y., Partridge, B., & Marwah, P. (1998) Steroids 63:158-165; 20. Reich, I., Lardy, H., Wei. Y., Marwah, P., Kneer, N., Powell, D., & Reich, H. J. (1998) Steroids 63:542-553; 21. Kelly, W. K., Slovin, S. & Scher, H. 1. (1997) Urol. Clin. North Am. 24:421-431; 22. Veldscholte, J., Ris-Stalpers, C., Kuiper, G. G. J. M., Jenster, G., Berrevoets, C., Claassen, E., van Rooij, H. C., Trapman, J., Brinkmann, A. O. & Mulder, E. (1990) Biochem. Biophys. Res. Commun. 173:534-540; 23. Suzuki, H., Akakura, K., Komiya, A., Aida, S., Akimoto, S. & Shimazaki, J. (1996) Prostate 29:153-158; 24. Kuil, C. W., Berrevoets, C. A. & Mulder E. (1995) J. Biol. Chem. 270: 27569-27576; 25. Wong, C., Kelce, W. R., Sar, M. & Wilson, E. M. (1995) J. Biol. Chem. 70:19998-20003; 26. Yeh, S., Miyamoto, H. & Chang, C. (1997) Lancet 349:852-853; 27. Miyamoto, H., Yeh, S., Wilding, G. & Chang, C. (1998) Proc. Natl. Acad. Sci. USA 95:7379-7984; 28. Chang, H. C, et al., Proc. Natl. Acad. Sci. USA 96:11173-11177 1999.

What is claimed is:
1. A group 9 compound having the structure

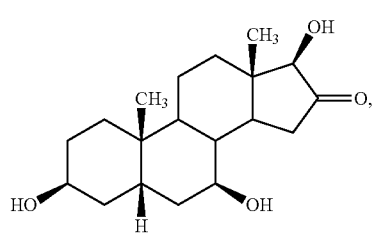

1.2.2.1

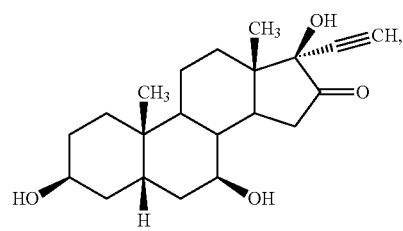

1.2.2.3

1.2.3.1
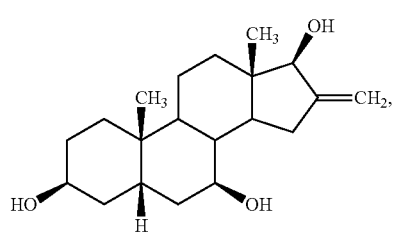
1.2.3.3
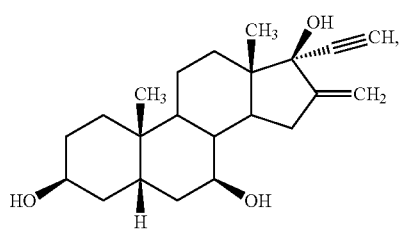
1.2.3.2
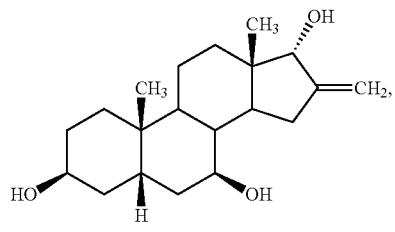
1.2.3.4
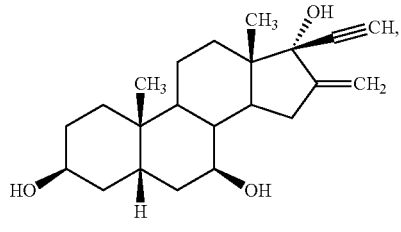
1.2.5.1
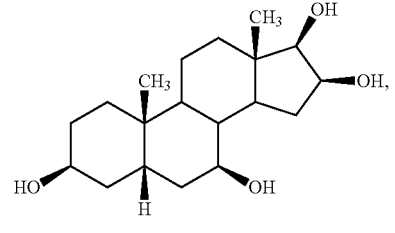
1.2.5.3
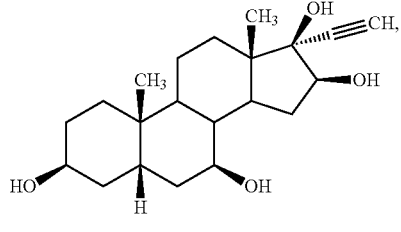
1.2.5.2
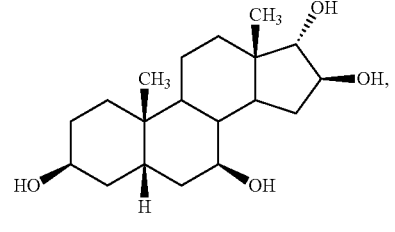
1.2.5.4
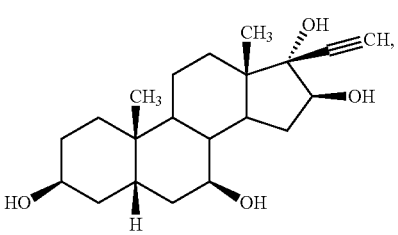
1.2.6.1
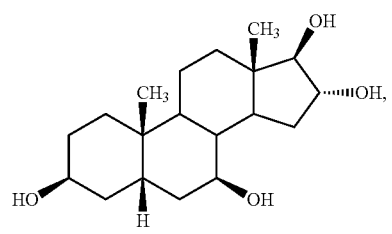
1.2.6.3
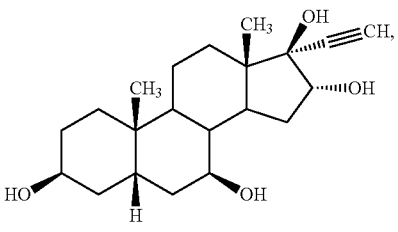
1.2.6.2
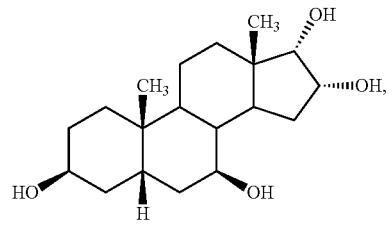
1.2.6.4
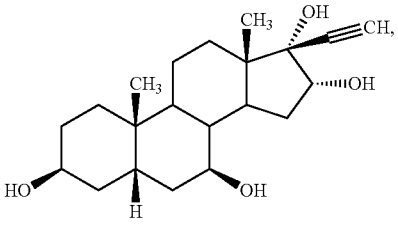
1.3.5.1
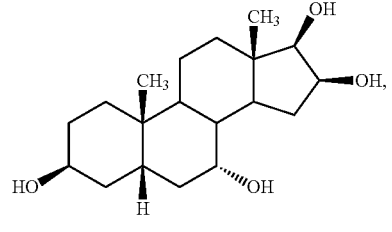
1.3.5.3
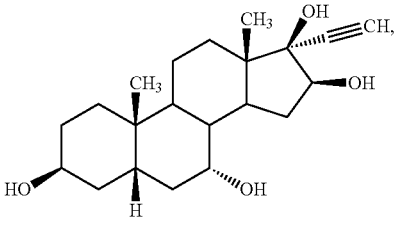

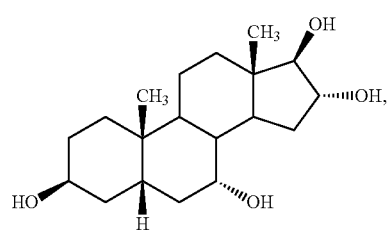
1.3.6.1
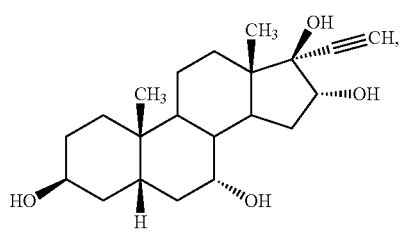
1.3.6.3
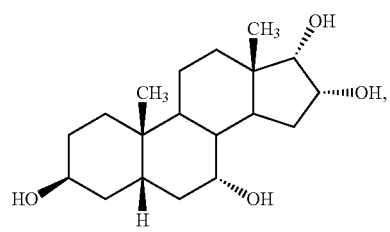
1.3.6.2
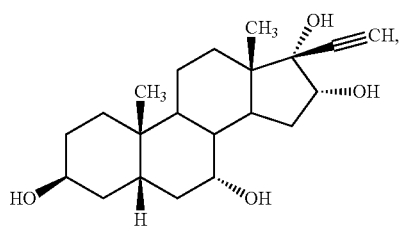
1.3.6.4
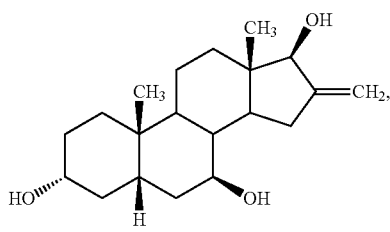
2.2.3.1
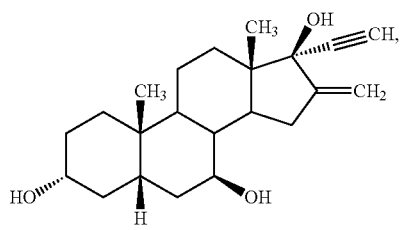
2.2.3.3
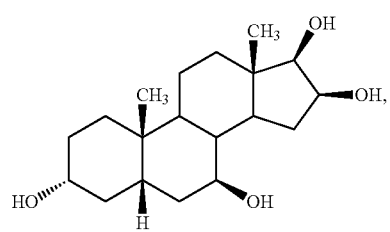
2.2.5.1
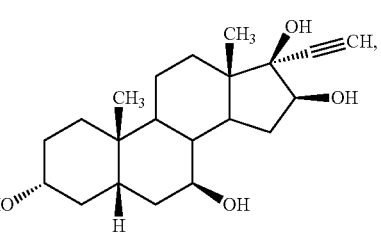
2.2.5.3
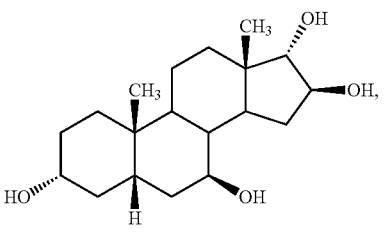
2.2.5.2
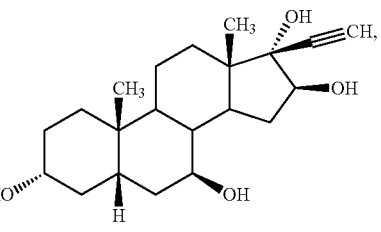
2.2.5.4
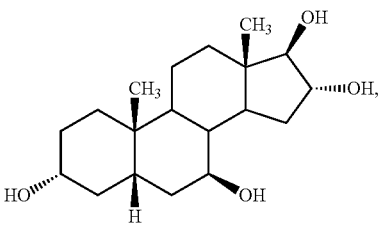
2.2.6.1
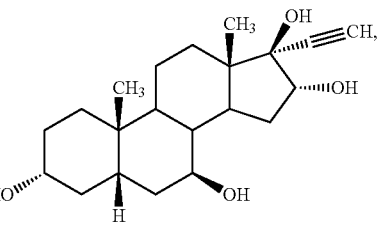
2.2.6.3
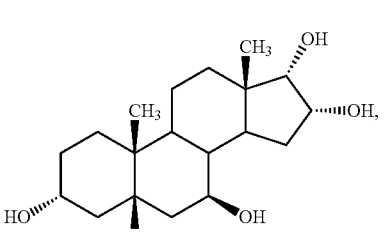
2.2.6.2
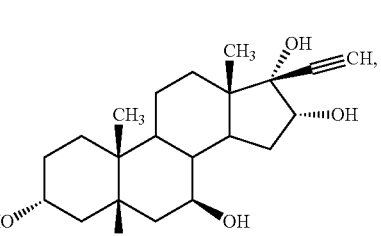
2.2.6.4

77
-continued
2.3.5.1
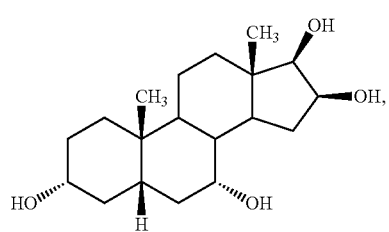
2.3.5.3
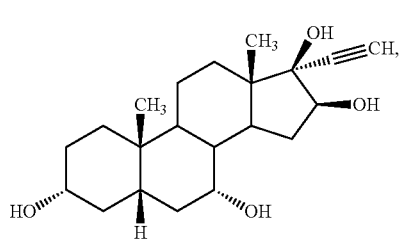
2.3.6.1
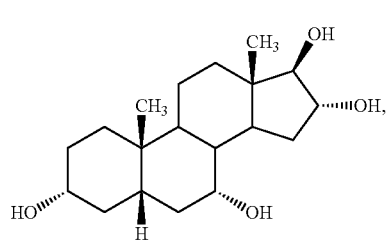
2.3.6.3
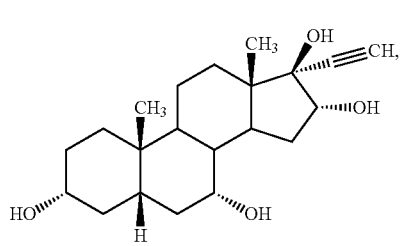
4.2.2.1
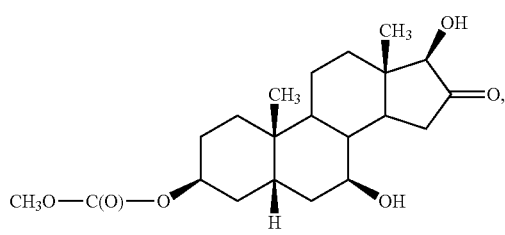
4.2.2.3
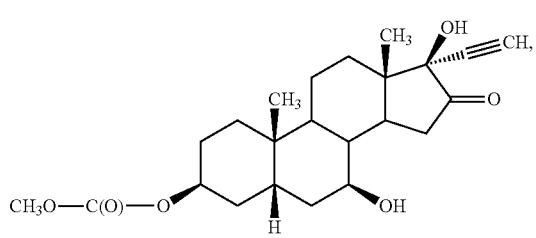
78
-continued
8.2.5.1
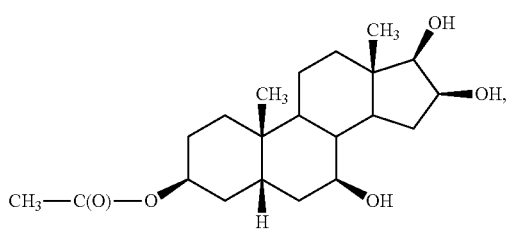
8.2.5.3
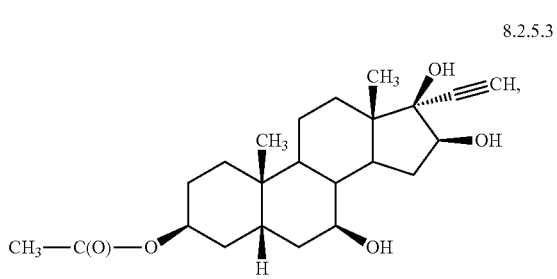
8.2.5.8
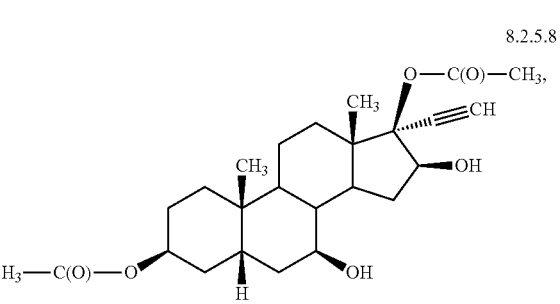
8.2.5.9
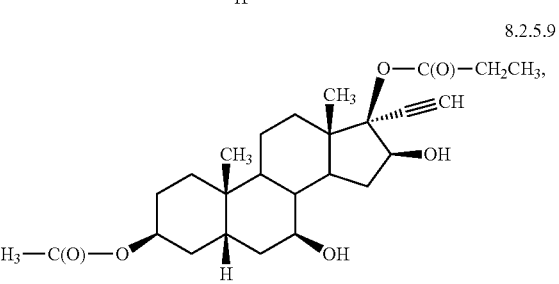
8.2.6.1
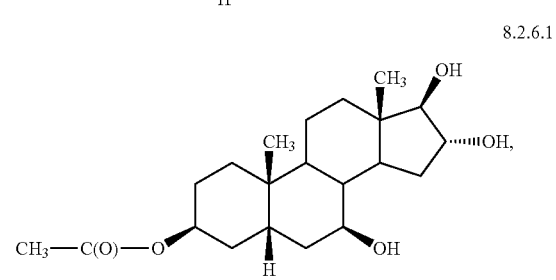
8.2.6.3
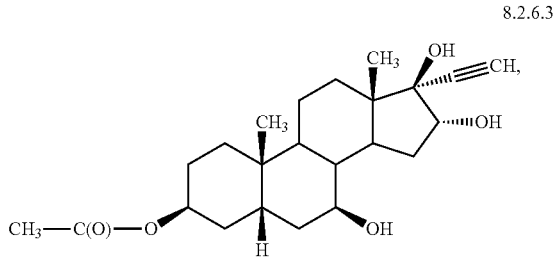

-continued 8.2.6.8
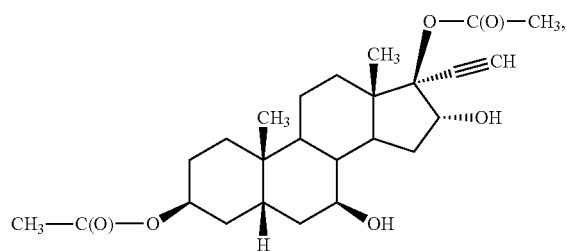

8.2.6.9
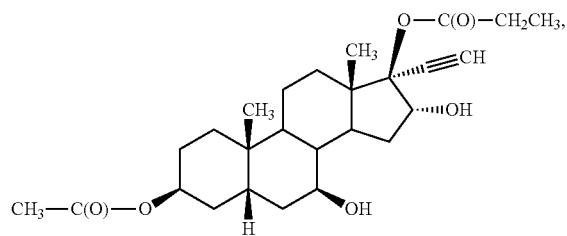

8.3.6.8
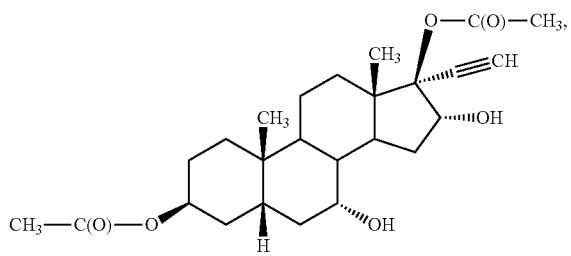

or 8.3.6.9
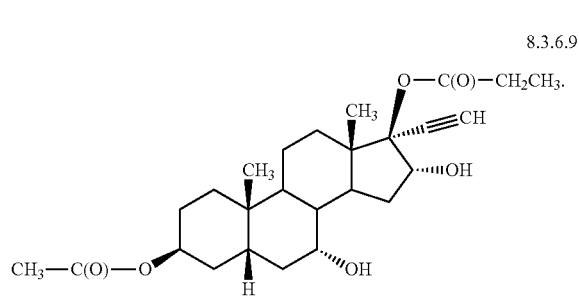

2. The group 9 compound of claim 1 having the structure 4.2.2.3
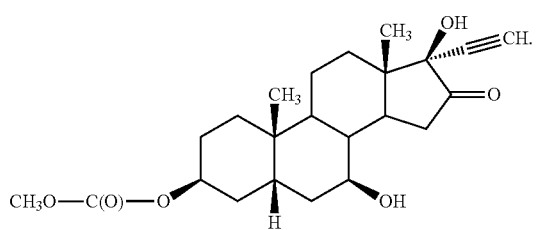

3. The compound of claim 1 wherein the compound is isolated and purified.

4. A pharmaceutical formulation comprising one or more excipients and a group 9 compound of claim 1.

5. The pharmaceutical formulation of claim 4 wherein the group 9 compound has the structure 4.2.2.3
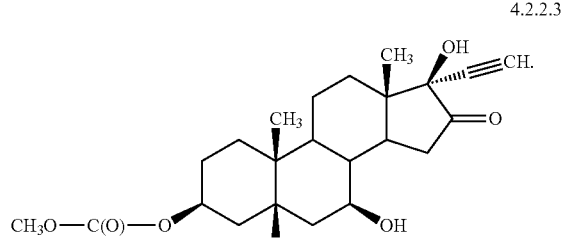

6. The pharmaceutical formulation of claim 4 wherein the group 9 compound has the structure 1.2.5.1
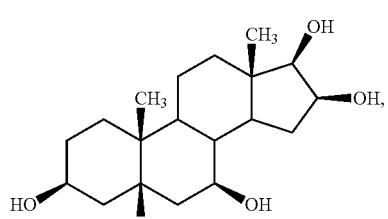

1.2.5.2
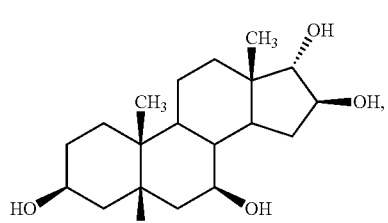

1.2.6.1
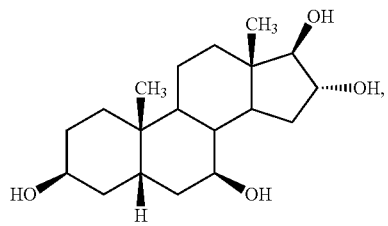

1.2.6.2
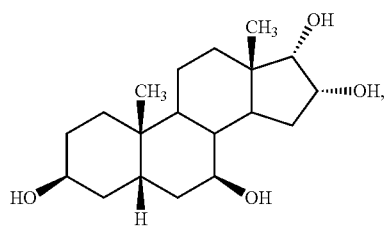

1.3.5.1
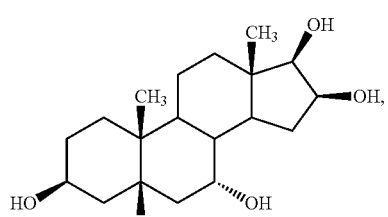

1.3.6.1
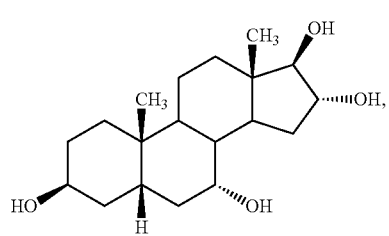
1.3.6.2
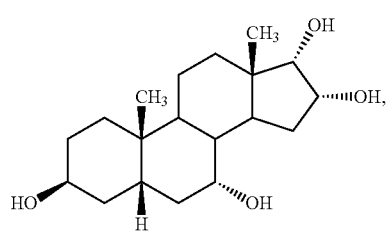
2.2.5.1
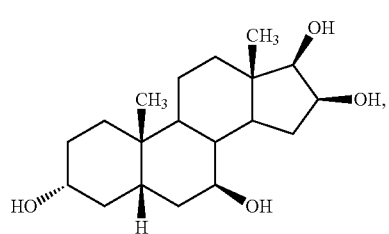
2.2.5.2
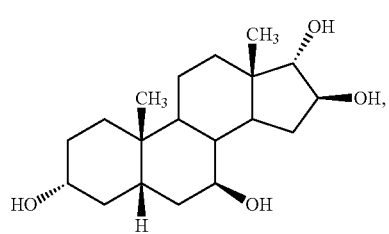
2.2.6.1
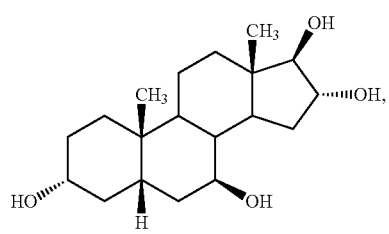
2.2.6.2
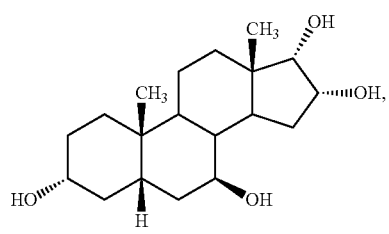
2.3.5.1
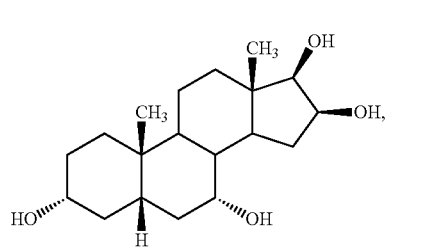 or
2.3.6.1
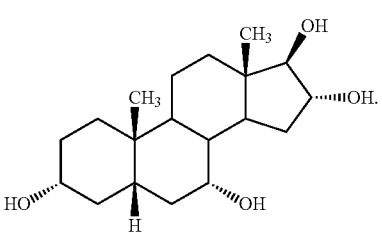
7. The pharmaceutical formulation of claim 4 wherein the group 9 compound has the structure
1.2.3.3
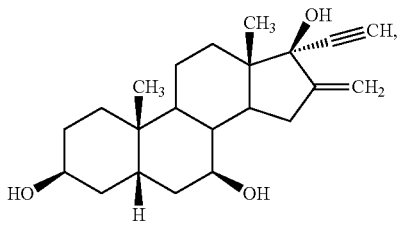
1.2.3.4
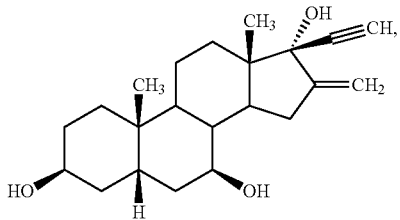
1.2.5.3
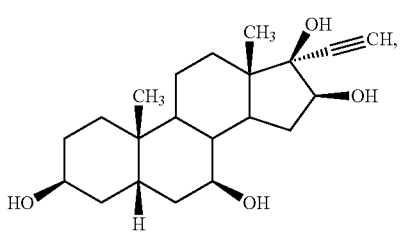
1.2.5.4
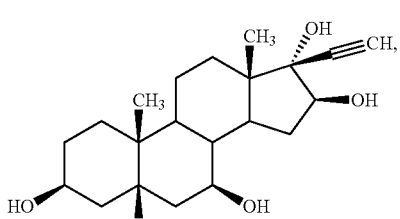
1.2.6.3
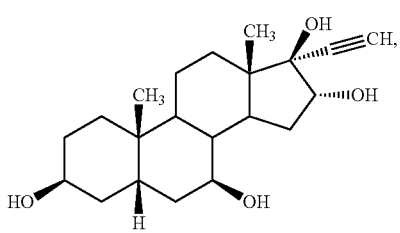

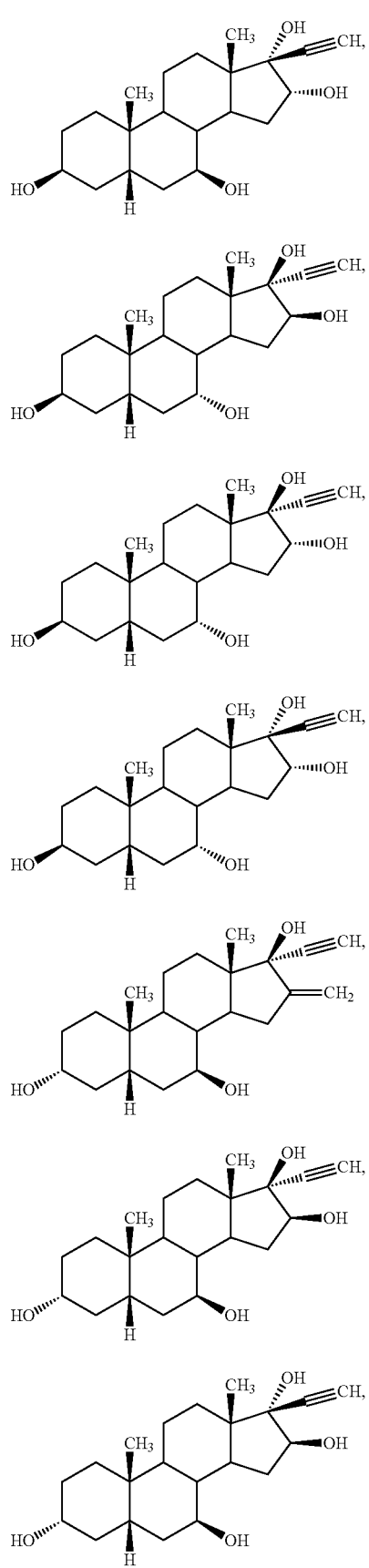
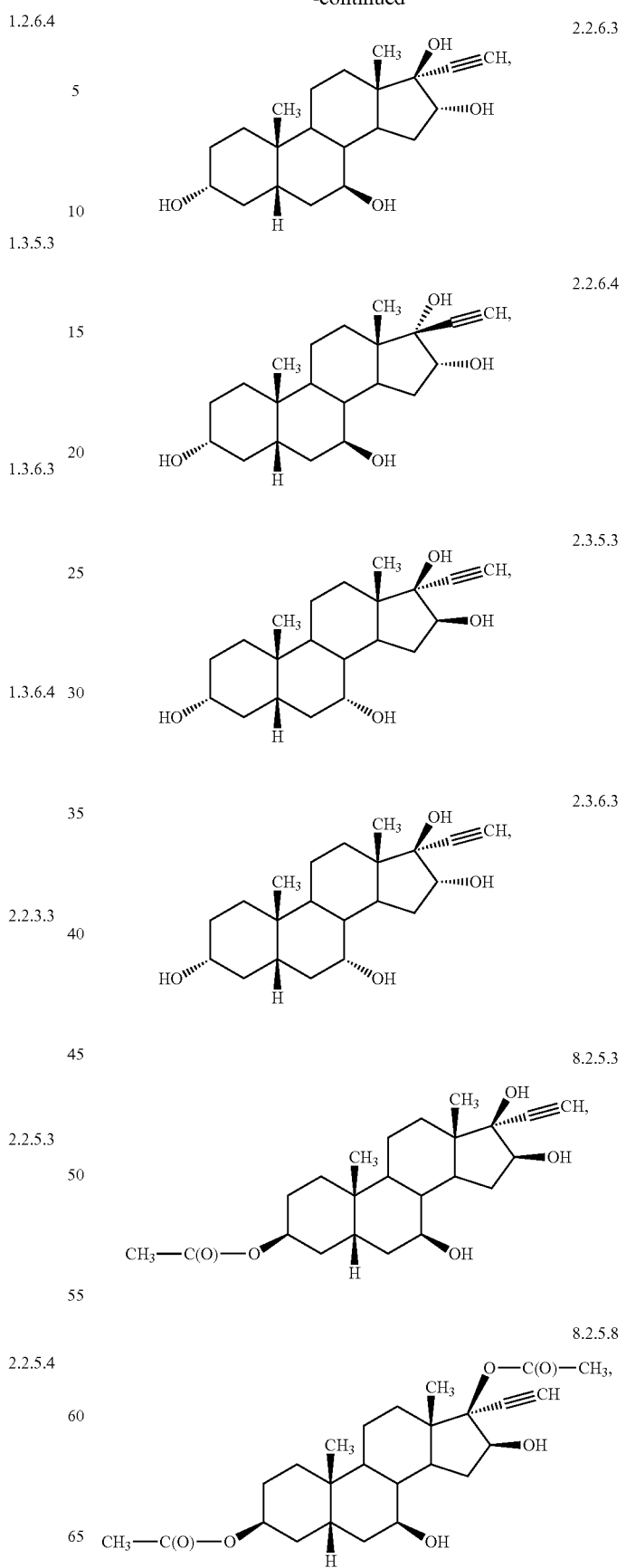

85
-continued
8.2.5.9
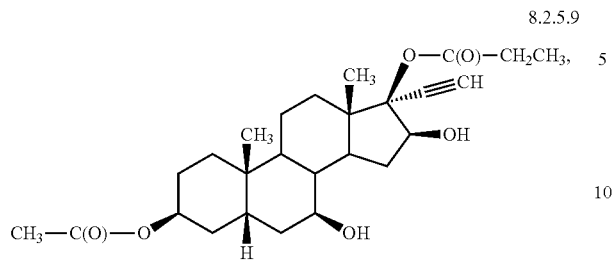
8.2.6.3
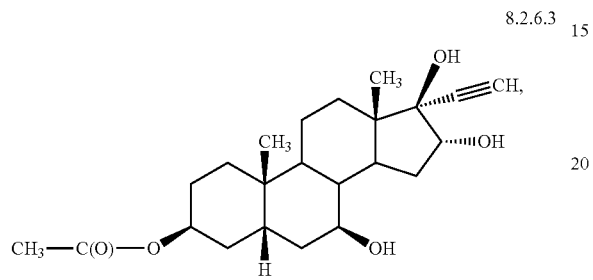
8.2.6.8
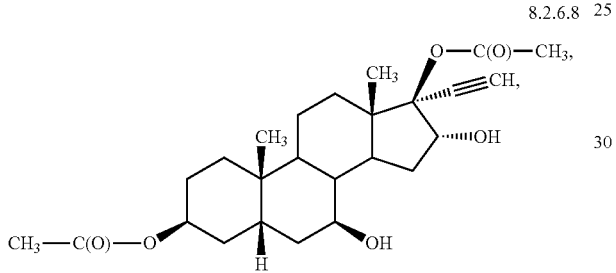
86
-continued
8.2.6.9
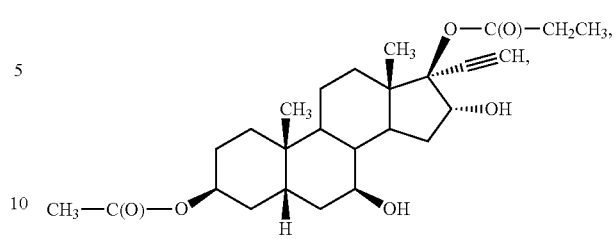
8.3.6.8
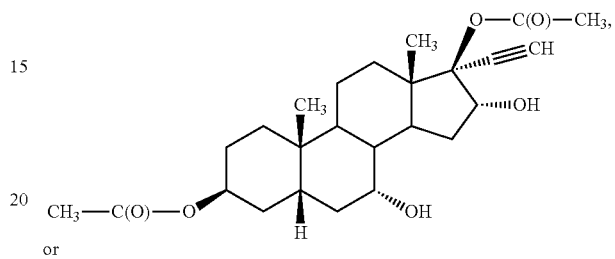
or
8.3.6.9
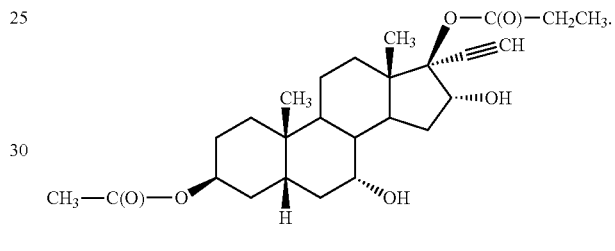
* * * * *